(12) United States Patent
Su et al.

(10) Patent No.: US 9,181,264 B2
(45) Date of Patent: Nov. 10, 2015

(54) FUSED HETEROARYLS AND THEIR USES

(75) Inventors: Weiguo Su, Shanghai (CN); Weihan Zhang, Shanghai (CN); Haibin Yang, Shanghai (CN)

(73) Assignee: Hutchison MediPharma Limited, Shanghai (CN)

( * ) Notice: Subject to any disclaimer, the term of this patent is extended or adjusted under 35 U.S.C. 154(b) by 0 days.

(21) Appl. No.: 13/823,604

(22) PCT Filed: Sep. 15, 2011

(86) PCT No.: PCT/CN2011/079684
§ 371 (c)(1),
(2), (4) Date: Mar. 14, 2013

(87) PCT Pub. No.: WO2012/034526
PCT Pub. Date: Mar. 22, 2012

(65) Prior Publication Data
US 2013/0190307 A1 Jul. 25, 2013

(51) Int. Cl.
*C07D 487/14* (2006.01)
*C07D 471/04* (2006.01)
*C07D 471/14* (2006.01)
*C07D 487/04* (2006.01)

(52) U.S. Cl.
CPC ............ *C07D 487/14* (2013.01); *C07D 471/04* (2013.01); *C07D 471/14* (2013.01); *C07D 487/04* (2013.01)

(58) Field of Classification Search
CPC ........................... C07D 487/14; C07D 471/04
See application file for complete search history.

(56) References Cited

U.S. PATENT DOCUMENTS

| 2010/0120762 A1 | 5/2010 | Stange et al. |
| 2010/0120763 A1 | 5/2010 | Stange et al. |
| 2011/0294799 A1 | 12/2011 | Hintermann et al. |

FOREIGN PATENT DOCUMENTS

| CN | 101330916 A | 12/2008 |
| CN | 101784547 A | 7/2010 |
| WO | WO 2005/054237 A1 | 6/2005 |
| WO | WO 2007/075468 A1 | 7/2007 |
| WO | WO 2009/155527 A2 | 12/2009 |
| WO | WO 2010/038164 A1 | 4/2010 |
| WO | WO 2010/038165 A1 | 4/2010 |
| WO | WO 2011/044157 A1 | 4/2011 |
| WO | WO 2011112731 A2 * | 9/2011 |

OTHER PUBLICATIONS

Extended European Search Report mailed Jan. 24, 2014 in European Patent Application No. 11824596.8.
International Search Report from the P.R. China Patent Office for International Application No. PCT/CN2011/079684, mailed Dec. 29, 2011.

* cited by examiner

*Primary Examiner* — Samira Jean-Louis
(74) *Attorney, Agent, or Firm* — Finnegan, Henderson, Farabow, Garrett & Dunner, LLP

(57) ABSTRACT

Provided are certain fused heteroaryls, compositions thereof and methods of use therefor.

2 Claims, No Drawings

FUSED HETEROARYLS AND THEIR USES

This application is the U.S. National Stage Application of International Application No. PCT/CN2011/079684, filed Sep. 15, 2011, which claims priority under 35 U.S.C. §365(b) to Internatioanl Application No. PCT/CN2010/076996 designating at least one country other than the U.S., filed Sep. 16, 2010.

Phosphoinositide 3-kinases (PI 3-kinases or PI3Ks) are a family of enzymes that may be involved in cellular functions such as cell growth, proliferation, differentiation, motility, survival and intracellular trafficking, which in turn can be involved in cancer.

The PI3K family may include four distinct classes defined by structural and functional characteristics and termed as Classes I-IV. The most fully characterized class may be the Class I-PI3Ks. Class I comprises three class I α isoforms—PI3Kα, PI3Kβ and PI3Kδ. PI3Kα appears to be highly relevant in human cancers and malignancies. PI3Kα can be overexpressed in human cancers.

Mammalian target of rapamycin (mTOR) is the downstream kinase of PI3K family. Inhibition of mTOR can inhibit the activity of PI3K. Therefore, the PI3K/mTOR pathway can be exploited for new cancer drug discovery.

Provided is at least one compound of formula 1:

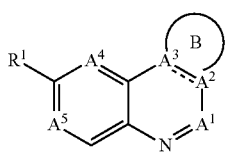

(1)

and/or at least one pharmaceutically acceptable salt thereof wherein $A^1$ is N or CH;

$A^4$ and $A^5$ are independently N or $CR^2$;

$A^2$ and $A^3$, together with B ring are a 5-membered heteroaryl or heterocycle containing 1 to 4 heteroatoms selected from N, O, and S, and said 5-membered heteroaryl or heterocycle is optionally substituted by one or more groups independently chosen from alkyl, alkenyl, alkynyl, aryl, cycloalkyl, oxo, —C(O)$R^a$, —C(O)O$R^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, —OR$^b$, —S(O)$_n$R$^e$, —S(O)$_n$NR$^c$R$^d$, halo, haloalkyl, heteroaryl, and heterocycle;

provided that $A^2$ and $A^3$, together with the B ring are not

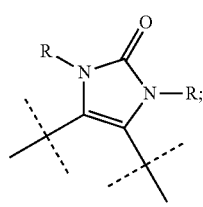

is a single bond or a double bond;

$R^1$ is heteroaryl, optionally substituted by one or more groups independently chosen from alkyl, alkenyl, alkynyl, aryl, cycloalkyl, oxo, —C(O)$R^a$, —C(O)O$R^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, —OR$^b$, —S(O)$_n$R$^e$, —S(O)$_n$NR$^c$R$^d$, halo, haloalkyl, heteroaryl, and heterocycle;

R and $R^2$ are independently chosen from H, alkyl, alkenyl, alkynyl, aryl, cycloalkyl, —C(O)$R^a$, —C(O)O$R^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, —OR$^b$, —OC(O)R$^a$, —OC(O)NR$^c$R$^d$, —S(O)$_n$R$^e$, —S(O)$_n$NR$^c$R$^d$, halo, haloalkyl, heteroaryl, and heterocycle;

and each of said above alkyl, alkenyl, alkynyl, aryl, cycloalkyl, haloalkyl, heteroaryl and heterocycle can be optionally substituted by one or more groups independently chosen from optionally substituted alkyl, optionally substituted alkenyl, optionally substituted alkynyl, optionally substituted aryl, optionally substituted cycloalkyl, —OH, oxo, —C(O)$R^a$, —C(O)O$R^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, OR$^b$, —S(O)$_n$R$^e$, —S(O)$_n$NR$^c$R$^d$, halo, optionally substituted haloalkyl, optionally substituted heteroaryl, and optionally substituted heterocycle;

$R^a$, $R^b$, $R^c$, $R^d$, $R^e$, $R^f$ and $R^g$ are each independently chosen from H, optionally substituted alkyl, optionally substituted alkenyl, optionally substituted alkynyl optionally substituted aryl, optionally substituted cycloalkyl, optionally substituted haloalkyl, optionally substituted heteroaryl, and optionally substituted heterocycle, or $R^a$ and $R^c$, and/or $R^c$ and $R^d$, and/or $R^c$ and $R^e$, and/or $R^c$ and $R^f$, and/or $R^d$ and $R^e$, and/or $R^g$ and $R^f$ together with the atom(s) to which they are attached, form a 3-10 membered optionally substituted heterocycle ring; and for each occurrence, n is independently 0, 1, or 2;

wherein each optionally substituted group above can be unsubstituted or independently substituted with one or more, such as one, two, or three, substituents independently selected from $C_1$-$C_4$ alkyl, cycloalkyl, oxo, aryl, heterocycle, heteroaryl, aryl-$C_1$-$C_4$ alkyl-, heterocycle-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —O$C_2$H, —C(O)O$C_1$-$C_4$ alkyl, —C(O)Ocycloalkyl, —C(O)Oaryl, —C(O)Oheteroaryl, —C(O)Oheterocycle, —CON($C_1$-$C_4$ alkyl)($C_1$-$C_4$ alkyl), —CONR'R" wherein R' and R" with the N to which they are attached form a heterocycle, —CON(cycloalkyl)(cycloalkyl), —CON(heterocycle)(heterocycle), —CONH($C_1$-$C_4$ alkyl), —CONH(cycloalkyl), —CONH(heterocycle), —CONH$_2$, —NHC(O)($C_1$-$C_4$ alkyl), —NHC(O)(cycloalkyl), —NHC(O)(heterocycle), —NHC(O)(aryl) such as —NHC(O)(phenyl), —NHC(O)(heteroaryl), —N($C_1$-$C_4$ alkyl)C(O)($C_1$-$C_4$ alkyl), —N($C_1$-$C_4$ alkyl)C(O)(cycloalkyl), —N($C_1$-$C_4$ alkyl)C(O)(heterocycle), —N($C_1$-$C_4$ alkyl)C(O)(aryl) such as —N($C_1$-$C_4$ alkyl)C(O)(phenyl), N($C_1$-$C_4$ alkyl)C(O)(heteroaryl), —C(O)$C_1$-$C_4$ alkyl, —C(O)(cycloalkyl), —C(O)(heterocycle), —C(O)(aryl) such as —C(O) phenyl, —C(O)(heteroaryl), —C(O)$C_1$-$C_4$ haloalkyl, —OC(O)$C_1$-$C_4$ alkyl, —OC(O)(cycloalkyl), —C(O)(heterocycle), —OC(O)(heteroaryl), OC(O)(aryl), such as —OC(O)phenyl, —SO$_2$($C_1$-$C_4$ alkyl), —SO$_2$(cycloalkyl), —SO$_2$(heterocycle), —SO$_2$(aryl) such as SO$_2$(phenyl), —SO$_2$(heteroaryl), —SO$_2$($C_1$-$C_4$ haloalkyl), —SO$_2$NH$_2$, —SO$_2$NR'R" wherein R' and R" with the N to which they are attached form a heterocycle, —SO$_2$NH($C_1$-$C_4$ alkyl), —SO$_2$NH(cycloalkyl), —SO$_2$NH(heterocycle), —SO$_2$NH(aryl) such as —SO$_2$NH(phenyl), —SO$_2$NH(heteroaryl), —NHSO$_2$(C$_1$-C$_4$ alkyl), NHSO$_2$(cycloalkyl), NHSO$_2$(heterocycle), NHSO$_2$(aryl) such as —NHSO$_2$(phenyl), NHSO$_2$(heteroaryl), and —NHSO$_2$(C$_1$-C$_4$ haloalkyl), in which each of alkyl, phenyl, aryl, cycloalkyl, heterocycle, and heteroaryl is optionally substituted by one or more groups independently chosen from —OH, halo, cycloalkyl, heterocycle, C$_1$-C$_4$ alkyl, C$_1$-C$_4$ haloalkyl-, —OC$_1$-C$_4$ alkyl, C$_1$-C$_4$ alkyl-OH, —C$_1$-C$_4$ alkyl-O—C$_1$-C$_4$ alkyl, —OC$_1$-C$_4$ haloalkyl, cyano, nitro, —NH$_2$, —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), and —N(C$_1$-C$_4$ alkyl)C(O)(C$_1$-C$_4$ alkyl).

Also provided is a pharmaceutical composition comprising at least one compound and/or at least one pharmaceutically acceptable salt thereof described herein and at least one pharmaceutically acceptable carrier.

Also provided is a method of inhibiting the activity of PI3K and/or mTOR comprising contacting the enzyme with an effective amount of at least one compound and/or at least one pharmaceutically acceptable salt thereof described herein.

Also provided is a method of treating cancer responsive to inhibition of PI3K and/or mTOR comprising administering to a subject in need of treating for said cancer an effective amount of at least one compound and/or at least one pharmaceutically acceptable salt thereof described herein.

Also provided is a use of at lease one compound and/or at least one pharmaceutically acceptable salt thereof described herein in the manufacture of a medicament for inhibiting the activity of PI3K and/or mTOR.

Also provided is a use of at lease one compound and/or at least one pharmaceutically acceptable salt thereof described herein in the manufacture of a medicament for treating cancer.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

The term "alkyl" herein refers to a straight or branched hydrocarbon, containing 1-18, such as 1-12, further such as 1-6 carbon atoms. Examples of alkyl groups include, but are not limited to, methyl, ethyl, n-propyl, i-propyl, n-butyl, i-butyl, and t-butyl. "Lower alkyl" refers to a straight or branched hydrocarbon, containing 1-6, such as 1-4 carbon atoms.

The term "alkoxy" herein refers to a straight or branched alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to a straight or branched alkoxy, wherein the alkyl portion contains 1-4 carbon atoms.

The term "alkenyl" herein refers to a straight or branched hydrocarbon, containing one or more C=C double bonds and 2-10, such as 2-6 carbon atoms. Examples of alkenyl groups include, but are not limited to, vinyl, 2-propenyl, and 2-butenyl.

The term "alkynyl" herein refers to a straight or branched hydrocarbon, containing one or more C≡O triple bonds and 2-10, such as 2-6 carbon atoms. Examples of alkynyl groups include, but are not limited to, ethynyl, 2-propynyl, and 2-butynyl.

The term "cycloalkyl" refers to saturated and partially unsaturated cyclic hydrocarbon groups having 3 to 12, such as 3 to 8 carbon atoms. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The ring may be saturated or have one or more double bonds (i.e. partially unsaturated), but not fully conjugated, and not aromatic, as defined herein.

"Aryl" encompasses:

5- and 6-membered carbocyclic aromatic rings, for example, phenyl;

bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene.

For example, aryl includes 5 and 6-membered carbocyclic aromatic rings fused to a 5- to 7-membered cycloalkyl or heterocyclic ring containing zero or more heteroatoms selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl when the carbocyclic aromatic ring fused with a cycloalkyl. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

The term "heteroaryl" refers to 5- to 7-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 4, or, in some embodiments, from 1 to 3, heteroatoms selected from N, O, and S, with the remaining ring atoms being carbon and wherein at least one ring is aromatic and at least one heteroatom is present in the aromatic ring; and 11- to 14-membered tricyclic rings containing one or more, for example, from 1 to 4, or in some embodiments, from 1 to 3, heteroatoms selected from N, O, and S, with the remaining ring atoms being carbon and wherein at least one ring is aromatic and at least one heteroatom is present in an aromatic ring.

For example, heteroaryl includes a 5- to 7-membered heterocyclic aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), pyridyl (such as 2-pyridyl, 3-pyridyl, or 4-pyridyl), pyrazinyl, 2,4-pyrimidinyl, 3,5-pyrimidinyl, 2,4-imidazolyl, isoxazolyl, oxazolyl, thiazolyl, thiadiazolyl, tetrazolyl, thienyl, benzothienyl, furyl, benzofuryl, benzoimidazolyl, indolyl, indolinyl, pyridizinyl, triazolyl, quinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), benzothiazolyl (such as benzo[d]thiazol-6-yl), indazolyl (such as 1H-indazol-5-yl) and 5,6,7,8-tetrahydroisoquinoline.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O⁻) substituents, such as pyridinyl N-oxides.

By "heterocycle" or "heterocyclic ring" is meant a 4- to 12-membered monocyclic, bicyclic or tricyclic saturated or partially unsaturated ring containing at least 2 carbon atoms in addition to 1-3 heteroatoms independently selected from oxygen, sulfur, and nitrogen. "Heterocycle" also refers to 5- to 7-membered heterocyclic ring containing one or more heteroatoms selected from N, O, and S fused with 5-, 6-, and/or 7-membered cycloalkyl, carbocyclic aromatic or heteroaromatic ring, provided that the point of attachment is at the heterocyclic ring when the heterocylice ring is fused with a carbocyclic aromatic or a heteroaromatic ring, and that the point of attachment can be at the cycloalkyl or heterocyclic ring when the heterocylic ring is fused with cycloalkyl. "Heterocycle" also refers to an aliphatic spirocyclic ring containing one or more heteroatoms selected from N, O, and S, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring. A heterocyle is not a heteroaryl as defined herein.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl and 3-morpholinyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogen atoms on the designated atom or group is replaced with a selection from the indicated group, provided that the designated atom's normal valence is not exceeded. When a substituent is oxo (i.e., =O) then 2 hydrogen atoms on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

In some embodiments, "substituted with one or more groups" refers to two hydrogen atoms on the designated atom or group being independently replaced with two selections from the indicated group of substituents. In some embodiments, "substituted with one or more groups" refers to three hydrogen atoms on the designated atom or group being independently replaced with three selections from the indicated group of substituents. In some embodiments, "substituted with one or more groups" refers to four hydrogen atoms on the designated atom or group being independently replaced with four selections from the indicated group of substituents.

Compounds described herein include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include, to the extent they can be made without undue experimentation, all tautomeric forms of the compound. Such compounds also include crystal forms including polymorphs and clathrates, to the extent they can be made by one of ordinary skill in the art by routine experimentation. Similarly, the term "salt" is intended to include all isomers, racemates, other mixtures, Z- and E-forms, tautomeric forms and crystal forms of the salt of the compound, to the extent they can be made by one of ordinary skill in the art without undue experimentation.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, alkanoate such as acetate, and salts with HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

A "solvate," such as a "hydrate," is formed by the interaction of a solvent and a compound. The term "compound" is intended to include solvates, including hydrates, of compounds, to the extent they can be made by one of ordinary skill in the art by routine experimentation. Similarly, "salts" includes solvates, such as hydrates, of salts, to the extent they can be made by one of ordinary skill in the art by routine experimentation. Suitable solvates are pharmaceutically acceptable solvates, such as hydrates, including monohydrates and hemi-hydrates, to the extent they can be made by one of ordinary skill in the art by routine experimentation.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound."

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

As used herein the terms "group", "radical" or "fragment" are synonymous and are intended to indicate functional groups or fragments of molecules attachable to a bond or other fragments of molecules.

The term "active agent" is used to indicate a chemical substance which has biological activity. In some embodiments, an "active agent" is a chemical substance having pharmaceutical utility.

"Treating," "treat," or "treatment" or "alleviation" refers to administering at least one compound and/or at least one pharmaceutically acceptable salt thereof described herein to a subject that has cancer, or has a symptom of cancer, or has a predisposition toward cancer, with the purpose to cure, heal, alleviate, relieve, alter, remedy, ameliorate, improve, or affect cancer, the symptoms of cancer, or the predisposition toward cancer.

The term "effective amount" refers to an amount of at least one compound and/or at least one pharmaceutically acceptable salt thereof described herein effective to "treat," as defined above, a disease or disorder in a subject. In the case of cancer, the effective amount may cause any of the changes observable or measurable in a subject as described in the definition of "treating," "treat," "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of PI3K/mTOR activity. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "inhibition" indicates a decrease in the baseline activity of a biological activity or process. "Inhibition of PI3K and/or mTOR activity" refers to a decrease in the activity of PI3K and/or mTOR as a direct or indirect response to the presence of at least one compound and/or at least one pharmaceutically acceptable salt described herein, relative to the activity of PI3K and/or mTOR in the absence of the at least one compound and/or the at least one pharmaceutically acceptable salt thereof. The decrease in activity is not bound by theory and may be due to the direct interaction of the at least one compound and/or at least one pharmaceutically acceptable salt thereof described herein with PI3K and/or mTOR, or due to the interaction of the at least one compound and/or at least one pharmaceutically acceptable salt described herein, with one or more other factors that in turn affect PI3K and/or mTOR activity. For example, the presence of at least one compound and/or at least one pharmaceutically acceptable salt thereof described herein, may decrease PI3K and/or mTOR activity by directly binding to the PI3K and/or mTOR, by causing (directly or indirectly) another factor to decrease PI3K and/or mTOR activity, or by (directly or indirectly) decreasing the amount of PI3K and/or mTOR present in the cell or organism.

The details of one or more embodiments of the invention are set forth below.

Provided herein is at least one compound of formula 1:

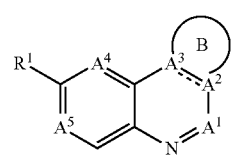

(1)

and/or at least one pharmaceutically acceptable salt thereof wherein $A^1$ is N or CH;

$A^4$ and $A^5$ are independently N or $CR^2$;

$A^2$ and $A^3$, together with B ring, are a 5-membered heteroaryl or heterocycle containing 1 to 4 heteroatoms selected from N, O, and S, and said 5-membered heteroaryl or heterocycle is optionally substituted by one or more groups independently chosen from alkyl, alkenyl, alkynyl, aryl, cycloalkyl, oxo, —C(O)$R^a$, —C(O)O$R^b$, —CN, —C(O)N$R^c R^d$, —N$R^c R^d$, —N$R^c$C(O)$R^a$, —N$R^c$S(O)$_n R^e$, —N$R^c$S $(O)_nNR^fR^g$, —$NR^cC(O)OR^b$, —$NR^cC(O)NR^dR^e$, —$NO_2$, —$OR^b$, —$S(O)_nR^e$, —$S(O)_nNR^cR^d$, halo, haloalkyl, heteroaryl, and heterocycle;

provided that $A^2$ and $A^3$, together with the B ring, are not

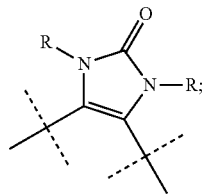

⋯ is a single bond or a double bond;

$R^1$ is heteroaryl, optionally substituted by one or more groups independently chosen from alkyl, alkenyl, alkynyl, aryl, cycloalkyl, oxo, —$C(O)R^a$, —$C(O)OR^b$, —CN, —$C(O)NR^cR^d$, —$NR^cR^d$, —$NR^cC(O)R^a$, —$NR^cS(O)_nR^e$, —$NR^cS(O)_nNR^fR^g$, —$NR^cC(O)OR^b$, —$NR^cC(O)NR^dR^e$, —$NO_2$, —$OR^b$, —$S(O)_nR^e$, —$S(O)_nNR^cR^d$, halo, haloalkyl, heteroaryl, and heterocycle;

R and $R^2$ are independently chosen from H, alkyl, alkenyl, alkynyl, aryl, cycloalkyl, —$C(O)R^a$, —$C(O)OR^b$, —CN, —$C(O)NR^cR^d$, —$NR^cR^d$, —$NR^cC(O)R^a$, —$NR^cS(O)_nR^e$, —$NR^cS(O)_nNR^fR^g$, —$NR^cC(O)OR^b$, —$NR^cC(O)NR^dR^e$, —$NO_2$, —$OR^b$, —$OC(O)R^a$, —$OC(O)NR^cR^d$, —$S(O)_nR^e$, —$S(O)_nNR^cR^d$, halo, haloalkyl, heteroaryl, and heterocycle;

and each of said above alkyl, alkenyl, alkynyl, aryl, cycloalkyl, haloalkyl, heteroaryl and heterocycle can be optionally substituted by one or more groups independently chosen from optionally substituted alkyl, optionally substituted alkenyl, optionally substituted alkynyl, optionally substituted aryl, optionally substituted cycloalkyl, —OH, oxo, —$C(O)R^a$, —$C(O)OR^b$, —CN, —$C(O)NR^cR^d$, —$NR^cR^d$, —$NR^cC(O)R^a$, —$NR^cS(O)_nR^e$, —$NR^cS(O)_nNR^fR^g$, —$NR^cC(O)OR^b$, —$NR^cC(O)NR^dR^e$, —$NO_2$, $OR^b$, —$S(O)_nR^e$, —$S(O)_nNR^cR^d$, halo, optionally substituted haloalkyl, optionally substituted heteroaryl, and optionally substituted heterocycle;

$R^a$, $R^b$, $R^c$, $R^d$, $R^e$, $R^f$ and $R^g$ are each independently chosen from H, optionally substituted alkyl, optionally substituted alkenyl, optionally substituted alkynyl optionally substituted aryl, optionally substituted cycloalkyl, optionally substituted haloalkyl, optionally substituted heteroaryl, and optionally substituted heterocycle, or $R^a$ and $R^c$, and/or $R^c$ and $R^d$, and/or $R^c$ and $R^e$, and/or $R^c$ and $R^f$, and/or $R^d$ and $R^e$, and/or $R^g$ and $R^f$ together with the atom(s) to which they are attached, form a 3-10 membered optionally substituted heterocycle ring; and for each occurrence, n is independently 0, 1, or 2;

wherein each optionally substituted group above can be unsubstituted or independently substituted with one or more, such as one, two, or three, substituents independently selected from, $C_1$-$C_4$ alkyl, cycloalkyl, oxo, aryl, heterocycle, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo, —$CO_2H$, —$C(O)OC_1$-$C_4$ alkyl, —$C(O)$ Ocycloalkyl, —$C(O)$Oaryl, —$C(O)$Oheteroaryl, —$C(O)$Oheterocycle, —$CON(C_1$-$C_4$ alkyl)($C_1$-$C_4$ alkyl), —CONR'R" wherein R' and R" with the N to which they are attached form a heterocycle, —CON(cycloalkyl)(cycloalkyl), —CON(heterocycle)(heterocycle), —CONH($C_1$-$C_4$ alkyl), —CONH(cycloalkyl), —CONH(heterocycle), —$CONH_2$, —$NHC(O)(C_1$-$C_4$ alkyl), —NHC(O)(cycloalkyl), —NHC(O)(heterocycle), —NHC(O)(aryl) such as —NHC(O)(phenyl), —NHC(O)(heteroaryl), —$N(C_1$-$C_4$ alkyl)C(O)($C_1$-$C_4$ alkyl), —$N(C_1$-$C_4$ alkyl)C(O)(cycloalkyl), —$N(C_1$-$C_4$ alkyl)C(O)(heterocycle), —$N(C_1$-$C_4$ alkyl)C(O)(aryl) such as —$N(C_1$-$C_4$ alkyl)C(O)(phenyl), —$N(C_1$-$C_4$ alkyl)C(O)(heteroaryl), —$C(O)C_1$-$C_4$ alkyl, —C(O)(cycloalkyl), —C(O)(heterocycle), —C(O)(aryl) such as —C(O) phenyl, —C(O)(heteroaryl), —$C(O)C_1$-$C_4$ haloalkyl, —$OC(O)C_1$-$C_4$ alkyl, —OC(O)(cycloalkyl), —OC(O)(heterocycle), —OC(O)(heteroaryl), OC(O)(aryl) such as —OC(O)phenyl, —$SO_2(C_1$-$C_4$ alkyl), —$SO_2$(cycloalkyl), —$SO_2$(heterocycle), —$SO_2$(aryl) such as $SO_2$(phenyl), —$SO_2$(heteroaryl), —$SO_2(C_1$-$C_4$ haloalkyl), —$SO_2NH_2$, —$SO_2NR'R"$ wherein R' and R" with the N to which they are attached form a heterocycle, —$SO_2NH(C_1$-$C_4$ alkyl), —$SO_2NH$(cycloalkyl), —$SO_2NH$(heterocycle), —$SO_2NH$(aryl) such as —$SO_2NH$(phenyl), —$SO_2NH$(heteroaryl), —$NHSO_2(C_1$-$C_4$ alkyl), $NHSO_2$(cycloalkyl), $NHSO_2$(heterocycle), $NHSO_2$(aryl) such as —$NHSO_2$(phenyl), —$NHSO_2$(heteroaryl), and —$NHSO_2(C_1$-$C_4$ haloalkyl), in which each of alkyl, phenyl, aryl, cycloalkyl, heterocycle, and heteroaryl is optionally substituted by one or more groups independently chosen from —OH, halo, cycloalkyl, heterocycle, $C_1$-$C_4$ alkyl, $C_1$-$C_4$ haloalkyl-, —$OC_1$-$C_4$ alkyl, $C_1$-$C_4$ alkyl-OH, —$C_1$-$C_4$ alkyl-O—$C_1$-$C_4$ alkyl, —$OC_1$-$C_4$ haloalkyl, cyano, nitro, —$NH_2$, —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), and —$N(C_1$-$C_4$ alkyl)C(O)($C_1$-$C_4$ alkyl).

In some embodiments, $A^2$ and $A^3$, together with B ring, are a 5-membered heteroaryl or heterocycle containing 1 to 3 heteroatoms selected from N, O and S. In some embodiments, $A^2$ and $A^3$, together with B ring, are a 5-membered heteroaryl or heterocycle containing 1 to 3 nitrogen heteroatoms.

In some embodiments, $A^2$ and $A^3$, together with B ring, can be selected from structures (2)-(6)

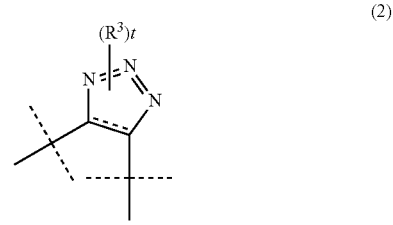

(2)

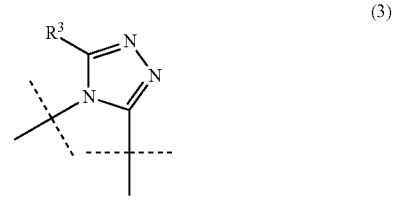

(3)

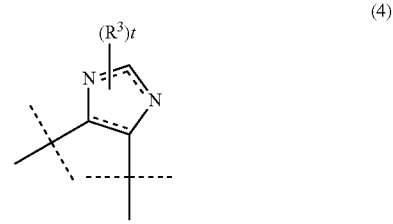

(4)

-continued

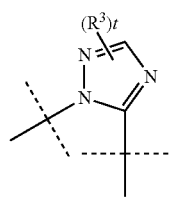
(5)

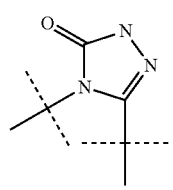
(6)

wherein, t is 1, 2 or 3; and $R^3$ is independently chosen from H, $C_1$-$C_6$alkyl, $C_2$-$C_8$ alkenyl, $C_2$-$C_8$ alkynyl, $C_6$-$C_{14}$aryl, $C_3$-$C_9$ cycloalkyl, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, —OR$^b$, —OC(O)R$^a$, —OC(O)NR$^c$R$^d$, —S(O)$_n$R$^e$, —S(O)$_n$NR$^c$R$^d$, halo, haloalkyl, heteroaryl, and heterocycle;

and each of said above alkyl, alkenyl, alkynyl, aryl, cycloalkyl, heteroaryl and heterocycle can be optionally substituted by one or more groups independently chosen from optionally substituted alkyl, optionally substituted alkenyl, optionally substituted alkynyl, optionally substituted aryl, optionally substituted cycloalkyl, —OH, oxo, —C(O)R$^a$, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, OR$^b$, —S(O)$_n$R$^e$, —S(O)$_n$NR$^c$R$^d$, halo, optionally substituted haloalkyl, optionally substituted heteroaryl, and optionally substituted heterocycle, and R$^a$, R$^b$, R$^c$, R$^d$, R$^e$, R$^f$ and R$^g$ are as defined above.

provided that, when $A^2$ and $A^3$, together with B ring, are structure (4), $A^4$ is not CR$^2$, wherein R$^2$ is as defined above.

For example, $R^3$ is independently chosen from H, OH, CN, NO$_2$, halo, $C_1$-$C_6$ alkyl, $C_2$-$C_8$ alkenyl, $C_2$-$C_8$ alkynyl, $C_6$-$C_{14}$ aryl, $C_3$-$C_9$ cycloalkyl, heteroaryl, and heterocycle, wherein each of the alkyl, alkenyl, alkynyl, aryl, cycloalkyl, heteroaryl, and heterocycle can be optionally substituted by one or more groups independently chosen from optionally substituted alkyl, optionally substituted alkenyl, optionally substituted alkynyl, optionally substituted aryl, optionally substituted cycloalkyl, —OH, oxo, —C(O)R$^a$, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, OR$^b$, —S(O)$_n$R$^e$, —S(O)$_n$NR$^c$R$^d$, halo, optionally substituted haloalkyl, optionally substituted heteroaryl, and optionally substituted heterocycle;

In some embodiments, $A^2$ and $A^3$ together with B ring, are chosen from the following structures (2)-(5), wherein $R^3$ and t are as defined above.

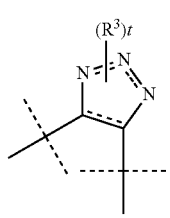
(2)

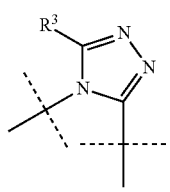
(3)

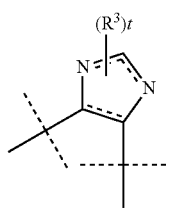
(4)

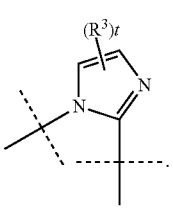
(5)

In some embodiments, $A^2$, $A^3$ and together with the B ring, are chosen from structure (3)-(4), wherein $R^3$ and t are as defined above.

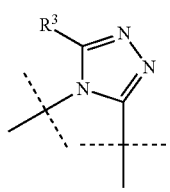
(3)

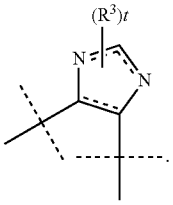
(4)

In some embodiments, $A^4$ is N or CH.

In some embodiments, $A^5$ is N or CH.

In some embodiments, $A_1$, $A_4$, and $A_5$ are CH.

In some embodiments, $A_1$ and $A_5$ are CH, and $A_4$ is N.

In some embodiments, $R^1$ is a heteroaryl that is chosen from the following structures

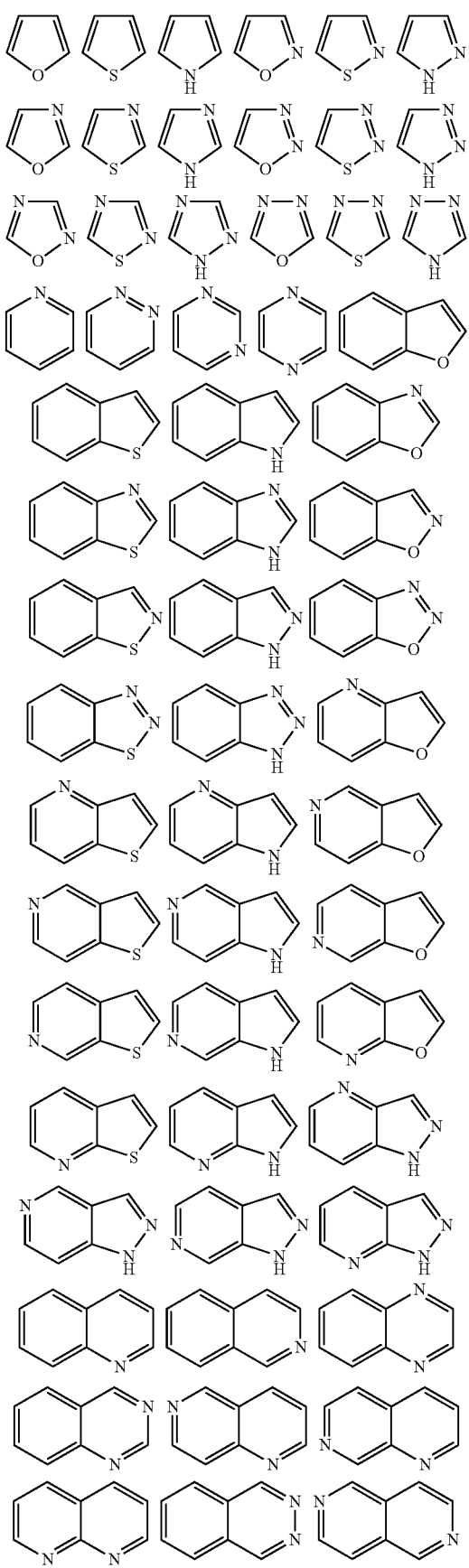

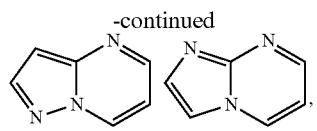

for example, R[1] is a heteroaryl chosen from

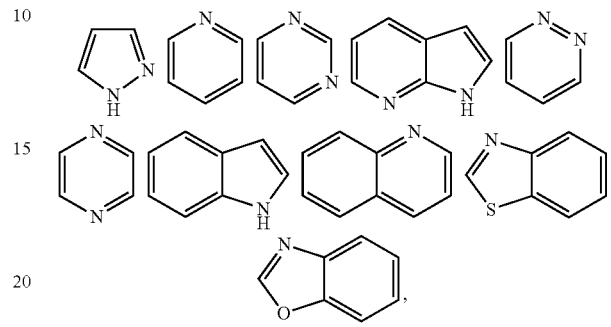

wherein each of which is optionally substituted by one or more groups independently chosen from alkyl, alkenyl, alkynyl, aryl, cycloalkyl, haloalkyl, heteroaryl, heterocycle, oxo, —C(O)R$^a$, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, —OR$^b$, —OC(O)R$^a$, —OC(O)NR$^c$R$^d$, —S(O)$_n$R$^e$, —S(O)$_n$NR$^c$R$^d$ and halo, wherein each of the alkyl, alkenyl, alkynyl, aryl, cycloalkyl, haloalkyl, heteroaryl and heterocycle can be optionally substituted by one or more groups independently chosen from optionally substituted alkyl, optionally substituted alkenyl, optionally substituted alkynyl, optionally substituted aryl, optionally substituted cycloalkyl, —OH, oxo, —C(O)R$^a$, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, OR$^b$, —S(O)$_n$R$^e$, —S(O)$_n$NR$^c$R$^d$, halo, optionally substituted haloalkyl, optionally substituted heteroaryl, and optionally substituted heterocycle;

wherein R$^a$, R$^b$, R$^c$, R$^d$, R$^e$, R$^f$ and R$^g$ are each independently chosen from H, alkyl, aryl, cycloalkyl, haloalkyl, heteroaryl, and heterocycle, wherein each of the alkyl, aryl, cycloalkyl, heteroaryl, and heterocycle in R$^a$, R$^b$, R$^c$, R$^d$, R$^e$, R$^f$ and R$^g$ is optionally substituted by one or more, such as one or two or three, substitutents independently selected from halo and alkyl.

In some embodiments, R[1] is

which is optionally substituted with one or more groups independently chosen from:
alkyl, alkenyl, and alkynyl, wherein each of which can be optionally substituted by groups independently chosen from optionally substituted alkyl, optionally substituted alkenyl, optionally substituted alkynyl, optionally substituted aryl, optionally substituted cycloalkyl, —OH, oxo, —C(O)R$^a$, —C(O)OR$^b$, —CN, —C(O)NR$^c$R$^d$, —NR$^c$R$^d$, —NR$^c$C(O)R$^a$, —NR$^c$S(O)$_n$R$^e$, —NR$^c$S(O)$_n$NR$^f$R$^g$, —NR$^c$C(O)OR$^b$, —NR$^c$C(O)NR$^d$R$^e$, —NO$_2$, OR$^b$, —S(O)$_n$R$^e$, —S(O)$_n$NR$^c$R$^d$, halo, optionally substituted haloalkyl, optionally substituted heteroaryl, and optionally substituted heterocycle;

C(O)NR$^c$R$^d$;

NR$^c$R$^d$;

OR$^b$;

halo;

cyano;

NR$^c$S(O)$_n$R$^e$, wherein R$^a$, R$^b$, R$^c$, R$^d$, R$^e$, R$^f$ and R$^g$ are each independently chosen from H, alkyl, aryl, cycloalkyl, haloalkyl, heteroaryl, and heterocycle, for example, R$^a$, R$^b$, R$^c$, R$^d$, R$^e$, R$^f$ and R$^g$ are each independently chosen from H, C$_1$-C$_6$ alkyl, phenyl, C$_3$-C$_6$ cycloalkyl, C$_1$-C$_3$ haloalkyl, heteroaryl, and heterocycle, wherein each of the alkyl, aryl, cycloalkyl, heteroaryl, and heterocycle in R$^a$, R$^b$, R$^c$, R$^d$, R$^e$, R$^f$ and R$^g$ is optionally substituted by one or more, such as one or two or three, substitutents independently selected from halo and alkyl.

Also provided is at least one compound selected from compounds 1 to 184 and/or at least one pharmaceutically acceptable salt described herein.

The compounds described herein, and/or the pharmaceutically acceptable salts thereof, can be synthesized from commercially available starting materials by methods well known in the art, taken together with the disclosure in this patent application. The following schemes illustrate methods for preparation of some of the compounds disclosed herein.

Scheme I

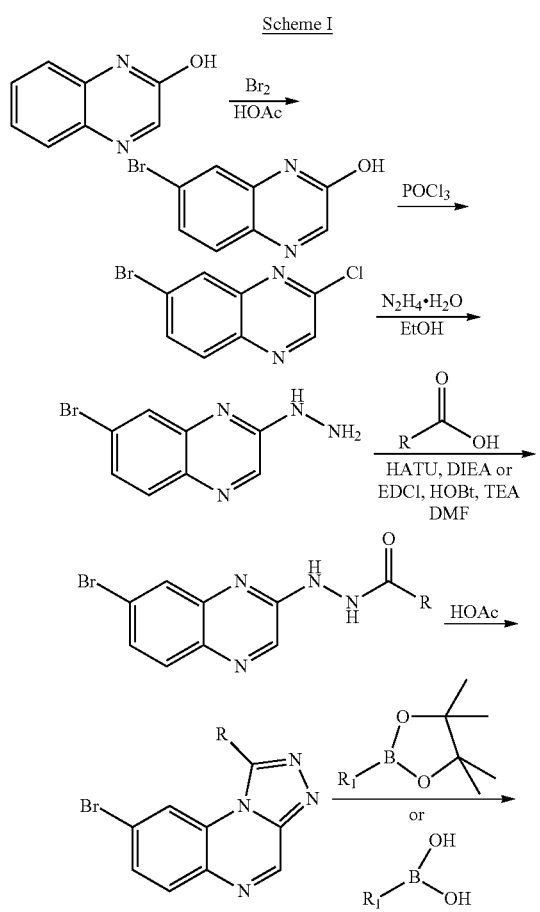

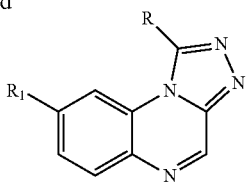

Scheme II

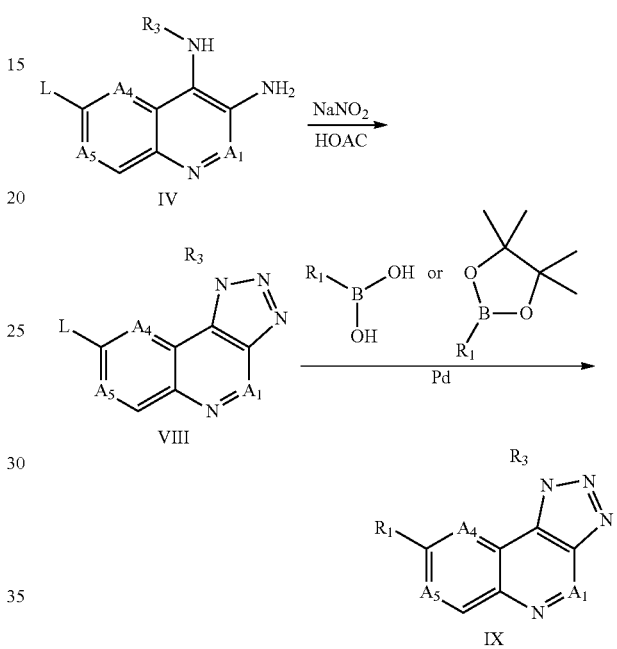

The compounds thus obtained can be further modified at their peripheral positions to provide the desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the at least one compound and/or at least one pharmaceutically acceptable salt described herein, can be purified by column chromatography, high performance liquid chromatography, crystallization, or other suitable methods.

Also provided is a composition comprising at least one compound and/or at least one pharmaceutically acceptable salt described herein, and at least one pharmaceutically acceptable carrier.

A composition comprising at least one compound and/or at least one pharmaceutically acceptable salt described herein, can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the at least one compound and/or at least one pharmaceutically acceptable salt described herein, in inhibiting the activity of PI3K and/or mTOR. The at least one compound and/or at least one pharmaceutically acceptable salt described herein, can further be examined for efficacy in treating cancer by in vivo assays. For example, the compounds described herein, and/or the pharmaceutically acceptable salts thereof, can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

Also provided is a method of inhibiting the activity of PI3K and/or mTOR. The method comprises contacting the enzyme with at least one compound and/or at least one pharmaceutically acceptable salt described herein in an amount effective to inhibit the activity of PI3K and/or mTOR.

The at least one compound and/or at least one pharmaceutically acceptable salt described herein can be used to achieve a beneficial therapeutic or prophylactic effect, for example, in subjects with cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma. For example, those solid tumors include pancreatic cancer; bladder cancer; colorectal cancer; breast cancer, and ovarian cancer.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

In some embodiments, the examples of the cancer to be treated include, but are not limited to, lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, and leukemia.

In some embodiments, the at least one compound and/or at least one pharmaceutically acceptable salt described herein, is administered in conjunction with another therapeutic agent. In some embodiments, the other therapeutic agent is one that is normally administered to patients with the disease or condition being treated. The at least one compound and/or at least one pharmaceutically acceptable salt described herein, may be administered with the other therapeutic agent in a single dosage form or as a separate dosage form. When administered as a separate dosage form, the other therapeutic agent may be administered prior to, at the same time as, or following administration of the at least one compound and/or at least one pharmaceutically acceptable salt described herein.

In some embodiments, at least one compound and/or at least one pharmaceutically acceptable salt described herein, is administered in conjunction with an anti-neoplastic agent. As used herein, the term "anti-neoplastic agent" refers to any agent that is administered to a subject with cancer for purposes of treating the cancer. Nonlimiting examples of anti-neoplastic agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The examples below are intended to be purely exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees Centigrade, and pressure is at or near atmospheric. All MS data were checked by agilent 6120 and/or agilent 1100. $^1$H NMR spectra were recorded on Varian 400 MHz NMR spectrometer using $CDCl_3$ or DMSO-$d_6$ as the solvent and tetramethylsilane (TMS) as the internal standard. Chemical shifts (δ) were expressed in ppm downfield from internal TMS, and J values were given in Hz. All reagents, except intermediates, used in this disclosure are commercially available. All compound names except the reagents were generated by Chemdraw 10.

In the following examples, the abbreviations below are used:
AcOH acetic acid
DCM dichloromethane
DMF N,N-dimethylformamide
DMF-DMA 1,1-dimethoxy-N,N-dimethylmethanamine
DMSO dimethyl sulfoxide
DTT dithiothreitol
EtOAc ethyl acetate
h hour
ISCO Flash chromatography
mL milliliter(s)
min minute(s)
Py pyridine
THF tetrahydrofuran
HATU 2-(1H-7-azabenzotriazol-1-yl)-1,1,3,3-tetramethyl uronium hexafluorophosphate Methanaminium
DIPEA N,N-diisopropylethylamine
DCM dichloromethane
EA ethyl acetate
PE petroleum ether
Pd(dppf)Cl$_2$ 1,1'-Bis(diphenylphosphino)ferrocene-palladium(II)dichloride dichloromethane complex
PTLC preparative thin-layer chromatography
HEPES 2-[4-(2-hydroxyethyl)piperazin-1-yl]ethanesulfonic acid
EGTA ethylene glycol tetraacetic acid)
CHAPS 3-[(3-Cholamidopropyl)-dimethylammonio]-1-propanesulfonate
TEA triethylamine
TLC thin-layer chromatography

INTERMEDIATE 1

2-(5-aminopyridin-2-yl)-2-methylpropanenitrile

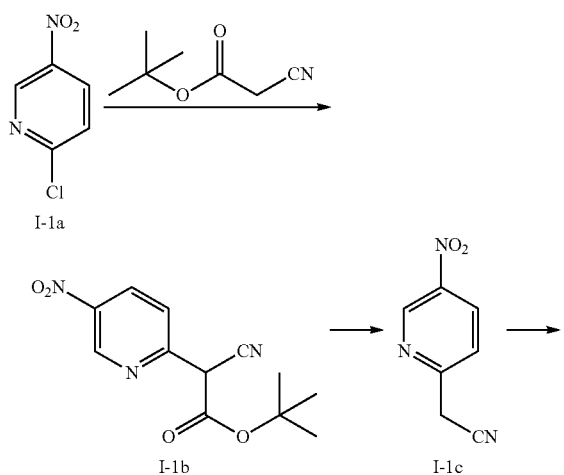

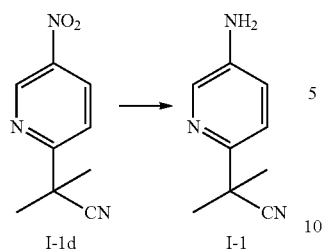

To a solution of 2-chloro-5-nitropyridine (10 g, 63 mmol) in THF (150 mL) at room temperature was added $K_2CO_3$ (17.4 g, 126 mmol) and tert-butyl 2-cyanoacetate (10.7 g, 76 mmol). The reaction mixture was heated to reflux and stirred overnight. Then the solid was filtered off, and the filtrate was concentrated to give the intermediate I-1b (16.6 g). m/z 208 $(M+H)^+$.

The crude product tert-butyl 2-cyano-2-(5-nitropyridin-2-yl)acetate (I-1b, 12 g, 47 mmol) was dissolved in 100 mL of HCl/EtOH (v/v 1:5) and stirred at 80° C. for 4 h. Then the mixture was concentrated, diluted with $H_2O$, and extracted with EtOAc (4×40 mL). The combined extracts were concentrated, and the residue was purified by chromatography on silica gel (PE:EtOAc=3:1) to afford 2-(5-nitropyridin-2-yl)acetonitrile (I-1c) as a solid (7.7 g, 42.0% yield).

To the mixture of 2-(5-nitropyridin-2-yl)acetonitrile (I-1c, 8 g, 46 mmol) and $K_2CO_3$ (18 g, 110 mmol) in $CH_3CN$ (200 mL) was added iodomethane (7.5 mL, 120 mmol) dropwise at room temperature. The reaction mixture was stirred at 40° C. overnight. Then the mixture was filtered, the filtrate was concentrated, and the residue was purified by chromatography on silica gel (PE:EtOAc=5:1) to afford 2-methyl-2-(5-nitropyridin-2-yl)propanenitrile (I-1d) (4.2 g, 48% yield). m/z 192 $(M+H)^+$.

The mixture of 2-methyl-2-(5-nitropyridin-2-yl)propanenitrile (I-1d, 2 g, 10.4 mmol) and $SnCl_2.2H_2O$ (9.3 g, 41.6 mmol) in EtOAc (10 mL) was stirred at reflux for 4 h. After cooling to room temperature, aqueous 2 M NaOH (80 mL) was added to adjust the pH to 8~9, the solid was filtered off, and the filtrate was extracted with ethyl acetate (3×40 mL). The combined organic layers were dried over anhydrous $Na_2SO_4$, and concentrated to afford 2-(5-aminopyridin-2-yl)-2-methylpropanenitrile (I-1) (1.7 g, 65.3% yield).

INTERMEDIATE 2

1,1,1-trifluoro-N-(2-methoxy-5-(4,4,5,5-tetramethyl-1,3,2-dioxaborolan-2-yl)pyridin-3-yl)methanesulfonamide

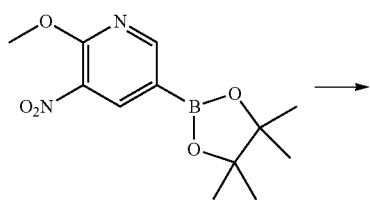

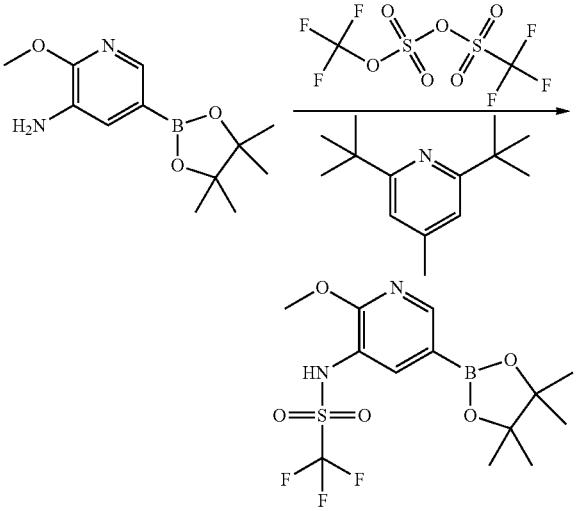

The mixture of 2-methoxy-3-nitro-5-(4,4,5,5-tetramethyl-1,3,2-dioxaborolan-2-yl) pyridine (300 mg, 1.1 mmol) and Raney-Ni (10 mg) in MeOH (10 mL) was subject to $H_2$ and stirred for 2 h. After filtration, the filtrate was concentrated to give the title compound as a white solid (261 mg). Yield: 95.0%.

To a solution of 2-methoxy-5-(4,4,5,5-tetramethyl-1,3,2-dioxaborolan-2-yl) pyridin-3-amine (100 mg, 0.4 mmol) and 2,6-di-tert-butyl-4-methylpyridine (115 mg, 0.56 mmol) in dichloromethane (5 mL) was added trifluoromethanesulfonic anhydride (147 mg, 0.52 mmol) drop wise at −20° C., and the mixture was stirred at this temperature for 2 h. Solvent was removed in vacuo and the residue was used in the next step without further purification (141 mg). Yield: 92.0%.

INTERMEDIATE 3

6-chloro-3-nitro-1,5-naphthyridin-4-ol

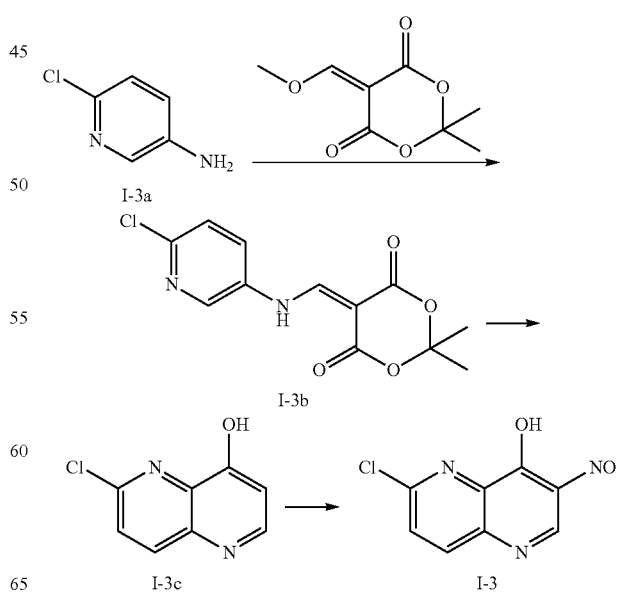

The mixture of 6-chloropyridin-3-amine (5.0 g, 38.8 mmol) and 5-(methoxymethylene)-2,2-dimethyl-1,3-dioxane-4,6-dione (7.2 g, 38.8 mmol) in i-PrOH (60 mL) was stirred at reflux for 2 h, and the solvent was removed to afford 5-((6-chloropyridin-3-ylamino)methylene)-2,2-dimethyl-1,3-dioxane-4,6-dione as a solid in 91% yield (10.0 g). m/z 283 (M+H)$^+$ To the heated Dowtherm A (200 mL) at 200° C. was added 5-((6-chloropyridin-3-ylamino)methylene)-2,2-dimethyl-1,3-dioxane-4,6-dione (3.5 g, 12.4 mmol) and then stirred for additional 5 min. After cooling to r.t., PE was added. The precipitate was collected, and dried in vacuo to afford 6-chloro-1,5-naphthyridin-4-ol as off-white solid in 42% yield (0.94 g). m/z 183 (M+H)$^+$ 6-chloro-1,5-naphthyridin-4-ol (1.45 g, 8 mmol) was added to ice-cooled conc. $H_2SO_4$ (15 mL) and followed by the addition of $KNO_3$ (1.62 g, 16 mmol) slowly at 0° C. The mixture was heated to 100° C. for 1 h, and then was poured into ice-water. The precipitate was collected and dried in vacuo to afford 6-chloro-3-nitro-1,5-naphthyridin-4-ol as a solid in 90% yield (1.97 g).

INTERMEDIATE 4

2,4-difluoro-N-(2-methoxy-5-(4,4,5,5-tetramethyl-1,3,2-dioxaborolan-2-yl)pyridin-3-yl)benzenesulfonamide

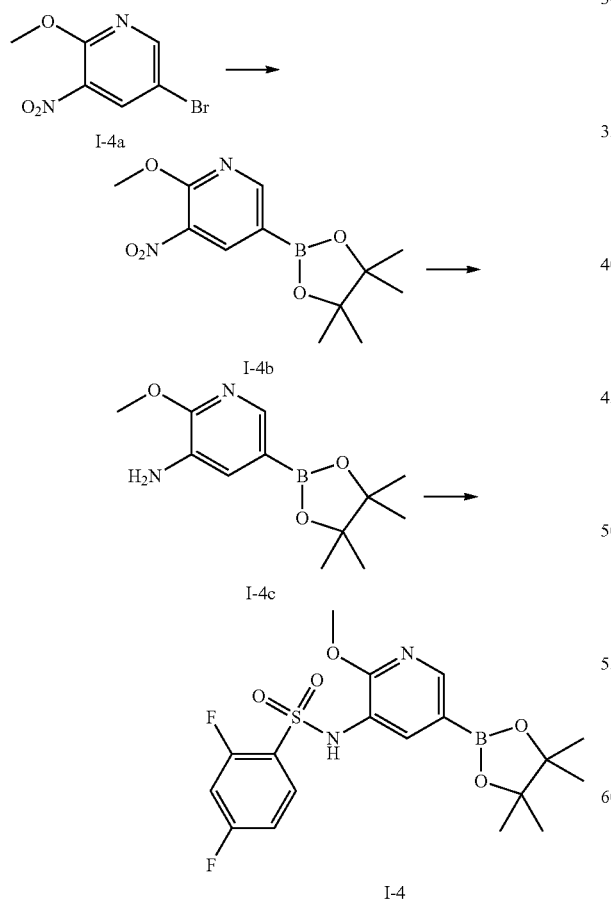

The mixture of 5-bromo-2-methoxy-3-nitropyridine (5 g, 21.5 mmol), 4,4,4',4',5,5,5',5'-octamethyl-2,2'-bi(1,3,2-dioxaborolane) (6.6 g, 25.8 mmol), $PdCl_2(dppf)\text{-}CH_2Cl_2$ (500 mg) and potassium acetate (6.3 g, 64.5 mmol) in anhydrous 1,4-dioxane (200 mL) was refluxed for 2 h. Then the solvents were removed. The crude product was purified by chromatography on silica gel using petroleum ether:EtOAc=10:1 as eluent to afford 2-methoxy-3-nitro-5-(4,4,5,5-tetramethyl-1,3,2-dioxaborolan-2-yl)pyridine in 81% yield (5 g). m/z 281 (M+H)$^+$.

To the solution of 2-methoxy-3-nitro-5-(4,4,5,5-tetramethyl-1,3,2-dioxaborolan-2-yl) pyridine (500 mg, 1.79 mmol) in MeOH (50 mL) was added Raney-Ni (50 mg). The reaction mixture was stirred at room temperature under $H_2$ for 2 h. Then the solid was filtered off, and the solvent was removed to afford 2-methoxy-5-(4,4,5,5-tetramethyl-1,3,2-dioxaborolan-2-yl)pyridin-3-amine in 89% yield (400 mg). m/z 251 (M+H)$^+$.

To the solution of 2-methoxy-5-(4,4,5,5-tetramethyl-1,3,2-dioxaborolan-2-yl)pyridin-3-amine (400 mg, 1.6 mmol) in pyridine (5 mL) was added 2,4-difluorobenzenesulfonyl chloride (407 mg, 1.9 mmol) slowly, the reaction mixture was stirred at room temperature overnight, the solvent was evaporated in vacuo, and the residue was treated with brine (5 mL) and extracted with EtOAc (3×10 mL). The combined organic layer was evaporated in vacuo, and the residue was purified by column chromatography using petroleum ether:EtOAc=5:1 as eluent to afford the desired product 2,4-difluoro-N-(2-methoxy-5-(4,4,5,5-tetramethyl-1,3,2-dioxaborolan-2-yl)pyridin-3-yl)benzenesulfonamide as white solid in 59% yield (400 mg). m/z 427 (M+H)$^+$.

INTERMEDIATE 5

8-bromo-[1,2,4]triazolo[4,3-a]quinoxaline

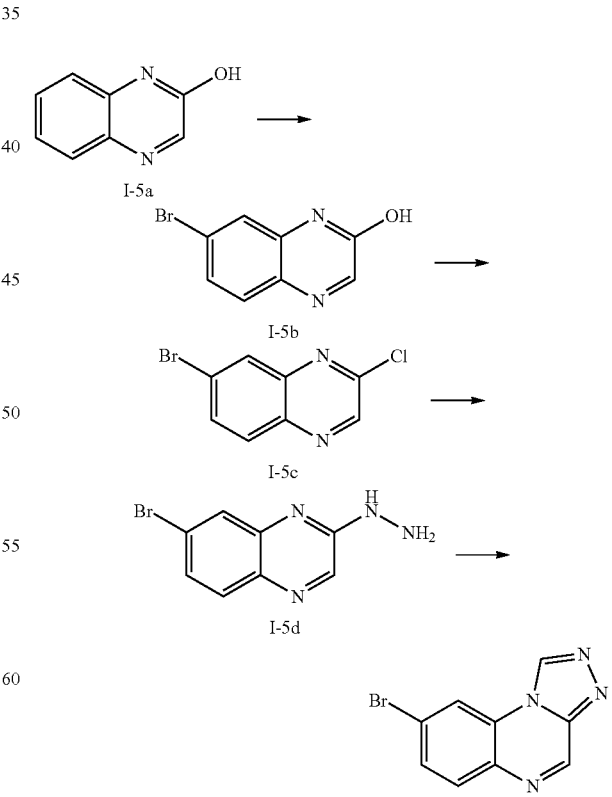

Bromine (0.895 mL, 15.5 mmol) was added to the solution of quinoxalin-2-ol (1.5 g, 10.3 mmol) in HOAc (15 mL), the mixture was stirred at r.t. for 6 h, and the precipitate was collected and washed with ethyl ether and dried to afford 7-bromoquinoxalin-2-ol as a solid in 90% yield (2 g).

To the suspension of 7-bromoquinoxalin-2-ol (2 g, 8.88 mmol) in neat phosphorus oxychloride (7 mL) was added DMF (2 drops). The mixture was heated to 100° C. for 3 h. Then it was cooled to room temperature. Phosphorus oxychloride was removed under vacuum, and the residue was dissolved into EtOAc and dropped into ice water with stirring. The mixture was extracted with EtOAc for three times, the combined organic layer was washed with saturated NaHCO$_3$ solution. Then the organic layer was concentrated to afford 7-bromo-2-chloroquinoxaline as a solid in 93% yield (2 g).

To the solution of 7-bromo-2-chloroquinoxaline (2 g, 8.2 mmol) in ethanol (20 mL) was added hydrazine hydrate (85%, 4.5 mL, 32.8 mmol). The mixture was heated to 78° C. for 2 h. After cooling to r.t., the precipitate was collected by filtration to afford 7-bromo-2-hydrazinylquinoxaline as white solid in 87% yield (1.7 g).

The solution of 7-bromo-2-hydrazinylquinoxaline (200 mg, 0.83 mmol) in triethyl orthoformate (3 mL) was heated to 100° C. for 4 h; after cooling to r.t., the mixture was diluted with ethyl ether, and the precipitate was collected by filtration and dried in vacuo to afford the title product 8-bromo-[1,2,4]triazolo[4,3-a]quinoxaline as yellow solid in 87% yield (180 mg). m/z 251 (M+H)$^+$.

INTERMEDIATE 6

8-bromo-1-cyclopropyl-[1,2,4]triazolo[4,3-a]quinoxaline

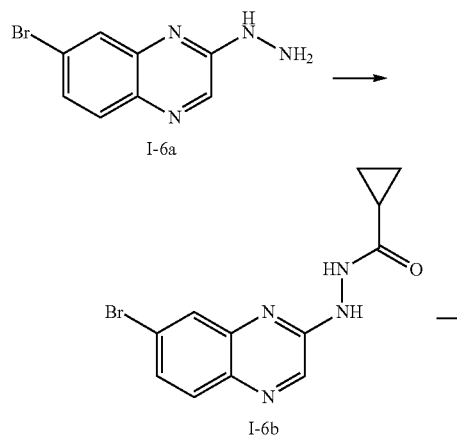

To the solution of 7-bromo-2-hydrazinylquinoxaline (200 mg, 0.83 mmol) in DMF (3 mL) was added HATU (380 mg, 1 mmol), DIPEA (0.205 mL, 1 mmol) and cyclopropanecarboxylic acid (71 mg, 0.83 mmol). After stirring at r.t. for 5 h, the mixture was diluted with EtOAc. The organic layer was washed with water for three times, then concentrated to afford N'-(7-bromoquinoxalin-2-yl)cyclopropane-carbohydrazide as yellow solid which was used directly in the next step. m/z 309 (M+H)$^+$.

The crude product N'-(7-bromoquinoxalin-2-yl)cyclopropanecarbohydrazide was dissolved in HOAc (5 mL) and then heated to 100° C. overnight. The solvent was removed under vacuum and the residue was washed with water and dried in vacuo to afford the title product 8-bromo-1-cyclopropyl-[1,2,4]triazolo[4,3-a]quinoxaline as yellow solid in 42% overall yield (100 mg). m/z 291 (M+H)$^+$.

INTERMEDIATE 7

8-bromo-[1,2,4]triazolo[4,3-a]quinoxalin-1(2H)-one

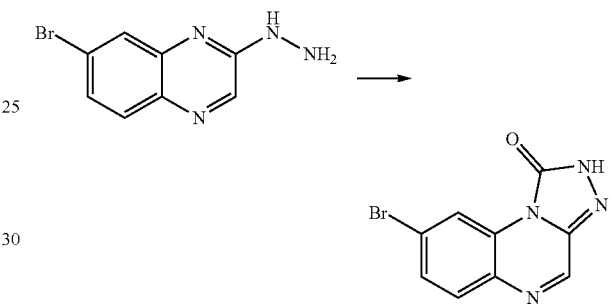

To the solution of 7-bromo-2-hydrazinylquinoxaline (200 mg, 0.83 mmol) in dichloromethane (5 mL) was added triethylamine (0.175 mL, 1.2 mmol), then the solution of diphosgene (0.055 mL, 0.46 mmol) in dichloromethane was added dropwise at 0° C. with stirring under nitrogen atmosphere. After stirring at r.t. for 5 h, the solvent was removed under vacuum, the residue was washed with water, and dried in vacuo to afford the title product 8-bromo-[1,2,4]triazolo[4,3-a]quinoxalin-1(2H)-one as yellow solid in 82% yield (180 mg). m/z 265 (M+H)$^+$.

INTERMEDIATE 8

5-(4,4,5,5-tetramethyl-1,3,2-dioxaborolan-2-yl)-3-(trifluoromethyl)pyridin-2-amine

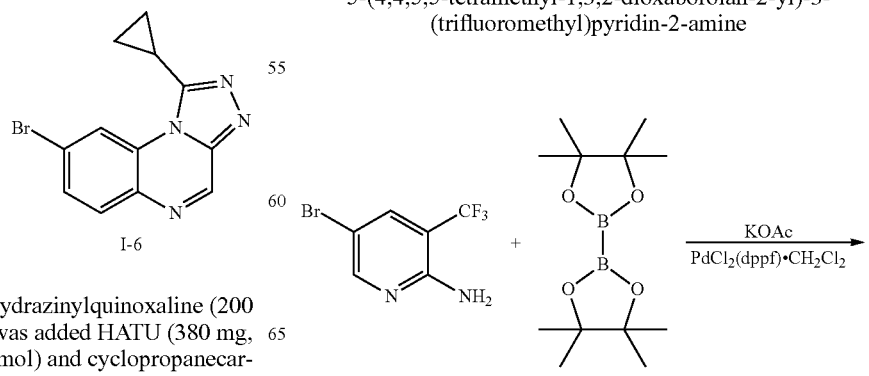

-continued

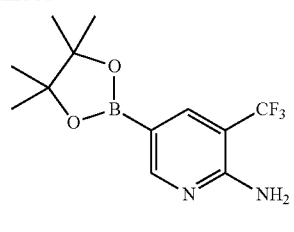

An orange suspension of 5-bromo-3-(trifluoromethyl)pyridin-2-amine (4 g, 16.60 mmol), 4,4,4',4',5,5,5',5'-octamethyl-2,2'-bi(1,3,2-dioxaborolane) (5.90 g, 23.24 mmol), KOAc (4.07 g, 41.5 mmol) and PdCl$_2$(dppf).CH$_2$Cl$_2$ (0.678 g, 0.830 mmol) in Dioxane (60 mL) was heated to 110° C. for 10 h under N$_2$. After concentration under vacuum to remove the solvent, the crude product was purified using a silica gel column, with PE/EtOAc as eluant to give pure product as pale yellow solid (4.5 g, yield 94%). MS (m/z): 289 (M+H)$^+$.

EXAMPLE 1

Synthesis of Compounds 1-20

Compound 1

(S)-1-(4-(8-(6-amino-5-(trifluoromethyl)pyridin-3-yl)-1H-[1,2,3]triazolo[4,5-c][1,5]naphthyridin-1-yl)piperidin-1-yl)-2-hydroxypropan-1-one

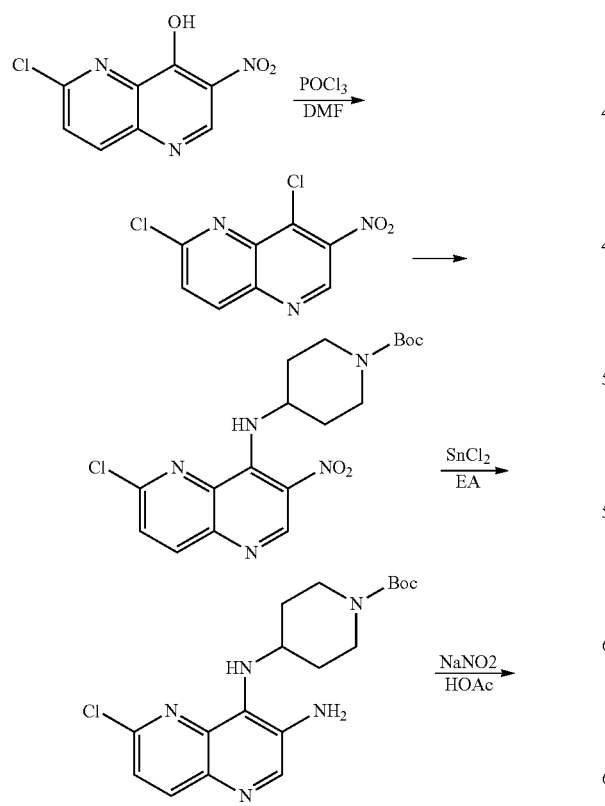

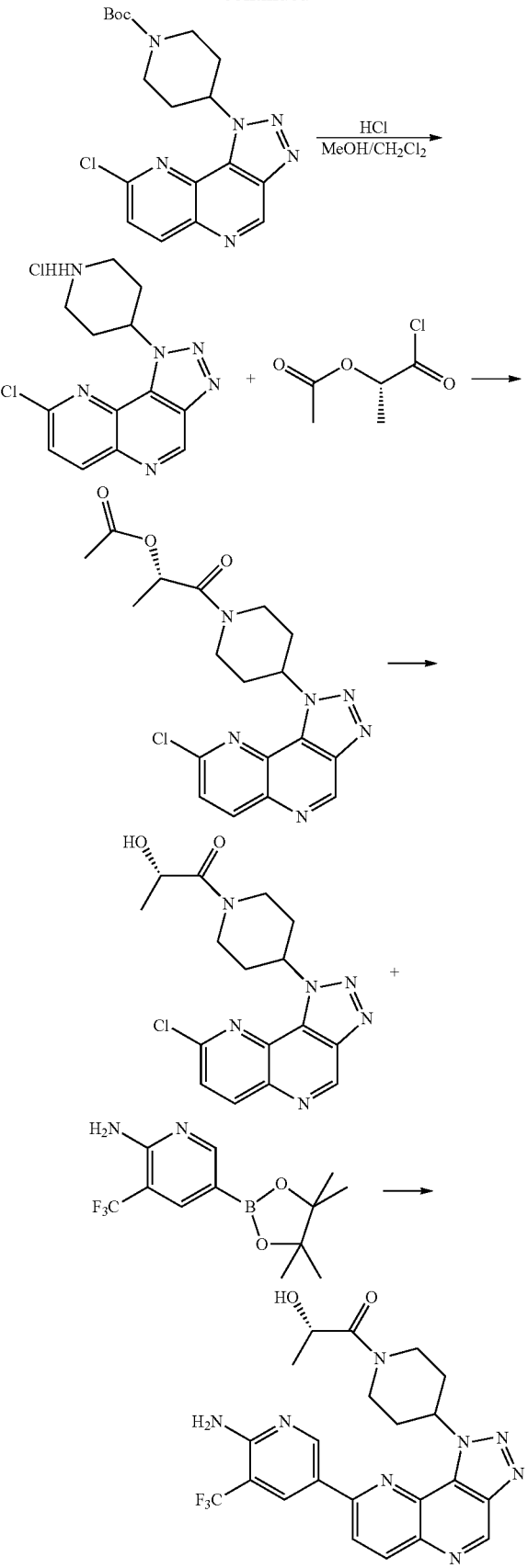

To a suspension of 6-chloro-3-nitro-1,5-naphthyridin-4-ol (5 g, 22.1 mmol) in 15 mL of DMF, was added a solution of phosphorous oxychloride (2.7 mL, 28.8 mmol) in anhydrous DMF (10 mL) over 3 min. The mixture was stirred at room temperature overnight. The mixture was then poured onto crushed ice. The resulting precipitate was collected by filtration, washed with $H_2O$, and dried in vacuo to afford 2,8-dichloro-7-nitro-1,5-naphthyridine as yellow solid (4 g, yield 74.0%). MS (m/z): 244 $(M+H)^+$.

A mixture of 2,8-dichloro-7-nitro-1,5-naphthyridine (4 g, 16.4 mmol), 4-amino-piperidine-1-carboxylic acid tert-butyl ester (4 g, 19.7 mmol) and triethylamine (3.5 mL) in DMF (15 mL) was stirred at room temperature overnight. The reaction mixture was poured into water (250 mL). The precipitate was collected by filtration, washed with $H_2O$, and dried in vacuo to afford tert-butyl 4-(6-chloro-3-nitro-1,5-naphthyridin-4-ylamino) piperidine-1-carboxylate as yellow solid (6.54 g, yield 97.8%). The crude product was used in the next step without further purification. MS (m/z): 408 $(M+H)^+$.

To the solution of tert-butyl 4-(6-chloro-3-nitro-1,5-naphthyridin-4-ylamino) piperidine-1-carboxylate (6.43 g, 15.7 mmol) in EtOAc (250 mL) was added $SnCl_2.2H_2O$ (18 g, 78.8 mmol), and the mixture was stirred at room temperature for 3 h. Then saturated $NaHCO_3$ was added to adjust the pH=8. The solid was filtered off. The filtrate was concentrated and the crude product was purified by silica gel chromatography using EtOAc:PE as eluant to afford tert-butyl 4-(3-amino-6-chloro-1,5-naphthyridin-4-ylamino) piperidine-1-carboxylate as yellow solid in 85.6% yield (5.1 g). MS (m/z): 378 $(M+H)^+$.

To a solution of tert-butyl 4-(3-amino-6-chloro-1,5-naphthyridin-4-ylamino) piperidine-1-carboxylate (2.5 g, 6.6 mmol) in acetic acid (8 mL) was added $NaNO_2$ (460 mg, 6.6 mmol) at 0° C. After the mixture was stirred at room temperature for 2 hours, saturated sodium bicarbonate and ice water were added. The resulting mixture was extracted with $CH_2Cl_2$. The organic layer was dried over anhydrous $Na_2SO_4$, and concentrated. The crude product was purified by silica gel chromatography using EtOAc:PE as eluant to afford tert-butyl 4-(8-chloro-1H-[1,2,3]triazolo[4,5-c][1,5]naphthyridin-1-yl) piperidine-1-carboxylate as yellow solid in 73.8% yield (1.9 g). MS (m/z): 388.8 $(M+H)^+$.

A solution of tert-butyl 4-(8-chloro-1H-[1,2,3]triazolo[4,5-c][1,5]naphthyridin-1-yl) piperidine-1-carboxylate (4 g) in $CH_2Cl_2$/MeOH was treated with 3 mL conc. HCl. The resulting solution was then concentrated to give 8-chloro-1-(piperidin-4-yl)-1H-[1,2,3]triazolo[4,5-c][1,5]naphthyridine hydrochloride as yellow solid. (3.81 g, yield 100%). MS (m/z): 289 $(M+H)^+$.

To a solution of 8-chloro-1-(piperidin-4-yl)-1H-[1,2,3]triazolo[4,5-c][1,5]naphthyridine hydrochloride (1 g, 3.08 mmol) in 10 mL of $CH_2Cl_2$ was added (S)-1-chloro-1-oxopropan-2-yl acetate (1.4 g, 9.23 mmol) and $Et_3N$ (2.2 mL). After the mixture was stirred at room temperature for 2 h, it was quenched with water (10 mL). The resulting mixture was extracted with $CH_2Cl_2$ (2×20 mL). The combined organic layer was dried over anhydrous $Na_2SO_4$, and then was concentrated in vacuo to afford the (S)-1-(4-(8-chloro-1H-[1,2,3]triazolo[4,5-c][1,5]naphthyridin-1-yl)piperidin-1-yl)-1-oxopropan-2-yl acetate (1.2 g). MS (m/z): 403 $(M+H)^+$.

To a solution of (S)-1-(4-(8-chloro-1H-[1,2,3]triazolo[4,5-c][1,5]naphthyridin-1-yl)piperidin-1-yl)-1-oxopropan-2-yl acetate (1.2 g, 2.97 mmol) in a mixture of THF (30 mL) and MeOH (30 mL), was added LiOH (650 mg, 14.9 mmol) drop-wise. The mixture was stirred at room temperature for 3 h. After concentration in vacuo, the residue was diluted with water and the pH was adjusted to 7 with 2N HCl. The resulting mixture was concentrated and the precipitate was collected by filtration, washed with $H_2O$, and dried in vacuo to afford (S)-1-(4-(8-chloro-1H-[1,2,3]triazolo[4,5-c][1,5] naphthyridin-1-yl)piperidin-1-yl)-2-hydroxypropan-1-one as yellow solid. The crude product was used in next step without further purification. (918 mg, yield 85.4%). MS (m/z): 361 $(M+H)^+$.

To a solution of (S)-1-(4-(8-chloro-1H-[1,2,3]triazolo[4,5-c][1,5]naphthyridin-1-yl)piperidin-1-yl)-2-hydroxypropan-1-one (150 mg, 0.42 mmol) in a mixture of 20 mL dixoane and 2 mL $H_2O$ was added 5-(4,4,5,5-tetramethyl-1,3,2-dioxaborolan-2-yl)-3-(trifluoromethyl)pyridin-2-amine (120 mg, 0.42 mmol), Pd(dppf)$Cl_2$ (20 mg, 0.02 mmol), and $Na_2CO_3$ (100 mg, 0.84 mmol). The resulting mixture was purged with $N_2$ and stirred at 100° C. overnight, then the resulting mixture was purified on silica gel using MeOH/$H_2O$ as eluent to afford compound 1 as yellow solid (59.1 mg). $^1$H NMR (400 MHz, DMSO-d$_6$) δ 9.60 (s, 1H), 9.20 (s, 1H), 8.67 (s, 1H), 8.64 (d, J=8.8 Hz, 1H), 8.54 (d, J=8.8 Hz, 1H), 7.09 (s, 2H), 6.23-6.02 (m, 1H), 5.17-5.01 (m, 1H), 4.75-4.50 (m, 2H), 4.46-4.27 (m, 1H), 3.00-2.79 (m, 1H), 2.39-1.90 (m, 3H), 1.36-1.16 (m, 6H). MS (m/z): 487 $(M+H)^+$.

The following compounds 2-20 were prepared according to the procedures for Compound 1 by using the corresponding intermediates and boronic acids or esters under appropriate conditions that could be recognized by one skilled in the art.

| Compound | Structure | LC/MS | NMR |
| --- | --- | --- | --- |
| 2 | 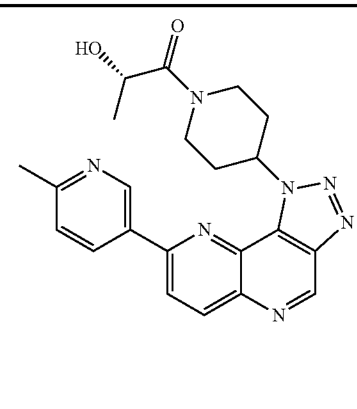 | 418$(M + H)^+$ | $^1$H NMR (400 MHz, dmso) δ 9.61 (s, 1H), 9.35 (s, 1H), 8.68 (d, J = 8.8 Hz, 1H), 8.53 (d, J = 8.8 Hz, 2H), 7.52-7.44 (m, 1H), 6.09-5.90 (m, 1H), 5.19-4.96 (m, 1H), 4.75-4.42 (m, 2H), 4.42-4.17 (m, 1H), 3.11-2.91 (m, 1H), 2.55 (m, 3H), 2.42 (m, 4H), 1.23 (m, 3H). |

-continued

| Compound | Structure | LC/MS | NMR |
|---|---|---|---|
| 3 | 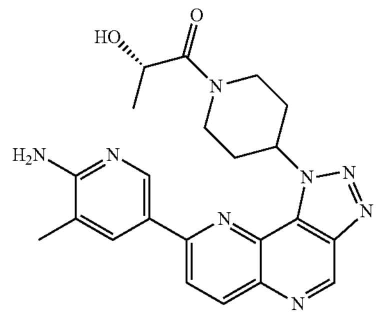 [SMILES: Cc1cc(-c2ccc3ncc4nnn(C5CCN(C(=O)[C@H](C)O)CC5)c4c3n2)cnc1N] | 433(M + H)+ | 1H NMR (400 MHz, dmso) δ 9.52 (s, 1H), 8.82 (s, 1H), 8.54 (d, J = 8.8 Hz, 1H), 8.37(d, J = 8.8 Hz, 1H), 8.17 (s, 1H), 6.34 (s, 2H), 6.13-5.96 (m, 1H), 5.79-5.66 (m, 1H), 5.17-5.01 (m, 1H), 4.72-4.25 (m, 3H), 3.14 (m, 5H), 3.04-2.93 (m, 1H), 2.16 (m, 7H), 1.23 (m,4H). |
| 4 | 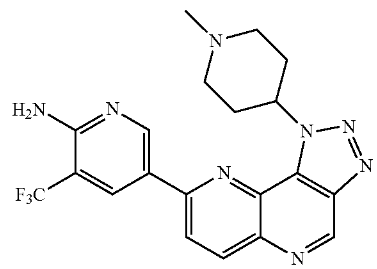 [SMILES: CN1CCC(n2nnc3cnc4ccc(-c5cnc(N)c(C(F)(F)F)c5)nc4c32)CC1] | 429(M + H)+ | 1H NMR (400 MHz, cd3od) δ 9.53 (s, 1H), 9.18-9.14 (m, 1H), 8.75 (d, J = 1.8 Hz, 1H), 8.66 (d, J = 8.9 Hz, 1H), 8.43 (d, J = 8.9 Hz, 1H), 6.31-6.03 (m, 1H), 3.58-3.48 (m, 2H), 3.40-3.36 (m, 1H), 3.30-3.26 (m, 1H), 2.76 (m, 3H), 2.68 (m, 4H). |
| 5 | 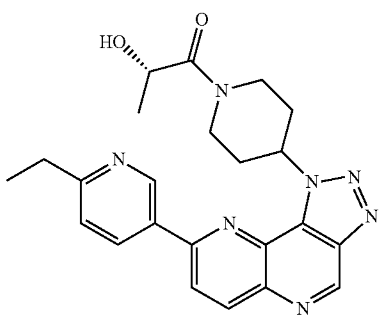 [SMILES: CCc1ccc(-c2ccc3ncc4nnn(C5CCN(C(=O)[C@H](C)O)CC5)c4c3n2)cn1] | 434(M + H)+ | 1H NMR (400 MHz, cdcl3) δ 9.60 (s, 1H), 9.02 (s, 1H), 8.70 (d, J = 8.8 Hz, 1H), 8.35-8.29 (m, 1H), 8.18 (d, J = 8.8 Hz, 1H), 7.01-6.92 (m, 1H), 6.22-5.98 (m, 1H), 4.89-4.68 (m, 1H), 4.68-4.52 (m, 1H), 4.23-4.08 (m, 1H), 4.07 (m, 3H), 3.59-3.39 (m, 1H), 3.38-3.14 (m, 1H), 2.83-2.45 (m, 5H), 1.43 (d, 3H). |
| 6 | 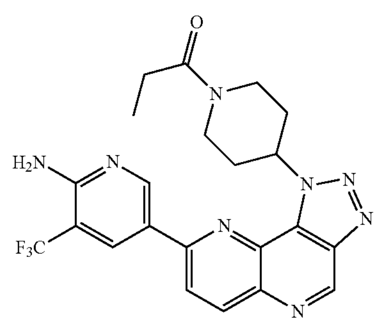 [SMILES: CCC(=O)N1CCC(n2nnc3cnc4ccc(-c5cnc(N)c(C(F)(F)F)c5)nc4c32)CC1] | 471(M + H)+ | 1H NMR (400 MHz, cdcl3) δ 9.58 (s, 1H), 9.06 (s, 1H), 8.66 (d, J = 8.8 Hz, 1H), 8.60 (d, J = 2.0 Hz, 1H), 8.17 (d, J = 8.8 Hz, 1H), 6.15 (m, 1H), 5.31 (m, 2H), 4.93 (m, 1H), 4.22 (m, 1H), 3.41 (m, 1H), 2.99 (m, 1H), 2.51 (m, 7H), 1.22 (m, 3H). |
| 7 | 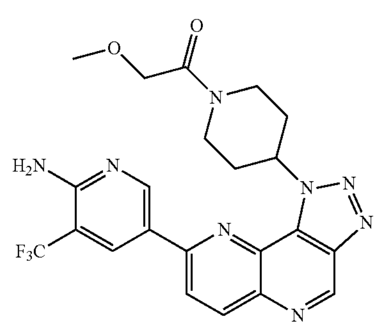 [SMILES: COCC(=O)N1CCC(n2nnc3cnc4ccc(-c5cnc(N)c(C(F)(F)F)c5)nc4c32)CC1] | 487(M + H)+ | 1H NMR (400 MHz, cdcl3) δ 9.57 (s, 1H), 9.05 (s, 1H), 8.65 (d, J = 8.8 Hz, 1H), 8.59 (s, 1H), 8.16 (d, J = 8.8 Hz, 1H), 6.15 (s, 1H), 5.31 (s, 2H), 4.84 (m, 1H), 4.24 (m, 3H), 3.48 (m, 3H), 3.39 (m, 1H), 3.12-2.96 (m, 1H), 2.53 (m, 5H). |

-continued

| Compound | Structure | LC/MS | NMR |
|---|---|---|---|
| 8 | 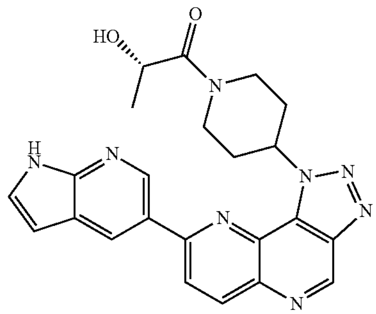 [SMILES: C[C@H](O)C(=O)N1CCC(n2nnc3cnc4ccc(-c5cnc6[nH]ccc6c5)nc4c32)CC1] | 443(M + H)+ | 1H NMR (400 MHz, dmso) δ 11.92 (s, 1H), 9.63 (s, 1H), 9.24 (d, J = 2.0 Hz, 1H), 8.89 (d, J = 1.8 Hz, 1H), 8.70 (d, J = 8.8 Hz, 1H), 8.61 (d, J = 8.9 Hz, 1H), 7.60 (s, 1H), 6.65 (s, 1H), 6.08 (m, 1H), 5.10-5.04 (m, 1H), 4.57 (m, 2H), 4.34 (m, 1H), 3.46 (m, 1H), 3.08 (m, 1H), 2.29 (m, 3H), 1.26 (m, 3H). |
| 9 | 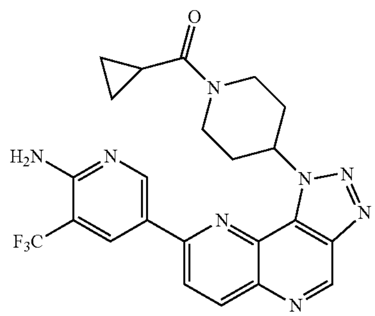 [SMILES: Nc1ncc(-c2ccc3ncc4nnn(C5CCN(C(=O)C6CC6)CC5)c4c3n2)cc1C(F)(F)F] | 483(M + H)+ | 1H NMR (400 MHz, cdcl3) δ 9.58 (s, 1H), 9.07 (d, J = 2.0 Hz, 1H), 8.66 (d, J = 8.8 Hz, 1H), 8.61 (d, J = 2.3 Hz, 1H), 8.17 (d, J = 8.8 Hz, 1H), 6.17 (s, 1H), 5.32 (m, 3H), 4.88 (m, 1H), 4.57 (m, 1H), 3.50 (m, 1H), 3.06 (m, 1H), 2.52 (m, 5H), 1.32 (m, 2H), 1.06 (m, 2H), 0.90 (m, 2H). |
| 10 | 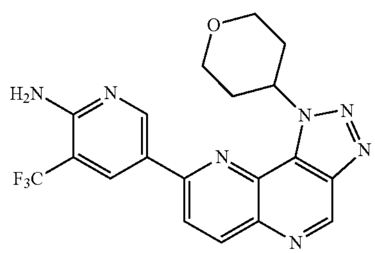 [SMILES: Nc1ncc(-c2ccc3ncc4nnn(C5CCOCC5)c4c3n2)cc1C(F)(F)F] | 416(M + H)+ | 1H NMR (400 MHz, cdcl3) δ 9.58 (s, 1H), 9.08 (s, 1H), 8.65 (d, J = 8.9 Hz, 2H), 8.17 (d, J = 8.8 Hz, 1H), 6.21-5.97 (m, 1H), 5.33 (s, 2H), 4.30 (m, 2H), 3.76 (m, 2H), 2.85-2.56 (m, 2H), 2.38 (m, 2H). |
| 11 | 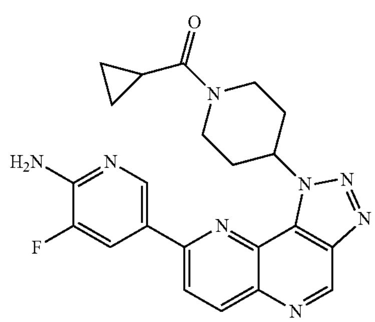 [SMILES: Nc1ncc(-c2ccc3ncc4nnn(C5CCN(C(=O)C6CC6)CC5)c4c3n2)cc1F] | 433(M + H)+ | 1H NMR (400 MHz, cdcl3) δ 9.57 (s, 1H), 8.74 (s, 1H), 8.63 (d, J = 8.6 Hz, 1H), 8.13 (d, J = 8.9 Hz, 1H), 8.04 (d, J = 12.5 Hz, 1H), 6.09 (s, 1H), 5.06-4.93 (m, 2H), 4.85 (m, 1H), 4.54 (m, 1H), 3.57 (sm, 1H), 3.10 (m, 1H), 2.54 (m, 5H), 1.86 (m, 1H), 1.07 (m, 2H), 0.85 (m, 2H). |
| 12 | 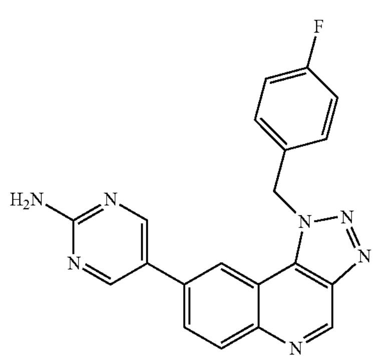 [SMILES: Nc1ncc(-c2ccc3ncc4nnn(Cc5ccc(F)cc5)c4c3c2)cn1] | 372(M + H)+ | 1H NMR (400 MHz, dmso) δ 9.55 (s, 1H), 8.35 (d, J = 2.3, 1H), 8.27 (d, J = 1.8, 1H), 8.22 (s, 1H), 8.10 (dd, J = 8.7, 2.0, 1H), 7.76-7.71 (m, 2H), 7.37 (t, J = 8.9, 1H), 7.10-7.06 (m, 1H), 6.61 (d, J = 8.6, 1H), 6.54 (s, 2H), 6.27 (s, 2H). |

-continued

| Compound | Structure | LC/MS | NMR |
|---|---|---|---|
| 13 | 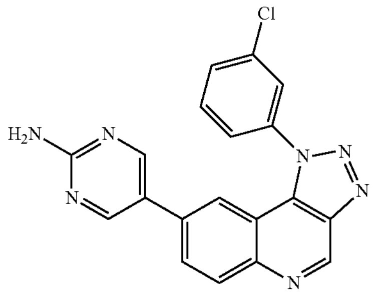 [SMILES: Nc1ncc(-c2ccc3ncc4nnn(-c5cccc(Cl)c5)c4c3c2)cn1] | 374(M + H)+ | 1H NMR (400 MHz, dmso) δ 9.62 (s, 1H), 8.42 (s, 2H), 8.29 (d, J = 8.7, 1H), 8.19-8.13 (m, 2H), 7.91 (dd, J = 15.2, 8.0, 2H), 7.82 (d, J = 8.0, 1H), 7.71 (s, 1H), 6.94 (s, 2H). |
| 14 | 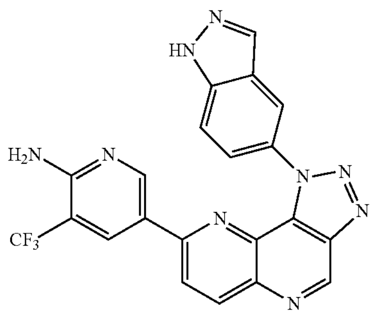 [SMILES: Nc1ncc(-c2ccc3ncc4nnn(-c5ccc6[nH]ncc6c5)c4c3n2)cc1C(F)(F)F] | 447(M + H)+ | 1HNMR (400 MHz, dmso) δ 13.61 (s, 1H), 9.63 (s, 1H), 8.37 (s, 1H), 8.31-8.25 (m, 3H), 8.18 (dd, J = 8.8, 1.8 Hz, 1H), 7.90 (d, J = 8.7 Hz, 1H), 7.79 (d, J = 8.7 Hz, 1H), 7.63 (s, 2H), 6.70 (s, 2H). |
| 15 | 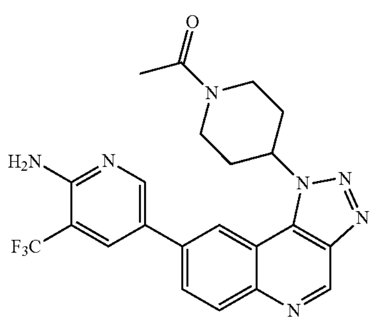 [SMILES: CC(=O)N1CCC(n2nnc3cnc4ccc(-c5cnc(N)c(C(F)(F)F)c5)cc4c32)CC1] | 456(M + H)+ | 1H NMR (400 MHz, dmso) δ 9.49 (s, 1H), 8.77 (s, 1H), 8.57 (s, 1H), 8.28 (d, J = 8.7, 1H), 8.23-8.16 (m, 2H), 6.70 (s, 2H), 5.80 (t, J = 10.7, 1H), 4.50 (d, J = 13.3, 1H), 4.02 (d, J = 13.5, 2H), 3.04 (t, J = 11.6, 1H), 2.40 (s, 2H), 2.31-2.20 (m, 1H), 2.10-2.02 (m, 4H). |
| 16 | 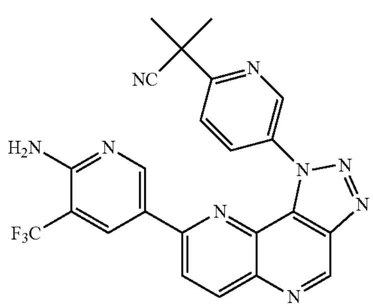 | 476(M + H)+ | 1H NMR (400 MHz, dmso) δ 9.72 (s, 1H), 9.24 (s, 1H), 8.87 (s, 1H), 8.65 (s, 2H), 8.53 (s, 1H), 8.23 (s, 1H), 7.97 (s, 1H), 6.98 (s, 2H), 1.86 (s, 6H). |
| 17 | 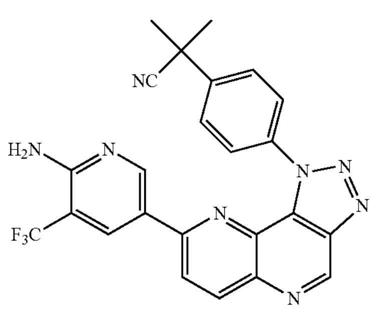 [SMILES: CC(C)(C#N)c1ccc(-n2nnc3cnc4ccc(-c5cnc(N)c(C(F)(F)F)c5)nc4c32)cc1] | 475(M + H)+ | 1H NMR (400 MHz, dmso) δ 9.71 (s, 1H), 8.90 (d, J = 1.9, 1H), 8.65 (d, J = 8.9, 1H), 8.52 (d, J = 8.9, 1H), 8.49-8.40 (m, 1H), 8.26 (d, J = 1.9, 1H), 8.09 (d, J = 8.6, 2H), 7.85 (d, J = 8.6, 2H), 6.99 (s, 2H), 1.84 (s, 6H). |

-continued
| Compound | Structure | LC/MS | NMR |
|---|---|---|---|
| 18 | 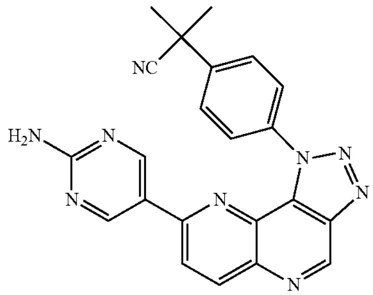 [SMILES: CC(C)(C#N)c1ccc(-n2nnc3cnc4ccc(-c5cnc(N)nc5)nc4c32)cc1] | 408(M + H)⁺ | ¹H NMR (400 MHz, dmso) δ 9.69 (s, 1H), 8.76 (s, 2H), 8.61 (d, J = 8.9, 1H), 8.41 (d, J = 8.9, 1H), 8.03 (d, J = 8.4, 2H), 7.88 (d, J = 8.4, 2H), 7.14 (s, 2H), 1.88 (s, 6H). |
| 19 | 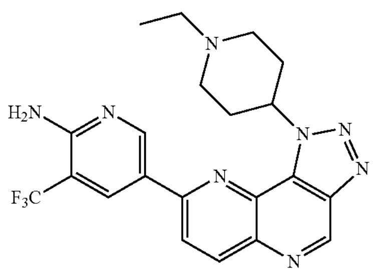 [SMILES: CCN1CCC(n2nnc3cnc4ccc(-c5cnc(N)c(C(F)(F)F)c5)nc4c32)CC1] | 443(M + H)⁺ | ¹H NMR (400 MHz, dmso) δ 9.58 (s, 1H), 9.19 (s, 1H), 8.67 (s, 1H), 8.62 (d, J = 8.8, 1H), 8.53 (d, J = 8.9, 1H), 7.11 (s, 2H), 5.88-5.77 (m, 1H), 3.19-3.14 (m, 2H), 2.49-2.44 (m, 2H), 2.37-2.32 (m, 4H), 2.24-2.21 (m, 2H), 1.10 (t, J = 7.1, 3H). |
| 20 | 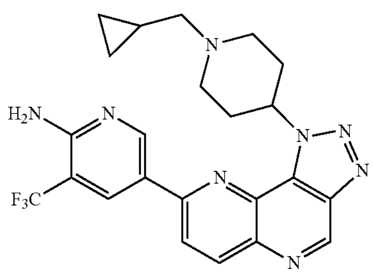 [SMILES: Nc1ncc(-c2ccc3ncc4nnn(C5CCN(CC6CC6)CC5)c4c3n2)cc1C(F)(F)F] | 469(M + H)⁺ | ¹H NMR (400 MHz, dmso) δ 9.59 (s, 1H), 9.19 (d, J = 1.8, 1H), 8.68 (d, J = 1.9, 1H), 8.62 (d, J = 8.9, 1H), 8.53 (d, J = 8.9, 1H), 7.10 (s, 2H), 5.87-5.76 (m, 1H), 3.28 (d, J = 11.3, 2H), 2.40-2.33 (m, 4H), 2.32-2.31 (m, 2H), 2.29-2.21 (m, 2H), 0.92-0.91 (m, 1H), 0.55-0.47 (m, 2H), 0.18-0.09 (m, 2H). |
EXAMPLE 2
Synthesis of Compounds 21-29
Compound 21
(R)-1-(4-(8-(6-amino-5-(trifluoromethyl)pyridin-3-yl)-1H-[1,2,3]triazolo[4,5-c][1,5]naphthyridin-1-yl)piperidin-1-yl)-2-hydroxypropan-1-one
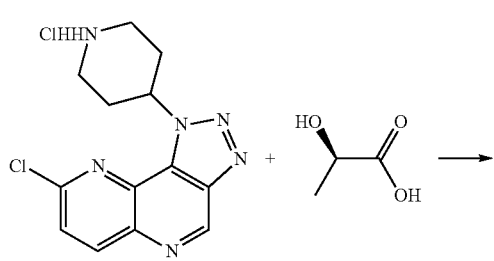
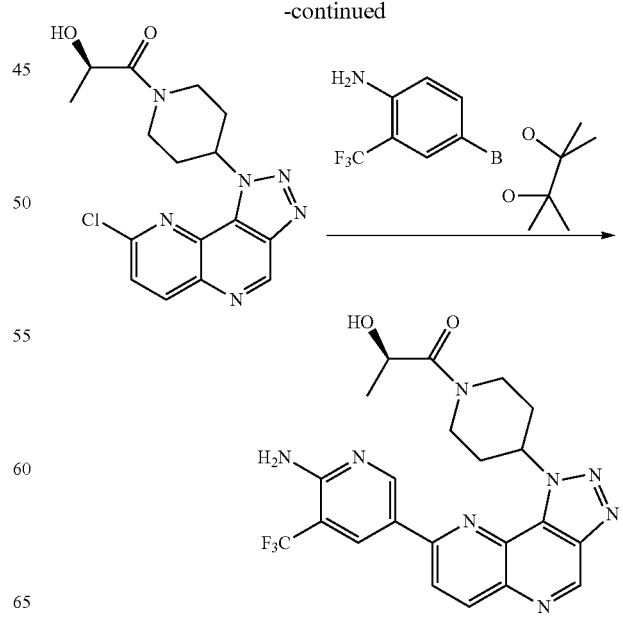

To a solution of 8-chloro-1-(piperidin-4-yl)-1H-[1,2,3]triazolo[4,5-c][1,5]naphthyridine hydrochloride (600 mg, 1.85 mmol) in DMF (15 mL) was added (R)-2-hydroxypropanoic acid (540 mg, 1.85 mmol), HATU (850 mg, 2.21 mmol) and DIEA (0.8 mL, 3.70 mmol). The mixture was stirred at room temperature overnight. Another 3 eq of HATU and 2 eq of DIEA were added because the reaction did not go to completion as shown by HPLC-MS. The mixture was stirred for another 30 min, and was then diluted with water. The resulting mixture was extracted with ethyl acetate twice. The combined organic layers were dried over anhydrous $Na_2SO_4$, and concentrated to give the crude product, which was subsequently purified by chromatography on silica gel using EtOAc:PE as eluent to afford (R)-1-(4-(8-chloro-1H-[1,2,3]triazolo[4,5-c][1,5]naphthyridin-1-yl)piperidin-1-yl)-2-hydroxypropan-1-one as a yellow solid (136 mg, yield 20.4%). MS (m/z): 361 (M+H)$^+$.

The next step for the synthesis of compound 21 was similar to the corresponding step used for the synthesis of Compound 1.

Compound 21: a solid, 31.0 mg. $^1$H NMR (400 MHz, dmso) δ 9.59 (s, 1H), 9.19 (s, 1H), 8.66 (s, 1H), 8.63 (d, J=8.9 Hz, 1H), 8.53 (d, J=8.9 Hz, 1H), 7.07 (s, 2H), 6.09 (m, 1H), 5.02 (m, 1H), 4.74-4.27 (m, 2H), 2.87 (m, 1H), 2.44-1.90 (m, 3H), 1.27-1.21 (m, 4H). MS (m/z): 487 (M+H)$^+$.

The following compounds 22-29 were prepared according to the procedures for Compound 21 by using the corresponding intermediates and boronic acid or ester under appropriate conditions that could be recognized by one skilled in the art.

| Compound | Structure | LC/MS | NMR |
|---|---|---|---|
| 22 | 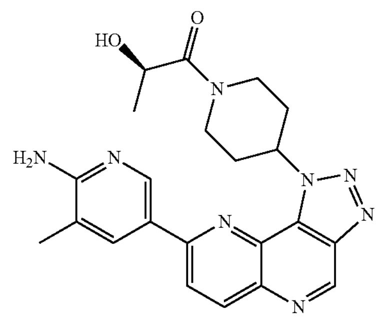 [SMILES: Cc1cc(-c2ccc3ncc4nnn(C5CCN(C(=O)[C@@H](C)O)CC5)c4c3n2)cnc1N] | 433(M + H)$^+$ | $^1$H NMR (400 MHz, dmso) δ 9.53 (s, 1H), 8.82 (s, 1H), 8.55 (d, J = 8.9 Hz, 1H), 8.37 (d, J = 8.9 Hz, 1H), 8.17 (s, 1H), 6.34 (s, 2H), 6.02 (m, 1H), 5.06 (m, 1H), 4.55 (m 2H), 4.32 (m, 1H), 2.99 (s, 1H), 2.29 (m, 1H), 2.17 (m, 5H), 1.97 (m, 1H), 1.23 (m, 3H). |
| 23 | 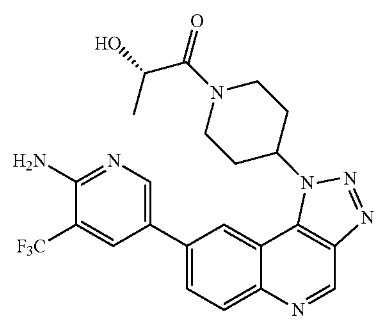 | 486(M + H)$^+$ | $^1$H NMR (400 MHz, dmso) δ 9.52 (s, 1H), 8.80 (s, 1H), 8.61 (s, 1H), 8.29 (d, J = 8.7, 1H), 8.22 (d, J = 6.4, 2H), 6.75 (s, 2H), 5.86 (s, 1H), 5.10-4.91 (m, 1H), 4.51 (s, 2H), 4.25 (s, 1H), 3.57-3.43 (m, 2H), 3.12 (d, J = 12.4, 2H), 2.35-2.18 (m, 1H), 2.08 (s, 1H), 1.22 (s, 3H). |
| 24 | 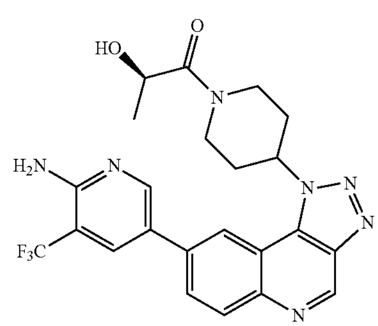 [SMILES: C[C@@H](O)C(=O)N1CCC(n2nnc3cnc4ccc(-c5cnc(N)c(C(F)(F)F)c5)cc4c32)CC1] | 486(M + H)$^+$ | $^1$H NMR (400 MHz, dmso) δ 8.16 (s, 1H), 7.80 (d, J = 8.2, 1H), 7.40 (s, 3H), 7.27 (t, J = 7.6, 2H), 7.16 (d, J = 7.4, 1H), 7.04 (d, J = 7.2, 1H), 6.97 (t, J = 8.0, 1H), 6.35-6.13 (m, 1H), 5.34-5.10 (m, 1H), 3.80 (s, 3H), 2.20 (s, 3H), 1.44 (d, J = 6.3, 3H). |

-continued

| Compound | Structure | LC/MS | NMR |
|---|---|---|---|
| 25 | 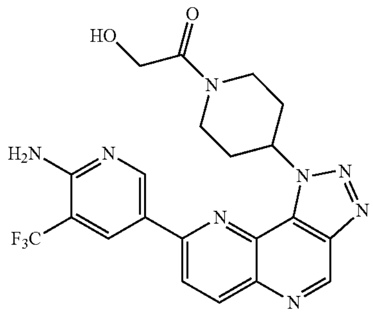 [SMILES: Nc1ncc(-c2ccc3ncc4nnn(C5CCN(C(=O)CO)CC5)c4c3n2)cc1C(F)(F)F] | 473(M + H)+ | $^1$H NMR (400 MHz, dmso) δ 9.62 (s, 1H), 9.22 (d, J = 1.6 Hz, 1H), 8.69 (d, J = 1.6 Hz, 1H), 8.66 (d, J = 8.9 Hz, 1H), 8.56 (d, J = 8.9 Hz, 1H), 7.09 (s, 2H), 6.13 (s, 1H), 5.34 (m, 1H), 4.65 (m, 2H), 4.17 (m, 3H), 2.94 (m, 2H), 2.07 (m, 4H). |
| 26 | 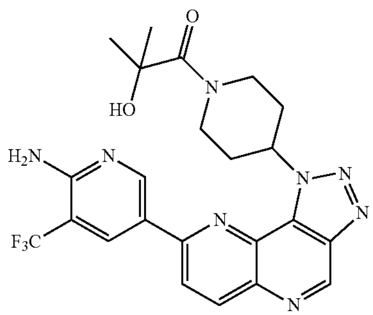 [SMILES: CC(C)(O)C(=O)N1CCC(n2nnc3cnc4ccc(-c5cnc(N)c(C(F)(F)F)c5)nc4c32)CC1] | 501(M + H)+ | $^1$H NMR (400 MHz, cdcl3) δ 9.59 (s, 1H), 9.21 (d, J = 2.2 Hz, 1H), 8.67 (d, J = 8.8 Hz, 1H), 8.53 (d, J = 2.1 Hz, 1H), 8.16 (d, J = 8.8 Hz, 1H), 5.98 (s, 1H), 5.30 (m, 2H), 4.97-4.88 (m, 3H), 3.22 (m, 2H), 2.80 (m, 2H), 2.41 (m, 2H), 1.62 (m, 6H). |
| 27 | 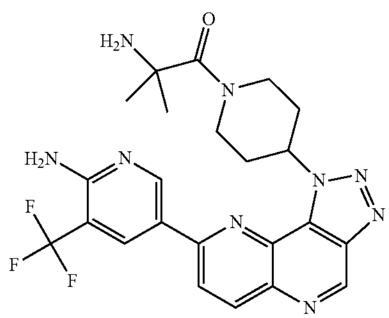 [SMILES: CC(C)(N)C(=O)N1CCC(n2nnc3cnc4ccc(-c5cnc(N)c(C(F)(F)F)c5)nc4c32)CC1] | 500(M + H)+ | 1H NMR (400 MHz, dmso) δ 9.62 (s, 1H), 9.21 (s, 1H), 8.73-8.63 (m, 2H), 8.56 (d, J = 8.9 Hz, 1H), 7.11 (s, 2H), 6.19-6.05 (m, 1H), 4.91-4.79 (m, 2H), 3.24-3.11 (m, 2H), 2.47-2.43 (mz, 2H), 2.29-2.19 (m, 2H), 1.49 (s, 6H). |
| 28 | 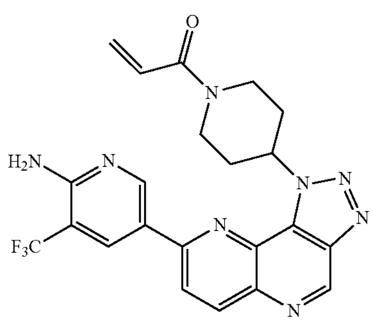 | 469(M + H)+ | $^1$H NMR (400 MHz, dmso) δ 9.58 (s, 1H), 9.18 (s, 1H), 8.65 (s, 1H), 8.62 (d, J = 8.9 Hz, 1H), 8.52 (d, J = 9.0 Hz, 1H), 7.08 (m, 2H), 6.89 (d, J = 6.0 Hz, 1H), 6.22-5.99 (m, 2H), 5.71 (m, 1H), 4.62 (m, 1H), 4.34 (m, 1H), 3.37 (m, 3H), 2.95 (m, 1H), 2.35-1.84 (m, 3H). |
| 29 | 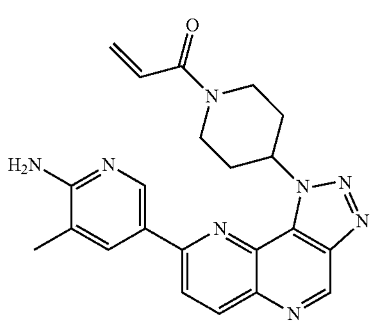 [SMILES: C=CC(=O)N1CCC(n2nnc3cnc4ccc(-c5cnc(N)c(C)c5)nc4c32)CC1] | 415(M + H)+ | $^1$H NMR (400 MHz, dmso) δ 9.53 (s, 1H), 8.82 (d, J = 2.1 Hz, 1H), 8.55 (d, J = 8.9 Hz, 1H), 8.38 (d, J = 8.9 Hz, 1H), 8.17 (s, 1H), 6.98-6.85 (m, 1H), 6.35 (s, 2H), 6.23-6.09 (m, 1H), 6.09-5.96 (m, 1H), 5.75-5.67 (m, 1H), 5.37-5.21 (m, 1H), 4.76-4.62 (m, 1H), 4.46-4.30 (m, 1H), 4.18-4.02 (m, 1H), 3.10-2.98 (m, 1H), 2.55-2.50 (m, 1H), 2.16 (m, 6H). |

EXAMPLE 3

Synthesis of Compounds 30-42

Compound 30

1-(4-(8-(6-amino-5-(trifluoromethyl)pyridin-3-yl)-1H-[1,2,3]triazolo[4,5-c][1,5]naphthyridin-1-yl)piperidin-1-yl)-2-methylpropan-1-one

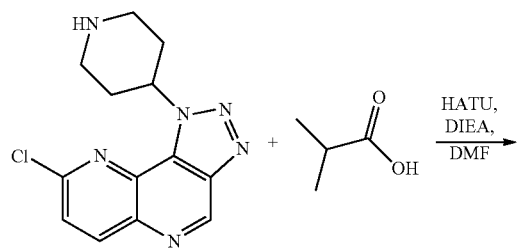

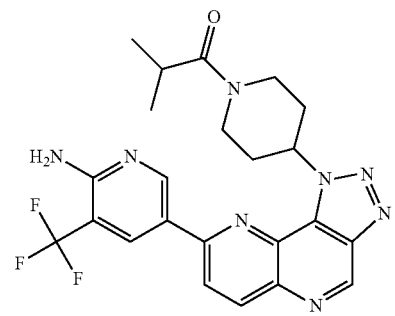

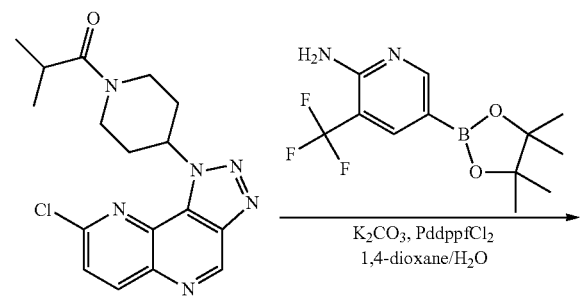

A mixture of 8-chloro-1-(piperidin-4-yl)-1H-[1,2,3]triazolo[4,5-c][1,5]naphthyridine (200 mg, 0.69 mmol), isobutyric acid (67 mg, 0.76 mmol), HATU (315 mg, 0.83 mmol) and DIEA (133 mg, 1.04 mmol) in DMF (5 mL) was stirred at r.t. overnight. Then water (10 mL) was added; the precipitate was collected and dried in vacuo to afford 1-(4-(8-chloro-1H-[1,2,3]triazolo[4,5-c][1,5]naphthyridin-1-yl)piperidin-1-yl)-2-methylpropan-1-one as a solid (200 mg).

A mixture of 1-(4-(8-chloro-1H-[1,2,3]triazolo[4,5-c][1,5]naphthyridin-1-yl)piperidin-1-yl)-2-methylpropan-1-one (60 mg, 0.17 mmol), 5-(4,4,5,5-tetramethyl-1,3,2-dioxaborolan-2-yl)-3-(trifluoromethyl)pyridin-2-amine (53 mg, 0.18 mmol), $K_2CO_3$ (70 mg, 0.51 mmol) and Pd(dppf)Cl$_2$ (6 mg) in dioxane/H$_2$O (3:1, 4 mL) was stirred and microwaved at 160° C. for 0.5 h. The solvent was removed, and the residue was purified by ISCO (MeOH/H$_2$O=20%-80%) to afford 1-(4-(8-(6-amino-5-(trifluoromethyl)pyridin-3-yl)-1H-[1,2,3]triazolo[4,5-c][1,5]naphthyridin-1-yl)piperidin-1-yl)-2-methylpropan-1-one as white solid (46 mg). $^1$HNMR (400 MHz, dmso) δ 9.61 (s, 1H), 9.21 (d, J=2.1 Hz, 1H), 8.66 (dd, J=12.5, 5.5 Hz, 2H), 8.55 (d, J=8.9 Hz, 1H), 7.10 (s, 2H), 6.17-6.01 (m, 1H), 4.78-4.59 (m, 1H), 4.35-4.26 (m, 1H), 3.40-3.37 (m, 2H), 3.05-2.97 (m, 1H), 2.93-2.82 (m, 1H), 2.64-2.52 (m, 1H), 2.39-2.21 (m, 1H), 2.16-1.96 (m, 1H), 1.07 (s, 6H). MS (m/z): 485 (M+H)$^+$.

The following compounds 31-42 were prepared according to the procedures for Compound 30 by using the corresponding intermediates and boronic acid or ester under appropriate conditions that could be recognized by one skilled in the art.

| Compound | Structure | LC/MS | NMR |
|---|---|---|---|
| 31 | 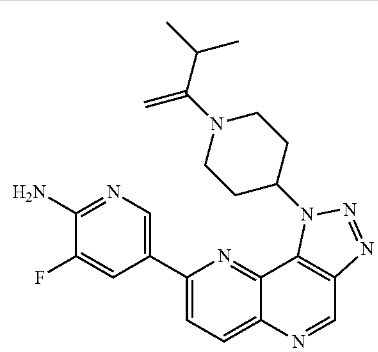 [SMILES: C=C(C(C)C)N1CCC(n2nnc3cnc4ccc(-c5cnc(N)c(F)c5)nc4c32)CC1] | 435(M + H)$^+$ | $^1$HNMR (400 MHz, dmso) δ 9.59 (s, 1H), 8.83 (s, 1H), 8.61 (d, J = 8.9 Hz, 1H), 8.45 (d, J = 8.9 Hz, 1H), 8.25 (dd, J = 12.7, 1.8 Hz, 1H), 6.87 (s, 2H), 6.15-5.91 (m, 1H), 4.68 (d, J = 12.7 Hz, 1H), 4.29 (d, J = 12.0 Hz, 1H), 3.49-3.38 (m, 2H), 3.06-2.95 (m, 2H), 2.58-2.52 (m, 1H), 2.36-2.24 (m, 1H), 2.17-2.05 (m, 1H), 1.07 (d, J = 6.4 Hz, 6H). |

-continued
| Compound | Structure | LC/MS | NMR |
|---|---|---|---|
| 32 | 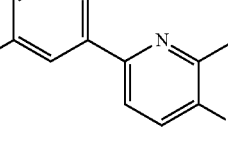 | 415(M + H)+ | 1HNMR (400 MHz, dmso) δ 9.61 (s, 1H), 9.22 (s, 1H), 8.65 (d, J = 8.9 Hz, 2H), 8.55 (d, J = 8.9 Hz, 1H), 8.25 (s, 2H), 7.11 (s, 2H), 6.09-5.96 (m, 1H), 3.43 (d, J = 13.4 Hz, 2H), 2.99 (t, J = 11.4 Hz, 2H), 2.46-2.31 (m, 4H). |
| 33 | 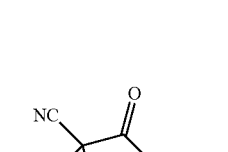 | 508(M + H)+ | 1HNMR (400 MHz, dmso) δ 9.63 (s, 1H), 9.23 (s, 1H), 8.67 (d, J = 9.0 Hz, 2H), 8.56 (d, J = 8.9 Hz, 1H), 7.09 (s, 2H), 6.21-6.12 (m, 1H), 4.61-4.48 (m, 2H), 3.40-3.52 (m, 2H), 2.61-2.53 (m, 2H), 2.41-2.27 (m, 2H), 1.68-1.56 (m, 4H). |
| 34 | 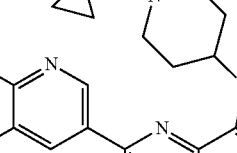 | 500(M + H)+ | 1HNMR (400 MHz, dmso) δ 9.61 (s, 1H), 9.21 (s, 1H), 8.74-8.61 (m, 2H), 8.55 (d, J = 8.9 Hz, 1H), 7.10 (s, 2H), 6.18-6.07 (m, 1H), 4.65 (d, J = 12.6 Hz, 1H), 4.24 (d, J = 12.7 Hz, 1H), 3.67 (d, J = 14.0 Hz, 1H), 3.57 (d, J = 14.1 Hz, 1H), 3.36 (dd, J = 32.3, 20.7 Hz, 2H), 2.95 (t, J = 12.3 Hz, 1H), 2.45 (s, 6H), 2.40-2.33 (m, 1H), 2.22-2.07 (m, 2H). |
| 35 | 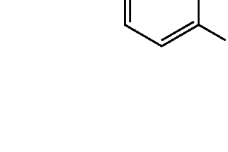 | 485(M + H)+ | 1H NMR (400 MHz, dmso) δ 9.51 (s, 1H), 9.11 (s, 1H), 8.58-8.45 (m, 3H), 7.03 (s, 2H), 5.98 (s, 1H), 4.64 (s, 1H), 4.16 (s, 1H), 2.38 (s, 4H), 2.05 (s, 2H), 1.54 (s, 2H), 1.17 (s, 2H), 0.89 (s, 3H). |

-continued

| Compound | Structure | LC/MS | NMR |
|---|---|---|---|
| 36 | 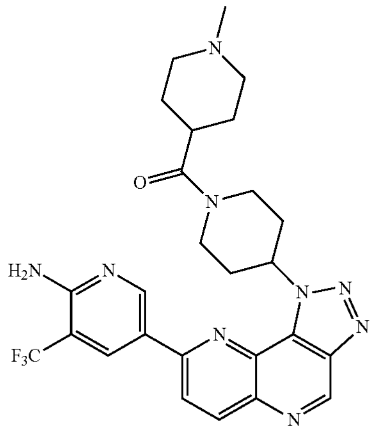 [SMILES: CN1CCC(C(=O)N2CCC(n3nnc4cnc5ccc(-c6cnc(N)c(C(F)(F)F)c6)nc5c43)CC2)CC1] | 540(M + H)+ | 1H NMR (400 MHz, cdcl3) δ 9.58 (s, 1H), 9.06 (s, 1H), 8.66 (d, J = 9.0, 1H), 8.60 (s, 1H), 8.17 (d, J = 8.8, 1H), 6.20-6.08 (m, 1H), 5.33 (s, 2H), 4.96-4.85 (m, 1H), 4.30-4.19 (m, 1H), 3.49-3.38 (m, 1H), 2.95 (m, 3H), 2.55 (m, 4H), 2.30 (m, 3H), 2.00 (m, 4H), 1.80 (m, 2H). |
| 37 | 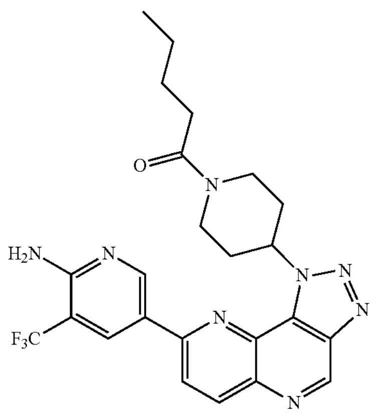 [SMILES: CCCCC(=O)N1CCC(n2nnc3cnc4ccc(-c5cnc(N)c(C(F)(F)F)c5)nc4c32)CC1] | 499(M + H)+ | 1H NMR (400 MHz, dmso) δ 9.53 (s, 1H), 9.13 (s, 1H), 8.54 (m, 3H), 7.06 (s, 2H), 6.01 (s, 1H), 4.64 (s, 1H), 4.18 (s, 1H), 2.43-1.92 (m, 7H), 1.50 (s, 2H), 1.25 (m, 3H), 0.87 (s, 3H). |
| 38 | 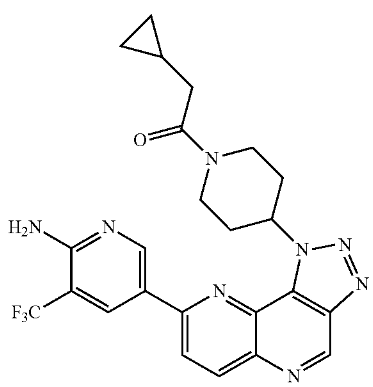 [SMILES: Nc1ncc(-c2ccc3ncc4nnn(C5CCN(C(=O)CC6CC6)CC5)c4c3n2)cc1C(F)(F)F] | 497(M + H)+ | 1H NMR (400 MHz, dmso) δ 9.39 (s, 1H), 9.00 (s, 1H), 8.44 (m, 2H), 8.34 (m, 1H), 6.91 (s, 2H), 5.88 (m, 1H), 4.50 (m, 1H), 3.99 (m, 1H), 2.14 (m, 7H), 1.04 (m, 1H), 0.84 (m, 1H), 0.32 (m, 2H), 0.00 (m, 2H). |
| 39 | 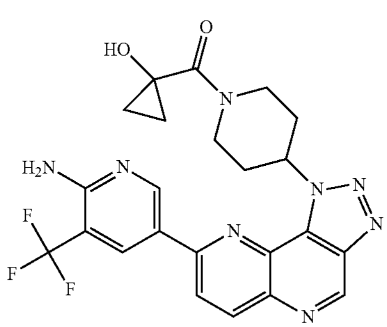 [SMILES: Nc1ncc(-c2ccc3ncc4nnn(C5CCN(C(=O)C6(O)CC6)CC5)c4c3n2)cc1C(F)(F)F] | 499(M + H)+ | 1HNMR (400 MHz, dmso) δ 9.62 (s, 1H), 9.21 (s, 1H), 8.66 (d, J = 8.7 Hz, 2H), 8.56 (d, J = 8.9 Hz, 1H), 7.10 (s, 2H), 6.21-6.09 (m, 1H), 4.61-4.49 (m, 1H), 3.95-3.81 (m, 1H), 3.45-3.36 (m, 1H), 3.17-3.07 (m, 1H), 2.85 (q, J = 7.2 Hz, 2H), 2.62-2.54 (m, 2H), 2.41-2.31 (m, 1H), 2.25-2.18 cm, 1H), 1.07 (t, J = 7.2 Hz, 2H). |

| Compound | Structure | LC/MS | NMR |
|---|---|---|---|
| 40 | 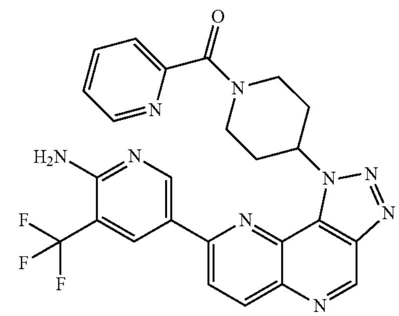 | 520(M + H)+ | 1H NMR (400 MHz, dmso) δ 9.62 (s, 1H), 9.22 (d, J = 1.9, 1H), 8.69-8.63 (m, 3H), 8.56 (d, J = 8.9, 1H), 7.97 (td, J = 7.7, 1.7, 1H), 7.69 (d, J = 7.8, 1H), 7.53-7.50 (m, 1H), 7.11 (s, 2H), 6.21-6.18 (m, 1H), 4.88-4.75 (m, 1H), 4.03-4.01 (m, 1H), 2.59-2.51 cm, 3H), 2.46-2.32 (m, 3H). |
| 41 | 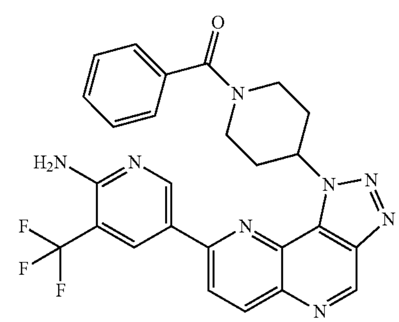 [SMILES: Nc1ncc(-c2ccc3ncc4nnn(C5CCN(C(=O)c6ccccc6)CC5)c4c3n2)cc1C(F)(F)F] | 519(M + H)+ | 1H NMR (400 MHz, dmso) δ 9.61 (s, 1H), 9.21 (d, J = 2.1, 1H), 8.65 (t, J = 5.5, 2H), 8.54 (d, J = 8.9, 1H), 7.55-7.46 (m, 5H), 7.10 (s, 2H), 6.18-6.07 (m, 1H), 4.95-4.57 (m, 1H), 4.01-3.74 (m, 1H), 2.57-2.54 (m, 1H), 2.48-2.45 (m, 1H), 2.38-2.28 (m, 3H), 2.08-1.91 (m, 1H). |
| 42 | 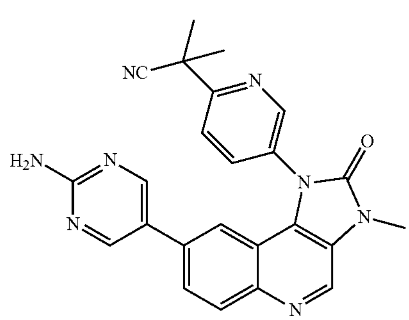 [SMILES: Cn1c(=O)n(-c2ccc(C(C)(C)C#N)nc2)c2c3cc(-c4cnc(N)nc4)ccc3ncc21] | 437(M + H)+ | 1H NMR (400 MHz, dmso) δ 9.00 (s, 1H), 8.93 (d, J = 1.8, 1H), 8.30-8.20 (m, 3H), 8.08 (d, J = 8.9, 1H), 7.98 (d, J = 8.4, 1H), 7.88 (d, J = 8.9, 1H), 6.92 (d, J = 25.9, 3H), 3.61 (s, 3H), 1.83 (s, 6H). |

EXAMPLE 4

Synthesis of Compounds 43-47

Compound 43

2-(4-(8-(6-amino-5-(trifluoromethyl)pyridin-3-yl)-1H-[1,2,3]triazolo[4,5-c][1,5]naphthyridin-1-yl)piperidin-1-yl)-N,N-dimethylacetamide

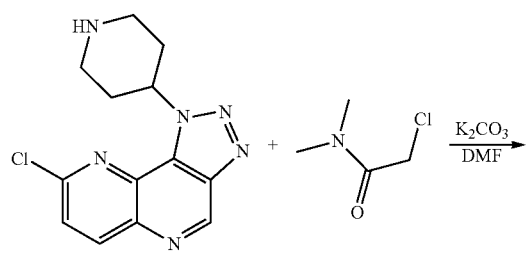

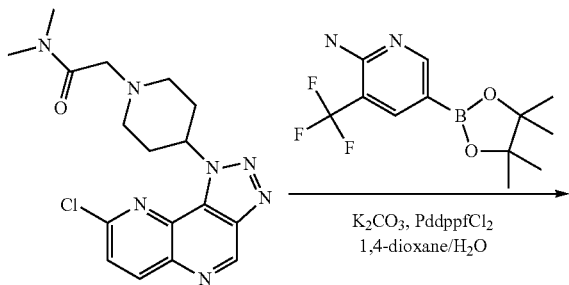

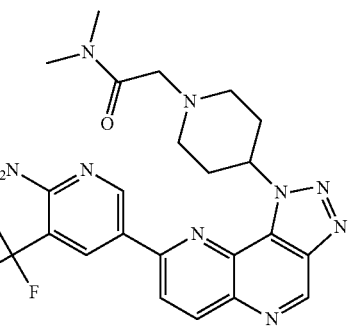

A mixture of 8-chloro-1-(piperidin-4-yl)-1H-[1,2,3]triazolo[4,5-c][1,5]naphthyridine (100 mg, 0.35 mmol), 2-chloro-N,N-dimethylacetamide (46 mg, 0.38 mmol), and $K_2CO_3$ (97 mg, 1.04 mmol) in DMF (5 mL) was stirred at r.t. overnight. The solvent was removed, and the residue was extracted with EtOAc (3×10 mL). The combined organic layers were dried over $Na_2SO_4$, and concentrated to afford crude 2-(4-(8-chloro-1H-[1,2,3]triazolo[4,5-c][1,5]naphthyridin-1-yl)piperidin-1-yl)-N,N-dimethylacetamide, which was used in the next step without further purification.

A mixture of the above product, 5-(4,4,5,5-tetramethyl-1,3,2-dioxaborolan-2-yl)-3-(trifluoromethyl)pyridin-2-amine (109 mg, 0.38 mmol), $K_2CO_3$ (145 mg, 1.05 mmol) and Pd(dppf)Cl$_2$ (10 mg) in dioxane/H$_2$O (3:1, 4 mL) was stirred and microwaved at 160° C. for 0.5 h. The solvent was removed, and the residue was purified by chromatography to afford compound 43 as a pale yellow solid (50 mg). $^1$HNMR (400 MHz, dmso-d$_6$) δ 9.60 (s, 1H), 9.20 (d, J=2.0 Hz, 1H), 8.66 (dd, J=16.5, 5.4 Hz, 2H), 8.54 (d, J=8.9 Hz, 1H), 7.12 (s, 2H), 5.97-5.77 (m, 1H), 3.40 (s, 2H), 3.29-3.14 (m, 4H), 3.10 (s, 3H), 2.86 (s, 3H), 2.44-2.35 (m, 4H). MS (m/z): 500 (M+H)$^+$.

The following compounds 44-47 were prepared according to the procedures for Compound 43 by using the corresponding intermediates, and boronic acid or ester under appropriate conditions that could be recognized by one skilled in the art:

| Compound | Structure | LC/MS | NMR |
|---|---|---|---|
| 44 | 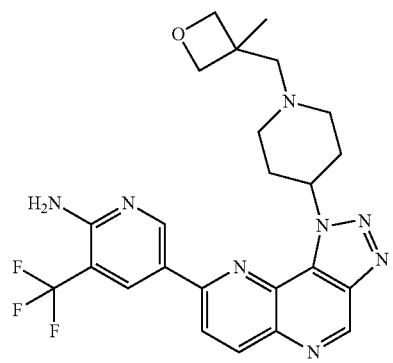 [SMILES: CC1(CN2CCC(n3nnc4cnc5ccc(-c6cnc(N)c(C(F)(F)F)c6)nc5c43)CC2)COC1] | 499(M + H)$^+$ | $^1$H NMR (400 MHz, dmso) δ 9.60 (s, 1H), 9.21 (d, J = 2.0, 1H), 8.71 (d, J = 2.1, 1H), 8.64 (d, J = 8.9, 1H), 8.55 (d, J = 8.9, 1H), 7.13 (s, 2H), 4.41 (d, J = 5.7, 2H), 4.25 (d, J = 5.7, 2H), 2.62 (s, 2H), 2.40-2.21 (m, 8H), 1.38 (s, 3H). |

-continued

| Compound | Structure | LC/MS | NMR |
| --- | --- | --- | --- |
| 45 | 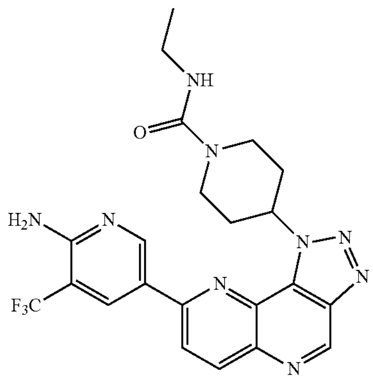 [SMILES: CCNC(=O)N1CCC(n2nnc3cnc4ccc(-c5cnc(N)c(C(F)(F)F)c5)nc4c32)CC1] | 486(M + H)+ | 1H NMR (400 MHz, dmso) δ 9.57 (s, 1H), 9.18 (d, J = 2.1, 1H), 8.65 (s, 1H), 8.62 (d, J = 8.9, 1H), 8.51 (d, J = 8.9, 1H), 7.07 (s, 2H), 6.66 (t, J = 5.4, 1H), 6.01 (s, 1H), 4.23 (d, J = 14.0, 2H), 2.93 (t, J = 12.2, 2H), 2.36-2.34 (m, 2H), 2.14-2.12 (m, 2H), 1.98-1.96 (m, 2H), 1.02 (t, J = 7.1, 3H). |
| 46 | 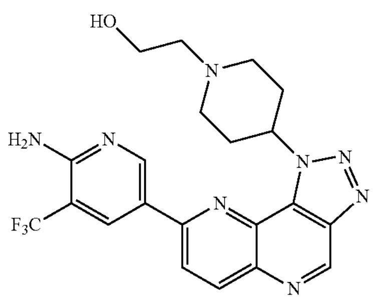 [SMILES: Nc1ncc(-c2ccc3ncc4nnn(C5CCN(CCO)CC5)c4c3n2)cc1C(F)(F)F] | 459(M + H)+ | 1H NMR (400 MHz, cdcl3) δ 9.73-9.68 (m, 1H), 9.57 (s, 1H), 8.64 (d, J = 8.8 Hz, 1H), 8.53-8.48 (m, 1H), 8.15 (d, J = 8.8 Hz, 1H), 5.75-5.60 (m, 1H), 5.40 (s, 2H), 3.78-3.71 (m, 2H), 3.34-3.26 (m, 2H), 3.21-3.07 (m, 2H), 2.76-2.65 (m, 2H), 2.48-2.34 (m, 2H), 1.31 (m, 4H). |
| 47 | 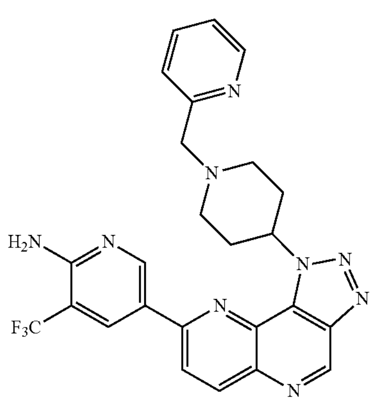 [SMILES: Nc1ncc(-c2ccc3ncc4nnn(C5CCN(Cc6ccccn6)CC5)c4c3n2)cc1C(F)(F)F] | 505(M + H)+ | 1H NMR (400 MHz, dmso) δ 9.57 (s, 1H), 9.18 (s, 1H), 8.67 (s, 1H), 8.61 (d, J = 8.7, 1H), 8.51 (d, J = 9.2, 2H), 7.79 (s, 1H), 7.53 (d, J = 7.4, 1H), 7.27 (s, 1H), 7.09 (s, 2H), 5.94-5.81 (m, 1H), 3.71 (s 2H), 3.13 (m, 2H), 2.35 (s, 6H). |

EXAMPLE 5

Synthesis of Compound 48

Compound 48

5-(1-(1-((tetrahydro-2H-pyran-4-yl)methyl)piperidin-4-yl)-1H-[1,2,3]triazolo[4,5-c][1,5]naphthyridin-8-yl)-3-(trifluoromethyl)pyridin-2-amine

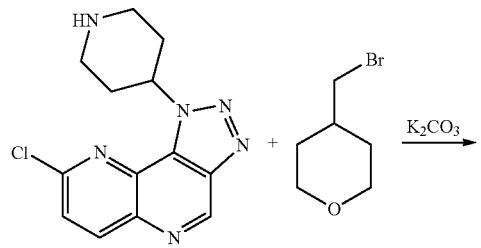

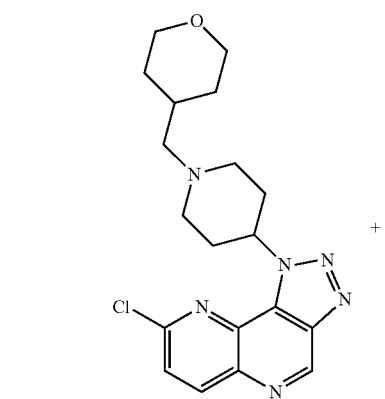

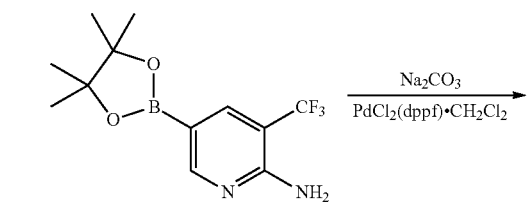

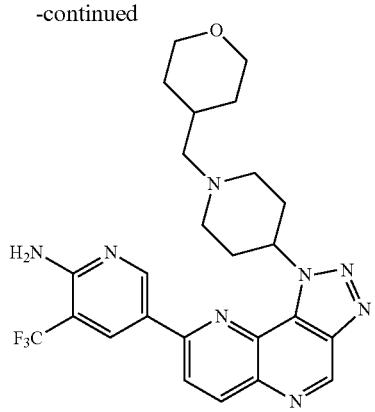

Under N$_2$, a white suspension of 8-chloro-1-(piperidin-4-yl)-1H-[1,2,3]triazolo[4,5-c][1,5]naphthyridine (130 mg, 0.450 mmol), 4-(bromomethyl)tetrahydro-2H-pyran (97 mg, 0.540 mmol) and K$_2$CO$_3$ (124 mg, 0.900 mmol) in acetonitrile (15 mL) was heated to reflux for 4 h. After cooling to room temperature, the mixture was diluted with EtOAc 20 mL. The mixture was then filtered through a Buchner funnel, and the organic phase was collected and concentrated. The crude product was used in the next step without further purification (35 mg). MS (m/z): 387 (M+H)$^+$.

Under N$_2$, an orange suspension of 8-chloro-1-(1-((tetrahydro-2H-pyran-4-yl)methyl)piperidin-4-yl)-H-[1,2,3]triazolo[4,5-c][1,5]naphthyridine (35 mg, 0.090 mmol), 5-(4,4,5,5-tetramethyl-1,3,2-dioxaborolan-2-yl)-3-(trifluoromethyl)pyridin-2-amine (26.1 mg, 0.090 mmol), Na$_2$CO$_3$ (19.18 mg, 0.181 mmol) and PdCl$_2$(dppf).CH$_2$Cl$_2$ (3.69 mg, 4.52 µmol) in a mixture of dioxane (20 mL) and H$_2$O (2 mL) was stirred for 10 minutes, before the resulting mixture was heated to 120° C. for 2 h. After concentration in vacuo, the resulting residue was purified by ISCO with 12 g silica gel (PE/EtOAc) to give the product as pale yellow powder (10 mg). $^1$H NMR (400 MHz, dmso) δ 9.53 (s, 1H), 9.15 (d, J=2.1, 1H), 8.65 (s, 1H), 8.61 (d, J=8.9, 1H), 8.51 (d, J=8.9, 1H), 7.07 (s, 2H), 5.99-5.80 (m, 1H), 3.91-3.85 (m, 4H), 3.22-3.08 (m, 4H), 2.41-2.15 (m, 10H), 1.73-1.58 (m, 2H). MS (m/z): 513 (M+H)$^+$.

EXAMPLE 6

Synthesis of Compounds 49-78

Compound 49

2-(4-(8-(6-amino-5-(trifluoromethyl)pyridin-3-yl)-[1,2,4]triazolo[4,3-a]quinoxalin-1-yl)phenyl)-2-methylpropanenitrile

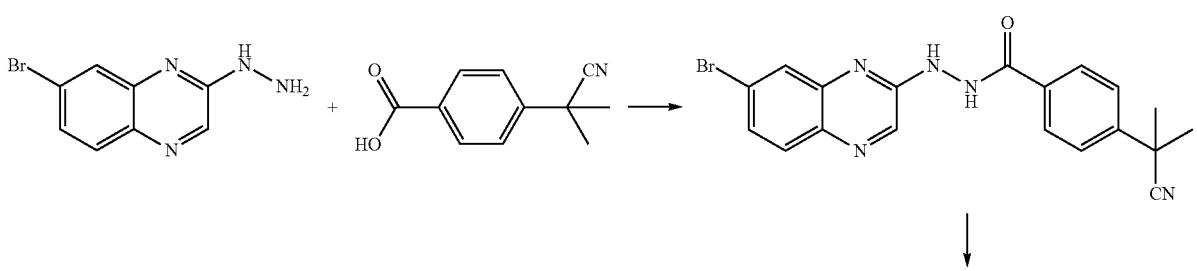

-continued

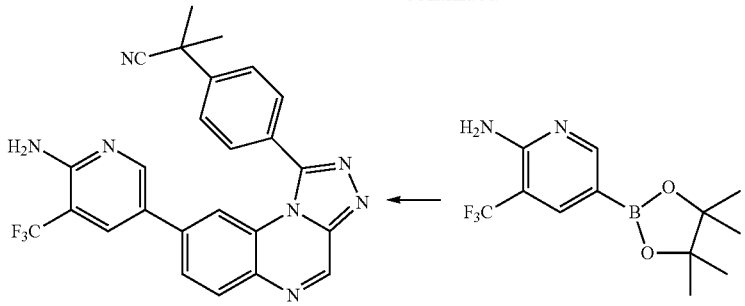

To a solution of 7-bromo-2-hydrazinylquinoxaline (1.5 g, 0.063 mol) and 4-(2-cyanopropan-2-yl) benzoic acid (1.1 g, 0.063 mol) in DMF (5 mL) was added HATU (2.4 g, 0.063 mol) and DIEA (1.2 g, 0.095 mol). The reaction mixture was then stirred at r.t. overnight. The solution was diluted with water (5 mL), and the solid was collected on a filter to give N'-(7-bromoquinoxalin-2-yl)-4-(2-cyanopropan-2-yl)benzohydrazide as a yellow solid (2.2 g, yield 85.0%). MS (m/z): 412 (M+H)$^+$.

A solution of N'-(7-bromoquinoxalin-2-yl)-4-(2-cyanopropan-2-yl)benzohydrazide (2.2 g, 0.054 mol) in 3 mL of AcOH was stirred at 100° C. overnight. After cooling to room temperature, the reaction mixture was diluted with water (5 mL). The solid was collected on a filter, and washed with Sat. NaHCO$_3$ (5 mL) to give 2-(4-(8-bromo-[1,2,4]triazolo[4,3-a]quinoxalin-1-yl) phenyl)-2-methylpropanenitrile as a yellow solid (1.8 g, yield 85.0%). MS (m/z): 392 (M+H)$^+$.

To a mixture of 2-(4-(8-bromo-[1,2,4]triazolo[4,3-a]quinoxalin-1-yl)phenyl)-2-methylpropanenitrile (80 mg, 0.21 mmol), 5-(4,4,5,5-tetramethyl-1,3,2-dioxaborolan-2-yl)-3-(trifluoromethyl)pyridin-2-amine (59 mg, 0.21 mmol) and K$_2$CO$_3$ (87 mg, 0.63 mmol) in dioxane (3 mL) and H$_2$O (1 mL) was added Pd(dppf)Cl$_2$ (3 mg). The reaction mixture was microwaved at 150° C. for 30 min. After cooling to room temperature, the mixture was concentrated and purified by chromatography to give compound 49 as a yellow solid (52 mg). $^1$H NMR (400 MHz, dmso) δ 9.38 (s, 1H), 8.26 (s, 1H), 8.11 (d, J=8.5, 1H), 7.99-7.95 (m, 1H), 7.92 (d, J=8.3, 2H), 7.83 (d, J=8.4, 2H), 7.63 (m, 1H), 7.52 (d, J=1.5, 1H), 6.77 (s, 2H), 1.77 (s, 6H). MS (m/z): 474 (M+H)$^+$.

The following compounds 50-78 were prepared according to the procedures for Compound 49 by using the corresponding intermediates and boronic acid or ester under appropriate conditions that could be recognized by one skilled in the art.

| Compound | Structure | LC/MS | NMR |
|---|---|---|---|
| 50 | 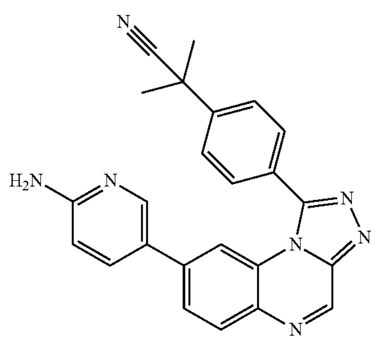 [SMILES: CC(C)(C#N)c1ccc(-c2nnc3cnc4ccc(-c5ccc(N)nc5)cc4n23)cc1] | 406(M + H)$^+$ | $^1$H NMR (400 MHz, dmso) δ 9.38 (s, 1H), 8.12 (d, J = 8.5, 1H), 7.96-7.87 (m, 5H), 7.74 (d, J = 1.8, 1H), 7.64 (s, 2H), 7.55 (d, J = 1.8, 1H), 7.27 (d, J = 8.4, 1H), 7.10 (dd, J = 8.4, 2.0, 1H), 1.81 (s, 6H). |
| 51 | 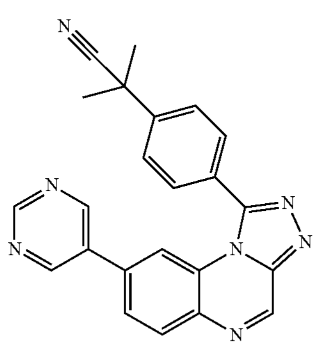 [SMILES: CC(C)(C#N)c1ccc(-c2nnc3cnc4ccc(-c5cncnc5)cc4n23)cc1] | 392(M + H)$^+$ | $^1$H NMR (400 MHz, dmso) δ 9.51 (s, 1H), 9.21 (s, 1H), 8.80 (s, 2H), 8.27 (d, J = 8.4, 1H), 8.16 (dd, J = 8.4, 1.9, 1H), 7.92 (dd, J = 11.7, 2.9, 5H), 7.49 (d, J = 1.8, 1H), 1.84 (s, 6H). |

| Compound | Structure | LC/MS | NMR |
|---|---|---|---|
| 52 | 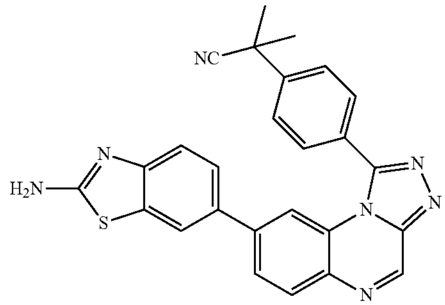 | 462(M + H)+ | ¹H NMR (400 MHz, dmso) δ 9.38 (s, 1H), 8.12 (d, J = 8.5, 1H), 7.96-7.87 (m, 5H), 7.74 (d, J = 1.8, 1H), 7.64 (s, 2H), 7.55 (d, J = 1.8, 1H), 7.27 (d, J = 8.4, 1H), 7.10 (dd, J = 8.4, 2.0, 1H), 1.81 (s, 6H). |
| 53 | 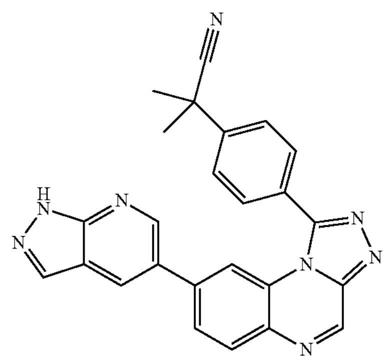 [SMILES: CC(C)(C#N)c1ccc(-c2nnc3cnc4ccc(-c5cnc6[nH]ncc6c5)cc4n23)cc1] | 431(M + H)+ | ¹HNMR (400 MHz, dmso) δ 13.81 (s, 1H), 9.43 (s, 1H), 8.46 (d, J = 2.2 Hz, 1H), 8.21-8.16 (m, 2H), 8.14 (s, 1H), 8.06 (dd, J = 8.5, 1.9 Hz, 1H), 7.92 (q, J = 8.5 Hz, 4H), 7.53 (d, J = 1.8 Hz, 1H), 1.79 (s, 6H). |
| 54 | 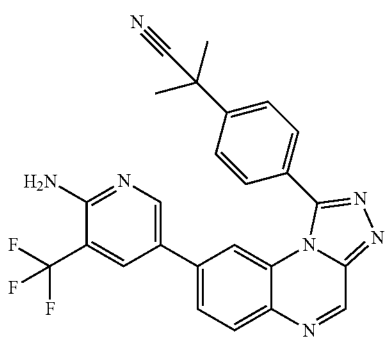 [SMILES: CC(C)(C#N)c1ccc(-c2nnc3cnc4ccc(-c5cnc(N)c(C(F)(F)F)c5)cc4n23)cc1] | 475(M + H)+ | ¹H NMR (400 MHz, dmso) δ 9.47 (s, 1H), 9.09 (dd, J = 2.3, 0.8, 1H), 8.50 (dd, J = 8.2, 2.3, 1H), 8.35 (d, J = 2.2, 1H), 8.19 (d, J = 8.5, 1H), 8.08-8.02 (m, 1H), 7.96 (dd, J = 8.2, 0.8, 1H), 7.71 (d, J = 2.2, 1H), 7.55 (d, J = 1.9, 1H), 6.83 (s, 2H), 1.82 (s, 6H). |
| 55 | 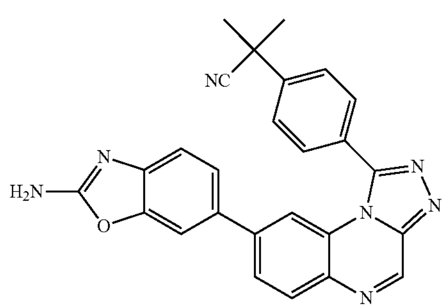 [SMILES: CC(C)(C#N)c1ccc(-c2nnc3cnc4ccc(-c5ccc6nc(N)oc6c5)cc4n23)cc1] | 446(M + H)+ | ¹H NMR (400 MHz, dmso) δ 9.38 (s, 1H), 8.11 (d, J = 8.5, 1H), 7.96 (dd, J = 8.5, 1.7, 1H), 7.90 (q, J = 8.5, 4H), 7.55 (s, 2H), 7.48 (d, J = 1.6, 1H), 7.38 (d, J = 1.3, 1H), 7.12 (d, J = 8.1, 1H), 7.00 (dd, J = 8.2, 1.5, 1H), 1.82 (s, 6H). |

| Compound | Structure | LC/MS | NMR |
|---|---|---|---|
| 56 | 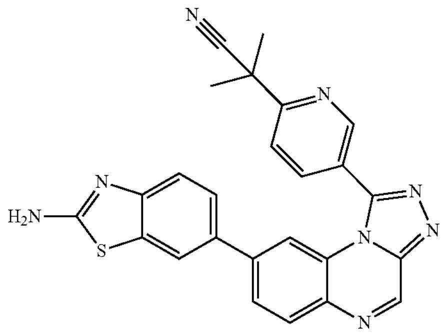 [SMILES: CC(C)(C#N)c1ccc(-c2nnc3cnc4ccc(-c5ccc6nc(N)sc6c5)cc4n23)cn1] | 463(M + H)+ | 1H NMR (400 MHz, dmso) δ 9.43 (s, 1H), 9.09 (s, 1H), 8.45 (dd, J = 8.2, 2.2, 1H), 8.16 (d, J = 8.5, 1H), 8.04-7.96 (m, 2H), 7.76 (d, J = 1.9, 1H), 7.66 (s, 2H), 7.53 (d, J = 1.8, 1H), 7.30 (d, J = 8.4, 1H), 7.16 (dd, J = 8.4, 2.0, 1H), 1.83 (s, 6H). |
| 57 | 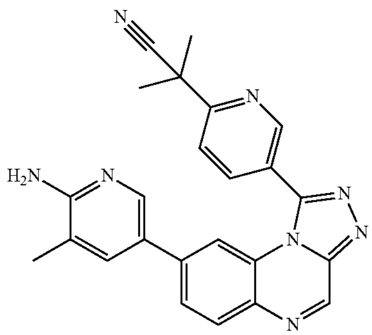 | 421(M + H)+ | 1H NMR (400 MHz, dmso) δ 9.39 (s, 1H), 9.07 (s, 1H), 8.45 (dd, J = 8.2, 2.3, 1H), 8.11 (d, J = 8.5, 1H), 8.00 (d, J = 8.2, 1H), 7.94-7.87 (m, 2H), 7.44 (d, J = 1.8, 1H), 7.23 (d, J = 1.7, 1H), 6.08 (s, 2H), 2.04 (s, 3H), 1.82 (s, 6H). |
| 58 | 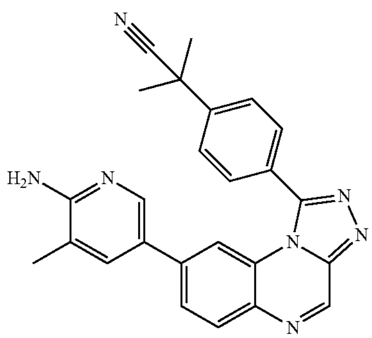 [SMILES: Cc1cc(-c2ccc3ncc4nnc(-c5ccc(C(C)(C)C#N)cc5)n4c3c2)cnc1N] | 420(M + H)+ | 1H NMR (400 MHz, dmso) δ 9.35 (s, 1H), 8.14 (s, 1H), 8.08 (d, J = 8.5, 1H), 7.94-7.84 (m, 6H), 7.47 (d, J = 1.8, 1H), 7.20 (d, J = 1.7, 1H), 6.05 (s, 2H), 2.03 (s, 3H), 1.81 (s, 6H). |
| 59 | 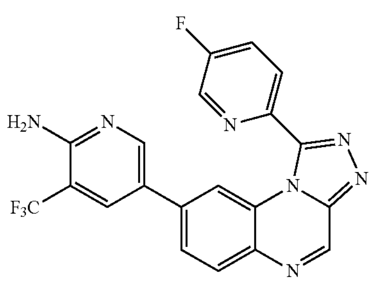 [SMILES: Nc1ncc(-c2ccc3ncc4nnc(-c5ccc(F)cn5)n4c3c2)cc1C(F)(F)F] | 426(M + H)+ | 1H NMR (400 MHz, dmso) δ 9.51 (s, 1H), 8.99 (d, J = 2.8, 1H), 8.58 (d, J = 2.1, 1H), 8.33-8.29 (m, 1H), 8.25-8.21 (m, 2H), 8.15 (d, J = 8.5, 1H), 8.05 (d, J = 1.8, 1H), 7.84 (d, J = 2.2, 1H), 6.93 (s, 2H). |
| 60 | 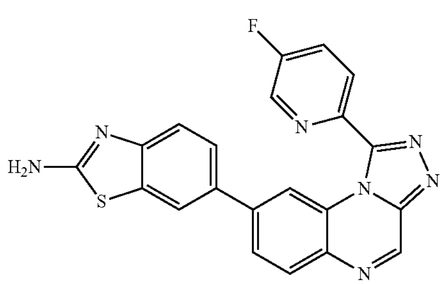 [SMILES: Nc1nc2ccc(-c3ccc4ncc5nnc(-c6ccc(F)cn6)n5c4c3)cc2s1] | 414(M + H)+ | 1H NMR (400 MHz, dmso) δ 9.50 (s, 1H), 9.13 (d, J = 2.8, 1H), 8.32-8.29 (m, 1H), 8.24-8.19 (m, 3H), 8.08 (dd, J = 8.5, 1.9, 1H), 7.94 (s, 1H), 7.74 (s, 2H), 7.46 (d, J = 2.4, 2H). |

| Compound | Structure | LC/MS | NMR |
|---|---|---|---|
| 61 | 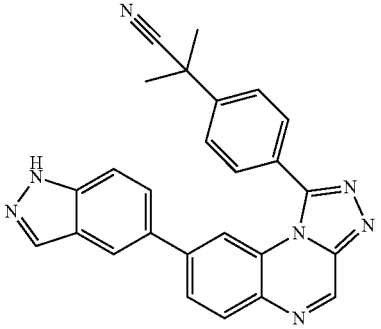 [SMILES: CC(C)(C#N)c1ccc(-c2nnc3cnc4ccc(-c5ccc6[nH]ncc6c5)cc4n23)cc1] | 430(M + H)+ | 1H NMR (400 MHz, dmso) δ 13.18 (s, 1H), 9.41 (s, 1H), 8.16 (d, J = 8.5, 1H), 8.09 (s, 1H), 8.01 (dd, J = 8.5, 1.9, 1H), 7.96-7.90 (m, 4H), 7.81 (s, 1H), 7.59 (d, J = 1.9, 1H), 7.54 (d, J = 8.7, 1H), 7.30 (dd, J = 8.7, 1.6, 1H), 1.79 (s, 6H). |
| 62 | 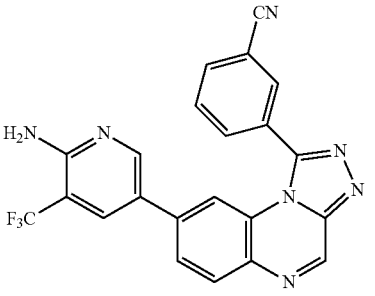 [SMILES: N#Cc1cccc(-c2nnc3cnc4ccc(-c5cnc(N)c(C(F)(F)F)c5)cc4n23)c1] | 432(M + H)+ | 1H NMR (400 MHz, dmso) δ 9.45 (s, 1H), 8.42 (s, 1H), 8.36 (d, J = 2.0, 1H), 8.27-8.22 (m, 2H), 8.18 (d, J = 8.5, 1H), 8.07 (dd, J = 8.5, 1.8, 1H), 7.94 (t, J = 7.8, 1H), 7.60 (d, J = 2.1, 1H), 7.42 (d, J = 1.8, 1H), 6.88 (s, 2H). |
| 63 | 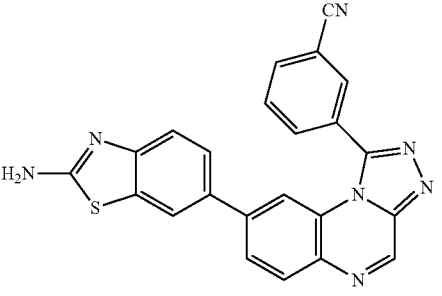 [SMILES: N#Cc1cccc(-c2nnc3cnc4ccc(-c5ccc6nc(N)sc6c5)cc4n23)c1] | 420(M + H)+ | 1H NMR (400 MHz, dmso) δ 9.42 (s, 1H), 8.49 (s, 1H), 8.29-8.10 (m, 3H), 7.95 (s, 2H), 7.69 (d, J = 8.1, 3H), 7.51 (s, 1H), 7.32 (d, J = 7.1, 1H), 7.21 (s, 1H). |
| 64 | 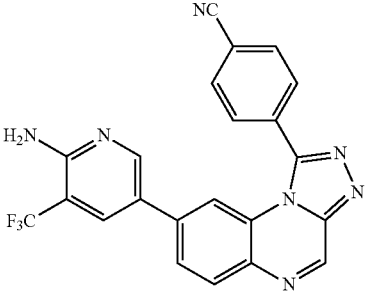 [SMILES: N#Cc1ccc(-c2nnc3cnc4ccc(-c5cnc(N)c(C(F)(F)F)c5)cc4n23)cc1] | 432(M + H)+ | 1H NMR (400 MHz, dmso) δ 9.45 (s, 1H), 8.44 (d, J = 2.2, 1H), 8.21 (d, J = 1.8, 1H), 8.19 (d, J = 3.0, 1H), 8.17 (s, 1H), 8.13 (d, J = 1.9, 1H), 8.12 (d, J = 1.9, 1H), 8.07 (dd, J = 8.5, 1.9, 1H), 7.56 (d, J = 2.2, 1H), 7.46 (d, J = 1.9, 1H), 6.87 (s, 2H). |
| 65 | 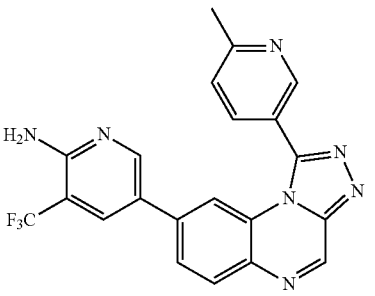 | 422(M + H)+ | 1H NMR (400 MHz, dmso) δ 9.40 (s, 1H), 8.88 (s, 1H), 8.41 (s, 2H), 8.21 (d, J = 8.1, 1H), 8.14 (d, J = 8.4, 1H), 8.02 (d, J = 7.9, 1H), 7.62-7.54 (m, 2H), 7.48 (s, 1H), 6.83 (s, 2H), 2.63 (s, 3H). |

| Compound | Structure | LC/MS | NMR |
|---|---|---|---|
| 66 | 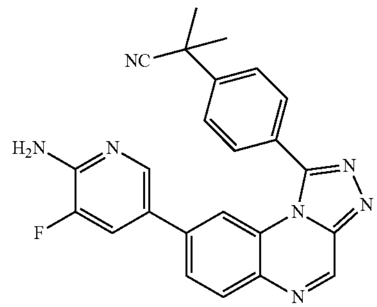 [SMILES: CC(C)(C#N)c1ccc(-c2nnc3cnc4ccc(-c5cnc(N)c(F)c5)cc4n23)cc1] | 424(M + H)+ | 1H NMR (400 MHz, dmso) δ 9.37 (s, 1H), 8.09 (d, J = 8.5, 1H), 7.94 (d, J = 8.8, 1H), 7.89 (d, J = 1.8, 3H), 7.87 (s, 1H), 7.83 (s, 1H), 7.37 (s, 1H), 7.21 (d, J = 12.5, 1H), 6.57 (s, 2H), 1.81 (s, 6H). |
| 67 | 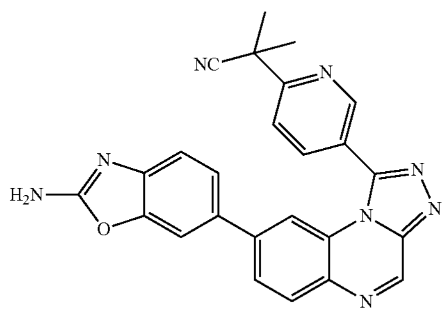 [SMILES: CC(C)(C#N)c1ccc(-c2nnc3cnc4ccc(-c5ccc6nc(N)oc6c5)cc4n23)cn1] | 447(M + H)+ | 1H NMR (400 MHz, dmso) δ 9.51 (s, 1H), 9.18 (d, J = 1.6, 1H), 8.51 (dd, J = 8.2, 2.2, 1H), 8.23 (d, J = 8.5, 1H), 8.08 (d, J = 8.3, 2H), 7.65 (s, 2H), 7.52 (dd, J = 19.9, 1.6, 2H), 7.23 (d, J = 8.1, 1H), 7.12 (dd, J = 8.2, 1.6, 1H), 1.92 (s, 6H). |
| 68 | 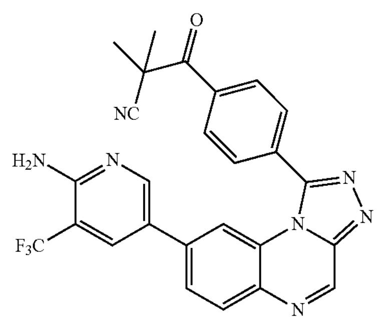 [SMILES: CC(C)(C#N)C(=O)c1ccc(-c2nnc3cnc4ccc(-c5cnc(N)c(C(F)(F)F)c5)cc4n23)cc1] | 502(M + H)+ | 1H NMR (400 MHz, dmso) δ 9.42 (s, 1H), 8.18 (d, J = 2.1, 2H), 8.15 (d, J = 2.8, 1H), 8.13 (s, 1H), 8.03 (s, 1H), 8.01 (d, J = 1.5, 2H), 7.99 (d, J = 1.9, 1H), 7.97 (d, J = 2.0, 1H), 7.81 (s, 1H), 7.79 (s, 1H), 1.94 (s, 6H). |
| 69 | 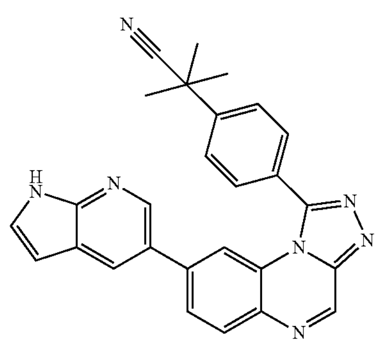 | 430(M + H)+ | 1H NMR (400 MHz, dmso) δ 11.82 (s, 1H), 9.41 (s, 1H), 8.24-8.13 (m, 2H), 8.04 (d, J = 8.2, 1H), 7.93-7.91 (m, 6H), 7.53 (d, J = 12.8, 2H), 6.46 (s, 1H), 1.80 s, 6H). |
| 70 | 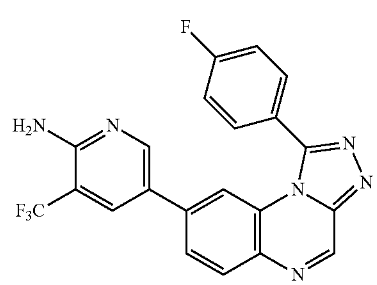 [SMILES: Nc1ncc(-c2ccc3ncc4nnc(-c5ccc(F)cc5)n4c3c2)cc1C(F)(F)F] | 425(M + H)+ | 1H NMR (400 MHz, dmso) δ 9.34 (s, 1H), 8.36 (d, J = 2.2, 1H), 8.11 (d, J = 8.5, 1H), 7.99 (dd, J = 8.5, 1.9, 1H), 7.92-7.83 (m, 2H), 7.53 (dd, J = 12.2, 5.4, 3H), 7.40 (d, J = 1.8, 1H), 6.76 (s, 2H). |

| Compound | Structure | LC/MS | NMR |
|---|---|---|---|
| 71 | 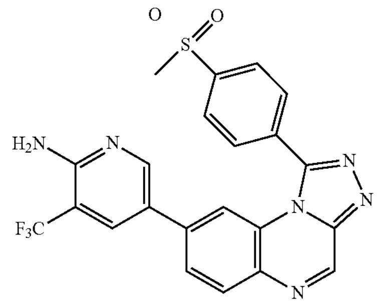 | 485(M + H)+ | 1H NMR (400 MHz, dmso) δ 9.46 (s, 1H), 8.26 (dd, J = 7.1, 5.0, 3H), 8.23-8.16 (m, 3H), 8.04 (dd, J = 8.5, 1.9, 1H), 7.78 (d, J = 2.2, 1H), 7.57 (d, J = 1.8, 1H), 6.83 (s, 2H), 3.35 (s, 3H). |
| 72 | 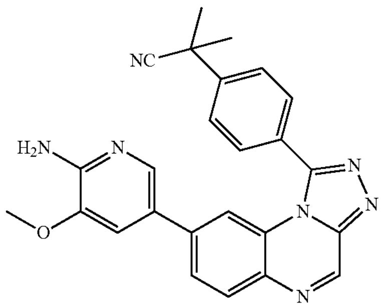 [SMILES: COc1cc(-c2ccc3ncc4nnc(-c5ccc(C(C)(C)C#N)cc5)n4c3c2)cnc1N] | 436(M + H)+ | 1H NMR (400 MHz, dmso) δ 9.39 (s, 1H), 8.12 (d, J = 8.5, 1H), 7.98-7.93 (m, 3H), 7.89 (d, J = 8.5, 2H), 7.53 (d, J = 1.8, 1H), 7.48 (d, J = 1.9, 1H), 7.08 (d, J = 1.8, 1H), 6.07 (s, 2H), 3.81 (s, 3H), 1.82 (s, 6H). |
| 73 | 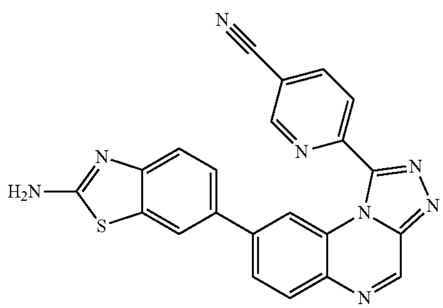 [SMILES: N#Cc1ccc(-c2nnc3cnc4ccc(-c5ccc6nc(N)sc6c5)cc4n23)nc1] | 421(M + H)+ | 1H NMR (400 MHz, dmso) δ 9.49 (d, J = 7.3, 2H), 8.71 (dd, J = 8.2, 2.1, 1H), 8.42 (dd, J = 4.8, 3.2, 2H), 8.19 (d, J = 8.5, 1H), 8.06 (dd, J = 8.5, 1.7, 1H), 7.94 (s, 1H), 7.70 (s, 2H), 7.47-7.44 (m, 3H). |
| 74 | 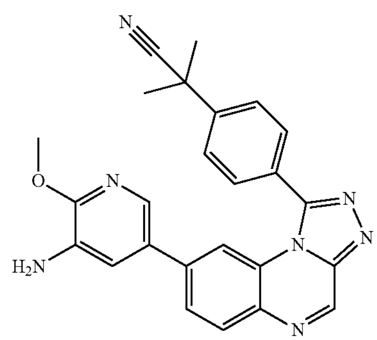 [SMILES: COc1ncc(-c2ccc3ncc4nnc(-c5ccc(C(C)(C)C#N)cc5)n4c3c2)cc1N] | 436(M + H)+ | 1H NMR (400 MHz, dmso) δ 9.42 (s, 1H), 8.16 (d, J = 8.4, 1H), 7.95-7.90 (m, 4H), 7.81 (dd, J = 8.5, 1.9, 1H), 7.40 (d, J = 1.9, 1H), 7.21 (d, J = 2.3, 1H), 6.96 (d, J = 2.3, 1H), 3.87 (s, 3H), 1.85 (s, 6H). |
| 75 | 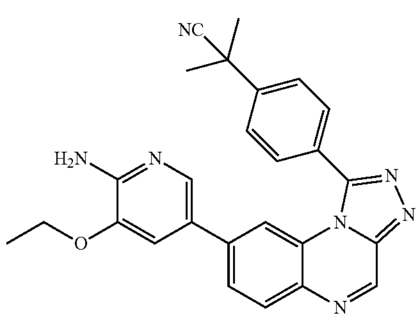 [SMILES: CCOc1cc(-c2ccc3ncc4nnc(-c5ccc(C(C)(C)C#N)cc5)n4c3c2)cnc1N] | 450(M + H)+ | 1H NMR (400 MHz, dmso) δ 9.35 (s, 1H), 8.09 (d, J = 8.5, 1H), 7.92-7.88 (m, 3H), 7.87-7.83 (m, 2H), 7.45 (dd, J = 14.5, 1.9, 2H), 7.03 (d, J = 2.0, 1H), 5.96 (s, 2H), 4.01 (q, J = 6.5, 2H), 1.79 (s, 6H), 1.35 (t, J = 6.9, 3H). |

| Compound | Structure | LC/MS | NMR |
|---|---|---|---|
| 76 | 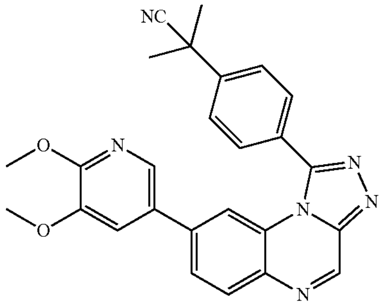 [SMILES: COc1cc(-c2ccc3ncc4nnc(-c5ccc(C(C)(C)C#N)cc5)n4c3c2)cnc1OC] | 451(M + H)⁺ | ¹H NMR (400 MHz, dmso) δ 9.41 (d, J = 1.5, 1H), 8.15 (d, J = 8.5, 1H), 8.00 (dd, J = 8.5, 1.8, 1H), 7.88 (q, J = 8.4, 4H), 7.45 (dd, J = 15.9, 1.9, 2H), 7.36 (d, J = 2.0, 1H), 3.84 (s, 3H), 3.80 (s, 3H), 1.80 (s, 6H). |
| 77 | 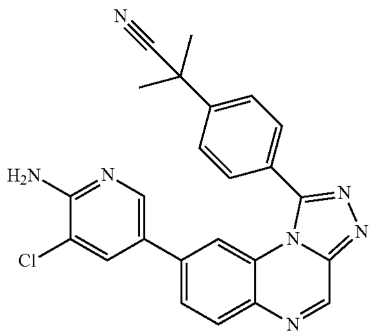 | 440(M + H)⁺ | ¹H NMR (400 MHz, dmso) δ 9.37 (s, 1H), 8.09 (d, J = 8.5, 1H), 7.97-7.86 (m, 6H), 7.50 (d, J = 2.2, 1H), 7.45 (d, J = 1.8, 1H), 6.62 (s, 2H), 1.81 (s, 6H). |
| 78 | 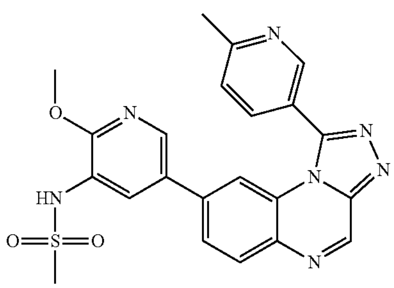 [SMILES: COc1ncc(-c2ccc3ncc4nnc(-c5ccc(C)nc5)n4c3c2)cc1NS(C)(=O)=O] | 462(M + H)⁺ | 1H NMR (400 MHz, dmso) δ 9.43 (s, 1H), 8.89-8.84 (m, 1H), 8.22-8.17 (m, 3H), 8.11 (s, 1H), 7.97 (d, J = 8.4, 1H), 7.61-7.54 (m, 3H), 3.94 (s, 3H), 3.02 (s, 3H), 2.65 (s, 3H). |
EXAMPLE 7
Synthesis of Compounds 79-87
Compound 79
(S)-1-(4-(8-(6-amino-5-(trifluoromethyl)pyridin-3-yl)-[1,2,4]triazolo[4,3-a]quinoxalin-1-yl)piperidin-1-yl)-2-hydroxypropan-1-one
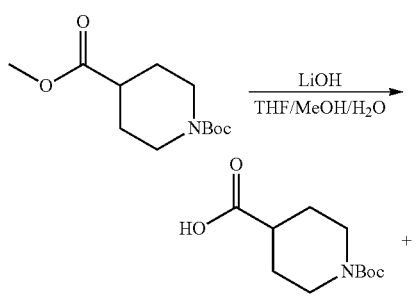
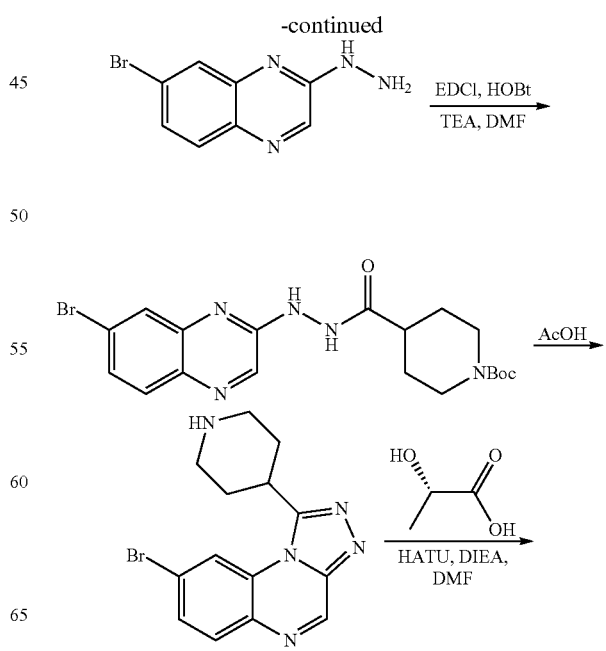

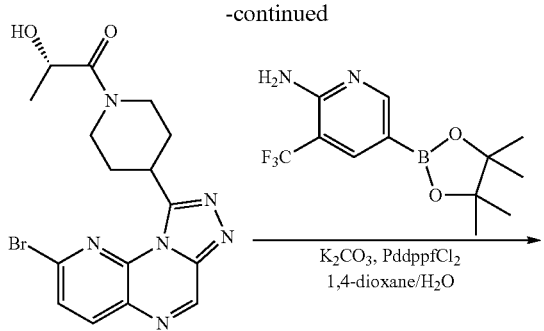

A mixture of 1-tert-butyl 4-methyl piperidine-1,4-dicarboxylate (4.84 g 20 mmol), and LiOH (2.52 g, 60 mmol) in THF (90 mL)/MeOH (90 mL)/H₂O (30 mL) was stirred at r.t overnight. Then the solvents were removed, and the pH of the residue was adjusted to 2 by using 2N HCl. The resulting mixture was extracted with EtOAc (3×20 mL). The combined organic layers were dried over Na₂SO₄, and concentrated to give 1-(tert-butoxycarbonyl)piperidine-4-carboxylic acid (4.6 g, yield 100.0%).

A mixture of 7-bromo-2-hydrazinylquinoxaline (3 g, 12.55 mmol), 1-(tert-butoxycarbonyl)piperidine-4-carboxylic acid (3.16 g, 13.81 mmol), EDCI (2.89 g, 15.06 mmol), HOBt (2.03 g, 15.06 mmol), and TEA (1.9 g, 18.83 mmol) in DMF (100 mL) was stirred at r.t. overnight. The mixture was diluted with water (10 mL), and extracted with EtOAc (3×100 mL). The combined layers were dried over Na₂SO₄, and concentrated in vacuo to afford tert-butyl 4-(2-(7-bromoquinoxalin-2-yl)hydrazinecarbonyl)piperidine-1-carboxylate as pale yellow solid (3.5 g, yield 62%).

A mixture of tert-butyl 4-(2-(7-bromoquinoxalin-2-yl)hydrazinecarbonyl)piperidine-1-carboxylate (900 mg, 2.0 mmol) in AcOH (10 mL) was refluxed overnight. Then the solvent was removed, and the residue was purified by ISCO (MeOH/H₂O=20%-90%) to afford 8-bromo-1-(piperidin-4-yl)[1,2,4]triazolo[4,3-a]quinoxaline as a pale yellow solid (550 mg, yield 83.0%). MS (m/z): 332 (M+H)⁺.

A mixture of 8-bromo-1-(piperidin-4-yl)[1,2,4]triazolo[4,3-a]quinoxaline (250 mg, 0.75 mmol), (S)-2-hydroxypropanoic acid (75 mg, 0.83 mmol), HATU (346 mg, 0.90 mmol), and DIEA (116 mg, 0.90 mmol) in DMF (5 mL) was stirred at r.t. for 6 h. Then the solvents was removed, and the residue was purified by ISCO (MeOH/H₂O=20%-90%) to afford (S)-1-(4-(8-bromo-[1,2,4]triazolo[4,3-a]quinoxalin-1-yl)piperidin-1-yl)-2-hydroxypropan-1-one as pale yellow solid (200 mg, yield 66.0%). MS (m/z): 404 (M+H)⁺.

A mixture of (S)-1-(4-(8-bromo-[1,2,4]triazolo[4,3-a]quinoxalin-1-yl) piperidin-1-yl)-2-hydroxypropan-1-one (65 mg, 0.16 mmol), 5-(4,4,5,5-tetramethyl-1,3,2-dioxaborolan-2-yl)-3-(trifluoromethyl)pyridin-2-amine (51 mg, 0.18 mmol), K₂CO₃ (67 mg, 0.48 mmol) and Pd(dppf)Cl₂ (5 mg) in dioxane/H₂O (3:1, 4 mL) was microwaved at 150° C. for 0.5 h. Then the solvents were removed, and the residue was purified by ISCO (MeOH/H₂O=20%-80%) to afford compound 72 as yellow solid (30 mg). ¹HNMR (400 MHz, dmso) δ 9.28 (s, 1H), 8.72 (d, J=2.0 Hz, 1H), 8.32 (s, 1H), 8.16-8.12 (m, 2H), 8.05 (dd, J=8.5, 1.5 Hz, 1H), 6.82 (s, 2H), 4.91 (dd, J=7.2, 6.5 Hz, 1H), 4.47 (dd, J=17.8, 11.8 Hz, 2H), 4.29 (t, J=10.6 Hz, 1H), 4.15 (t, J=11.2 Hz, 1H), 3.09-2.97 (m, 1H), 2.27 (dd, J=15.6, 14.5 Hz, 2H), 1.97 (dd, J=12.0, 4.5 Hz, 1H), 1.78 (dd, J=7.1, 5.0 Hz, 1H), 1.25-1.15 (m, 3H). MS (m/z): 486 (M+H)⁺.

The following compounds 80-87 were prepared according to the procedures for Compound 79 by using the corresponding intermediates and boronic acid or ester under appropriate conditions that could be recognized by one skilled in the art:

| Compound | Structure | LC/MS | NMR |
|---|---|---|---|
| 80 | 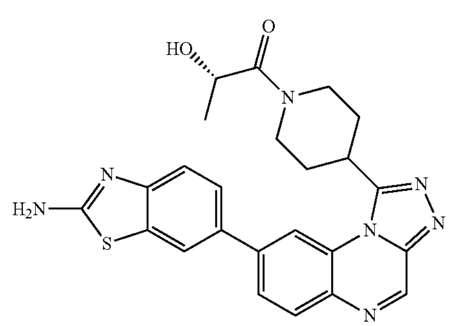 [SMILES: C[C@H](O)C(=O)N1CCC(c2nnc3cnc4ccc(-c5ccc6nc(N)sc6c5)cc4n23)CC1] | 474(M + H)⁺ | ¹HNMR (400 MHz, dmso) δ 9.27 (s, 1H), 8.33 (s, 1H), 8.19-8.08 (m, 2H), 8.02 (d, J = 8.5 Hz, 1H), 7.72-7.59 (m, 3H), 7.48 (d, J = 8.3 Hz, 1H), 4.88 (dd, J = 18.5, 12.3 Hz, 1H), 4.42 (dd, J = 24.2, 18.1 Hz, 2H), 4.17 (dd, J = 26.5, 14.0 Hz, 2H), 3.06 (d, J = 7.2 Hz, 1H), 2.34-2.22 (m, 2H), 2.00 (d, J = 14.6 Hz, 1H), 1.90-1.75 (m, 1H), 1.29-1.15 (m, 3H). |

-continued

| Compound | Structure | LC/MS | NMR |
|---|---|---|---|
| 81 | 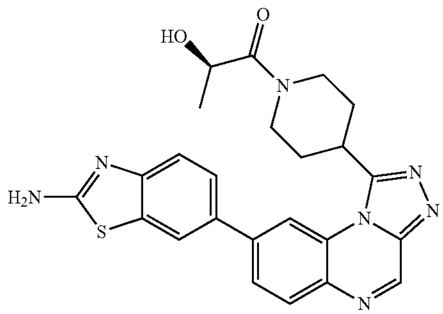 | 474(M + H)+ | ¹HNMR (400 MHz, dmso) δ 9.27 (s, 1H), 8.33 (s, 1H), 8.20-8.12 (m, 2H), 8.02 (d, J = 8.6 Hz, 1H), 7.71-7.61 (m, 3H), 7.48 (d, J = 8.4 Hz, 1H), 4.98-4.76 (m, 1H), 4.51-4.37 (m, 2H), 4.25-4.11 (m, 2H), 3.12-3.01 (m, 1H), 2.35-2.21 (m, 2H), 2.04-1.94 (dd, J = 33.4, 10.8 Hz, 1H), 1.90-1.77 (m, 1H), 1.20 (d, J = 6.5 Hz, 3H). |
| 82 | 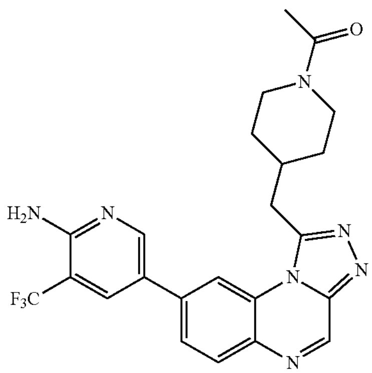 [SMILES: CC(=O)N1CCC(Cc2nnc3cnc4ccc(-c5cnc(N)c(C(F)(F)F)c5)cc4n23)CC1] | 470(M + H)+ | ¹HNMR (400 MHz, dmso) δ 9.26 (s, 1H), 8.72 (d, J = 2.0 Hz, 1H), 8.27 (s, 1H), 8.13 (d, J = 8.4 Hz, 2H), 8.03 (dd, J = 8.4, 1.5 Hz, 1H), 6.82 (s, 2H), 4.33 (d, J = 12.5 Hz, 1H), 3.78 (d, J = 13.3 Hz, 1H), 3.57 (d, J = 4.4 Hz, 2H), 3.04-2.96 (m, 1H), 2.60-2.48 (m, 1H), 2.38-2.29 (m, 1H), 1.97 (s, 3H), 1.78 (d, J = 12.6 Hz, 2H), 1.43-1.31 (m, 1H), 1.28-1.18 (m, 1H). |
| 83 | 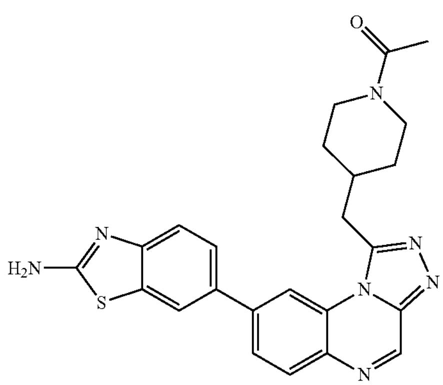 [SMILES: CC(=O)N1CCC(Cc2nnc3cnc4ccc(-c5ccc6nc(N)sc6c5)cc4n23)CC1] | 458(M + H)+ | ¹HNMR (400 MHz, dmso) δ 9.26 (s, 1H), 8.30 (s, 1H), 8.14 (dd, J = 7.5, 5.1 Hz, 2H), 7.99 (dd, J = 8.5, 1.5 Hz, 1H), 7.72-7.60 (m, 3H), 7.46 (d, J = 8.4 Hz, 1H), 4.38 (d, J = 12.6 Hz, 1H), 3.81 (d, J = 14.0 Hz, 1H), 3.54 (d, J = 6.5 Hz, 2H), 3.03 (t, J = 11.8 Hz, 1H), 2.60-2.51 (m, 1H), 2.42-2.28 (m, 1H), 1.97 (s, 3H), 1.83 (d, J = 12.8 Hz, 2H), 1.40 (dt, J = 10.5, 6.7 Hz, 1H), 1.29-1.20 (m, 1H). |
| 84 | 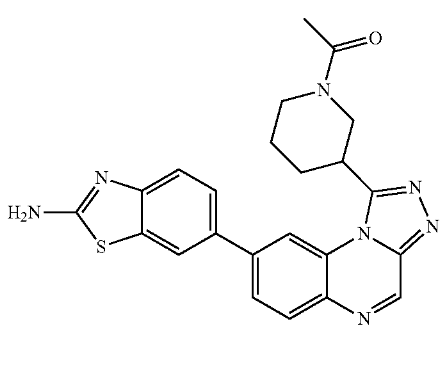 [SMILES: CC(=O)N1CCCC(c2nnc3cnc4ccc(-c5ccc6nc(N)sc6c5)cc4n23)C1] | 444(M + H)+ | ¹HNMR (400 MHz, dmso) δ 9.26 (s, 1H), 8.32 (s, 1H), 8.19-8.10 (m, 2H), 8.05-8.78 (m, 1H), 7.72-7.58 m, 3H), 7.41 (d, J = 8.1 Hz, 1H), 4.38-4.23 (m, 1H), 4.17-4.02 (m, 1H), 3.98-3.91 (m, 1H), 3.88-3.80 (m, 1H), 2.89-2.78 (m, 1H), 2.36-2.23 (m, 2H), 2.15 (s, 3H), 1.84 (d, J = 21.4 Hz, 1H), 1.79-1.62 (m, 1H). |

| Compound | Structure | LC/MS | NMR |
|---|---|---|---|
| 85 | 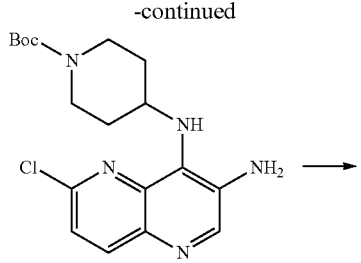 | 429(M + H)+ | 1HNMR (400 MHz, dmso) δ 9.22 (d, J = 2.1 Hz, 1H), 8.68 (s, 1H), 8.23 (d, J = 3.7 Hz, 1H), 8.12 (d, J = 8.4 Hz, 2H), 8.01 (d, J = 8.5 Hz, 1H), 6.77 (d, J = 6.2 Hz, 2H), 4.67-4.55 (m, 1H), 3.39-3.35 (m, 1H), 2.22-2.10 (m, 2H), 2.03-2.93 (m, 2H), 1.87-1.77 (m, 2H), 1.77-1.66 (m, 2H). |
| 86 | 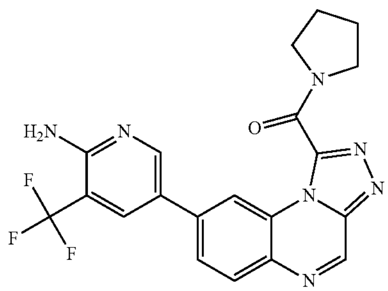 [SMILES: Nc1ncc(-c2ccc3ncc4nnc(C(=O)N5CCCC5)n4c3c2)cc1C(F)(F)F] | 428(M + H)+ | 1H NMR (400 MHz, dmso) δ 9.45 (s, 1H), 8.67 (s, 1H), 8.52 (s, 1H), 8.18 (d, J = 8.4, Hz, 1H), 8.14 (dd, J = 8.4 Hz, 2.0 Hz, 1H), 8.11-8.08 (m, 1H), 6.90 (s, 2H), 3.76-3.61 (m, 4H), 1.99 (m, 2H), 1.92 (m, 2H). |
| 87 | 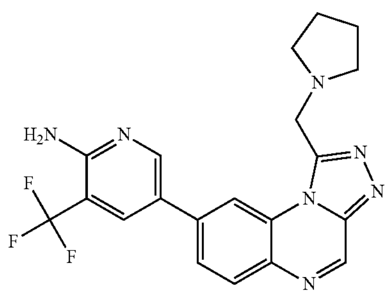 [SMILES: Nc1ncc(-c2ccc3ncc4nnc(CN5CCCC5)n4c3c2)cc1C(F)(F)F] | 414(M + H)+ | 1H NMR (400 MHz, cd3od) δ 9.23 (s, 1H), 8.99 (d, J = 1.9 Hz, 1H), 8.61 (d, J = 2.1 Hz, 1H), 8.23 (d, J = 8.5 Hz, 1H), 8.14 (d, J = 1.9 Hz, 1H), 7.97 (dd, J = 8.5, 1.9 Hz, 1H), 4.47 (m 2H), 4.38 (m 2H), 2.73 (m, 4H), 1.88 (m, 4H). |

EXAMPLE 8

Synthesis of Compounds 88-118

Compound 88

(4-(8-(6-amino-5-(trifluoromethyl)pyridine-3-yl)-1H-imidazo[4,5-c][1,5]naphthyridin-1-yl)piperidin-1-yl)(cyclopropyl)methanone

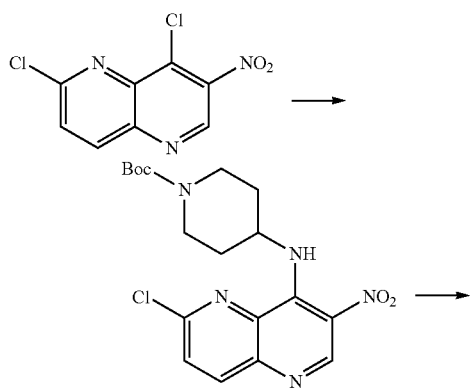

-continued

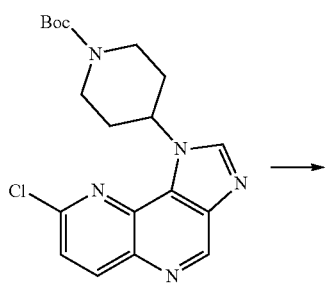

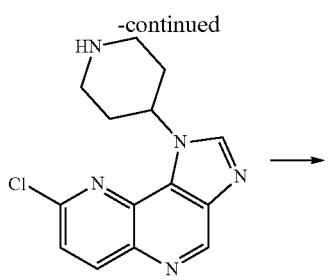

A mixture of 2,8-dichloro-7-nitro-1,5-naphthyridine (3.55 g, 14.55 mmol) and K$_2$CO$_3$ (6.02 g, 43.65 mmol) in DMF (8 mL) was stirred at r.t. overnight, and then poured into ice-water (~20 mL). The precipitate was collected, washed with water three times, and dried in vacuo to afford tert-butyl 4-(6-chloro-3-nitro-1,5-naphthyridin-4-ylamino)piperidine-1-carboxylate as yellow solid (5.22 g, yield 88%) which was used in next step without further purification. MS (m/z): 409 (M+H)$^+$.

A mixture of tert-butyl 4-(6-chloro-3-nitro-1,5-naphthyridin-4-ylamino) piperidine-1-carboxylate (600 mg, 1.47 mmol) and SnCl$_2$.H$_2$O (996 mg, 4.41 mmol) in ethyl acetate (20 mL) was stirred at r.t. for 2 h, and was then alkalized with 5% NaOH solution. The mixture was filtered through a pad of celite. The filtrate was extracted with ethyl acetate (3×15 mL). The organic layers were combined and washed with brine (10 mL), dried over anhydrous Na$_2$SO$_4$, filtered, and concentrated to give tert-butyl 4-(3-amino-6-chloro-1,5-naphthyridin-4-ylamino) piperidine-1-carboxylate as a yellow solid (499 mg, yield 90%) which was used in the next step without further purification. MS (m/z): 378 (M+H)$^+$.

A mixture of tert-butyl 4-(3-amino-6-chloro-1,5-naphthyridin-4-ylamino)piperidine-1-carboxylate (200 mg, 0.53 mmol), triethyl orthoformate (94 mg, 0.64 mmol), and PyHCl (6 mg, 0.053 mmol) in Toluene (5 mL) was refluxed for 3.5 h. The solvent was removed under vacuum and the residue was added to a solution of HCl in MeOH (6N, 3 mL). The reaction mixture was stirred at r.t. for 3 h, and was then concentrated under vacuum. The residue was dissolved in dichloromethane (20 mL). the resulting solution was washed with saturated NaHCO$_3$ (10 mL) and brine (10 mL), dried over anhydrous Na$_2$SO$_4$, filtered, and concentrated to to give 8-chloro-1-(piperidin-4-yl)-1H-imidazo[4,5-c][1,5]naphthayridine as a yellow solid (110 mg, yield 72%) which was used in next step without further purification.

To a solution of 8-chloro-1-(piperidin-4-yl)-1H-imidazo[4,5-c][1,5]naphthayridine (110 mg, 0.382 mmol) and Et$_3$N (106 µL, 0.764 mmol) in THF (15 mL) was added cyclopropanecarbonyl chloride (38 µL, 0.420 mmol) while cooling with an ice-water bath. The reaction mixture was stirred at r.t. for 3 h, and was then concentrated under vacuum. The residue was dissolved in ethyl acetate (20 mL). The resulting solution was washed with saturated NaHCO$_3$ (10 mL) and brine (10 mL), dried over anhydrous Na$_2$SO$_4$, filtered, and concentrated to give (4-(8-chloro-1H-imidazo[4,5-c][1,5]naphthyridin-1-yl)piperidin-1-yl)(cyclopropyl)methanone as a yellow solid (100 mg, yield 73%) which was used in the next step without further purification. MS (m/z): 356 (M+H)$^+$.

A mixture of (4-(8-chloro-1H-imidazo[4,5-c][1,5]naphthyridin-1-yl)piperidin-1-yl)(cyclopropyl)methanone (100 mg, 0.281 mmol), PdCl$_2$(dppf)$_2$ (12 mg, 0.014 mmol), 5-(4,4,5,5-tetramethyl-1,3,2-dioxaborolan-2-yl)-3-(trifluoromethyl)pyridine-2-amine (97 mg, 0.337 mmol), and 2 N K$_2$CO$_3$ solution (1 mL) in dioxane (4 mL) was microwaved at 150° C. for 30 min. The solvent was removed and the residue was purified by ISCO (MeOH/H$_2$O 0%~100%) to give compound 88 as a yellowish solid (70 mg). $^1$H NMR (400 MHz, dmso) δ 9.20 (s, 1H), 9.13 (d, J=1.9, 1H), 8.71 (s, 1H), 8.59 (d, J=2.0, 1H), 8.49 (d, J=8.9, 1H), 8.32 (d, J=8.9, 1H), 6.99 (s, 2H), 5.98-5.92 (m, 1H), 4.66 (s, 1H), 4.58 (s, 1H), 3.25 (s, 2H), 2.35 (s, 2H), 2.09-2.01 (m, 2H), 2.01-1.90 (m, 1H), 0.80-0.71 (m, 4H). MS (m/z): 482 (M+H)$^+$.

The following compounds 89-118 were prepared according to the procedures for Compound 88 by using the corresponding intermediates and boronic acid or ester under appropriate conditions that could be recognized by one skilled in the art.

| Compound | Structure | LC/MS | NMR |
|---|---|---|---|
| 89 | 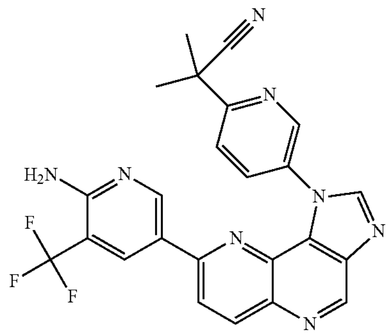 [SMILES: CC(C)(C#N)c1ccc(-n2cnc3cnc4ccc(-c5cnc(N)c(C(F)(F)F)c5)nc4c32)cn1] | 475(M + H)+ | ¹HNMR (400 MHz, dmso) δ 9.38 (s, 1H), 9.08 (d, J = 2.6 Hz, 1H), 8.79 (s, 1H), 8.70 (d, J = 2.0 Hz, 1H), 8.55 (d, J = 8.9 Hz, 1H), 8.47 (dd, J = 8.4, 2.5 Hz, 1H), 8.34 (d, J = 8.9 Hz, 1H), 8.16 (d, J = 2.1 Hz, 1H), 7.88 (d, J = 8.4 Hz, 1H), 6.90 (s, 2H), 1.85 (s, 6H). |
| 90 | 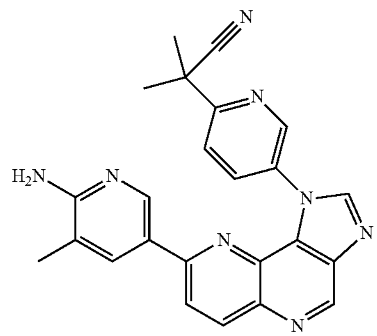 [SMILES: Cc1cc(-c2ccc3ncc4ncn(-c5ccc(C(C)(C)C#N)nc5)c4c3n2)cnc1N] | 421(M + H)+ | ¹HNMR (400 MHz, dmso) δ 9.32 (d, J = 1.2 Hz, 1H), 9.11 (s, 1H), 8.77 (d, J = 1.2 Hz, 1H), 8.49-8.43 (m, 2H), 8.37 (s, 1H), 8.22 (d, J = 9.0 Hz, 1H), 7.95 (d, J = 8.4 Hz, 1H), 7.72 (s, 1H), 6.20 (s, 2H), 2.10 (s, 3H), 1.87 (s, 6H). |
| 91 | 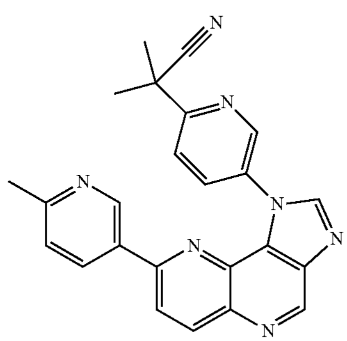 [SMILES: Cc1ccc(-c2ccc3ncc4ncn(-c5ccc(C(C)(C)C#N)nc5)c4c3n2)cn1] | 406(M + H)+ | ¹HNMR (400 MHz, dmso) δ 9.41 (s, 1H), 9.11 (d, J = 2.0 Hz, 1H), 8.87 (s, 1H), 8.82 (s, 1H), 8.60 (d, J = 8.8 Hz, 1H), 8.39 (t, J = 7.5 Hz, 2H), 8.05 (d, J = 6.2 Hz, 1H), 7.94 (d, J = 8.4 Hz, 1H), 7.28 (d, J = 8.2 Hz, 1H), 2.49 (s, 3H), 1.89 (s, 6H). |
| 92 | 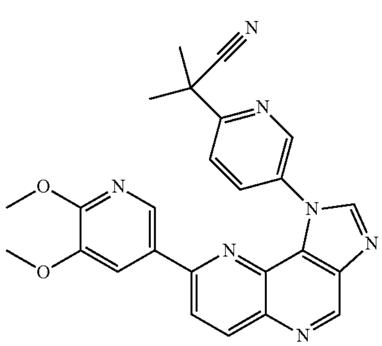 [SMILES: COc1cc(-c2ccc3ncc4ncn(-c5ccc(C(C)(C)C#N)nc5)c4c3n2)cnc1OC] | 452(M + H)+ | ¹HNMR (400 MHz, dmso) δ 9.40 (s, 1H), 9.12 (d, J = 2.5 Hz, 1H), 8.81 (s, 1H), 8.60 (d, J = 8.8 Hz, 1H), 8.40-8.35 (m, 2H), 7.97-7.92 (m, 2H), 7.80 (d, J = 2.0 Hz, 1H), 3.91 (s, 3H), 3.87 (s, 3H), 1.90 (s, 6H). |

-continued

| Compound | Structure | LC/MS | NMR |
|---|---|---|---|
| 93 | 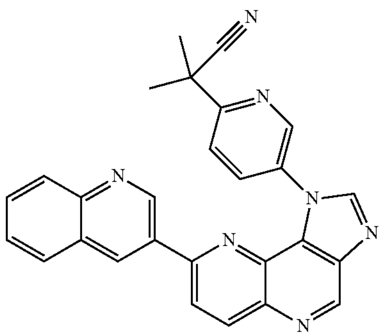 [SMILES: CC(C)(C#N)c1ccc(-n2cnc3cnc4ccc(-c5cnc6ccccc6c5)nc4c32)cn1] | 442(M + H)+ | ¹HNMR (400 MHz, dmso) δ 9.45 (s, 1H), 9.16 (s, 1H), 9.10 (s, 1H), 8.96 (s, 1H), 8.86 (s, 1H), 8.69 (d, J = 8.8 Hz, 1H), 8.55 (d, J = 8.8 Hz, 1H), 8.48 (d, J = 8.3 Hz, 1H), 8.08-7.98 (m, 3H), 7.82 (t, J = 7.5 Hz, 1H), 7.66 (t, J = 7.4 Hz, 1H), 1.93 (s, 6H). |
| 94 | 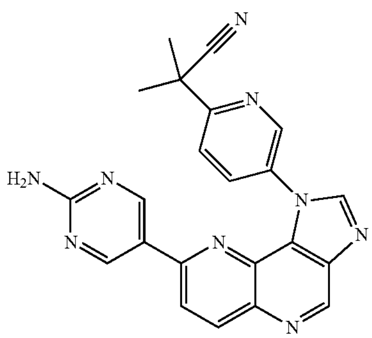 [SMILES: CC(C)(C#N)c1ccc(-n2cnc3cnc4ccc(-c5cnc(N)nc5)nc4c32)cn1] | 408(M + H)+ | ¹HNMR (400 MHz, dmso) δ 9.36 (s, 1H), 9.10 (s, 1H), 8.80 (s, 1H), 8.64 (s, 2H), 8.52 (d, J = 8.8 Hz, 1H), 8.39 (d, J = 8.5 Hz, 1H), 8.25 (d, J = 8.9 Hz, 1H), 7.93 (d, J = 8.4 Hz, 1H), 7.07 (s, 2H), 1.91 (s, 6H). |
| 95 | 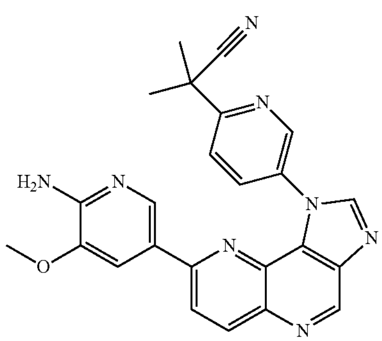 [SMILES: COc1cc(-c2ccc3ncc4ncn(-c5ccc(C(C)(C)C#N)nc5)c4c3n2)cnc1N] | 437(M + H)+ | 1HNMR (400 MHz, dmso) δ 9.34 (s, 1H), 9.13 (d, J = 2.4 Hz, 1H), 8.76 (s, 1H), 8.50 (d, J = 8.8 Hz, 1H), 8.44-8.38 (m, 1H), 8.26 (d, J = 9.0 Hz, 1H), 8.16 (s, 1H), 8.02 (s, 1H), 7.91 (d, J = 8.4 Hz, 1H), 6.18 (s, 2H), 3.83 (s, 3H), 1.86 (s, 6H). |
| 96 | 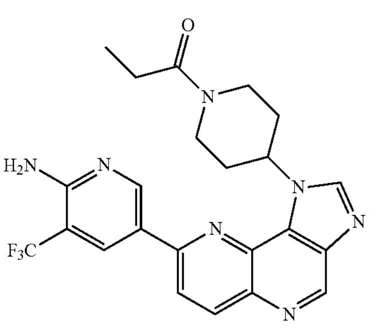 | 470(M + H)+ | ¹H NMR (400 MHz, cdcl3) δ 9.37 (s, 1H), 9.04 (d, J = 1.3 Hz, 1H), 8.61 (d, J = 8.8 Hz, 1H), 8.57 (d, J = 1.7 Hz, 1H), 8.22 (s, 1H), 8.06 (d, J = 8.8 Hz, 1H), 6.17-5.98 (m, 1H), 5.32 (m, 2H), 5.00 (m, 1H), 4.13 (s, 1H), 3.35 (m, 1H), 2.83 (s, 1H), 2.57 (m, 2H), 2.46 (m, 2H), 2.03 (m, 4H), 1.32-1.31 (m, 3H). |

| Compound | Structure | LC/MS | NMR |
|---|---|---|---|
| 97 | 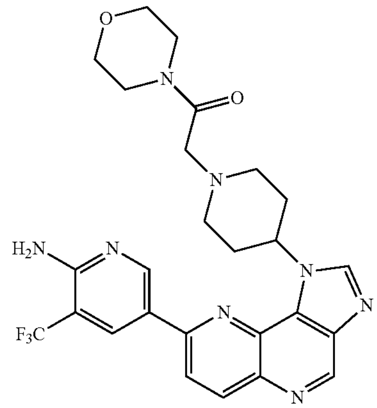 [SMILES: Nc1ncc(-c2ccc3ncc4ncn(C5CCN(CC(=O)N6CCOCC6)CC5)c4c3n2)cc1C(F)(F)F] | 541(M + H)⁺ | ¹H NMR (400 MHz, dmso) δ 9.31 (s, 1H), 9.22 (s, 1H), 8.85 (s, 1H), 8.72 (s, 1H), 8.59 (d, J = 8.9, 1H), 8.44 (d, J = 8.9, 1H), 7.11 (s, 2H), 3.69 (m, 4H), 3.63 (m, 3H), 3.51 (m, 3H), 3.31 (m, 2H), 3.16 (m, 2H), 2.39-2.25 (m, 5H). |
| 98 | 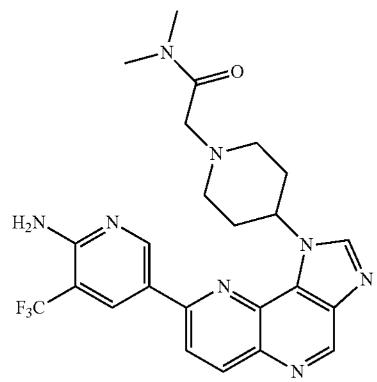 [SMILES: CN(C)C(=O)CN1CCC(n2cnc3cnc4ccc(-c5cnc(N)c(C(F)(F)F)c5)nc4c32)CC1] | 499(M + H)⁺ | ¹H NMR (400 MHz, dmso) δ 9.31 (s, 1H), 9.22 (s, 1H), 8.84 (s, 1H), 8.72 (s, 1H), 8.60 (d, J = 8.9, 1H), 8.43 (d, J = 8.9, 1H), 7.11 (s, 2H), 3.27 (s, 2H), 3.18 (m, 2H), 3.14 (s, 3H), 2.89 (s, 3H), 2.40-2.18 (m, 7H). |
| 99 | 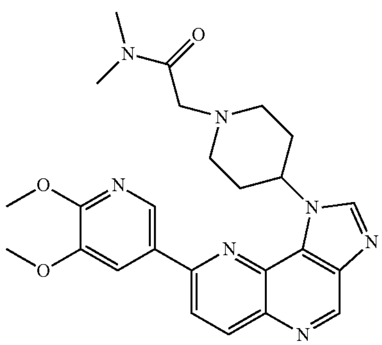 [SMILES: COc1cc(-c2ccc3ncc4ncn(C5CCN(CC(=O)N(C)C)CC5)c4c3n2)cnc1OC] | 476(M + H)⁺ | ¹H NMR (400 MHz, cdcl3) δ 9.36 (s, 1H), 8.60 (d, J = 8.8 Hz, 1H), 8.50 (m 1H), 8.31 (s, 1H), 8.03 (d, J = 8.8 Hz, 1H), 7.83 (m, 1H), 6.06-5.77 (m, 1H), 4.10 (d, 6H), 3.25 (m, 2H), 3.09 (s, 3H), 2.98 (s, 3H), 2.74-2.60 (m, 2H), 2.45 (m, 2H), 2.31-2.20 (m, 4H). |
| 100 | 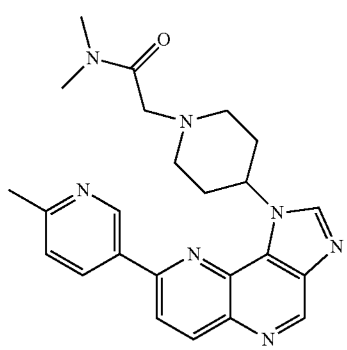 [SMILES: Cc1ccc(-c2ccc3ncc4ncn(C5CCN(CC(=O)N(C)C)CC5)c4c3n2)cn1] | 430(M + H)⁺ | ¹H NMR (400 MHz, cdcl3) δ 9.35 (s, 1H), 9.29 (d, J = 2.0 Hz, 1H), 8.59 (d, J = 8.8 Hz, 1H), 8.33 (m, 1H), 8.27 (s, 1H), 8.07 (d, J = 8.8 Hz, 1H), 7.36 (d, J = 8.1 Hz, 1H), 5.91-5.71 (m, 1H), 3.34 (m, 2H), 3.23 (m, 2H), 3.10 (s 3H), 2.98 (s 3H), 2.67 (s 3H), 2.54 (m, 2H), 2.45 (m, 2H), 2.26 (m, 2H). |

| Compound | Structure | LC/MS | NMR |
|---|---|---|---|
| 101 | 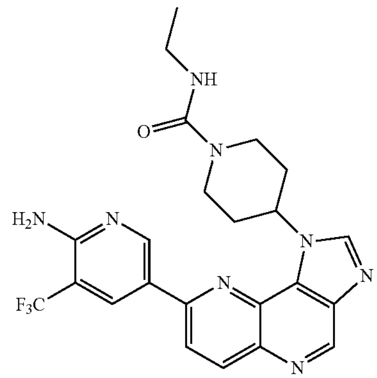 | 485(M + H)⁺ | ¹H NMR (400 MHz, dmso) δ 9.21 (s, 1H), 9.15 (s, 1H), 8.73 (s, 1H), 8.61 (s, 1H), 8.50 (d, J = 8.8, 1H), 8.34 (d, J = 8.8, 1H), 7.01 (s, 2H), 6.63 (s, 1H), 5.87 (s, 1H), 4.26 (m, 2H), 3.07 (m, 2H), 2.84 (m, 2H), 2.26 (m, 2H), 1.99 (m, 2H), 1.02 (m, 3H). |
| 102 | 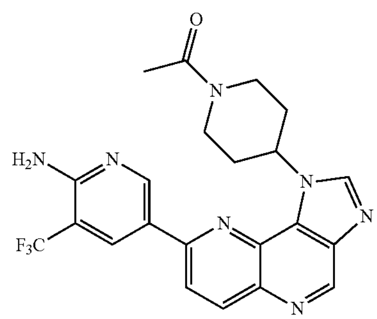 [SMILES: CC(=O)N1CCC(n2cnc3cnc4ccc(-c5cnc(N)c(C(F)(F)F)c5)nc4c32)CC1] | 456(M + H)⁺ | ¹H NMR (400 MHz, dmso) δ 9.25 (s, 1H), 9.17 (s, 1H), 8.73 (s, 1H), 8.64 (s, 1H), 8.54 (d, J = 8.7, 1H), 8.37 (d, J = 8.9, 1H), 7.04 (s, 2H), 5.98 (s, 1H), 4.72 (m, 1H), 4.15 (m, 1H), 3.24 (m, 1H), 2.73 (m, 1H), 2.34 (m, 2H), 2.11 (s, 3H), 2.00 (m, 2H). |
| 103 | 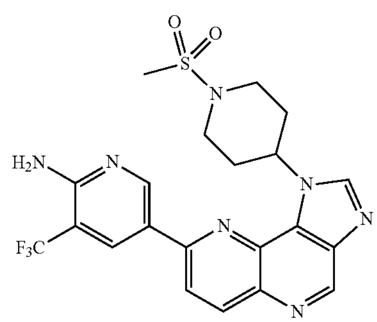 [SMILES: CS(=O)(=O)N1CCC(n2cnc3cnc4ccc(-c5cnc(N)c(C(F)(F)F)c5)nc4c32)CC1] | 492(M + H)⁺ | ¹H NMR (400 MHz, dmso) δ 9.26 (s, 1H), 9.14 (d, J = 1.9, 1H), 8.79 (s, 1H), 8.63 (d, J = 2.1, 1H), 8.55 (d, J = 8.9, 1H), 8.37 (d, J = 8.9, 1H), 7.04 (s, 2H), 5.84 (m, 1H), 3.90 (m, 2H), 2.98 (s, 3H), 2.46 (m, 2H), 2.29-2.19 (m, 2H), 2.08-1.88 (m, 2H). |
| 104 | 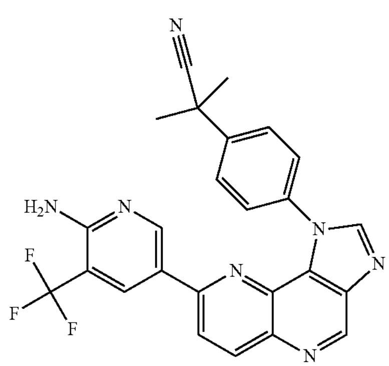 [SMILES: CC(C)(C#N)c1ccc(-n2cnc3cnc4ccc(-c5cnc(N)c(C(F)(F)F)c5)nc4c32)cc1] | 474(M + H)⁺ | ¹H NMR (400 MHz, dmso) δ 9.44-9.29 (m, 1H), 8.71 (dd, J = 7.7, 5.4, 2H), 8.59-8.50 (m, 1H), 8.32 (d, J = 8.9, 1H), 8.18 (s, 1H), 7.90 (d, J = 5.9, 2H), 7.84-7.74 (m, 2H), 6.89 (s, 2H), 1.83 (s, 6H). |

| Compound | Structure | LC/MS | NMR |
|---|---|---|---|
| 105 | 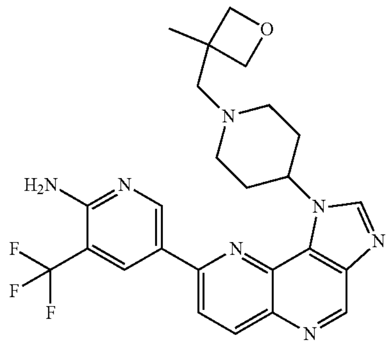 [SMILES: CC1(CN2CCC(n3cnc4cnc5ccc(-c6cnc(N)c(C(F)(F)F)c6)nc5c43)CC2)COC1] | 498(M + H)+ | ¹H NMR (400 MHz, dmso) δ 9.25 (d, J = 5.7, 1H), 9.16 (s, 1H), 8.78-8.76 (m, 1H), 8.70-8.67 (m, 1H), 8.53 (d, J = 8.8, 1H), 8.37 (d, J = 8.9, 1H), 7.06 (s, 2H), 5.77-5.73 (m, 1H), 4.40 (d, J = 5.4, 2H), 4.24 (d, J = 5.6, 2H), 2.86-2.83 (m, 2H), 2.61 (s, 2H), 2.29-2.13 (m, 6H), 1.37 (s, 3H). |
| 106 | 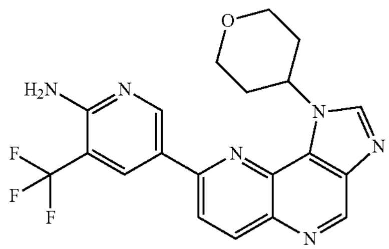 [SMILES: Nc1ncc(-c2ccc3ncc4ncn(C5CCOCC5)c4c3n2)cc1C(F)(F)F] | 415(M + H)+ | ¹H NMR (400 MHz, dmso) δ 9.27 (d, J = 12.4, 1H), 9.20 (d, J = 10.7, 1H), 8.79 (d, J = 12.4, 1H), 8.66 (d, J = 10.7, 1H), 8.60-8.50 (m, 1H), 8.39 (t, J = 10.6, 1H), 7.06 (d, J = 11.0, 2H), 5.97-5.93 (m, 1H), 4.17-4.12 (m, 2H), 3.61-3.55 (m, 2H), 2.31-2.23 (m, 4H). |
| 107 | 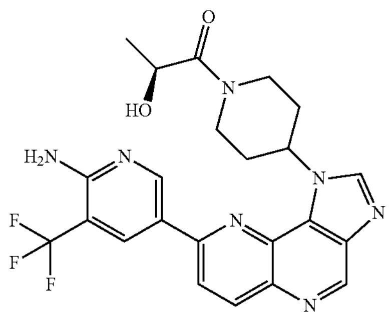 [SMILES: C[C@H](O)C(=O)N1CCC(n2cnc3cnc4ccc(-c5cnc(N)c(C(F)(F)F)c5)nc4c32)CC1] | 486(M + H)+ | ¹H NMR (400 MHz, dmso) δ 9.25 (d, J = 4.2, 1H), 9.18 (s, 1H), 8.74 (s, 1H), 8.64 (s, 1H), 8.54 (dd, J = 8.5, 3.5, 1H), 8.42-8.34 (m, 1H), 7.05 (s, 2H), 6.00-5.95 (m, 1H), 4.74-4.71 (m, 1H), 4.56-4.54 (m, 1H), 4.39-4.36 (m, 1H), 3.22-3.18 (m, 1H), 2.82-2.79 (m, 1H), 2.41-2.38 (m, 2H), 2.17-1.98 (m, 2H), 1.27-1.25 (m, 3H). |
| 108 | 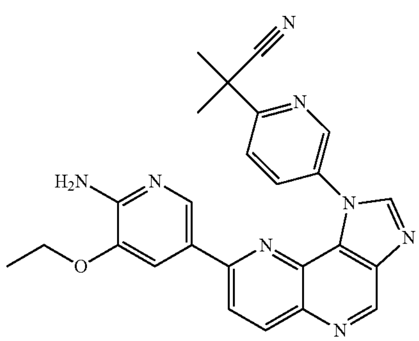 [SMILES: CCOc1cc(-c2ccc3ncc4ncn(-c5ccc(C(C)(C)C#N)nc5)c4c3n2)cnc1N] | 451(M + H)+ | ¹HNMR (400 MHz, dmso) δ 9.30 (d, J = 1.4 Hz, 1H), 9.08 (d, J = 2.5 Hz, 1H), 8.73 (d, J = 1.3 Hz, 1H), 8.46 (d, J = 8.9 Hz, 1H), 8.36 (dd, J = 8.4, 2.6 Hz, 1H), 8.20 (d, J = 9.0 Hz, 1H), 7.94 (d, J = 1.8 Hz, 1H), 7.86 (d, J = 8.4 Hz, 1H), 7.42 (s, 1H), 6.07 (s, 2H), 4.05 (q, J = 6.9 Hz, 2H), 1.81 (s, 6H), 1.35 (t, J = 6.9 Hz, 3H). |
| 109 | 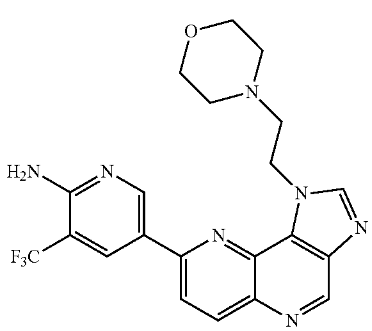 [SMILES: Nc1ncc(-c2ccc3ncc4ncn(CCN5CCOCC5)c4c3n2)cc1C(F)(F)F] | 444(M + H)+ | ¹H NMR (400 MHz, dmso) δ 9.19 (s, 1H), 9.14 (s, 1H), 8.57 (s, 1H), 8.49 (d, J = 7.7, 3H), 8.31 (d, J = 7.7, 1H), 6.95 (s, 2H), 5.01 (d, J = 6.2, 2H), 3.41 (t, J = 7.0, 4H), 2.88 (t, J = 7.0, 2H), 2.39 (m 4H). |

| Compound | Structure | LC/MS | NMR |
|---|---|---|---|
| 110 | 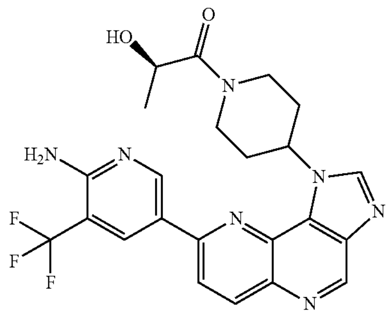 [SMILES: C[C@@H](O)C(=O)N1CCC(n2cnc3cnc4ccc(-c5cnc(N)c(C(F)(F)F)c5)nc4c32)CC1] | 486(M + H)+ | ¹H NMR (400 MHz, dmso) δ 9.26 (s, 1H), 9.18 (s, 1H), 8.74 (s, 1H), 8.64 (s, 1H), 8.55 (d, J = 8.9, 1H), 8.38 (d, J = 8.9, 1H), 7.04 (s, 2H), 6.05-5.92 (m, 1H), 4.73-4.70 (m, 1H), 4.55-4.52 (m, 1H), 4.38-4.35 (m, 1H), 3.24-3.21 (m, 1H), 2.83-2.77 (m, 1H), 2.40-2.37 (m, 2H), 2.15-1.97 (m, 2H), 1.28-1.22 (m, 3H). |
| 111 | 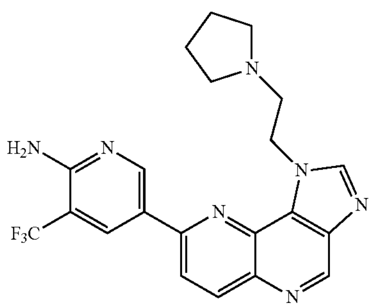 [SMILES: Nc1ncc(-c2ccc3ncc4ncn(CCN5CCCC5)c4c3n2)cc1C(F)(F)F] | 428(M + H)+ | ¹H NMR (400 MHz, dmso) δ 9.24 (s, 1H), 9.18 (d, J = 2.0, 1H), 8.64 (d, J = 2.1, 1H), 8.56-8.51 (m, 2H), 8.37 (d, J = 8.9, 1H), 7.01 (s, 2H), 5.04 (t, J = 6.3, 2H), 3.07 (t, J = 6.3, 3H), 2.51 (d, J = 1.7, 4H), 1.65 (s, 4H). |
| 112 | 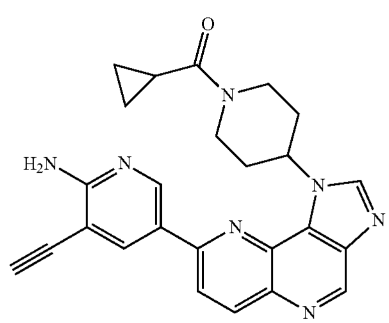 [SMILES: C#Cc1cc(-c2ccc3ncc4ncn(C5CCN(C(=O)C6CC6)CC5)c4c3n2)cnc1N] | 438(M + H)+ | ¹HNMR (400 MHz, dmso) δ 9.32 (s, 1H), 8.77 (s, 1H), 8.57 (d, J = 8.7 Hz, 1H), 8.16 (d, J = 8.7 Hz, 1H), 8.07 (dd, J = 4.9, 1.9 Hz, 1H), 7.78 (dd, J = 7.5, 1.9 Hz, 1H), 6.64 (dd, J = 7.5, 4.9 Hz, 1H), 6.57 (s, 2H), 5.85-5.77 (m, 1H), 4.75-4.67 (m, 1H), 4.62-4.54 (m, 1H), 2.93-2.76 (m, 1H), 2.42-2.28 (m, 2H), 2.18-1.96 (m, 4H), 0.81-0.72 (m, 4H). |
| 113 | 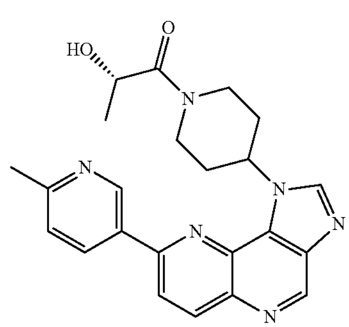 [SMILES: Cc1ccc(-c2ccc3ncc4ncn(C5CCN(C(=O)[C@H](C)O)CC5)c4c3n2)cn1] | 417(M + H)+ | ¹H NMR (400 MHz, dmso) δ 9.38 (d, J = 1.9, 1H), 9.32 (s, 1H), 8.75 (s, 1H), 8.64 (d, J = 8.8, 1H), 8.54 (dd, J = 8.1, 2.3, 1H), 8.42 (d, J = 8.8, 1H), 7.52 (d, J = 7.9, 1H), 5.89-5.84 (m, 1H), 4.78-4.64 (m, 1H), 4.61-4.47 (m, 1H), 4.42-4.26 (m, 1H), 3.31-3.27 (m, 1H), 2.94-2.82 (m, 1H), 2.58 (s, 3H), 2.45-2.34 (m, 2H), 2.22-2.03 (m, 2H), 1.28-1.24 (m, 3H). |

-continued

| Compound | Structure | LC/MS | NMR |
|---|---|---|---|
| 114 | 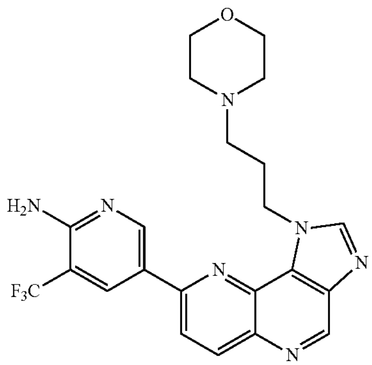 [SMILES: Nc1ncc(-c2ccc3ncc4ncn(CCCN5CCOCC5)c4c3n2)cc1C(F)(F)F] | 458(M + H)+ | ¹H NMR (400 MHz, dmso) δ 9.18 (s, 1H), 9.11 (s, 1H), 8.58 (s, 1H), 8.51-8.39 (m, 2H), 8.29 (d, J = 8.9 Hz, 1H), 6.97 (s, 2H), 4.88 (t, J = 6.7 Hz, 2H), 3.39 (d, J = 4.2 Hz, 4H), 2.20 (tt, J = 13.7, 6.9 Hz, 8H). |
| 115 | 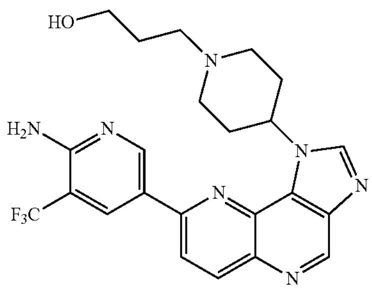 [SMILES: Nc1ncc(-c2ccc3ncc4ncn(C5CCN(CCCO)CC5)c4c3n2)cc1C(F)(F)F] | 472(M + H)+ | 1H NMR (400 MHz, dmso) δ 9.22 (s, 1H), 9.13 (s, 1H), 8.74 (s, 1H), 8.63 (s, 1H), 8.51 (d, J = 8.9 Hz, 1H), 8.34 (d, J = 8.9 Hz, 1H), 7.00 (s, 2H), 5.71 (m, 1H), 3.47 (m, 3H), 3.10 (m, 2H), 2.41 (m, 2H), 2.24 (m, 2H), 2.13 (m, 5H), 1.67-1.57 (m, 2H). |
| 116 | 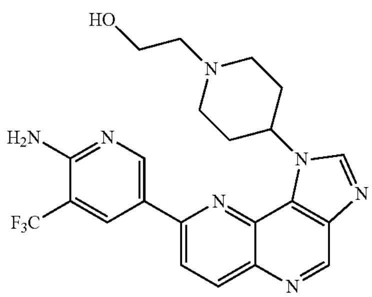 | 458(M + H)+ | 1H NMR (400 MHz, dmso) δ 9.22 (s, 1H), 9.15 (d, J = 2.0 Hz, 1H), 8.73 (s, 1H), 8.64 (d, J = 2.0 Hz, 1H), 8.51 (d, J = 8.9 Hz, 1H), 8.35 (d, J = 8.9 Hz, 1H), 7.00 (s, 2H), 5.69 (s, 1H), 4.61-4.34 (m, 1H), 3.54 (s, 2H), 3.12 (d, J = 14.3 Hz, 4H), 2.20 (d, J = 7.9 Hz, 6H). |
| 117 | 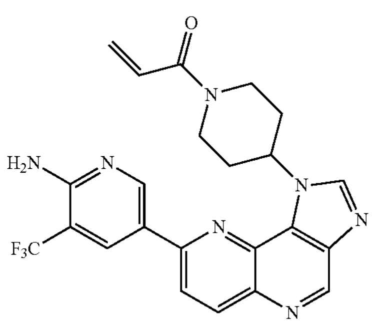 | 468(M + H)+ | 1HNMR (400 MHz, dmso) δ 9.30-9.09 (m, 2H), 8.84-8.44 (m, 4H), 8.37 (s, 1H), 7.01 (s, 2H), 6.93-6.82 (m, 1H), 6.27-6.09 (m, 1H), 6.07-5.90 (m, 1H), 5.81-5.62 (m, 1H), 4.81-4.67 (m, 1H), 4.49-4.32 (m, 1H), 2.86-2.75 (m, 1H), 2.42-2.24 (m, 3H), 2.15-1.97 (m, 2H). |
| 118 | 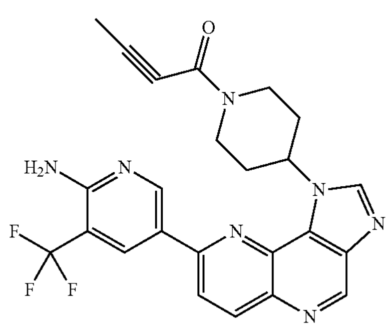 [SMILES: CC#CC(=O)N1CCC(n2cnc3cnc4ccc(-c5cnc(N)c(C(F)(F)F)c5)nc4c32)CC1] | 480(M + H)+ | 1H NMR (400 MHz, dmso) δ 9.26 (d, J = 2.7, 1H), 9.18 (d, J = 2.1, 1H), 8.74 (d, J = 5.9, 1H), 8.64 (d, J = 2.1, 1H), 8.55 (d, J = 8.9, 1H), 8.38 (d, J = 8.9, 1H), 7.04 (s, 2H), 6.08-5.96 (m, 1H), 4.67-4.58 (m, 2H), 2.92-2.83 (m, 1H), 2.47-2.34 (m, 3H), 2.21-2.11 (m, 1H), 2.06 (s, 3H), 2.03-1.97 (m, 1H). |

EXAMPLE 9

Synthesis of Compound 119-146

Compound 119

(4-(8-(6-amino-5-(trifluoromethyl)pyridine-3yl)-2-methyl-1H-imidazo[4,5-c][1,5]naphthyridin-1-yl)piperidin-1-yl)(cyclopropyl)methanone

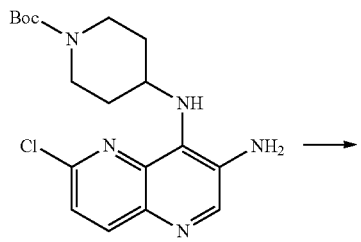

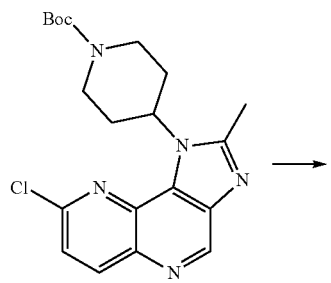

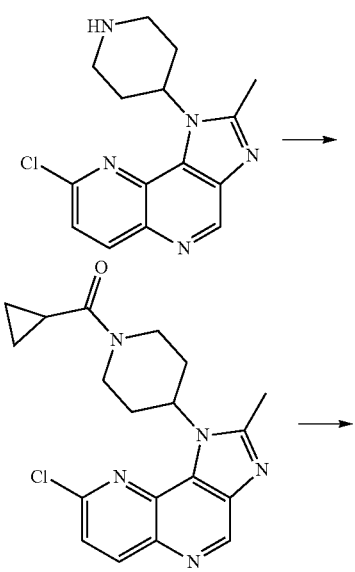

-continued

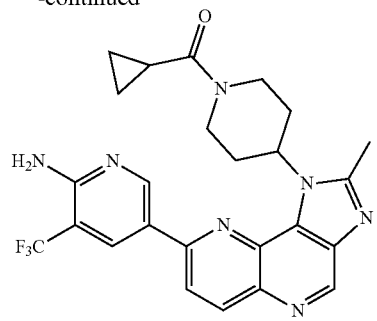

A mixture of tert-butyl 4-(3amino-6-chloro-1,5-naphthyridin-4-ylamino) piperidine-1-carboxylate (200 mg, 0.53 mmol) in acetic acid (3 mL) was stirred at 100° C. overnight. The solvent was removed under vacuum and the residue was added to a solution of HCl in MeOH (6N, 3 mL). The reaction mixture was stirred at r.t. for 2 h, and was then concentrated under vacuum. The residue was dissolved in dichloromethane (20 mL). The resulting solution was washed with saturated NaHCO$_3$ (10 mL) and brine (10 mL), dried over anhydrous Na$_2$SO$_4$, filtered, and concentrated to give crude 8-chloro-2-methyl-1-(piperidin-4-yl)-1H-imidazo[4,5-c][1,5]naphthyridine as a yellow solid (110 mg, yield 68%) which was used in the next step without further purification.

To a solution of 8-chloro-2-methyl-1-(piperidin-4-yl)-1H-imidazo[4,5-c][1,5]naphthyridine (110 mg, 0.364 mmol) and Et$_3$N (101 µL, 0.728 mmol) in THF (15 mL) was added cyclopropanecarbonyl chloride (36 µL, 0.401 mmol) while cooling with an ice-water bath. The reaction mixture was stirred at r.t. for 3 h, and was then concentrated under vacuum. The residue was dissolved in a mixture of CH$_2$Cl$_2$ (10 mL) and H$_2$O (10 mL). The resulting solution was then extracted with EA (2×10 mL). The combined organic layers were concentrated to give crude (4-(8-chloro-2-methyl-1H-imidazo[4,5-c][1,5]naphthyridin-1-yl) piperidin-1-yl)(cyclopropyl) methanone as a yellow solid (105 mg, yield 80%) which was used in the next step without further purification. MS (m/z): 370 (M+H)$^+$.

A mixture of crude (4-(8-chloro-2-methyl-1H-imidazo[4,5-c][1,5]naphthyridin-1-yl) piperidin-1-yl)(cyclopropyl) methanone (105 mg, 0.284 mmol), PdCl$_2$(dppf)$_2$ (12 mg, 0.014 mmol), 5-(4,4,5,5-tetramethyl-1,3,2-dioxaborolan-2-yl)-3-(trifluoromethyl) pyridine-2-amine (98 mg, 0.340 mmol), and 2 N K$_2$CO$_3$ solution (1 mL) in dioxane (4 mL) was microwaved at 150° C. for 30 min. The solvent was removed and the residue was purified by ISCO (MeOH/H2O 0%~100%) to obtain compound 119 as a yellowish solid (57 mg). $^1$H NMR (400 MHz, dmso) δ 9.11 (d, J=6.8, 2H), 8.58 (s, 1H), 8.48 (d, J=8.8, 1H), 8.29 (d, J=8.3, 1H), 6.97 (s, 2H), 4.67-4.58 (m, 2H), 4.06 (s, 1H), 2.75 (m, 5H), 2.11-2.04 (m, 4H), 0.81 (s, 1H), 0.71 (m, 4H). MS (m/z): 496 (M+H)$^+$.

The following compounds 120-146 were prepared according to the procedures for Compound 119 by using the corresponding intermediates and boronic acid or ester under appropriate conditions that could be recognized by one skilled in the art.

| Compound | Structure | LC/MS | NMR |
|---|---|---|---|
| 120 | 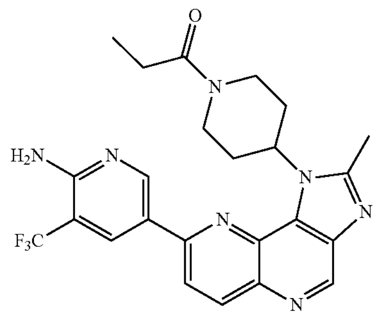 [SMILES: CCC(=O)N1CCC(n2c(C)nc3cnc4ccc(-c5cnc(N)c(C(F)(F)F)c5)nc4c32)CC1] | 484(M + H)+ | 1H NMR (400 MHz, cdcl3) δ 9.24 (s, 1H), 9.03 (s, 1H), 8.57 (d, J = 8.7 Hz, 1H), 8.51 (d, J = 8.7 Hz, 1H), 7.98 (s, 1H), 5.25 (s, 3H), 5.11-4.92 (m, 1H), 4.16 (m, 1H), 3.28 (m, 2H), 2.78 (m, 5H), 2.45 (m, 3H), 2.20 (m, 3H), 1.24 (m, 4H). |
| 121 | 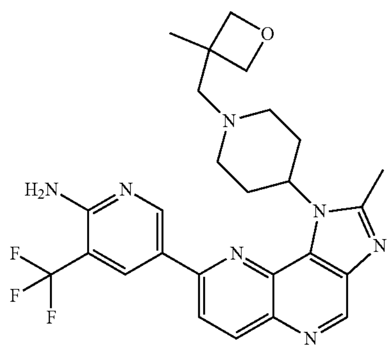 [SMILES: Cc1nc2cnc3ccc(-c4cnc(N)c(C(F)(F)F)c4)nc3c2n1C1CCN(CC2(C)COC2)CC1] | 512(M + H)+ | 1H NMR (400 MHz, dmso) δ 9.39-9.11 (m, 2H), 8.62 (s, 1H), 8.51 (t, J = 8.5, 1H), 8.31 (d, J = 8.3, 1H), 7.02 (s, 2H), 6.82-6.36 (m, 1H), 4.39-4.37 (m, 2H), 4.26-4.23 (m, 2H), 2.84-2.79 (m, 5H), 2.64-2.61 (m, 2H), 2.27-2.19 (m, 3H), 2.09-1.98 (m, 3H), 1.35 (s, 3H). |
| 122 | 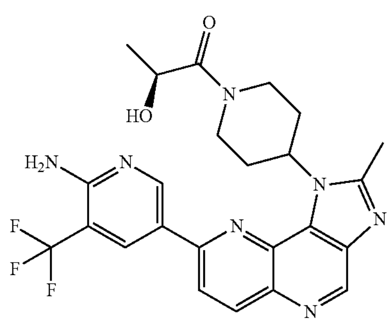 | 500(M + H)+ | 1H NMR (400 MHz, dmso) δ 9.14 (d, J = 3.9, 1H), 8.66-8.62 (m, 1H), 8.52 (dd, J = 8.8, 3.3, 1H), 8.37-8.33 (m, 1H), 8.21-8.18 (m, 1H), 7.01 (s, 2H), 5.36-4.93 (m, 1H), 4.75-4.72 (m, 1H), 4.58-4.55 (m, 1H), 4.47-4.32 (m, 1H), 3.19-3.16 (m, 2H), 2.79 (s, 3H), 2.21-1.91 (m, 4H), 1.28-1.24 (m, 3H). |
| 123 | 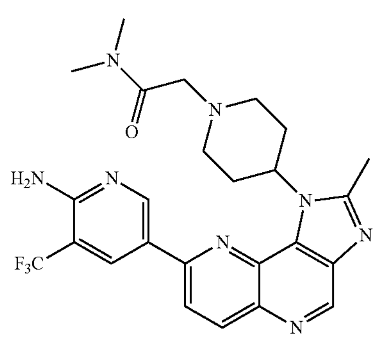 [SMILES: Cc1nc2cnc3ccc(-c4cnc(N)c(C(F)(F)F)c4)nc3c2n1C1CCN(CC(=O)N(C)C)CC1] | 513(M + H)+ | 1H NMR (400 MHz, dmso) δ 9.19 (s, 1H), 9.13 (s, 1H), 8.62 (s, 1H), 8.51 (d, J = 8.9, 1H), 8.32 (d, J = 8.8, 1H), 7.01 (s, 2H), 3.24 (s, 2H), 3.12 (m, 3H), 2.83 (m, 6H), 2.32 (m, 2H), 2.01 (s, 3H), 1.23 (s, 3H). |

| Compound | Structure | LC/MS | NMR |
|---|---|---|---|
| 124 | 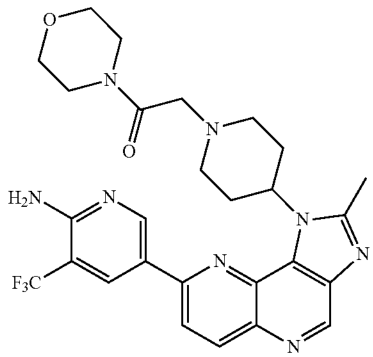 [SMILES: Cc1nc2cnc3ccc(-c4cnc(N)c(C(F)(F)F)c4)nc3c2n1C1CCN(CC(=O)N2CCOCC2)CC1] | 555(M + H)+ | ¹H NMR (400 MHz, dmso) δ 9.15 (d, J = 22.8, 2H), 8.61 (s, 1H), 8.49 (d, J = 8.0, 1H), 8.31 (d, J = 8.3, 1H), 7.04 (s, 2H), 4.12 (s, 1H), 3.65-3.44 (m, 8H), 3.26-3.03 (m, 7H), 2.81 (s 3H), 2.30 (m, 2H), 2.02 (m, 2H). |
| 125 | 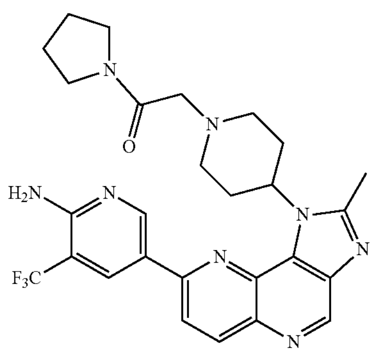 [SMILES: Cc1nc2cnc3ccc(-c4cnc(N)c(C(F)(F)F)c4)nc3c2n1C1CCN(CC(=O)N2CCCC2)CC1] | 539(M + H)+ | ¹H NMR (400 MHz, dmso) δ 9.19 (s, 1H), 9.13 (s, 1H), 8.63 (s, 1H), 8.51 (d, J = 8.9, 1H), 8.32 (d, J = 8.9, 1H), 7.01 (s, 2H), 3.51 (m, 2H), 3.23-3.09 (m, 8H), 2.82 (s 3H), 2.34 (m, 2H), 2.05-1.72 (m, 7H). |
| 126 | 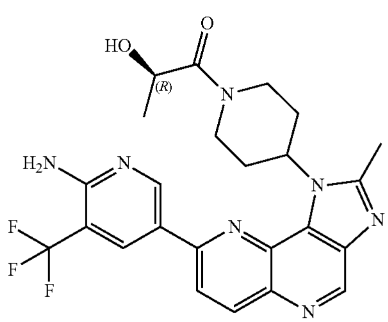 | 500(M + H)+ | ¹H NMR (400 MHz, dmso) δ 9.18-9.14 (m, 1H), 8.64-8.59 (m, 1H), 8.52 (d, J = 8.8, 1H), 8.34 (d, J = 7.8, 1H), 8.26-8.23 (m, 1H), 7.00 (s, 2H), 5.44-4.86 (m, 1H), 4.74-4.70 (m, 1H), 4.58-4.55 (m, 1H), 4.50-4.28 (m, 1H), 3.21-3.16 (m, 2H), 2.79 (s, 3H), 2.21-2.06 (m, 3H), 2.04-1.92 (m, 1H), 1.28-1.23 (m, 3H). |
| 127 | 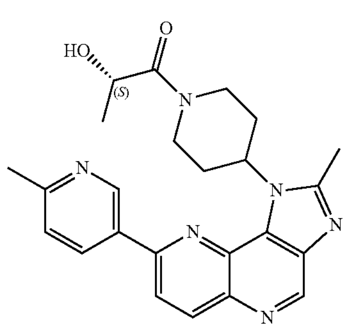 | 431(M + H)+ | ¹H NMR (400 MHz, dmso) δ 9.32 (s, 1H), 9.21 (s, 1H), 8.60 (d, J = 8.8, 1H), 8.55-8.49 (m, 1H), 8.38 (d, J = 6.9, 1H), 7.52 (d, J = 7.7, 1H), 4.73-4.68 (m, 2H), 4.52-4.33 (m, 2H), 2.96-2.80 (m, 5H), 2.59-2.53 (m, 5H), 2.06-1.88 (m, 2H), 1.29-1.21 (m, 3H). |

-continued

| Compound | Structure | LC/MS | NMR |
|---|---|---|---|
| 128 | 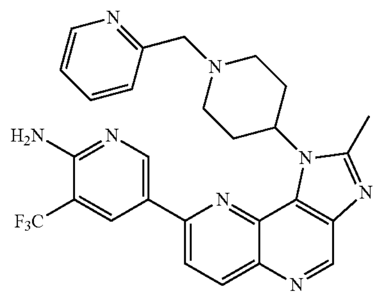 [SMILES: Cc1nc2cnc3ccc(-c4cnc(N)c(C(F)(F)F)c4)nc3c2n1C1CCN(Cc2ccccn2)CC1] | 519(M + H)+ | 1H NMR (400 MHz, dmso) δ 9.10 (s, 1H), 8.59 (s, 1H), 8.47 (d, J = 8.8 Hz, 2H), 8.27 (d, J = 8.8 Hz, 1H), 7.86-7.63 (m, 1H), 7.53 (d, J = 7.7 Hz, 1H), 7.25 (s, 1H), 6.99 (m, 2H), 3.69 (m, 2H), 3.12 (m, 4H), 2.80 (s, 3H), 2.13 (m, 5H). |
| 129 | 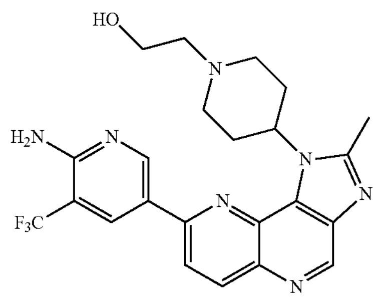 | 472(M + H)+ | 1H NMR (400 MHz, dmso) δ 9.13 (s, 1H), 8.63 (s, 1H), 8.51 (d, J = 8.9 Hz, 1H), 8.42 (s, 1H), 8.34 (d, J = 8.9 Hz, 1H), 4.33-4.13 (m, 1H), 3.62 (s, 6H), 3.14 (s, 3H), 2.81 (s, 4H), 2.27 (s, 3H), 2.00 (m, 3H). |
| 130 | 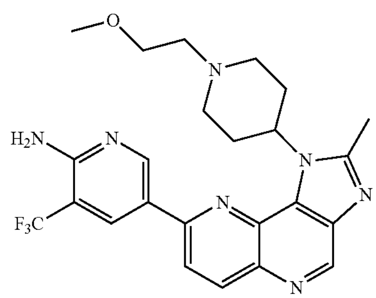 [SMILES: COCCN1CCC(n2c(C)nc3cnc4ccc(-c5cnc(N)c(C(F)(F)F)c5)nc4c32)CC1] | 486(M + H)+ | 1H NMR (400 MHz, dmso) δ 9.09 (s, 1H), 8.57 (s, 1H), 8.45 (d, J = 8.8 Hz, 1H), 8.32 (s, 1H), 8.26 (d, J = 8.9 Hz, 1H), 6.97 (s, 2H), 3.75 (s, 6H), 3.52 (s, 3H), 3.26 (s, 3H), 3.11 (d, J = 10.1 Hz, 3H), 2.78 (s, 3H), 2.57 (t, J = 5.9 Hz, 2H), 2.24 (d, J = 10.0 Hz, 3H). |
| 131 | 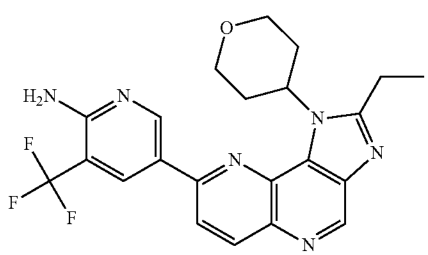 [SMILES: CCc1nc2cnc3ccc(-c4cnc(N)c(C(F)(F)F)c4)nc3c2n1C1CCOCC1] | 443(M + H)+ | 1H NMR (400 MHz, cdcl3) δ 9.32 (d, J = 1.4, 1H), 8.64-8.48 (m, 2H), 8.01 (dd, J = 8.8, 1.5, 1H), 7.27 (d, J = 0.9, 1H), 5.47 (s, 2H), 4.31 (d, J = 8.3, 2H), 3.71 (t, J = 11.6, 2H), 3.17 (d, J = 7.3, 2H), 1.65 (m 4H), 1.58 (t, J = 7.4, 3H). |
| 132 | 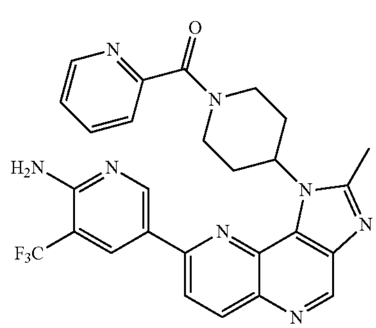 [SMILES: Cc1nc2cnc3ccc(-c4cnc(N)c(C(F)(F)F)c4)nc3c2n1C1CCN(C(=O)c2ccccn2)CC1] | 533(M + H)+ | 1H NMR (400 MHz, dmso) δ 9.11 (m, 2H), 8.59 (m, 2H), 8.48 (d, J = 8.9 Hz, 1H), 8.36-8.22 (m, 1H), 8.01-7.87 (m, 1H), 7.72-7.63 (m, 1H), 7.54-7.41 (m, 1H), 7.01 (s, 2H), 4.92-4.76 (m, 1H), 4.05-3.92 (m, 1H), 3.26-3.19 (m, 1H), 3.11-2.88 (m, 2H), 2.78 (s, 3H), 2.43-1.83 (m, 4H). |

| Compound | Structure | LC/MS | NMR |
| --- | --- | --- | --- |
| 133 | 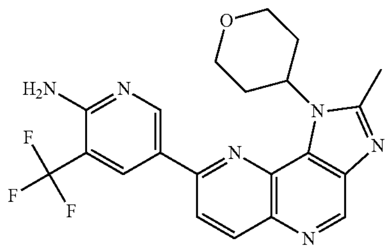 [SMILES: Cc1nc2cnc3ccc(-c4cnc(N)c(C(F)(F)F)c4)nc3c2n1C1CCOCC1] | 429(M + H)+ | 1H NMR (400 MHz, cd3od) δ 9.24 (s, 1H), 9.09 (s, 1H), 8.67 (s, 1H), 8.53 (d, J = 9.2 Hz, 1H), 8.22 (d, J = 9.2 Hz, 1H), 4.26-4.17 (m, 2H), 3.77-3.70 (m, 2H), 2.87 (s, 3H), 2.17-1.73 (m, 4H) |
| 134 | 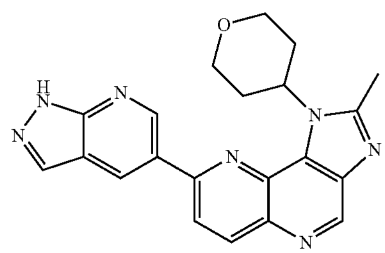 [SMILES: Cc1nc2cnc3ccc(-c4cnc5[nH]ncc5c4)nc3c2n1C1CCOCC1] | 386(M + H)+ | 1H NMR (400 MHz, dmso-d6) δ 9.64 (s, 1H), 9.42 (s, 1H), 8.21 (s, 1H), 8.63 (d, J = 8.8 Hz, 1H), 8.51 (d, J = 8.8 Hz, 1H), 8.26 (s, 1H), 4.25-4.14 (m, 2H), 3.78-3.67 (m, 2H), 2.85 (s, 3H), 2.02-1.76 (m, 4H) |
| 135 | 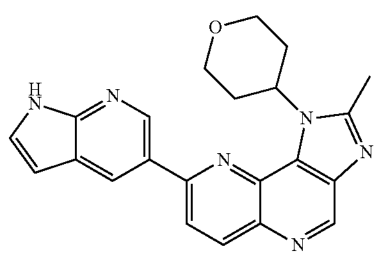 [SMILES: Cc1nc2cnc3ccc(-c4cnc5[nH]ccc5c4)nc3c2n1C1CCOCC1] | 385(M + H)+ | 1H NMR (400 MHz, dmso-d6) δ 11.81 (s, 1H), 9.27 (s, 1H), 9.13 (s, 1H), 8.53 (d, J = 8.8 Hz, 1H), 8.42 (d, J = 8.8 Hz, 1H), 7.53 (d, J = 3.2 Hz, 1H), 6.53 (d, J = 3.2 Hz, 1H), 4.18-4.10 (m, 2H), 3.70-3.62 (m, 2H), 2.79 (s, 3H), 2.01-1.70 (m, 4H) |
| 136 | 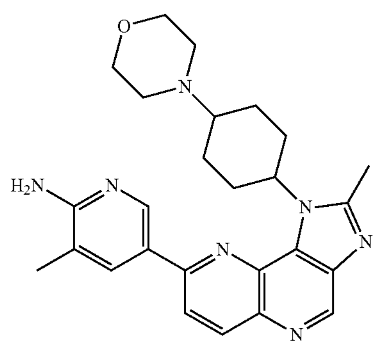 [SMILES: Cc1cc(-c2ccc3ncc4nc(C)n(C5CCC(N6CCOCC6)CC5)c4c3n2)cnc1N] | 458(M + H)+ | 1H NMR (400 MHz, cdcl3) δ 9.20 (s, 1H), 8.81 (d, J = 2.1, 1H), 8.50 (d, J = 8.8, 1H), 8.15 (s, 1H), 7.98 (d, J = 8.8, 1H), 7.10-6.96 (m, 1H), 4.71 (s, 2H), 3.81 (m, 4H), 2.95 (s, 3H), 2.52 (m, 6H), 2.40 (s, 1H), 2.30 (m, 2H), 2.28 (s, 3H), 1.92 (m, 2H), 1.70 (m, 2H) |
| 137 | 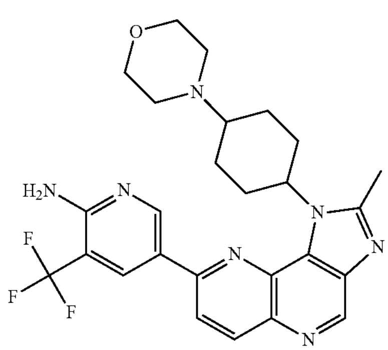 [SMILES: Cc1nc2cnc3ccc(-c4cnc(N)c(C(F)(F)F)c4)nc3c2n1C1CCC(N2CCOCC2)CC1] | 512(M + H)+ | 1H NMR (400 MHz, cdcl3) δ 9.23 (s, 1H), 9.02 (d, J = 1.7, 1H), 8.66 (d, J = 1.9, 1H), 8.56 (d, J = 8.8, 1H), 8.01 (d, J = 8.8, 1H), 7.00-6.86 (m, 1H), 5.25 (s, 2H), 3.80 (m, 4H), 3.49 (m, 1H), 2.97 (s, 3H), 2.56 (m, 3H), 2.48 (m, 2H), 2.40 (s, 1H), 2.28 (m, 2H), 1.90 (m, 2H), 1.68 (m, 2H) |

-continued

| Compound | Structure | LC/MS | NMR |
|---|---|---|---|
| 138 | 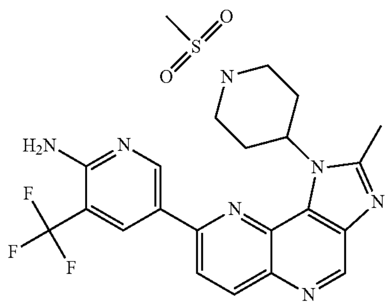 | 506(M + H)⁺ | ¹H NMR (400 MHz, dmso) δ 9.19 (s, 1H), 9.15 (s, 1H), 8.65-8.48 (m, 2H), 8.32 (d, J = 8.8, 1H), 7.00 (s, 2H), 3.92-3.89 (m, 2H), 3.06 (s, 3H), 2.94 (d, J = 11.2, 2H), 2.82 (s, 3H), 2.50 (s, 3H), 2.18 (s, 2H). |
| 139 | 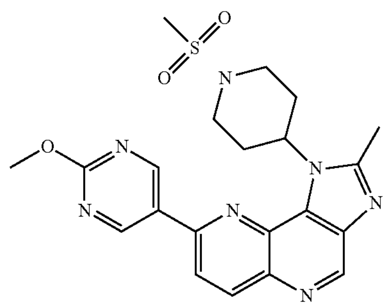 | 454(M + H)⁺ | ¹H NMR (400 MHz, dmso) δ 9.54 (s, 2H), 9.21 (s, 1H), 8.62 (d, J = 8.8, 1H), 8.38 (d, J = 8.8, 1H), 4.92-4.56 (m, 1H), 4.02 (s, 3H), 3.85 (d, J = 11.5, 2H), 3.17 (s, 3H), 3.03 (d, J = 11.6, 2H), 2.82 (s, 3H), 2.53-2.51 (m, 2H), 2.29-1.81 (m, 2H). |
| 140 | 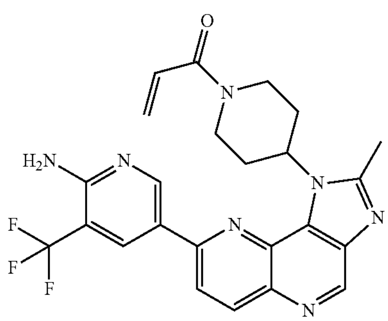 [SMILES: C=CC(=O)N1CCC(n2c(C)nc3cnc4ccc(-c5cnc(N)c(C(F)(F)F)c5)nc4c32)CC1] | 482(M + H)⁺ | ¹H NMR (400 MHz, dmso) δ 9.23-9.08 (m, 2H), 8.52 (d, J = 8.8, 1H), 8.33 (d, J = 8.7, 1H), 7.03-6.86 (m, 3H), 6.16 (d, J = 16.7, 1H), 5.78-5.68 (m, 1H), 4.78-4.75 (m, 1H), 4.42-4.36 (m, 1H), 3.32-3.19 (m, 4H), 2.86-2.79 (m, 1H), 2.78 (s, 3H), 2.22-2.06 (m, 3H). |
| 141 | 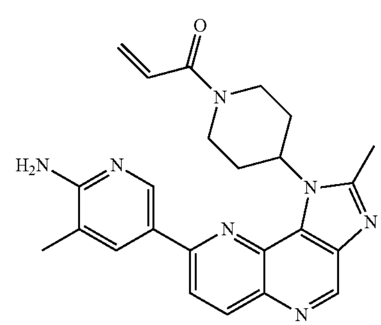 [SMILES: C=CC(=O)N1CCC(n2c(C)nc3cnc4ccc(-c5cnc(N)c(C)c5)nc4c32)CC1] | 428(M + H)⁺ | ¹H NMR (400 MHz, dmso) δ 9.06 (s, 1H), 8.73 (s, 1H), 8.41 (d, J = 8.9, 1H), 8.28-8.25 (m, 2H), 8.17-7.97 (m, 2H), 6.95-6.80 (m, 1H), 6.25-6.06 (m, 2H), 5.73-5.66 (m, 1H), 4.83-4.68 (m, 1H), 4.61-4.45 (m, 1H), 4.42-4.28 (m, 1H), 3.53 (s, 3H), 3.28-3.19 (m, 2H), 2.95-2.86 (m, 1H), 2.74 (s, 3H), 2.13-2.07 (m, 3H). |
| 142 | 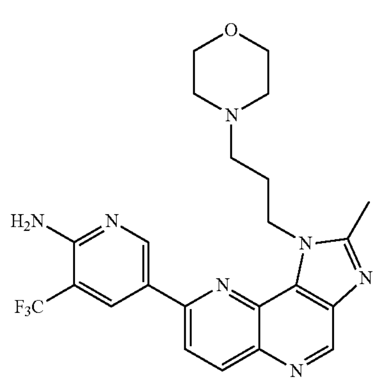 [SMILES: Cc1nc2cnc3ccc(-c4cnc(N)c(C(F)(F)F)c4)nc3c2n1CCCN1CCOCC1] | 472(M + H)⁺ | ¹H NMR (400 MHz, dmso) δ 9.18 (s, 1H), 9.11 (s, 1H), 8.58 (s, 1H), 8.51-8.39 (m, 2H), 8.29 (d, J = 8.9 Hz, 1H), 6.97 (s, 2H), 4.88 (t, J = 6.7 Hz, 2H), 3.39 (d, J = 4.2 Hz, 4H), 2.20 (m, 8H). |

| Compound | Structure | LC/MS | NMR |
|---|---|---|---|
| 143 | 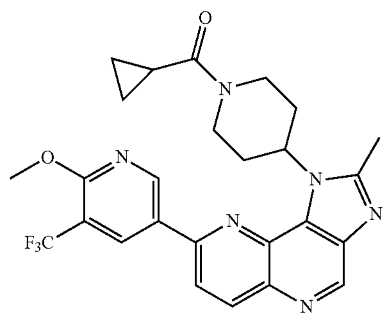 | 511(M + H)⁺ | ¹H NMR (400 MHz, dmso) δ 9.25 (s, 1H), 9.15 (s, 1H), 8.82 (s, 1H), 8.56 (d, J = 8.8, 1H), 8.38 (s, 1H), 4.57 (d, J = 39.0, 2H), 4.06 (s, 4H), 2.76 (s, 5H), 2.01 (s, 4H), 0.79 (d, J = 6.9, 1H), 0.68 (s, 4H). |
| 144 | 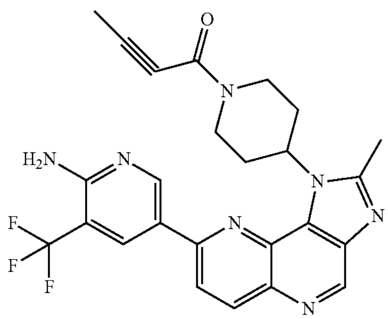 [SMILES: CC#CC(=O)N1CCC(n2c(C)nc3cnc4ccc(-c5cnc(N)c(C(F)(F)F)c5)nc4c32)CC1] | 494(M + H)⁺ | ¹H NMR (400 MHz, dmso) δ 9.14 (s, 2H), 8.61 (s, 1H), 8.52 (d, J = 8.8, 1H), 8.33 (d, J = 8.8, 1H), 7.01 (s, 2H), 4.69-4.56 (m, 2H), 3.35-3.26 (m, 3H), 2.88-2.83 (m, 1H), 2.79 (s, 3H), 2.28-2.13 (m, 3H), 2.06 (s, 3H). |
| 145 | 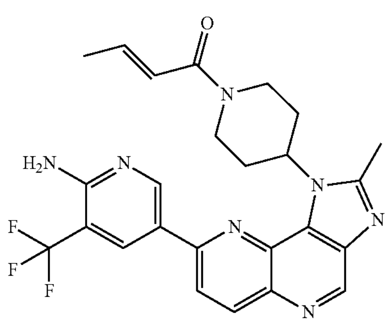 [SMILES: C/C=C/C(=O)N1CCC(n2c(C)nc3cnc4ccc(-c5cnc(N)c(C(F)(F)F)c5)nc4c32)CC1] | 496(M + H)⁺ | ¹H NMR (400 MHz, dmso) δ 9.13 (s, 2H), 8.60 (s, 1H), 8.51 (d, J = 8.8, 1H), 8.32 (d, J = 8.7, 1H), 7.00 (s, 2H), 6.75 (td, J = 13.4, 6.6, 1H), 6.61 (d, J = 15.2, 1H), 4.81-4.68 (m, 1H), 4.46-4.22 (m, 1H), 3.81-3.72 (m, 1H), 3.28-3.18 (m, 2H), 2.80-2.78 (m, 1H), 2.77 (s, 3H), 2.22-2.02 (m, 3H), 1.87 (d, J = 6.7, 3H) |
| 146 | 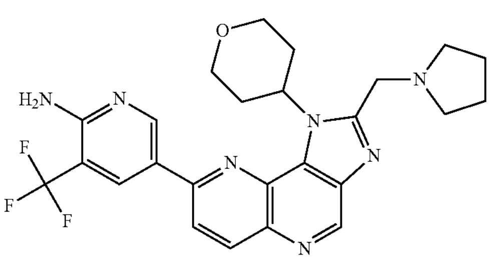 [SMILES: Nc1ncc(-c2ccc3ncc4nc(CN5CCCC5)n(C5CCOCC5)c4c3n2)cc1C(F)(F)F] | 498(M + H)⁺ | ¹H NMR (400 MHz, cdcl3) δ 9.48 (s, 1H), 9.30 (s, 1H), 8.67-8.44 (m, 2H), 8.01 (s, 1H), 5.64 (s, 2H), 4.30-4.29 (d, 2H), 4.11 (s, 2H), 3.71-3.65 (m, 3H), 2.63 (m, 4H), 1.81 (m, 4H), 1.68 (m, 4H). |

EXAMPLE 10

Synthesis of Compounds 147-178

Compound 147

2,4-difluoro-N-(2-methoxy-5-(1-methyl-[1,2,4]triazolo[4,3-a]quinoxalin-8-yl)pyridin-3-yl)benzenesulfonamide

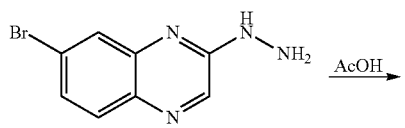

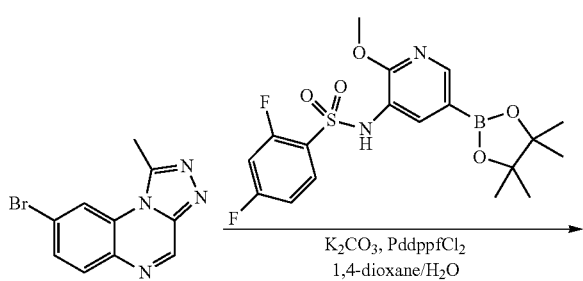

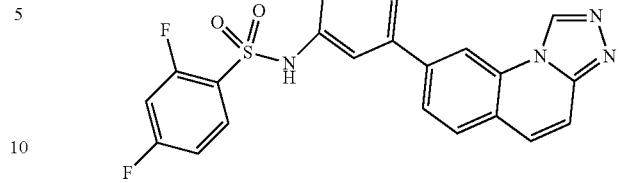

A mixture of 7-bromo-2-hydrazinylquinoxaline (200 mg, 0.84 mmol) and AcOH (5 mL) was refluxed overnight. After cooling to r.t., the mixture was treated with water (10 mL); the solid was collected on a filter and dried by vacuum to give 8-bromo-1-methyl-[1,2,4]triazolo[4,3-a]quinoxaline as gray solid (200 mg, yield: 91.0%).

A mixture of 8-bromo-1-methyl-[1,2,4]triazolo[4,3-a]quinoxaline (60 mg, 0.23 mmol), 2,4-difluoro-N-(2-methoxy-5-(4,4,5,5-tetramethyl-1,3,2-dioxaborolan-2-yl)pyridine-3-yl)benzenesulfonamide (107 mg, 0.25 mmol), $K_2CO_3$ (95 mg, 0.69 mmol) and Pd(dppf)$Cl_2$ (6 mg) in dioxane/$H_2O$ (3:1, 4 mL) was microwaved at 160° C. for 0.5 h. Then the solvent was removed, and the residue was purified by ISCO (MeOH/$H_2O$=20%-80%) to give compound 147 as white solid (60 mg). $^1$HNMR (400 MHz, dmso) δ 10.44 (s, 1H), 9.26 (s, 1H), 8.47 (d, J=1.7 Hz, 1H), 8.34 (d, J=1.5 Hz, 1H), 8.13 (t, J=10.3 Hz, 1H), 8.02 (d, J=2.1 Hz, 1H), 7.92 (dd, J=8.4, 1.5 Hz, 1H), 7.76 (dd, J=14.9, 8.5 Hz, 1H), 7.51 (dd, J=14.2, 5.4 Hz, 1H), 7.18 (t, J=7.5 Hz, 1H), 3.68 (s, 3H), 3.17 (s, 3H). MS (m/z): 483 (M+H)$^+$.

The following compounds 148-178 were prepared according to the procedures for Compound 147 by using the corresponding intermediates and boronic acid or ester under appropriate conditions that could be recognized by one skilled in the art.

| Compounds | Structure | LC/MS | NMR |
|---|---|---|---|
| 148 | 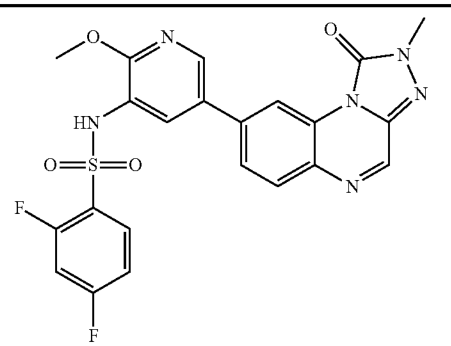 | 499(M + H)$^+$ | $^1$H NMR (400 MHz, dmso) δ 10.39 (s, 1H), 8.82 (s, 2H), 8.30 (s, 1H), 7.92 (d, J = 8.4, 1H), 7.86 (d, J = 2.2, 1H), 7.82 (d, J = 6.4, 1H), 7.78 (dd, J = 8.4, 1.9, 1H), 7.51 (t, J = 8.8, 1H), 7.21 (t, J = 8.6, 1H), 3.69 (s, 3H), 3.62 (s, 3H). |
| 149 | 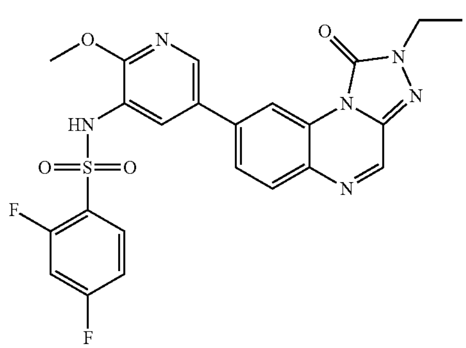 [SMILES: CCn1nc2cnc3ccc(-c4cnc(OC)c(NS(=O)(=O)c5ccc(F)cc5F)c4)cc3n2c1=O] | 513(M + H)$^+$ | $^1$H NMR (400 MHz, dmso) δ 10.38 (s, 1H), 8.83-8.77 (m, 2H), 8.32 (d, J = 2.2, 1H), 7.90 (d, J = 8.4, 1H), 7.86 (d, J = 2.3, 1H), 7.84-7.79 (m, 1H), 7.78-7.74 (m, 1H), 7.56-7.49 (m, 1H), 7.23-7.18 (m, 2.2, 1H), 3.99 (q, J = 7.2, 2H), 3.69 (s, 3H), 1.34 (t, J = 7.2, 3H). |

| Compounds | Structure | LC/MS | NMR |
|---|---|---|---|
| 150 | 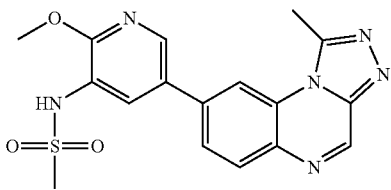 [SMILES: COc1ncc(-c2ccc3ncc4nnc(C)n4c3c2)cc1NS(C)(=O)=O] | 385(M + H)+ | 1H NMR (400 MHz, dmso) δ 9.30 (s, 1H), 8.52 (d, J = 2.3, 1H), 8.43 (d, J = 1.7, 1H), 8.19 (d, J = 8.4, 1H), 8.07 (d, J = 2.3, 1H), 8.00 (dd, J = 8.4, 1.8, 1H), 4.00 (s, 3H), 3.22 (s, 3H), 3.10 (s, 3H). |
| 151 | 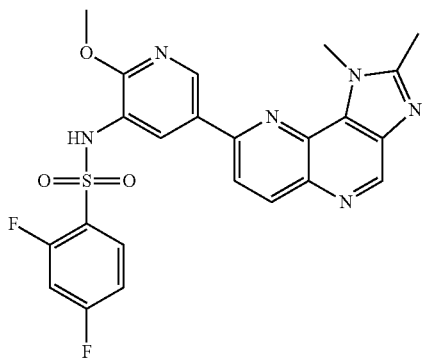 | 497(M + H)+ | 1H NMR (400 MHz, dmso) δ 9.15 (s, 1H), 8.82 (s, 1H), 8.54 (d, J = 3.5, 1H), 8.52 (s, 1H), 8.28 (d, J = 8.9, 1H), 8.14 (s, 1H), 7.84-7.76 (m, 1H), 7.53 (t, J = 8.7, 1H), 7.20 (td, J = 8.6, 2.2, 1H), 4.45 (s, 3H), 3.78 (s, 3H), 2.69 (s, 3H). |
| 152 | 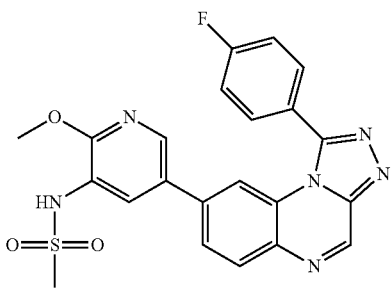 [SMILES: COc1ncc(-c2ccc3ncc4nnc(-c5ccc(F)cc5)n4c3c2)cc1NS(C)(=O)=O] | 465(M + H)+ | 1H NMR (400 MHz, dmso) δ 9.45 (s, 1H), 8.21 (d, J = 8.4, 1H), 8.03 (d, J = 2.3, 1H), 7.99-7.90 (m, 3H), 7.66 (d, J = 2.3, 1H), 7.62 (d, J = 1.9, 1H), 7.59-7.53 (m, 2H), 3.96 (s, 3H), 3.02 (s, 3H). |
| 153 | 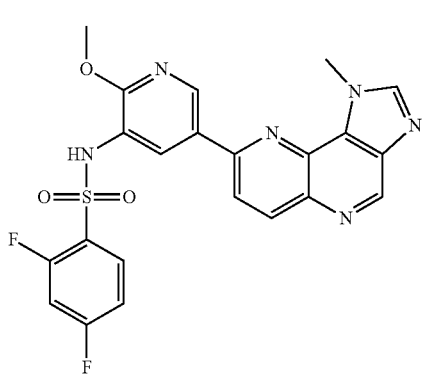 | 483(M + H)+ | 1H NMR (400 MHz, dmso) δ 10.41 (s, 1H), 9.27 (s, 1H), 8.92 (d, J = 2.0, 1H), 8.60-8.56 (m, 2H), 8.51 (s, 1H), 8.35 (d, J = 8.9, 1H), 7.79 (td, J = 8.6, 6.4, 1H), 7.61-7.52 (m, 1H), 7.21 (td, J = 8.4, 2.1, 1H), 4.47 (s, 3H), 3.77 (s, 3H). |
| 154 | 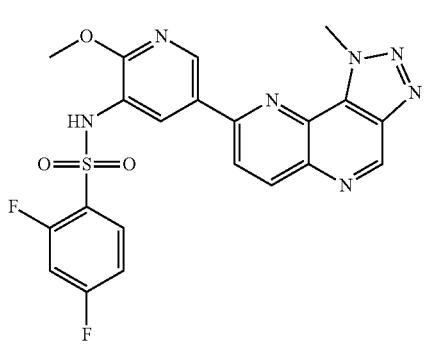 [SMILES: COc1ncc(-c2ccc3ncc4nnn(C)c4c3n2)cc1NS(=O)(=O)c1ccc(F)cc1F] | 484(M + H)+ | 1H NMR (400 MHz, dmso) δ 9.51 (s, 1H), 8.54 (d, J = 8.1, 1H), 8.28-8.21 (m, 4H), 7.79 (d, J = 7.0, 1H), 7.21-7.18 (m, 1H), 7.03-6.99 (m, 1H), 4.73 (s, 3H), 3.83 (s, 3H). |

-continued
| Compounds | Structure | LC/MS | NMR |
|---|---|---|---|
| 155 | 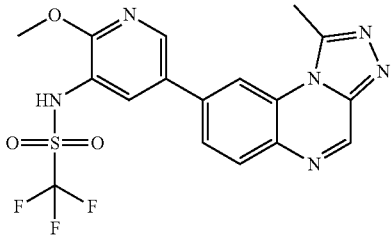 [SMILES: COc1ncc(-c2ccc3ncc4nnc(C)n4c3c2)cc1NS(=O)(=O)C(F)(F)F] | 439(M + H)+ | ¹H NMR (400 MHz, dmso) δ 9.31 (s, 1H), 8.64 (d, J = 2.0, 1H), 8.44 (d, J = 1.7, 1H), 8.18 (dd, J = 11.1, 5.4, 2H), 8.01 (dd, J = 8.4, 1.8, 1H), 4.00 (s, 3H), 3.23 (s, 3H). |
| 156 | 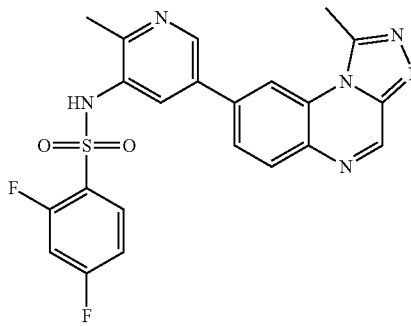 | 467(M + H)+ | ¹H NMR (400 MHz, dmso) δ 9.31 (s, 1H), 8.62 (s, 1H), 8.35 (d, J = 1.6, 1H), 8.19 (d, J = 8.4, 1H), 8.14 (s, 1H), 7.95-7.76 (m, 3H), 7.51-7.47 (m, 1H), 7.22-7.19 (m, 1H), 3.16 (s, 3H), 2.36 (s, 3H). |
| 157 | 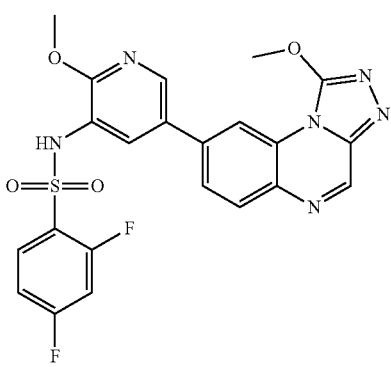 [SMILES: COc1ncc(-c2ccc3ncc4nnc(OC)n4c3c2)cc1NS(=O)(=O)c1ccc(F)cc1F] | 499(M + H)+ | ¹H NMR (400 MHz, dmso) δ 9.12 (s, 1H), 8.45 (d, J = 1.9, 1H), 8.34 (d, J = 2.1, 1H), 8.15 (s, 1H), 8.08 (d, J = 8.4, 1H), 7.94 (d, J = 2.3, 1H), 7.88 (dd, J = 8.4, 2.0, 1H), 7.82-7.77 (m, 1H), 7.56-7.48 (m, 1H), 7.21 (td, J = 8.2, 2.2, 1H), 4.42 (s, 3H), 3.72 (s, 3H). |
| 158 | 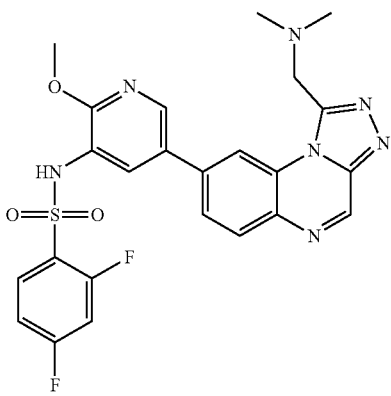 [SMILES: COc1ncc(-c2ccc3ncc4nnc(CN(C)C)n4c3c2)cc1NS(=O)(=O)c1ccc(F)cc1F] | 526(M + H)+ | ¹H NMR (400 MHz, dmso) δ 9.36 (s, 1H), 8.81 (d, J = 1.8, 1H), 8.50 (d, J = 2.3, 1H), 8.18 (d, J = 8.4, 1H), 8.15 (s, 1H), 8.08 (d, J = 2.3, 1H), 8.01-7.97 (m, 1H), 7.77 (td, J = 8.6, 6.4, 1H), 7.58-7.53 (m, 1H), 7.20 (td, J = 8.4, 2.3, 1H), 4.29 (m 2H), 3.69 (s, 3H), 2.31 (s, 6H). |
| 159 | 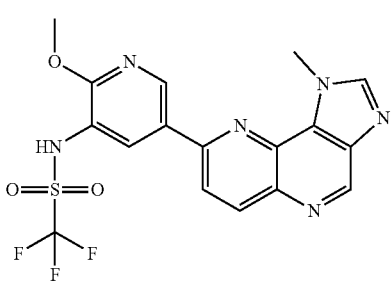 [SMILES: COc1ncc(-c2ccc3ncc4ncn(C)c4c3n2)cc1NS(=O)(=O)C(F)(F)F] | 439(M + H)+ | ¹H NMR (400 MHz, dmso) δ 9.37 (s, 1H), 8.99 (d, J = 2.0, 1H), 8.67-8.55 (m, 3H), 8.42 (d, J = 8.9, 1H), 4.50 (s, 3H), 4.02 (s, 3H). |

-continued

| Compounds | Structure | LC/MS | NMR |
|---|---|---|---|
| 160 | 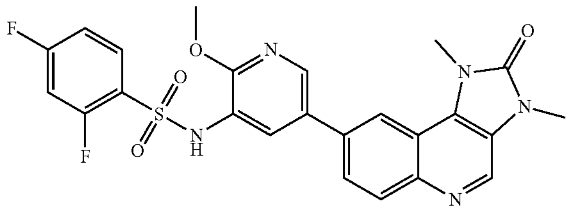 [SMILES: COc1ncc(-c2ccc3ncc4c(c3c2)n(C)c(=O)n4C)cc1NS(=O)(=O)c1ccc(F)cc1F] | 512(M + H)+ | ¹H NMR (400 MHz, dmso) δ 10.38-10.29 (m, 1H), 8.87 (s, 1H), 8.51 (d, J = 2.1, 1H), 8.41 (d, J = 1.6, 1H), 8.10 (d, J = 8.8, 1H), 8.02 (d, J = 2.2, 1H), 7.86 (dd, J = 8.9, 1.8, 1H), 7.76 (dd, J = 14.9, 8.5, 1H), 7.56 (dd, J = 14.3, 5.5, 1H), 7.20 (t, J = 7.3, 1H), 3.89 (s, 3H), 3.66 (m, 3H), 3.52 (s, 3H). |
| 161 | 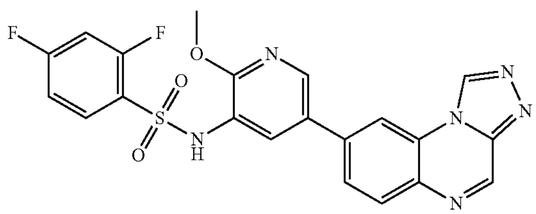 [SMILES: COc1ncc(-c2ccc3ncc4nncn4c3c2)cc1NS(=O)(=O)c1ccc(F)cc1F] | 469 (M + H)⁺ | ¹H NMR (400 MHz, dmso) δ 10.46-10.31 (m, 1H), 10.22 (s, 1H), 9.38 (s, 1H), 8.82 (d, J = 1.9, 1H), 8.59 (d, J = 2.3, 1H), 8.16 (dd, J = 5.4, 3.1, 2H), 8.00 (dd, J = 8.5, 1.9, 1H), 7.77-7.69 (m, 1H), 7.59-7.51 (m, 1H), 7.23-7.14 (m, 1H), 3.63 (s, 3H). |
| 162 | 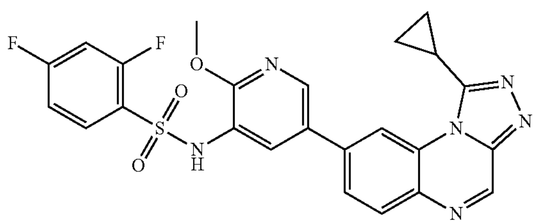 [SMILES: COc1ncc(-c2ccc3ncc4nnc(C5CC5)n4c3c2)cc1NS(=O)(=O)c1ccc(F)cc1F] | 509 (M + H)⁺ | ¹H NMR (400 MHz, dmso) δ 13.11 (s, 1H), 10.60-10.24 (m, 1H), 8.83 (d, J = 2.0, 1H), 8.80 (s, 1H), 8.36 (d, J = 2.1, 1H), 7.92 (d, J = 8.4, 1H), 7.87 (d, J = 2.3, 1H), 7.82-7.76 (m, 2H), 7.53 (dd, J = 14.3, 5.4, 1H), 7.20 (td, J = 8.3, 2.0, 1H), 3.68 (s, 3H). |
| 163 | 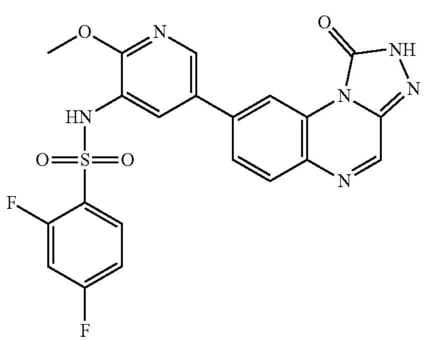 [SMILES: COc1ncc(-c2ccc3ncc4n[nH]c(=O)n4c3c2)cc1NS(=O)(=O)c1ccc(F)cc1F] | 485 (M + H)⁺ | ¹H NMR (400 MHz, dmso) δ 10.50-10.35 (m, 1H), 9.26 (d, J = 4.8, 1H), 8.87 (d, J = 1.8, 1H), 8.51 (d, J = 2.3, 1H), 8.16 (d, J = 8.4, 1H), 8.07 (d, J = 2.4, 1H), 8.01-7.99 (m, 1H), 7.74 (dt, J = 4.1, 1.9, 1H), 7.53 (dd, J = 14.4, 5.3, 1H), 7.22-7.17 (m, 1H), 3.68 (s, 3H), 1.30 (dt, J = 8.0, 2.9, 2H), 1.20 (dt, J = 11.4, 5.6, 3H). |
| 164 | 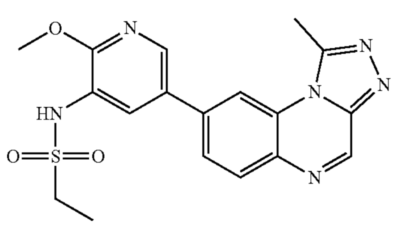 [SMILES: CCS(=O)(=O)Nc1cc(-c2ccc3ncc4nnc(C)n4c3c2)cnc1OC] | 399(M + H)⁺ | 1H NMR (400 MHz, dmso) δ 9.44 (s, 1H), 9.27 (s, 1H), 8.53 (d, J = 2.2, 1H), 8.40 (s, 1H), 8.16 (d, J = 8.4, 1H), 8.06 (d, J = 2.2, 1H), 7.97 (dd, J = 8.5, 1.5, 1H), 4.00 (s, 3H), 3.18-3.13 (m, 2H), 1.27 (t, J = 7.3, 3H), 1.20 (s, 3H). |

-continued

| Compounds | Structure | LC/MS | NMR |
|---|---|---|---|
| 165 | 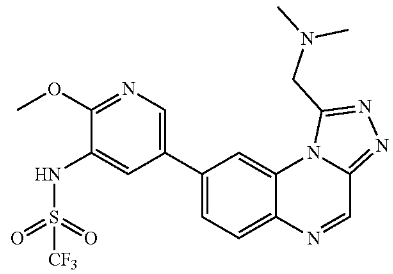 [SMILES: COc1ncc(-c2ccc3ncc4nnc(CN(C)C)n4c3c2)cc1NS(=O)(=O)C(F)(F)F] | 482(M + H)+ | 1H NMR (400 MHz, dmso) δ 9.39 (s, 1H), 8.21 (d, J = 8.5, 3H), 7.95 (d, J = 6.7, 3H), 3.89 (s, 3H), 3.17 (s, 2H), 2.50 (s, 6H). |
| 166 | 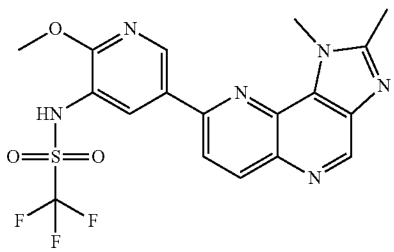 [SMILES: COc1ncc(-c2ccc3ncc4nc(C)n(C)c4c3n2)cc1NS(=O)(=O)C(F)(F)F] | 453(M + H)+ | 1H NMR (400 MHz, dmso) δ 9.26 (s, 1H), 8.80 (d, J = 2.1, 1H), 8.60 (d, J = 2.2, 1H), 8.56 (d, J = 8.9, 1H), 8.35 (d, J = 8.9, 1H), 4.48 (s, 3H), 3.97 (s, 3H), 2.70 (s, 3H). |
| 167 | 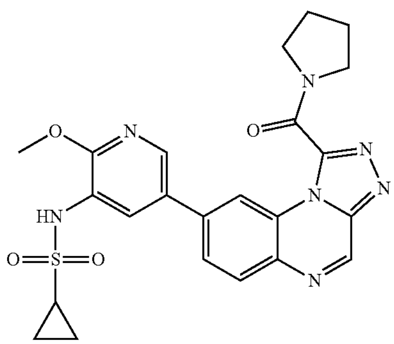 [SMILES: COc1ncc(-c2ccc3ncc4nnc(C(=O)N5CCCC5)n4c3c2)cc1NS(=O)(=O)C1CC1] | 494(M + H)+ | 1H NMR (400 MHz, dmso) δ 9.49 (d, J = 9.7, 1H), 8.57 (d, J = 1.8, 1H), 8.45 (d, J = 2.3, 1H), 8.23 (d, J = 8.5, 1H), 8.10 (dd, J = 8.5, 1.9, 1H), 8.00 (d, J = 2.3, 1H), 4.01 (s, 3H), 3.71 (dt, J = 18.0, 6.8, 4H), 2.89-2.77 (m, 1H), 2.03-1.79 (m, 5H), 1.03-0.92 (m, 4H). |
| 168 | 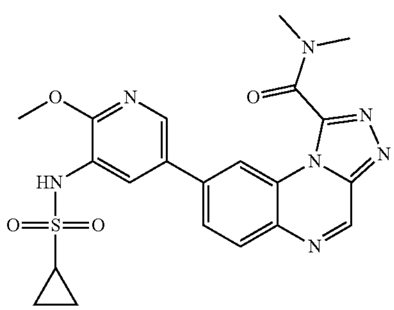 [SMILES: COc1ncc(-c2ccc3ncc4nnc(C(=O)N(C)C)n4c3c2)cc1NS(=O)(=O)C1CC1] | 468(M + H)+ | 1H NMR (400 MHz, dmso) δ 9.48 (d, J = 2.7, 1H), 8.42 (d, J = 2.3, 1H), 8.27 (d, J = 1.8, 1H), 8.25 (d, J = 8.5, 1H), 8.09 (dd, J = 8.5, 1.9, 1H), 7.98 (d, J = 2.3, 1H), 4.01 (s, 3H), 3.26 (s, 3H), 3.13 (s, 3H), 2.80 (s, 1H), 1.04-0.93 (m, 4H). |
| 169 | 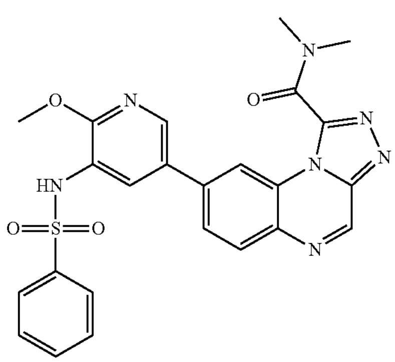 [SMILES: COc1ncc(-c2ccc3ncc4nnc(C(=O)N(C)C)n4c3c2)cc1NS(=O)(=O)c1ccccc1] | (M + H)+ | 1H NMR (400 MHz, dmso) δ 10.13 (s, 1H), 9.49 (s, 1H), 8.37 (d, J = 2.2, 1H), 8.28-8.21 (m, 2H), 8.04 (dd, J = 8.5, 1.8, 1H), 7.95 (d, J = 2.2, 1H), 7.89-7.81 (m, 2H), 7.63 (t, J = 7.3, 1H), 7.56 (t, J = 7.4, 2H), 3.72 (s, 3H), 3.30 (s, 3H), 3.17 (s, 3H). |

-continued

| Compounds | Structure | LC/MS | NMR |
|---|---|---|---|
| 170 | 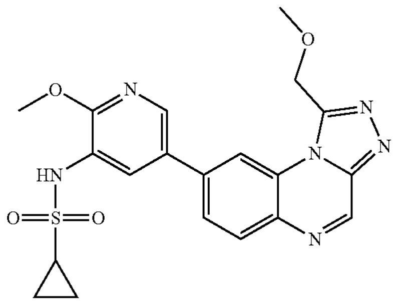 [SMILES: COCc1nnc2cnc3ccc(-c4cnc(OC)c(NS(=O)(=O)C5CC5)c4)cc3n12] | 441(M + H)+ | 1H NMR (400 MHz, dmso) δ 9.51 (s, 1H), 9.41 (s, 1H), 8.52 (t, J = 2.3, 2H), 8.23 (d, J = 8.4, 1H), 8.10 (d, J = 2.3, 1H), 8.06 (dd, J = 8.4, 1.9, 1H), 5.33 (s, 2H), 4.02 (s, 3H), 3.43 (s, 3H), 2.80 (m, 1H), 1.06-0.91 (m, 4H). |
| 171 | 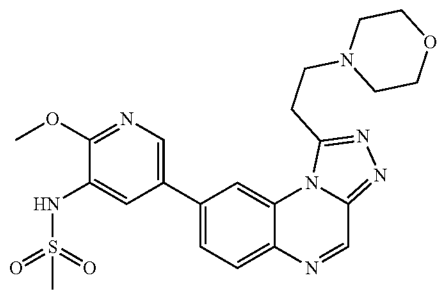 [SMILES: COc1ncc(-c2ccc3ncc4nnc(CCN5CCOCC5)n4c3c2)cc1NS(C)(=O)=O] | 484(M + H)+ | 1H NMR (400 MHz, dmso) δ 9.29 (s, 1H), 8.53 (d, J = 2.3, 1H), 8.39 (d, J = 1.6, 1H), 8.17 (d, J = 8.4, 1H), 8.06 (d, J = 2.3, 1H), 8.00 (dd, J = 8.4, 1.7, 1H), 3.98 (s, 3H), 3.79-3.74 (m, 2H), 3.57-3.53 (m, 4H), 3.08 (s, 3H), 2.96-2.91 (m, 2H), 2.48 (m 4H). |
| 172 | 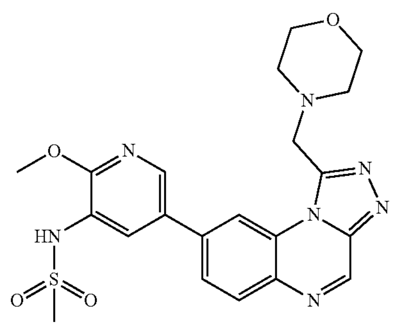 [SMILES: COc1ncc(-c2ccc3ncc4nnc(CN5CCOCC5)n4c3c2)cc1NS(C)(=O)=O] | 470(M + H)+ | 1H NMR (400 MHz, dmso) δ 9.33 (s, 1H), 8.84 (d, J = 1.8, 1H), 8.51 (d, J = 2.3, 1H), 8.17 (d, J = 8.4, 1H), 8.03 (dd, J = 6.9, 2.1, 2H), 4.34 (s, 2H), 3.98 (s, 3H), 3.50 (s, 4H), 3.06 (s, 3H), 2.52 (m, 4H). |
| 173 | 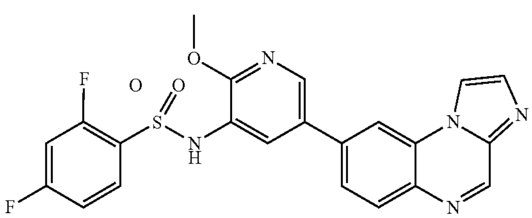 | 468(M + H)+ | 1H NMR (400 MHz, dmso) δ 10.44 (s, 1H), 9.18 (s, 1H), 9.06 (s, 1H), 8.81 (s, 1H), 8.66 (s, 1H), 8.32-8.17 (m, 2H), 8.06-7.91 (m, 2H), 7.83 (s, 1H), 7.64 (s, 1H), 7.27 (s, 1H), 3.72 (s, 3H). |
| 174 | 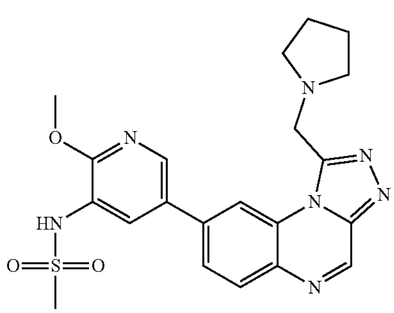 [SMILES: COc1ncc(-c2ccc3ncc4nnc(CN5CCCC5)n4c3c2)cc1NS(C)(=O)=O] | 454(M + H)+ | 1H NMR (400 MHz, cd3od) δ 9.23 (s, 1H), 9.00 (s, 1H), 8.37 (d, J = 2.1 Hz, 1H), 8.23-8.18 (m, 1H), 8.14 (d, J = 1.9 Hz, 1H), 7.96 (d, J = 8.5 Hz, 1H), 4.46 (s, 2H), 4.11 (s, 3H), 3.05 (s, 3H), 2.74 (m, 4H), 1.88 (m, 4H). |

-continued

| Compounds | Structure | LC/MS | NMR |
|---|---|---|---|
| 175 | 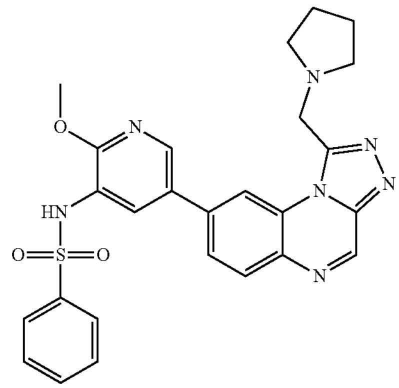 [SMILES: COc1ncc(-c2ccc3ncc4nnc(CN5CCCC5)n4c3c2)cc1NS(=O)(=O)c1ccccc1] | 516(M + H)+ | 1H NMR (400 MHz, cd3od) δ 9.20 (s, 1H), 8.88 (s, 1H), 8.15 (d, J = 8.5 Hz, 1H), 7.98 (s, 1H), 7.88 (d, J = 6.5 Hz, 3H), 7.78 (d, J = 9.3 Hz, 1H), 7.49-7.39 (m, 3H), 4.45 (m 2H), 3.88 (s, 3H), 2.70 (m, 4H), 1.83 (m, 4H). |
| 176 | 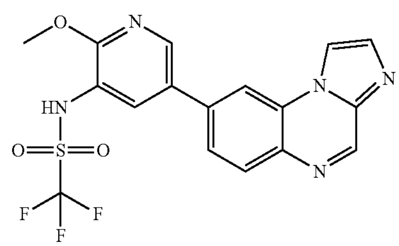 [SMILES: COc1ncc(-c2ccc3ncc4nccn4c3c2)cc1NS(=O)(=O)C(F)(F)F] | 424(M + H)+ | 1H NMR (400 MHz, dmso) δ 9.13 (s, 1H), 9.00 (s, 1H), 8.75 (d, J = 1.8, 1H), 8.61 (s, 1H), 8.17-8.14 (m, 2H), 7.97-7.94 (m, 1H), 7.92-7.90 (m, 1H), 3.98 (s, 3H). |
| 177 | 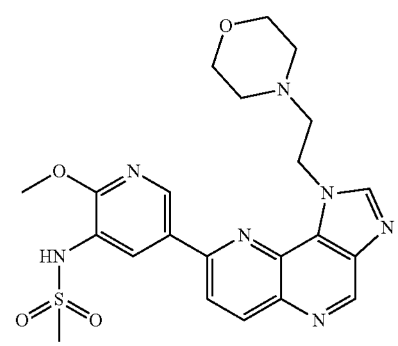 [SMILES: COc1ncc(-c2ccc3ncc4ncn(CCN5CCOCC5)c4c3n2)cc1NS(C)(=O)=O] | 484(M + H)+ | 1H NMR (400 MHz, dmso) δ 9.22 (s, 1H), 8.89 (d, J = 2.2, 1H), 8.54 (dd, J = 5.5, 3.3, 2H), 8.50 (s, 1H), 8.32 (d, J = 8.9, 1H), 5.04 (t, J = 5.9, 2H), 4.00 (s, 3H), 3.45-3.42 (m, 4H), 3.09 (s, 3H), 2.90 (t, J = 6.0, 2H), 2.38 (m 4H). |
| 178 | 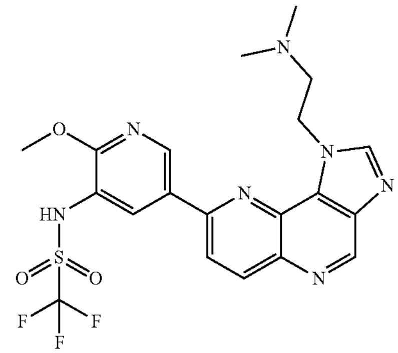 [SMILES: COc1ncc(-c2ccc3ncc4ncn(CCN(C)C)c4c3n2)cc1NS(=O)(=O)C(F)(F)F] | 496(M + H)+ | 1H NMR (400 MHz, dmso) δ 9.22 (s, 1H), 8.52 (d, J = 8.9, 1H), 8.47 (dd, J = 4.8, 1.6, 3H), 8.24 (d, J = 8.9, 2H), 5.11-5.05 (m, 2H), 3.87 (s, 3H), 2.94-2.90 (m, 2H), 2.14 (s, 6H). |

EXAMPLE 11

Synthesis of Compounds 179-182

Compound 179

N-(2-methoxy-5-(1-methyl-[1,2,4]triazolo[4,3-a]quinoxalin-8-yl)pyridin-3-yl)-4-methylbenzenesulfonamide

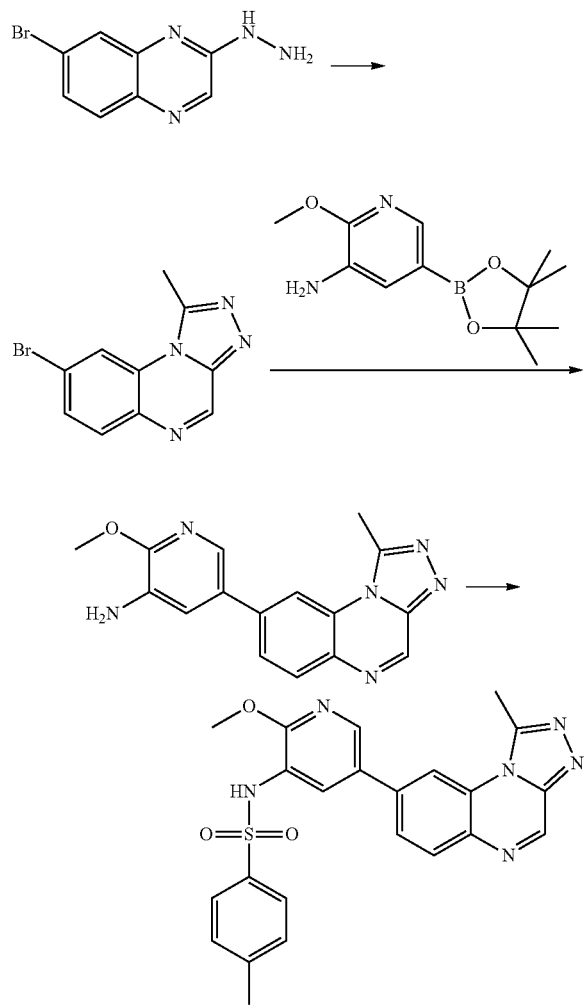

A mixture of 7-bromo-2-hydrazinylquinoxaline (1 g, 4.18 mmol) in acetic acid (10 mL) was refluxed for 18 h. Half of the acetic acid was removed under vacuum and the residue was poured into ice-water. The precipitate was collected on a filter, washed with water, and dried under vacuo to afford crude 8-bromo-1-methyl-[1,2,4]triazolo[4,3-a]quinoxaline as a dark red solid (1 g, yield 90%) which was used in the next step without further purification. MS (m/z): 263 (M+H)$^+$.

A mixture of crude 8-bromo-1-methyl-[1,2,4]triazolo[4,3-a]quinoxaline (809 mg, 3.07 mmol), PdCl$_2$(dppf)$_2$ (132.6 mg, 0.153 mmol), 2-methoxy-5-(4,4,5,5-tetramethyl-1,3,2-dioxaborolan-2-yl)pyridin-3-amine (1 g, 4.3 mmol) and K$_2$CO$_3$ (1.7 g, 12.28 mmol) in DMF (40 mL) and water (15 mL) was stirred at 100° C. overnight. Half of solvent was removed. After cooling to room temperature, the resulting mixture was poured into ice-water. The precipitate was collected, washed with water three times, and dried in vacuo to afford crude 2-methoxy-5-(1-methyl-[1,2,4]triazolo[4,3-a]quinoxalin-8-yl)pyridin-3-amine as grey solid (730 mg, yield 77%) which was used in next step without further purification. MS (m/z): 307 (M+H)$^+$.

To a mixture of crude 2-methoxy-5-(1-methyl-[1,2,4]triazolo[4,3-a]quinoxalin-8-yl)pyridin-3-amine (50 mg, 0.163 mmol) in pyridine (2 mL) was added 4-methylbenzene-1-sulfonyl chloride (31.3 mg, 0.164 mmol). The mixture was stirred at room temperature overnight, and was then heated at 50° C. for 5 h. The solvent was removed, and the residue was purified by PTLC to afford compound 179 as a grey solid (22 mg). $^1$H NMR (400 MHz, dmso) δ 10.00 (s, 1H), 9.27 (s, 1H), 8.44 (d, J=2.3, 1H), 8.32 (d, J=1.8, 1H), 8.15 (d, J=8.4, 1H), 7.98 (d, J=2.3, 1H), 7.89 (dd, J=8.4, 1.8, 1H), 7.68 (dd, J=8.4, 1.8, 2H), 7.35 (d, J=8.0, 2H), 3.71 (s, 3H), 3.17 (s, 3H), 2.33 (s, 3H). MS (m/z): 461 (M+H)$^+$.

The following compounds 180-182 were prepared according to the procedures for Compound 179 by using the corresponding intermediates and boronic acid or ester under appropriate conditions that could be recognized by one skilled in the art.

| Compound | Structure | LC/MS | NMR |
|---|---|---|---|
| 180 | 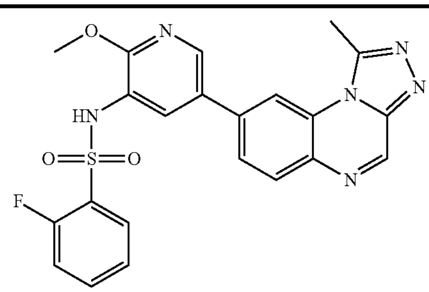 | 465(M + H)$^+$ | $^1$H NMR (400 MHz, dmso) δ 10.31 (s, 1H), 9.28 (s, 1H), 8.51 (d, J = 2.0, 1H), 8.36 (s, 1H), 8.16 (d, J = 8.4, 1H), 8.04 (d, J = 2.2, 1H), 7.93 (d, J = 8.5, 1H), 7.72 (t, J = 7.5, 2H), 7.48-7.39 (m, 1H), 7.31 (t, J = 7.6, 1H), 3.66 (s, 3H), 3.18 (s, 3H). |

| Compound | Structure | LC/MS | NMR |
|---|---|---|---|
| 181 | 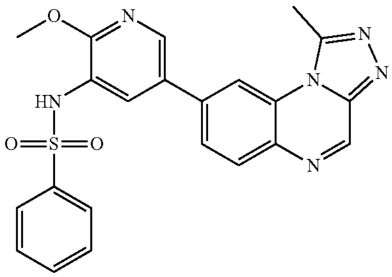 [SMILES: COc1ncc(-c2ccc3ncc4nnc(C)n4c3c2)cc1NS(=O)(=O)c1ccccc1] | 447(M + H)+ | ¹H NMR (400 MHz, dmso) δ 10.09 (s, 1H), 9.28 (s, 1H), 8.47 (d, J = 2.3, 1H), 8.34 (d, J = 1.8, 1H), 8.16 (d, J = 8.4, 1H), 8.00 (d, J = 2.3, 1H), 7.91 (dd, J = 8.4, 1.8, 1H), 7.79-7.77 (m, 2H), 7.65-7.61 (m, 1H), 7.57-7.54 (m, 2H), 3.68 (s, 3H), 3.18 (s, 3H). |
| 182 | 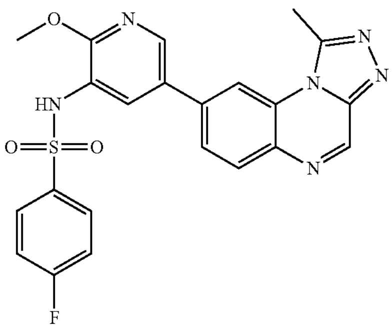 [SMILES: COc1ncc(-c2ccc3ncc4nnc(C)n4c3c2)cc1NS(=O)(=O)c1ccc(F)cc1] | 465(M + H)+ | ¹H NMR (400 MHz, dmso) δ 10.14 (s, 1H), 9.28 (s, 1H), 8.49 (d, J = 2.0, 1H), 8.34 (s, 1H), 8.16 (d, J = 8.4, 1H), 8.02 (d, J = 2.0, 1H), 7.92 (d, J = 8.5, 1H), 7.83 (dd, J = 8.6, 5.1, 2H), 7.40 (t, J = 8.8, 2H), 3.69 (s, 3H), 3.18 (s, 3H). |
EXAMPLE 12
Synthesis of Compounds 183 and 184
Compound 183
2-(4-(8-(6-amino-5-(trifluoromethyl)pyridin-3-yl)-1H-imidazo[4,5-c]cinnolin-1-yl)phenyl)-2-methyl-propanenitrile
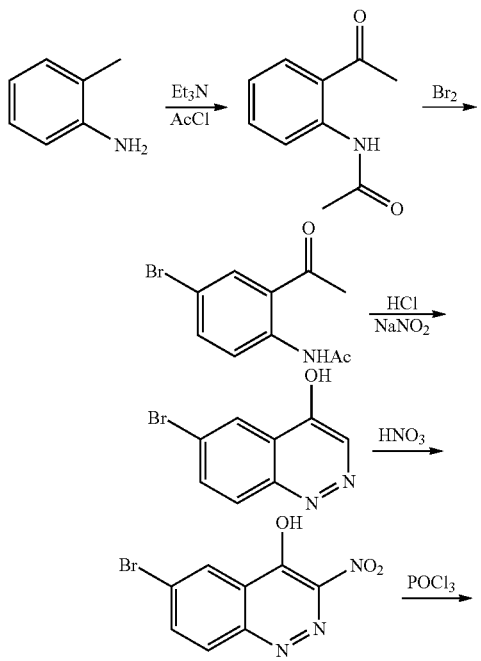
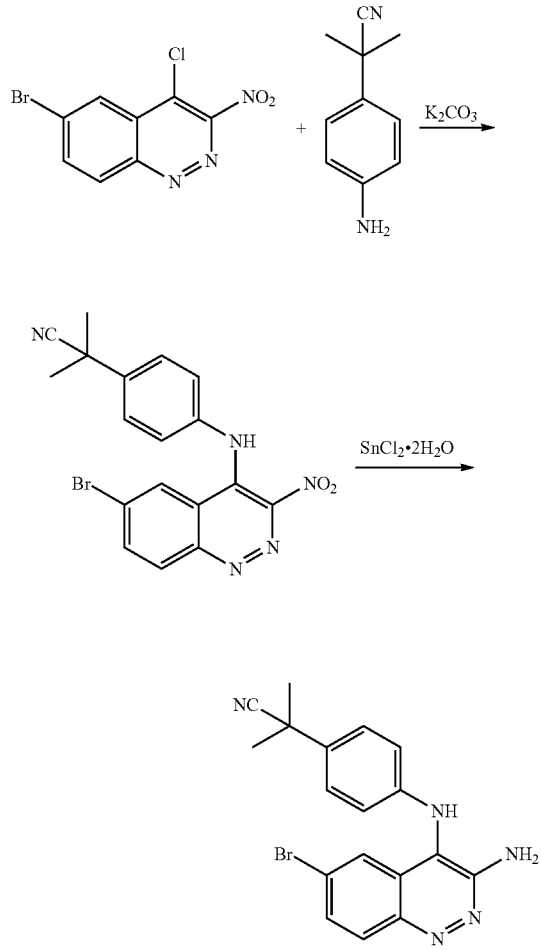

-continued

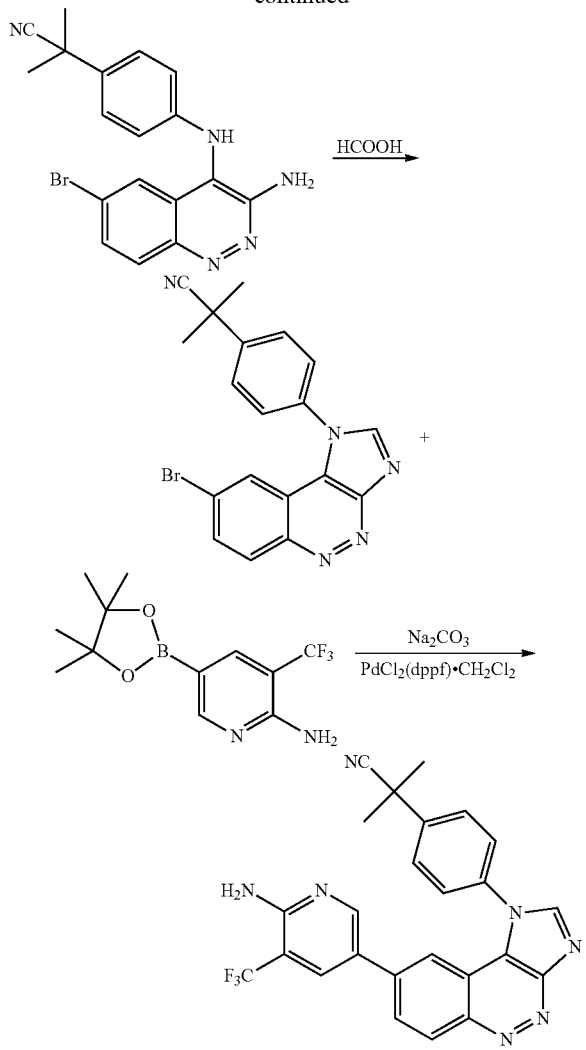

To a white suspension of 1-(2-aminophenyl)ethanone (25 g, 185 mmol) and Et₃N (33.4 mL, 240 mmol) in DCM at 0° C. was added dropwise AcCl (15.70 mL, 222 mmol) in 25 mL DCM. The reaction mixture was then stirred at r.t. for 2 h. After the reaction went to completion as monitored by LC-MS, the reaction mixture was cooled to 0° C., and was then quenched with H₂O (100 mL). The organic phase was isolated; the aqueous layer was extracted with DCM. The organic phases were combined, and washed with H₂O and brine. The resulting organic phase was dried over anhydrous MgSO₄, filtered and concentrated to dryness to give crude N-(2-acetylphenyl)acetamide, which was used in the next step without further purification (30 g, yield 92%). MS (m/z): 136 (M+H)⁺.

Under N₂, a pale yellow suspension of crude N-(2-acetylphenyl)acetamide (28 g, 158 mmol) in AcOH (300 mL) was stirred for about 5 min, and Br₂ (12.95 mL, 253 mmol) was added within 1 h at room temperature. The resulting mixture was then stirred at room temperature for 75 min. After the reaction went to completion as monitored by LC-MS, the reaction mixture was quenched with H₂O (200 mL). The mixture was filtered through Buchner funnel, and the solid was collected as N-(2-acetyl-4-bromophenyl)acetamide (35 g, yield 86%). MS (m/z): 216 (M+H)⁺.

Under N₂, a mixture of N-(2-acetyl-4-bromophenyl)acetamide (35 g, 137 mmol) and HCl (100 mL, 600 mmol) in THF (400 mL) was heated to reflux for 1 h. After being concentrated under vacuum to remove the solvent, the mixture was treated with EtOAc (100 mL). The aqueous layer was concentrated to remove THF, and 6N HCl (100 mL, 600 mmol) was added at room temperature. After cooling to 0° C., the resulting mixture was treated dropwise with NaNO₂ (9.43 g, 137 mmol) in 20 mL H₂O. The reaction mixture was then stirred at r.t. for 15 h. Then the resulting mixture was heated to reflux for another 6 h. The mixture was cooled to r.t. The solid was collected and dried in vacuo, to afford the desired product as a white solid. The crude product was used directly in next step without further purification. (19.5 g, yield 63.4%) MS (m/z): 227 (M+H)⁺.

Under N₂, an orange solution of 6-bromocinnolin-4-ol (18.5 g, 82 mmol) in HNO₃ (90 mL, 82 mmol) was cooled to 0° C., and H₂SO₄ (30 mL) was added. The resulting mixture was then heated at 60° C. for 3 h. After the reaction went to completion as monitored by LC-MS, the reaction mixture was cooled to 0° C., and was then quenched with H₂O (20 mL). The mixture was diluted with EtOAc (25 mL). Following general workup procedures, the crude residue was added to silica gel, and eluted with PE/EtOAc to give 6-bromo-3-nitrocinnolin-4-ol as a pale yellow solid (13 g, yield 58.6%).

Under N₂, a brown solution of 6-bromo-3-nitrocinnolin-4-ol (2 g, 7.41 mmol) in DMF (10 mL) was cooled to 0° C., and POCl₃ (0.897 mL, 9.63 mmol) was added dropwise. The reaction mixture was stirred at r.t. for 5 h. After the reaction went to completion as monitored by LC-MS, the reaction mixture was cooled to 0° C., and then quenched with H₂O (50 mL). The mixture was filtered through a Buchner funnel, and the solid was collected. The crude 6-bromo-4-chloro-3-nitrocinnoline was used in the next step without further purification (1.75 g, yield 82%). MS (m/z): 290 (M+H)⁺.

A yellow suspension of 6-bromo-4-chloro-3-nitrocinnoline (1.75 g, 6.07 mmol), 2-(4-aminophenyl)-2-methylpropanenitrile (1.069 g, 6.67 mmol) and K₂CO₃ (1.677 g, 12.13 mmol) in MeCN (2 mL) was heated to reflux for 5 min. The workup followed general workup procedures, and the crude was purified on silica gel with PE/EtOAc as eluant to give 2-(4-(6-bromo-3-nitrocinnolin-4-ylamino)phenyl)-2-methylpropanenitrile as yellow solid (2.5 g, yield 100%). MS (m/z): 414 (M+H)⁺.

Under N₂, an orange solution of 2-(4-(6-bromo-3-nitrocinnolin-4-ylamino)phenyl)-2-methylpropanenitrile (2.5 g, 6.06 mmol) and SnCl₂.2H₂O (5.21 g, 24.26 mmol) in EtOAc (50 mL) was heated at 45° C. for 3 h. After cooling to r.t., the pH of the mixture was adjusted to 8 with saturated Na₂CO₃. The mixture was filtered through a Buchner funnel, and the filtrate was collected and concentrated to give 2-(4-(3-amino-6-bromocinnolin-4-ylamino)phenyl)-2-methylpropanenitrile (1.6 g, yield 69%). MS (m/z): 384 (M+H)⁺.

Under N₂, a brown solution of 2-(4-(3-amino-6-bromocinnolin-4-ylamino)phenyl)-2-methyl-propanenitrile (250 mg, 0.654 mmol) in HCO₂H (3 mL) was heated to reflux for 4 h. The reaction mixture was quenched with H₂O, and was then concentrated to remove the solvent. The crude product was used in the next step directly without further purification (250 mg, yield 97%). MS (m/z): 394 (M+H)⁺.

Under N₂, an orange suspension of 2-(4-(8-bromo-1H-imidazo[4,5-c]cinnolin-1-yl)phenyl)-2-methylpropanenitrile (100 mg, 0.255 mmol), 5-(4,4,5,5-tetramethyl-1,3,2-dioxaborolan-2-yl)-3-(trifluoromethyl)pyridin-2-amine (95 mg, 0.331 mmol), Na₂CO₃ (54.0 mg, 0.510 mmol) and PdCl₂(dppf).CH₂Cl₂ (10.41 mg, 0.013 mmol) in dioxane (20 mL) and H₂O (2 mL) was stirred for 10 minutes at r.t. The resulting mixture was then heated at 120° C. for 2 h. The mixture was concentrated in vacuo, and the residue was then purified by chromatography to give compound 183 as a pale yellow powder (50 mg). $^1$H NMR (400 MHz, dmso) δ 8.87 (s, 1H), 8.63 (d, J=8.9, 1H), 8.48 (d, J=2.0, 1H), 8.22 (dd, J=9.0, 1.9, 1H), 7.95 (d, J=8.6, 2H), 7.88 (d, J=8.6, 2H), 7.76 (d, J=2.1, 1H), 7.52 (d, J=1.8, 1H), 6.84 (5, 2H), 1.78 (5, 6H). MS (m/z): 474 (M+H)+.

The following compound 184 was prepared according to the procedures of Compound 183 by using the corresponding intermediates and boronic acid or ester under appropriate conditions that could be recognized by one skilled in the art.

Results

Above compounds 1, 2, 3, 5, 6, 7, 8, 9, 10, 11, 12, 13, 14, 15, 16, 17, 18, 20, 21, 22, 23, 24, 25, 26, 28, 29, 30, 31, 33, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 79, 80, 81, 82, 83, 84, 85, 87, 88, 89, 90, 92, 94, 95, 96, 97, 98, 99, 100, 101, 102, 103, 104, 105, 106, 107, 108, 109, 110, 111, 112, 113, 119, 120, 121, 122, 123, 124, 125, 126, 127, 128, 129, 130, 131, 132, 133, 134, 135, 136, 137, 138, 139, 140, 142, 143, 144, 145, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184 inhibited the PI3Kα kinase receptor with IC₅₀<100 nM.

| Compound | Structure | LC/MS | NMR |
|---|---|---|---|
| 184 | 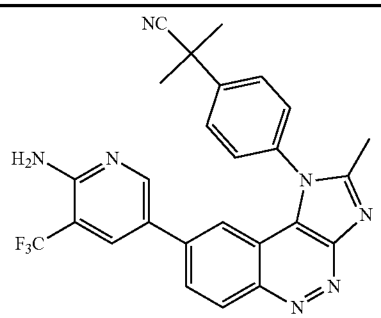 | 488(M + H)+ | $^1$H NMR (400 MHz, dmso) δ 8.56 (d, J = 8.9, 1H), 8.33 (d, J = 2.1, 1H), 8.13 (dd, J = 9.0, 2.0, 1H), 7.88 (d, J = 9.3, 4H), 7.69 (d, J = 1.9, 1H), 7.10 (d, J = 1.7, 1H), 6.80 (s, 2H), 2.51 (s, 3H), 1.79 (s, 6H). |

EXAMPLE 13

PI3Ka Transcreener ADP Assay

Fluorescence polarization was used in this assay. The final conditions for kinase assay are 10 μM of ATP, 0.2 ng/μL of PI3Kα kinase, 30 μmol/L of lipid substrate and assay buffer (50 mmol/L of HEPES (pH 7.5), 100 mmol/L of NaCl, 1 mmol/L of EGTA, 3 mmol/L of MgCl₂, 1 mmol/L of DTT and 0.03% CHAPS and 2% DMSO).

5 μL of test compounds in 10% DMSO and 10 μL of 0.5 ng/μL PI3K kinase (Invitrogen, PV4788) in assay buffer are put into a 96-well plate (Greiner, Cat. 675076), and then the reaction is started by the addition of 10 μL of 75 μmol/L PIP2, (PS Lipid Substrate Invitrogen, PV5100), and 25 μmol/L ATP mixture. After the mixture is incubated for 60 minutes at room temperature, 25 μL of transcreener Kinase Kit reagent—ADP Detection Mix—(Bellbrook Labs) is added, and the reaction is continued for an additional 1.5 hours. At the end, the plate is read in a Tecan Infinite F500 at excitation of 610 nm and emission of 670 nm.

A standard curve for ADP is obtained in a parallel way by replacing compound and PI3Kα kinase with DMSO and assay buffer, respectively. Different concentration of ADP, 0-10 μM, and ATP, 10-0 μM (ATP+ADP equal to 10 μM) are applied instead of a fixed concentration of ATP in this standard curve assay. Other conditions are the same as described above. The standard curve is plotted using Origin 8.0 software. The inhibition of test compound on ADP production is calculated based on ADP concentration from standard curve. IC50 is obtained using XLfit 2.0 software.

EXAMPLE 14

P-Akt Acumen Assay

Compounds are tested using p-Akt Acumen cell-based assay. The human prostate cancer cell line PC3 (ATCC) is cultured in F-12 medium with 10% fetal bovine serum. For p-Akt Acumen assay, PC3 cells are seeded at a density of 5000 cells/90 μL in Poly-D-Lysine 96-well plate (BD, 356692). After incubation for 24 hours, different concentrations of test compounds (10 μL) is added and cells are incubated for another 2 hours. 100 μL of 4% prewarmed paraformaldehyde is added, and cells are fixed for 45 min at room temperature. After the removal of paraformaldehyde, 100 μL of 0.1% Triton X-100 is added, and cells are incubated for extra 30 min at room temperature. After the cells are washed twice with 160 μL of PBS, 100 μL of blocking buffer (1% BSA, in PBS) is added, and the cells are continued to incubate for 2~3 hours. Cells are washed with 160 μL of PBS again, treated with 30 μL of Ser473-p-Akt (Cell signaling, CAT: 4060) which is diluted in 0.1% BSA at 1:250, and incubated at 4° C. overnight. Cells are then washed twice with 160 μL of PBS. 35 μL of Alexa Fluor 488 goat anti-rabbit IgG (Invitrogen, A11034), in a 1:1000 dilution buffer (0.1% BSA in PBS), is added, and the reaction mixture is incubated for 1.5 hours in the dark. It is washed twice with 160 μL of PBS, and then 35 μL of 1.5 μM propidium iodide (Sigma, P4170) is added to each well, and reaction plate is incubated at 37° C., 5% CO₂ for 30 min. Finally, the plate is loaded into the Acumen eX3 (TTP LabTech) and scanned with the appropriate instrument settings.

The inhibition of test compound is calculated based on the ratio of compound treated and untreated cells. IC₅₀ is generated using XLfit 2.0 software. Each compound specifically exemplified in the invention inhibited the PI3Kα kinase receptor with $IC_{50}<1.0$ μM.

EXAMPLE 15 mTOR TR-FRET Assay

Compounds are tested using LanthaScreen TR-FRET Assay. The kinase reaction is completed in 384-well black plate (Corning, Cat. 3676). The final conditions for kinase assay are: 10 μmol/L of ATP, 0.2 ng/μL of mTOR kinase, 0.4 μmol/L of GFP-4EBP1 substrate and assay buffer (50 mmol/L of HEPES, pH 7.5, 0.01% of Tween 20, 1 mmol/L of EGTA, 10 mmol/L of $MnCl_2$, 2 mmol/L of DTT and 1% DMSO).

To each well, 2.5 μL of test compounds in 4% DMSO and 2.5 μL of 0.8 ng/μL mTOR kinase (Invitrogen, PV4753) diluted in assay buffer are added. The reaction is initiated by the addition of 5 μL mixture of 0.8 μmol/L GFP-4EBP1 Substrate (Invitorgen, PV4759) and 20 μmol/L ATP mixtures. The mixture is incubated at room temperature for 60 minutes. 10 μL of 20 mmol/L EDTA and 4 nmol/L Tb-anti-p4EBP1 [pThr46] antibody (Invitrogen, PV4755) diluted in TR-FRET dilution buffer are added and incubated for an additional 1 hour. The plate is then read in a BioTek Synergy2 Reader at excitation of 340 nm and emission of 490 nm and 528 nm.

The inhibition of test compound is calculated based on the ratio of 528 nm/490 nm. $IC_{50}$ of test compound is obtained using XLfit 2.0 software.

Results: Above compounds 1, 6, 7, 9, 10, 12, 14, 16, 17, 21, 25, 26, 30, 33, 35, 42, 43, 44, 45, 46, 49, 50, 52, 53, 55, 56, 58, 63, 66, 72, 75, 88, 96, 98, 102, 103, 105, 106, 107, 119, 120, 121, 122, 123, 129, 131, 147, 148, 149, 151, 152, 153, 154, 155, 156, 157, 158, 159, 160, 165, 166, 178, 180, 181 inhibited mTOR with $IC_{50}<100$ nM.

EXAMPLE 16

P-S6 Acumen Assay

Compounds are tested using p-Akt Acumen cell-based assay. The human prostate cancer cell line PC3 (ATCC) is cultured in F-12 medium with 10% fetal bovine serum. For p-S6 Acumen assay, PC3 cells are seeded at density of 5000 cells/90 μL in Poly-D-Lysine 96-well plate (BD, 356692). After incubation for 24 hours, 10 μL of different concentration of test compounds is added and cells are incubated for 2 hours, followed by the addition of 100 μL of 4% pre-warmed paraformaldehyde. The cells are fixed at room temperature for 45 min. After removal of the paraformaldehyde solution, 100 μL of 0.1% Triton X-100 is added, and cells are incubated at room temperature for 30 min. After the cells are washed twice with 160 μL of PBS, 100 μL of blocking buffer (1% BSA, in PBS) is added, and the cells are incubated for an additional 2~3 hours. Again, cells are washed with 160 μL of PBS, treated with 30 μL of p-S6 antibody (Cell signaling, CAT: 4858) which is diluted in 0.1% BSA at 1:250, and incubated at 4° C. overnight. After the cells are washed twice with 160 μL of PBS, 35 μL of Alexa Fluor 488 goat anti-rabbit IgG (Invitrogen, A11034), in a 1:1000 dilution buffer (0.1% BSA in PBS) is added and the reaction mixture is incubated in the dark for 1.5 hours. After washing twice with 160 μL of PBS, 35 μL of 1.5 μM propidium iodide (Sigma, P4170) is added to each well and reaction plate is incubated at 37° C., 5% $CO_2$ for 30 min. Finally, the plate is loaded into the Acumen eX3 (TTP LabTech) and scanned with the appropriate instrument settings.

The inhibition of the test compound is calculated based on the ratio of compound treated and untreated cells. $IC_{50}$ is generated using XLfit 2.0 software. Each compound specifically exemplified in the invention inhibited mTOR with $IC_{50}<10.0$ μM.

What is claimed is:

1. A compound selected from the following compounds 1 to 184,

| No. | Structure |
| --- | --- |
| 1 | 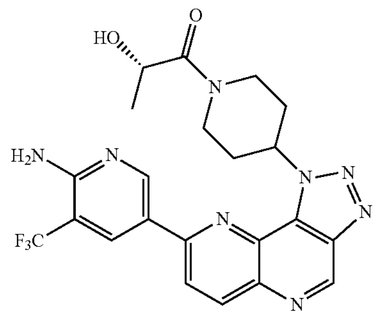 |
| 2 | 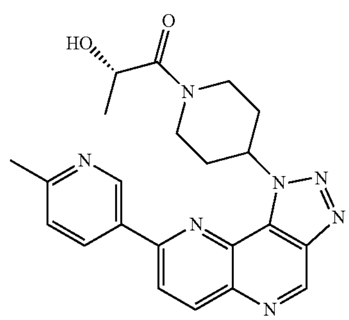 [SMILES: Cc1ccc(-c2ccc3ncc4nnn(C5CCN(C(=O)[C@H](C)O)CC5)c4c3n2)cn1] |
| 3 | 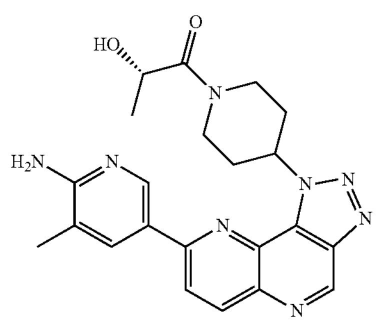 [SMILES: Cc1cc(-c2ccc3ncc4nnn(C5CCN(C(=O)[C@H](C)O)CC5)c4c3n2)cnc1N] |
| 4 | 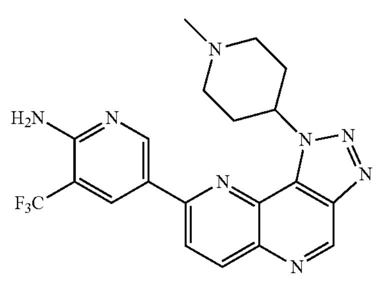 [SMILES: CN1CCC(n2nnc3cnc4ccc(-c5cnc(N)c(C(F)(F)F)c5)nc4c32)CC1] |

131
-continued

| No. | Structure |
|---|---|
| 5 | 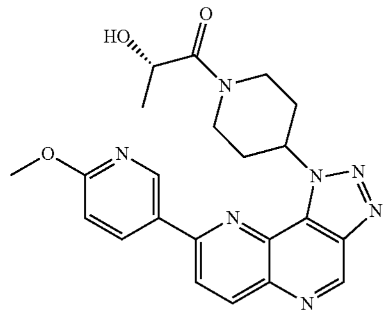 |
| 6 | 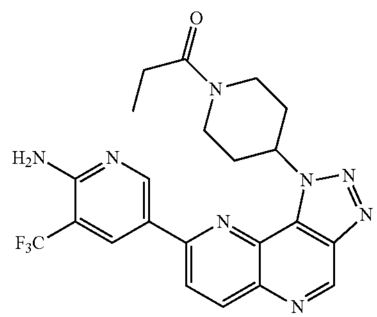 [SMILES: CCC(=O)N1CCC(n2nnc3cnc4ccc(-c5cnc(N)c(C(F)(F)F)c5)nc4c32)CC1] |
| 7 | 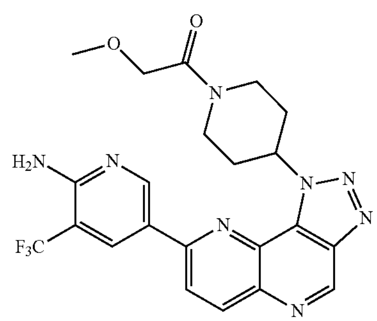 [SMILES: COCC(=O)N1CCC(n2nnc3cnc4ccc(-c5cnc(N)c(C(F)(F)F)c5)nc4c32)CC1] |
| 8 | 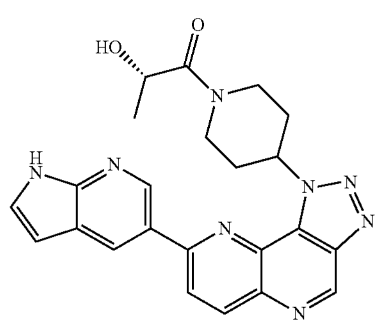 [SMILES: C[C@H](O)C(=O)N1CCC(n2nnc3cnc4ccc(-c5cnc6[nH]ccc6c5)nc4c32)CC1] |
| 9 | 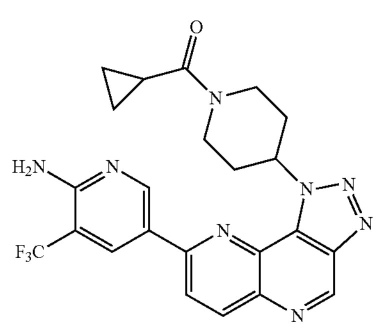 [SMILES: Nc1ncc(-c2ccc3ncc4nnn(C5CCN(C(=O)C6CC6)CC5)c4c3n2)cc1C(F)(F)F] |

132
-continued

| No. | Structure |
|---|---|
| 10 | 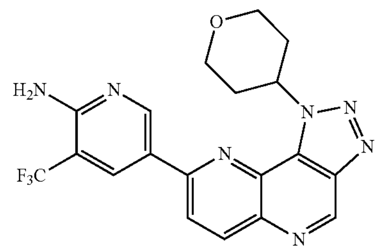 [SMILES: Nc1ncc(-c2ccc3ncc4nnn(C5CCOCC5)c4c3n2)cc1C(F)(F)F] |
| 11 | 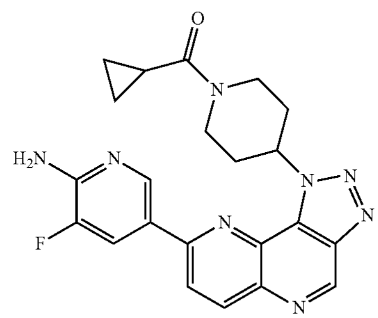 [SMILES: Nc1ncc(-c2ccc3ncc4nnn(C5CCN(C(=O)C6CC6)CC5)c4c3n2)cc1F] |
| 12 | 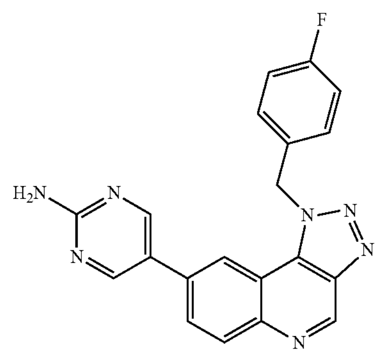 [SMILES: Nc1ncc(-c2ccc3ncc4nnn(Cc5ccc(F)cc5)c4c3c2)cn1] |
| 13 | 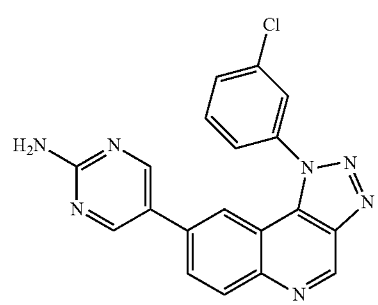 [SMILES: Nc1ncc(-c2ccc3ncc4nnn(-c5cccc(Cl)c5)c4c3c2)cn1] |
| 14 | 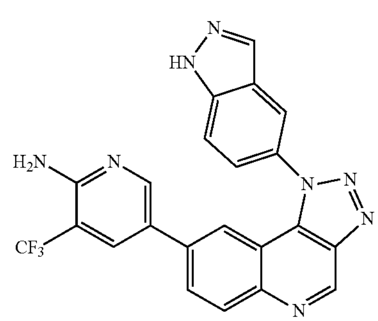 [SMILES: Nc1ncc(-c2ccc3ncc4nnn(-c5ccc6[nH]ncc6c5)c4c3c2)cc1C(F)(F)F] |

| No. | Structure |
|---|---|
| 15 | 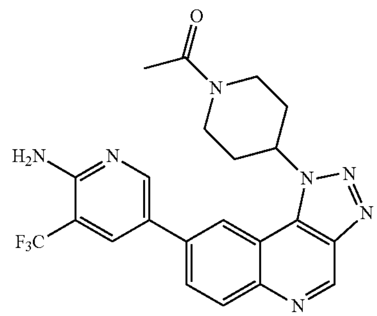 [SMILES: CC(=O)N1CCC(n2nnc3cnc4ccc(-c5cnc(N)c(C(F)(F)F)c5)cc4c32)CC1] |
| 16 | 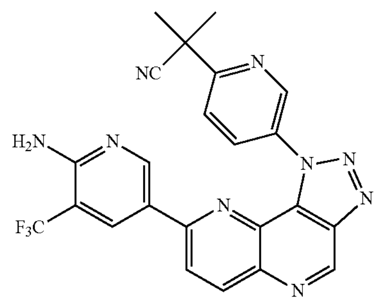 [SMILES: CC(C)(C#N)c1ccc(-n2nnc3cnc4ccc(-c5cnc(N)c(C(F)(F)F)c5)nc4c32)cn1] |
| 17 | 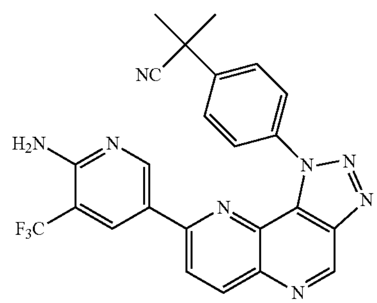 [SMILES: CC(C)(C#N)c1ccc(-n2nnc3cnc4ccc(-c5cnc(N)c(C(F)(F)F)c5)nc4c32)cc1] |
| 18 | 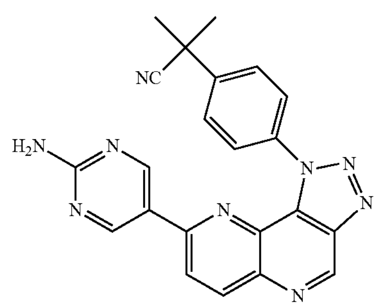 [SMILES: CC(C)(C#N)c1ccc(-n2nnc3cnc4ccc(-c5cnc(N)nc5)nc4c32)cc1] |
| 19 | 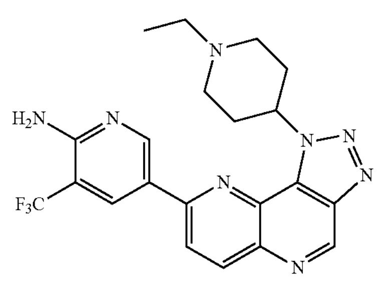 [SMILES: CCN1CCC(n2nnc3cnc4ccc(-c5cnc(N)c(C(F)(F)F)c5)nc4c32)CC1] |

| No. | Structure |
|---|---|
| 20 | 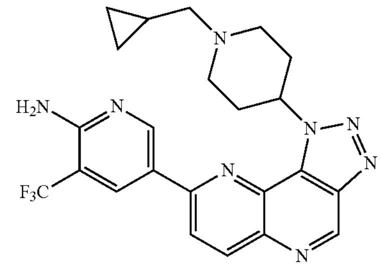 [SMILES: Nc1ncc(-c2ccc3ncc4nnn(C5CCN(CC6CC6)CC5)c4c3n2)cc1C(F)(F)F] |
| 21 | 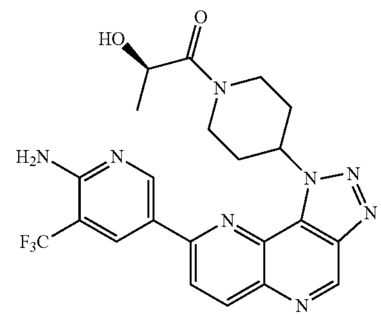 [SMILES: C[C@@H](O)C(=O)N1CCC(n2nnc3cnc4ccc(-c5cnc(N)c(C(F)(F)F)c5)nc4c32)CC1] |
| 22 | 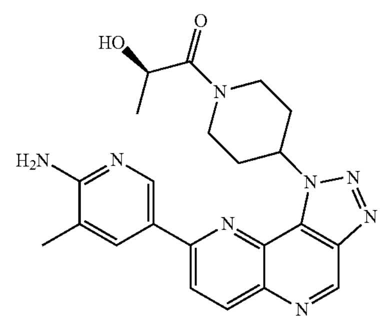 [SMILES: Cc1cc(-c2ccc3ncc4nnn(C5CCN(C(=O)[C@@H](C)O)CC5)c4c3n2)cnc1N] |
| 23 | 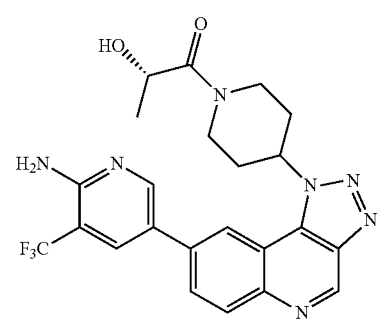 [SMILES: C[C@H](O)C(=O)N1CCC(n2nnc3cnc4ccc(-c5cnc(N)c(C(F)(F)F)c5)cc4c32)CC1] |
| 24 | 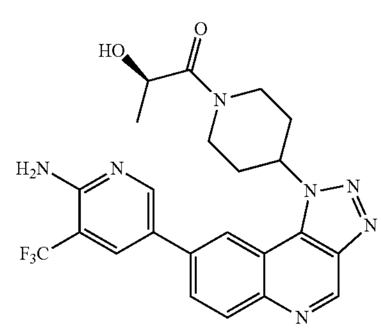 [SMILES: C[C@@H](O)C(=O)N1CCC(n2nnc3cnc4ccc(-c5cnc(N)c(C(F)(F)F)c5)cc4c32)CC1] |

| No. | Structure |
|---|---|
| 25 | 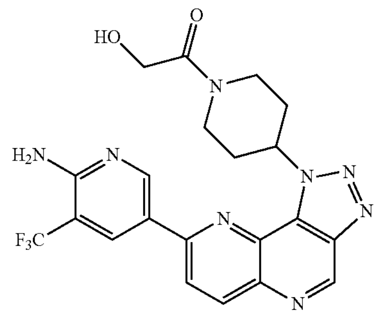 [SMILES: Nc1ncc(-c2ccc3ncc4nnn(C5CCN(C(=O)CO)CC5)c4c3n2)cc1C(F)(F)F] |
| 26 | 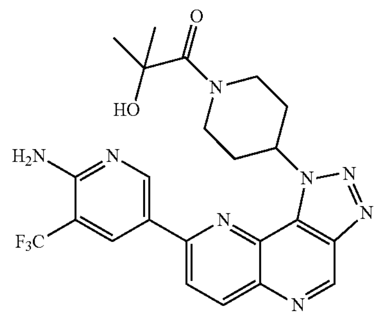 [SMILES: CC(C)(O)C(=O)N1CCC(n2nnc3cnc4ccc(-c5cnc(N)c(C(F)(F)F)c5)nc4c32)CC1] |
| 27 | 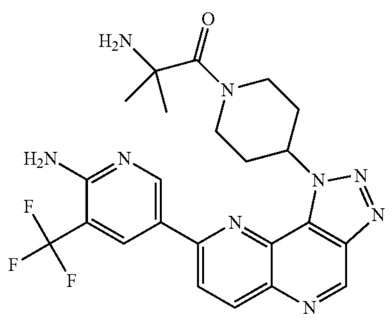 [SMILES: CC(C)(N)C(=O)N1CCC(n2nnc3cnc4ccc(-c5cnc(N)c(C(F)(F)F)c5)nc4c32)CC1] |
| 28 | 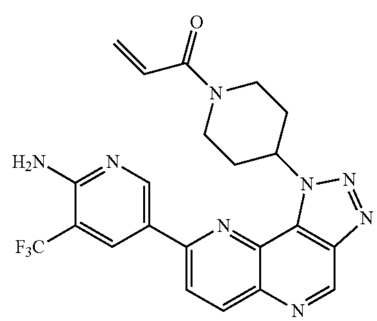 [SMILES: C=CC(=O)N1CCC(n2nnc3cnc4ccc(-c5cnc(N)c(C(F)(F)F)c5)nc4c32)CC1] |
| 29 | 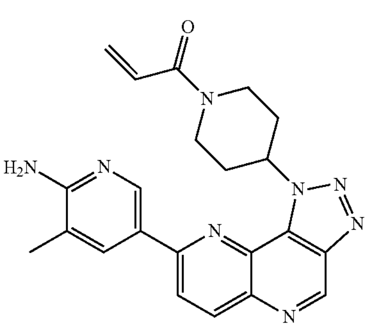 [SMILES: C=CC(=O)N1CCC(n2nnc3cnc4ccc(-c5cnc(N)c(C)c5)nc4c32)CC1] |
| 30 | |
| 31 | |
| 32 | |
| 33 | |
| 34 | |

| No. | Structure |
|---|---|
| 35 | 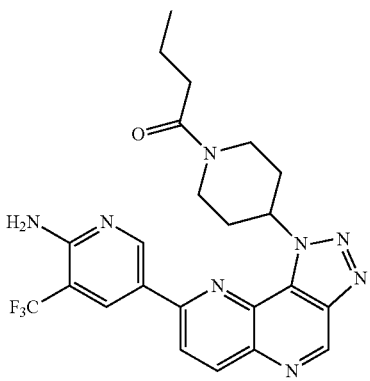 [SMILES: CCCC(=O)N1CCC(n2nnc3cnc4ccc(-c5cnc(N)c(C(F)(F)F)c5)nc4c32)CC1] |
| 36 | 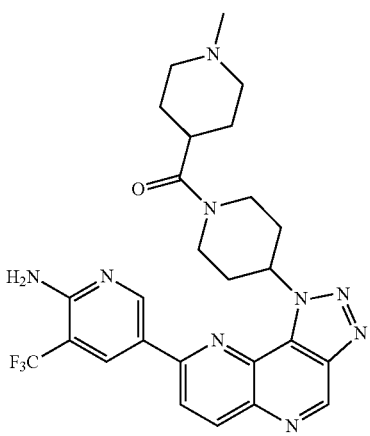 [SMILES: CN1CCC(C(=O)N2CCC(n3nnc4cnc5ccc(-c6cnc(N)c(C(F)(F)F)c6)nc5c43)CC2)CC1] |
| 37 | 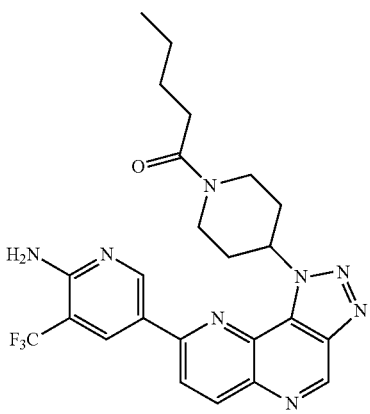 [SMILES: CCCCC(=O)N1CCC(n2nnc3cnc4ccc(-c5cnc(N)c(C(F)(F)F)c5)nc4c32)CC1] |
| 38 | 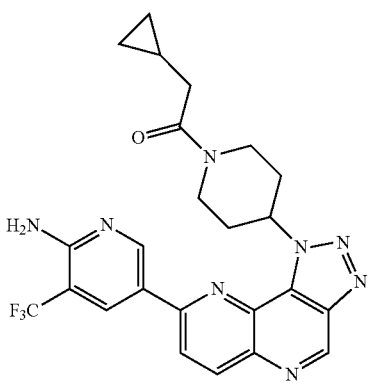 [SMILES: Nc1ncc(-c2ccc3ncc4nnn(C5CCN(C(=O)CC6CC6)CC5)c4c3n2)cc1C(F)(F)F] |
| No. | Structure |
|---|---|
| 39 | 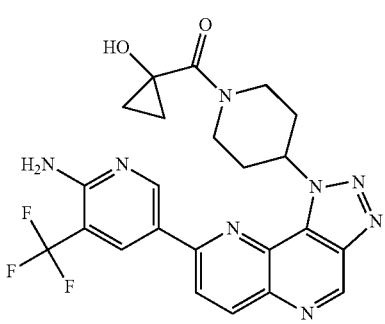 [SMILES: Nc1ncc(-c2ccc3ncc4nnn(C5CCN(C(=O)C6(O)CC6)CC5)c4c3n2)cc1C(F)(F)F] |
| 40 | 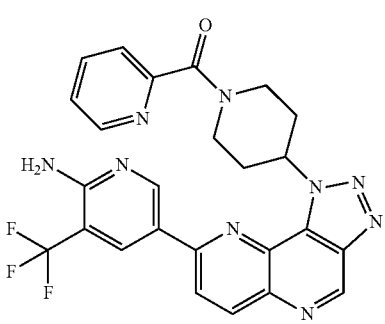 [SMILES: Nc1ncc(-c2ccc3ncc4nnn(C5CCN(C(=O)c6ccccn6)CC5)c4c3n2)cc1C(F)(F)F] |
| 41 | |
| 42 | 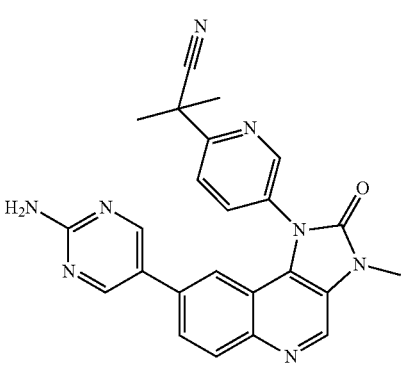 [SMILES: Cn1c(=O)n(-c2ccc(C(C)(C)C#N)nc2)c2c3cc(-c4cnc(N)nc4)ccc3ncc21] |

| No. | Structure | | No. | Structure |
|---|---|---|---|---|
| 43 | 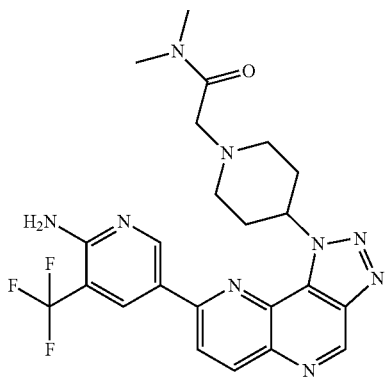 [SMILES: CN(C)C(=O)CN1CCC(n2nnc3cnc4ccc(-c5cnc(N)c(C(F)(F)F)c5)nc4c32)CC1] | | 47 | 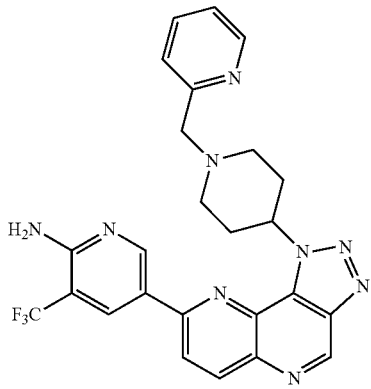 |
| 44 | 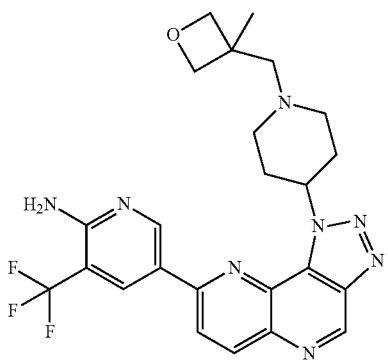 [SMILES: CC1(CN2CCC(n3nnc4cnc5ccc(-c6cnc(N)c(C(F)(F)F)c6)nc5c43)CC2)COC1] | | 48 | 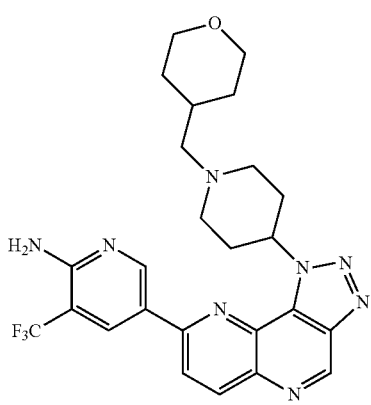 [SMILES: Nc1ncc(-c2ccc3ncc4nnn(C5CCN(CC6CCOCC6)CC5)c4c3n2)cc1C(F)(F)F] |
| 45 | 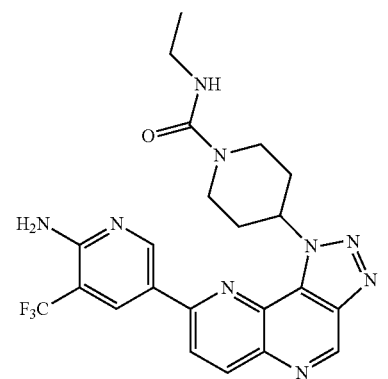 | | 49 | 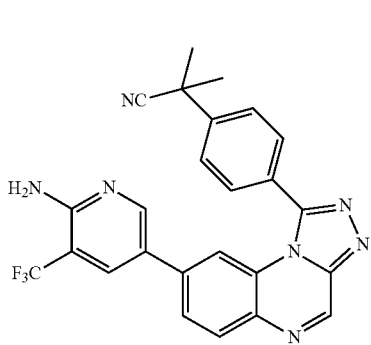 [SMILES: CC(C)(C#N)c1ccc(-c2nnc3cnc4ccc(-c5cnc(N)c(C(F)(F)F)c5)cc4n23)cc1] |
| 46 | 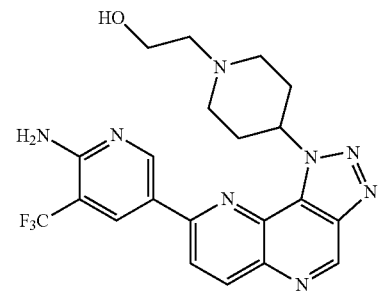 | | 50 | 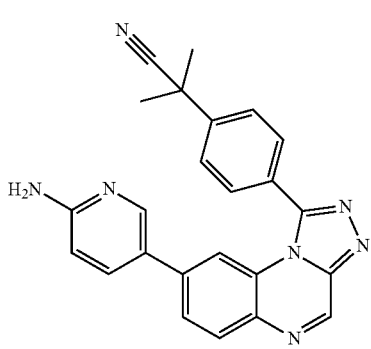 [SMILES: CC(C)(C#N)c1ccc(-c2nnc3cnc4ccc(-c5ccc(N)nc5)cc4n23)cc1] |

141
-continued
| No. | Structure |
|---|---|
| 51 | |
| 52 | |
| 53 | |
| 54 | |
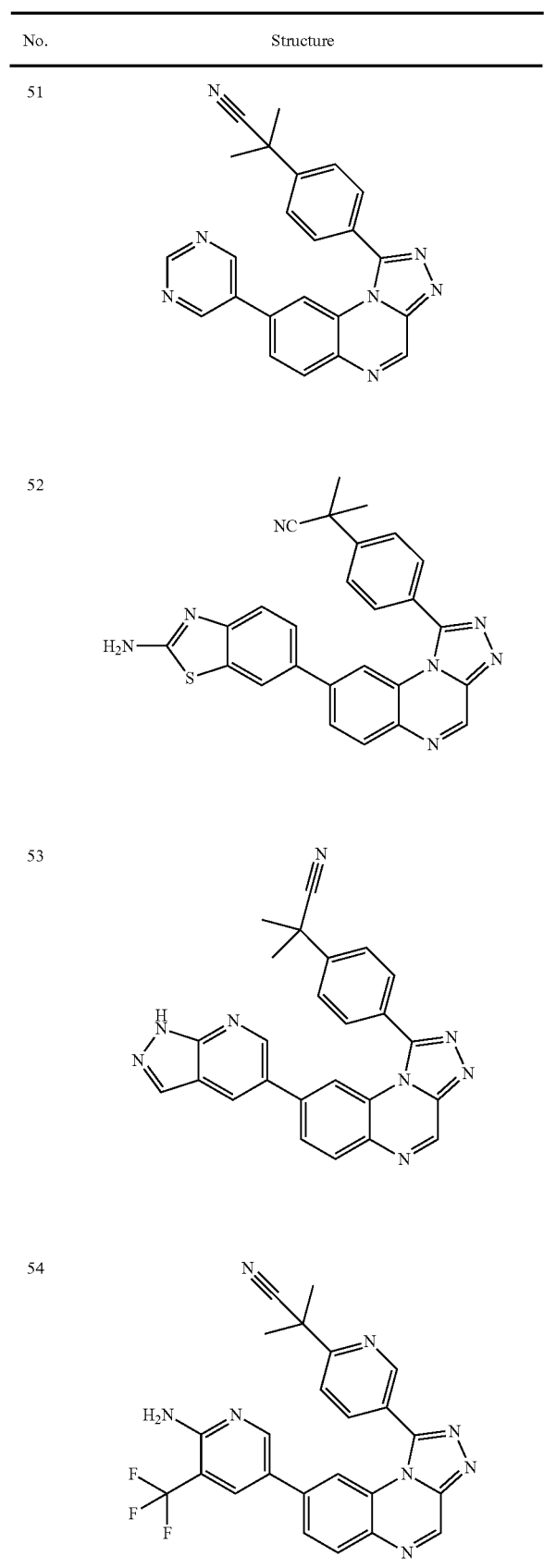
142
-continued
| No. | Structure |
|---|---|
| 55 | 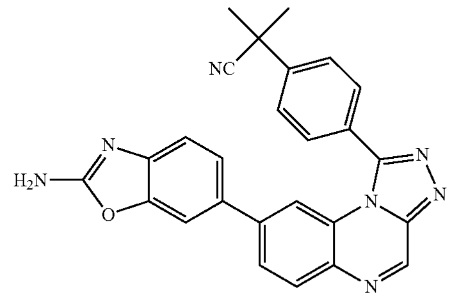 [SMILES: CC(C)(C#N)c1ccc(-c2nnc3cnc4ccc(-c5ccc6nc(N)oc6c5)cc4n23)cc1] |
| 56 | 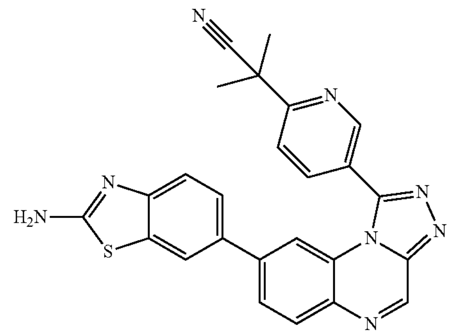 [SMILES: CC(C)(C#N)c1ccc(-c2nnc3cnc4ccc(-c5ccc6nc(N)sc6c5)cc4n23)cn1] |
| 57 | 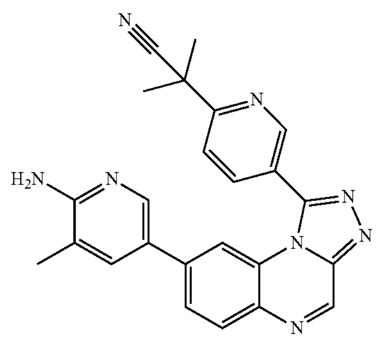 [SMILES: Cc1cc(-c2ccc3ncc4nnc(-c5ccc(C(C)(C)C#N)nc5)n4c3c2)cnc1N] |
| 58 | 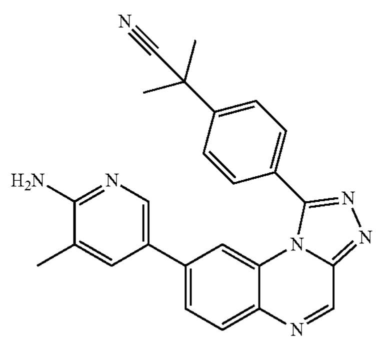 [SMILES: Cc1cc(-c2ccc3ncc4nnc(-c5ccc(C(C)(C)C#N)cc5)n4c3c2)cnc1N] |
| 59 | 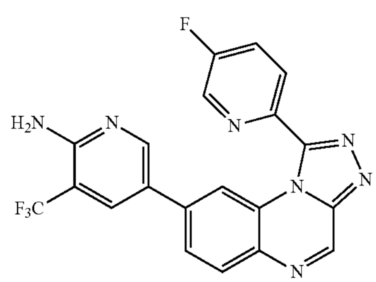 [SMILES: Nc1ncc(-c2ccc3ncc4nnc(-c5ccc(F)cn5)n4c3c2)cc1C(F)(F)F] |
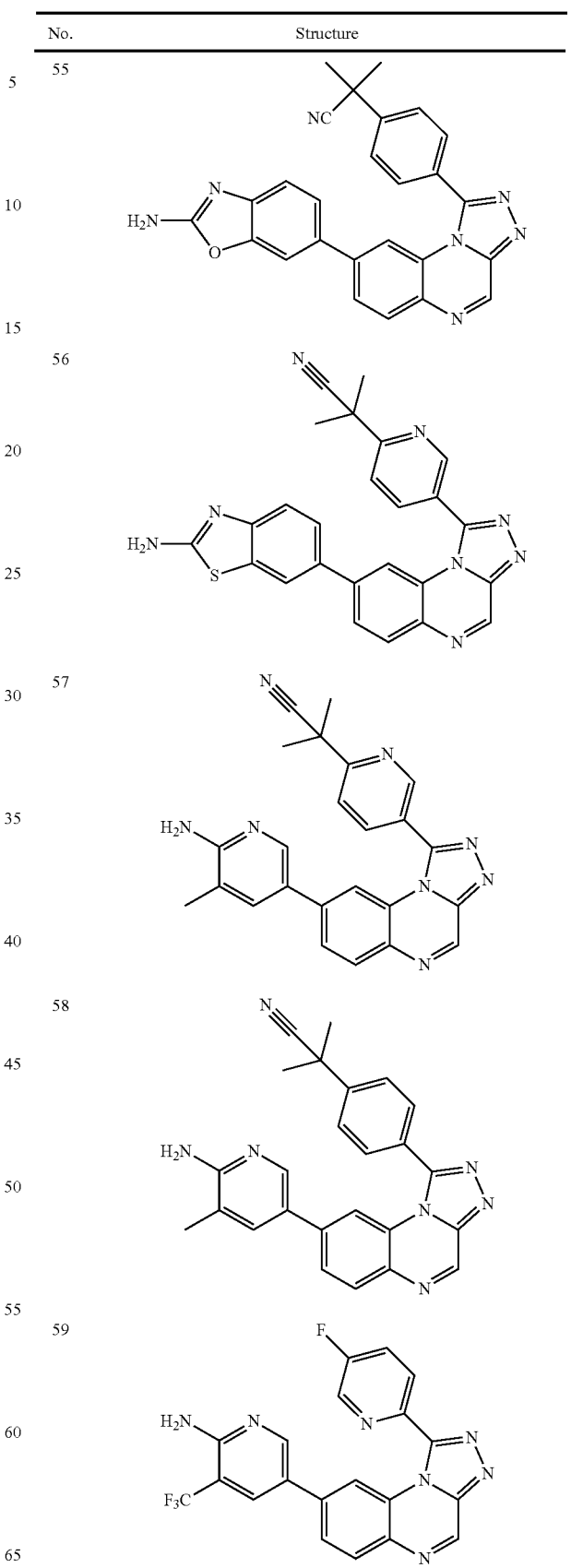

TABLE-continued
| No. | Structure |
|---|---|
| 60 | 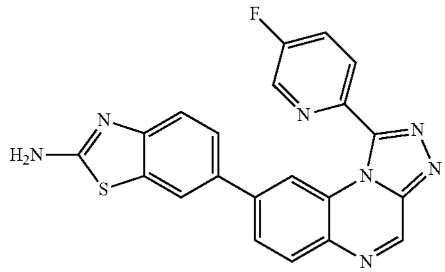 [SMILES: Nc1nc2ccc(-c3ccc4ncc5nnc(-c6ccc(F)cn6)n5c4c3)cc2s1] |
| 61 | 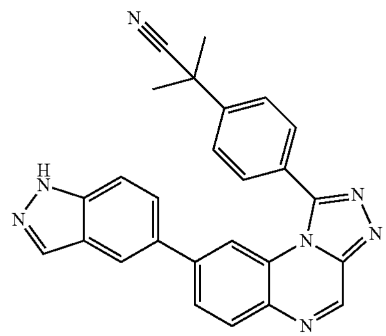 [SMILES: CC(C)(C#N)c1ccc(-c2nnc3cnc4ccc(-c5ccc6[nH]ncc6c5)cc4n23)cc1] |
| 62 | 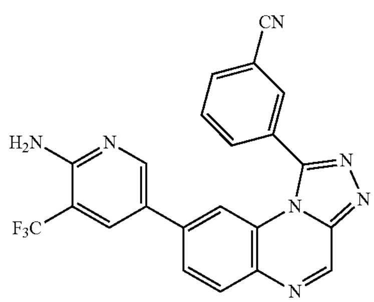 [SMILES: N#Cc1cccc(-c2nnc3cnc4ccc(-c5cnc(N)c(C(F)(F)F)c5)cc4n23)c1] |
| 63 | 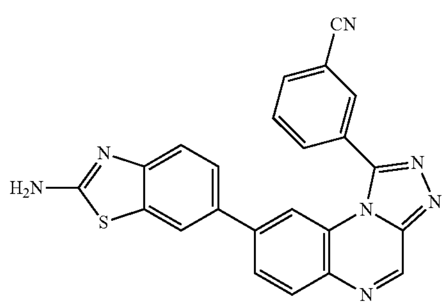 [SMILES: N#Cc1cccc(-c2nnc3cnc4ccc(-c5ccc6nc(N)sc6c5)cc4n23)c1] |
| 64 | 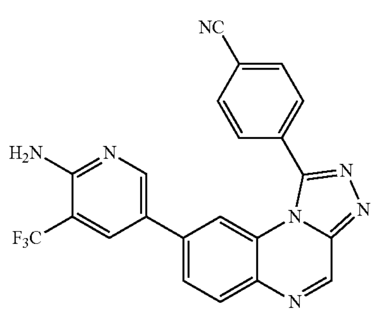 [SMILES: N#Cc1ccc(-c2nnc3cnc4ccc(-c5cnc(N)c(C(F)(F)F)c5)cc4n23)cc1] |
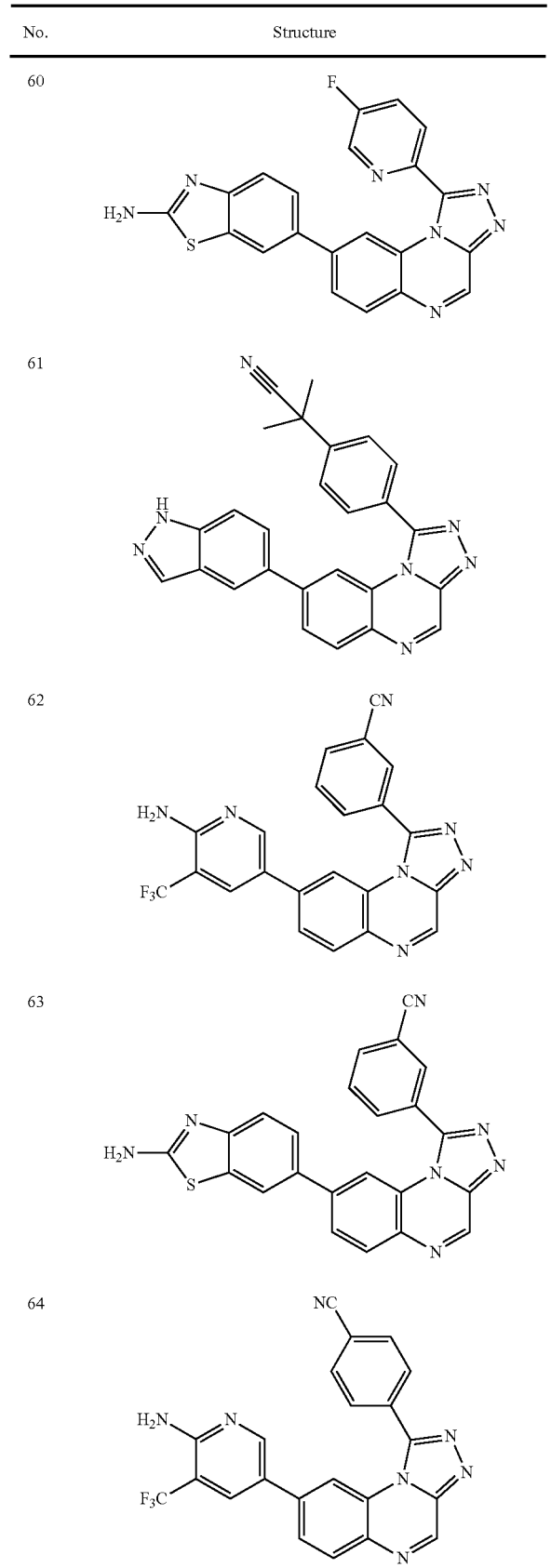
TABLE-continued
| No. | Structure |
|---|---|
| 65 | 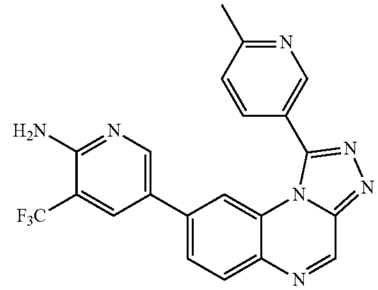 [SMILES: Cc1ccc(-c2nnc3cnc4ccc(-c5cnc(N)c(C(F)(F)F)c5)cc4n23)cn1] |
| 66 | 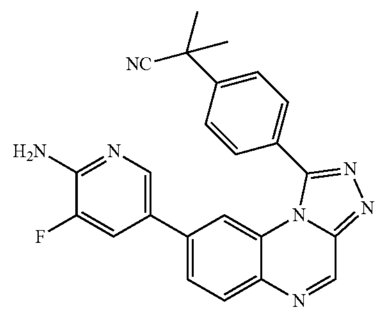 [SMILES: CC(C)(C#N)c1ccc(-c2nnc3cnc4ccc(-c5cnc(N)c(F)c5)cc4n23)cc1] |
| 67 | 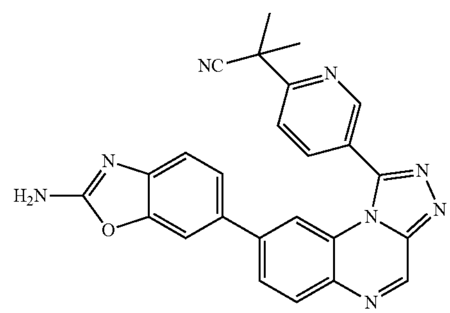 [SMILES: CC(C)(C#N)c1ccc(-c2nnc3cnc4ccc(-c5ccc6nc(N)oc6c5)cc4n23)cn1] |
| 68 | 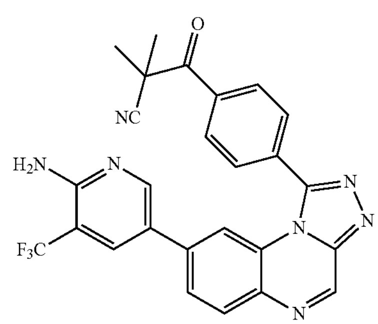 [SMILES: CC(C)(C#N)C(=O)c1ccc(-c2nnc3cnc4ccc(-c5cnc(N)c(C(F)(F)F)c5)cc4n23)cc1] |
| 69 | 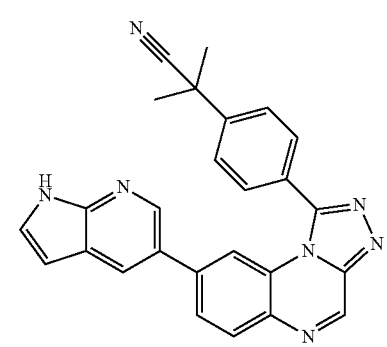 [SMILES: CC(C)(C#N)c1ccc(-c2nnc3cnc4ccc(-c5cnc6[nH]ccc6c5)cc4n23)cc1] |
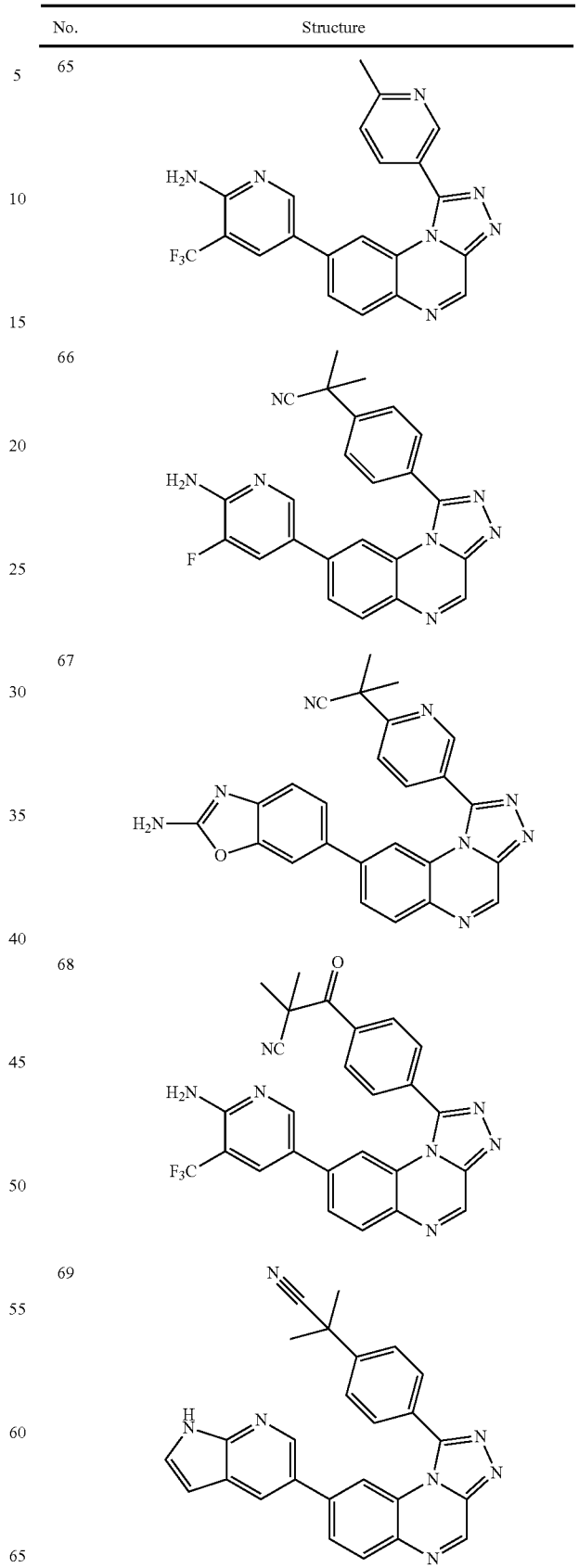

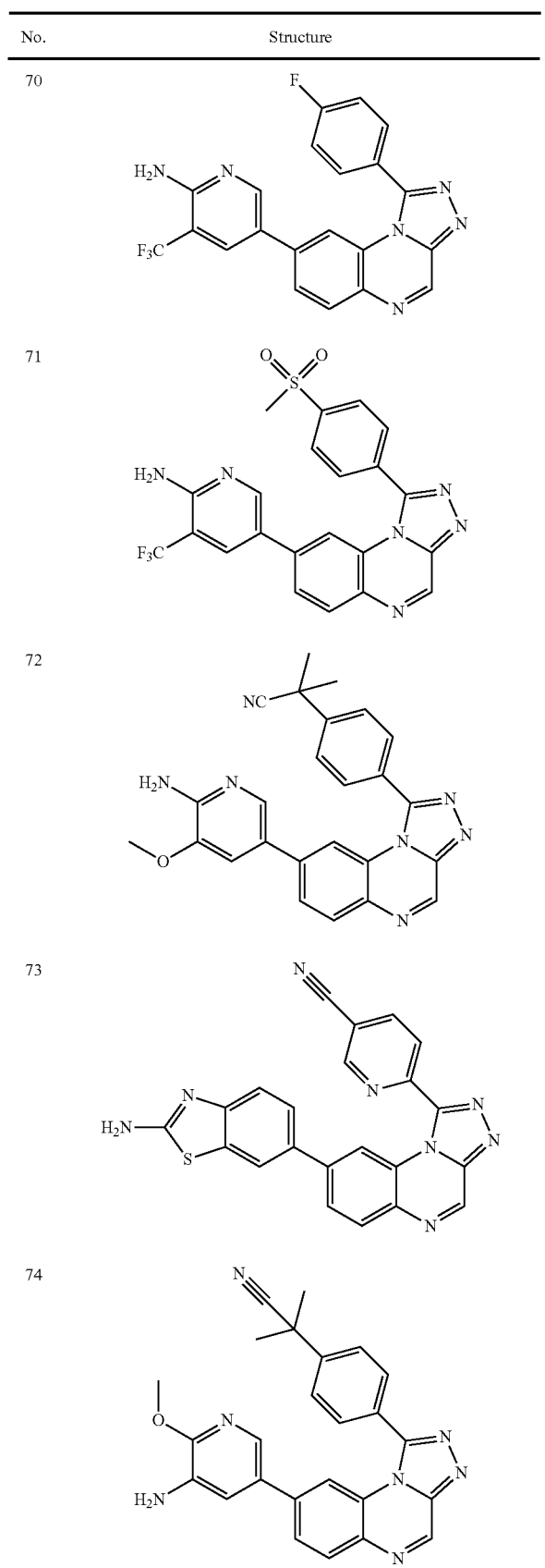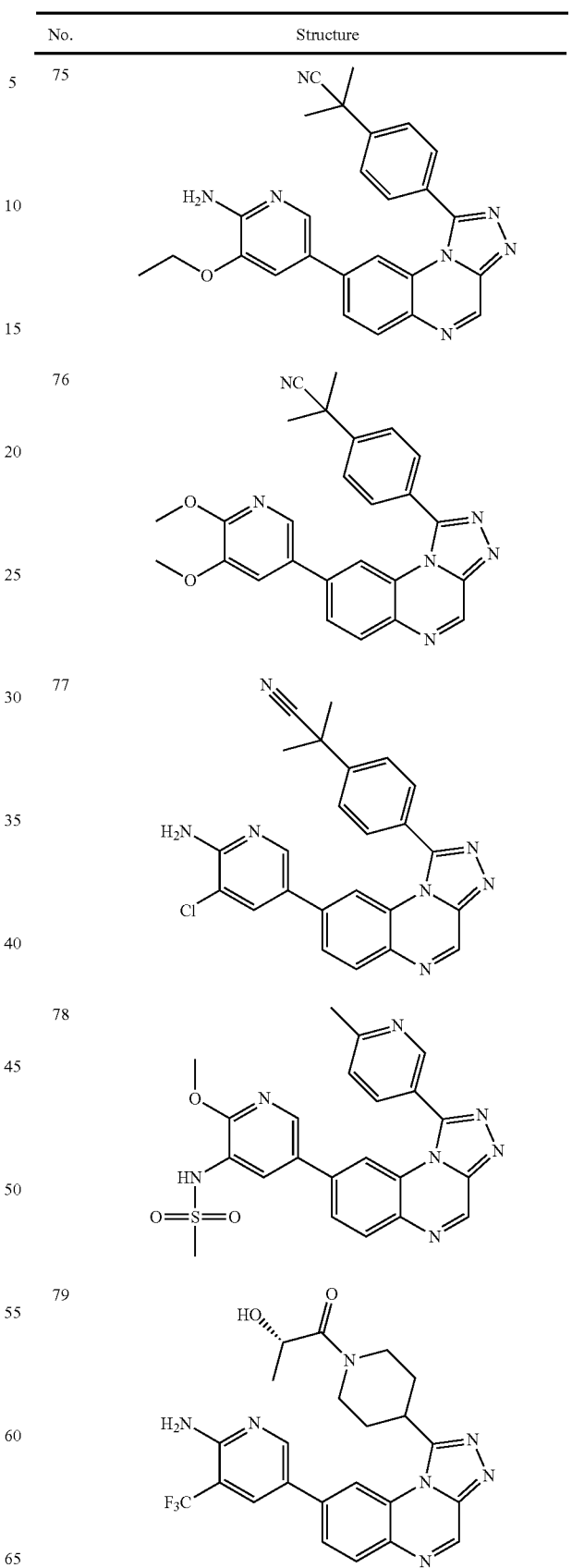

147
-continued

| No. | Structure |
|---|---|
| 80 | |
| 81 | |
| 82 | |
| 83 | |

148
-continued

| No. | Structure |
|---|---|
| 84 | 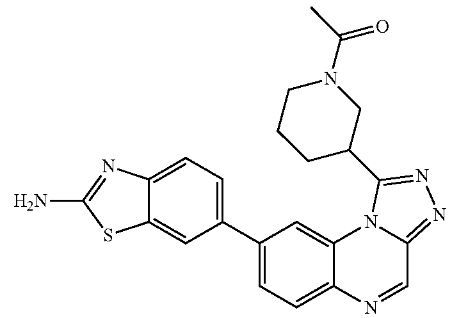 [SMILES: CC(=O)N1CCCC(c2nnc3cnc4ccc(-c5ccc6nc(N)sc6c5)cc4n23)C1] |
| 85 | 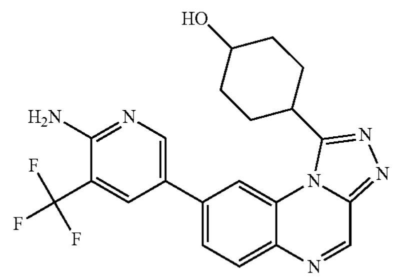 [SMILES: Nc1ncc(-c2ccc3ncc4nnc(C5CCC(O)CC5)n4c3c2)cc1C(F)(F)F] |
| 86 | 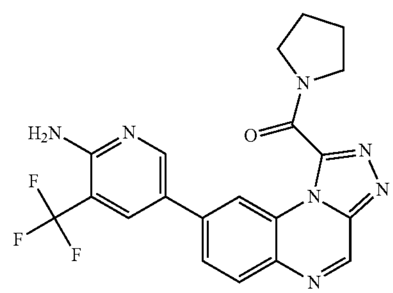 [SMILES: Nc1ncc(-c2ccc3ncc4nnc(C(=O)N5CCCC5)n4c3c2)cc1C(F)(F)F] |
| 87 | 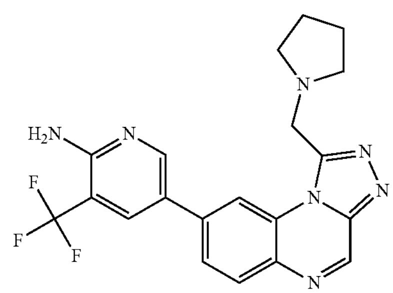 [SMILES: Nc1ncc(-c2ccc3ncc4nnc(CN5CCCC5)n4c3c2)cc1C(F)(F)F] |
| 88 | 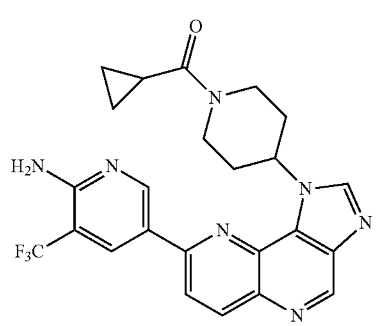 [SMILES: Nc1ncc(-c2ccc3ncc4ncn(C5CCN(C(=O)C6CC6)CC5)c4c3n2)cc1C(F)(F)F] |

| No. | Structure |
|---|---|
| 89 | 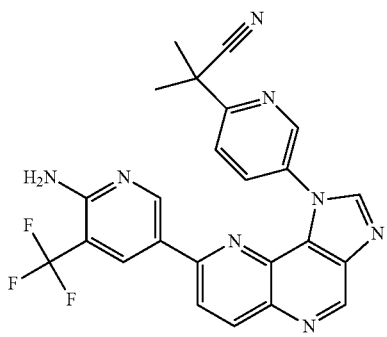 [SMILES: CC(C)(C#N)c1ccc(-n2cnc3cnc4ccc(-c5cnc(N)c(C(F)(F)F)c5)nc4c32)cn1] |
| 90 | 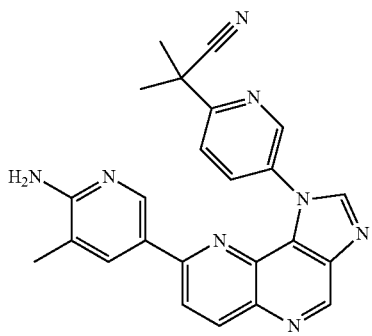 [SMILES: Cc1cc(-c2ccc3ncc4ncn(-c5ccc(C(C)(C)C#N)nc5)c4c3n2)cnc1N] |
| 91 | 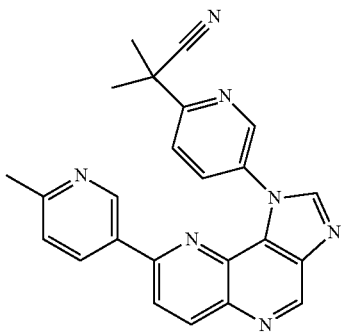 [SMILES: Cc1ccc(-c2ccc3ncc4ncn(-c5ccc(C(C)(C)C#N)nc5)c4c3n2)cn1] |
| 92 | 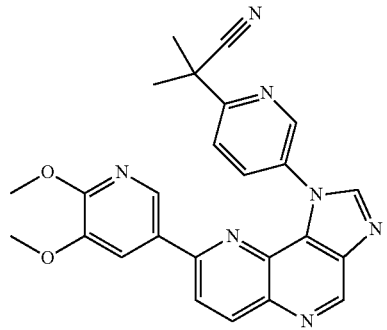 [SMILES: COc1cc(-c2ccc3ncc4ncn(-c5ccc(C(C)(C)C#N)nc5)c4c3n2)cnc1OC] |
| No. | Structure |
|---|---|
| 93 | 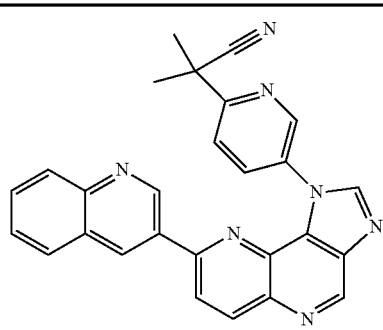 |
| 94 | 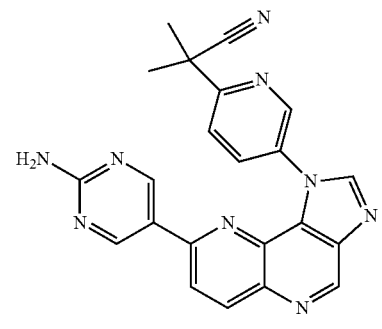 [SMILES: CC(C)(C#N)c1ccc(-n2cnc3cnc4ccc(-c5cnc(N)nc5)nc4c32)cn1] |
| 95 | 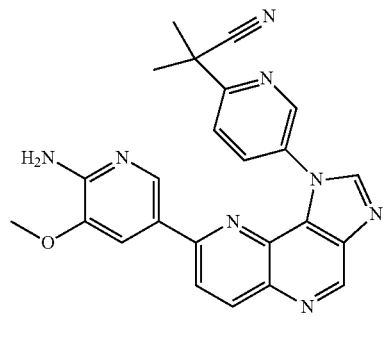 [SMILES: COc1cc(-c2ccc3ncc4ncn(-c5ccc(C(C)(C)C#N)nc5)c4c3n2)cnc1N] |
| 96 | 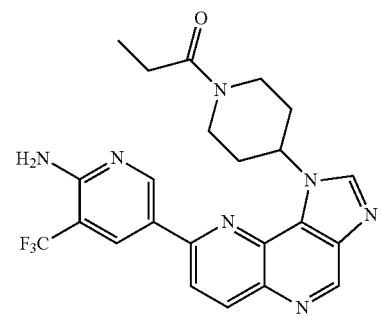 [SMILES: CCC(=O)N1CCC(n2cnc3cnc4ccc(-c5cnc(N)c(C(F)(F)F)c5)nc4c32)CC1] |

| No. | Structure |
|---|---|
| 97 | 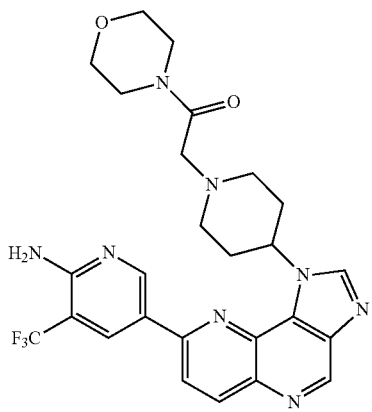 [SMILES: Nc1ncc(-c2ccc3ncc4ncn(C5CCN(CC(=O)N6CCOCC6)CC5)c4c3n2)cc1C(F)(F)F] |
| 98 | 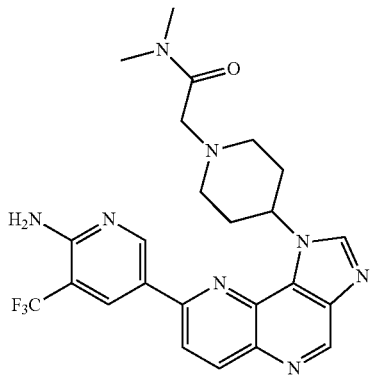 [SMILES: CN(C)C(=O)CN1CCC(n2cnc3cnc4ccc(-c5cnc(N)c(C(F)(F)F)c5)nc4c32)CC1] |
| 99 | 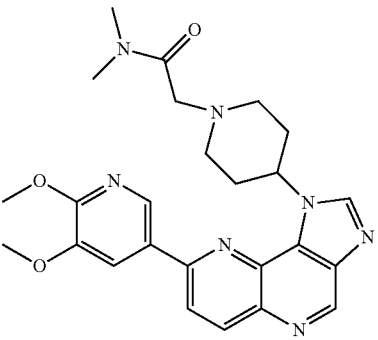 [SMILES: COc1cc(-c2ccc3ncc4ncn(C5CCN(CC(=O)N(C)C)CC5)c4c3n2)cnc1OC] |
| 100 | 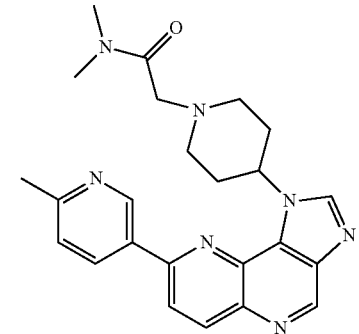 [SMILES: Cc1ccc(-c2ccc3ncc4ncn(C5CCN(CC(=O)N(C)C)CC5)c4c3n2)cn1] |
| No. | Structure |
|---|---|
| 101 | 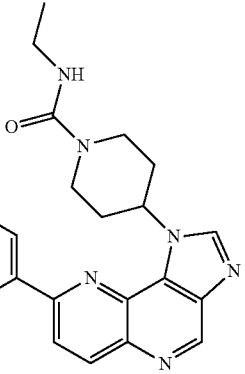 |
| 102 | 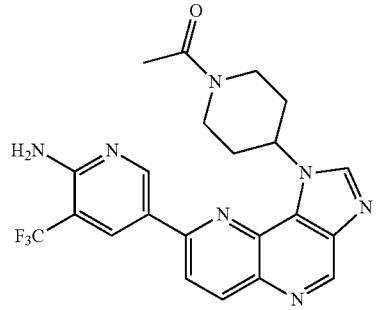 [SMILES: CC(=O)N1CCC(n2cnc3cnc4ccc(-c5cnc(N)c(C(F)(F)F)c5)nc4c32)CC1] |
| 103 | 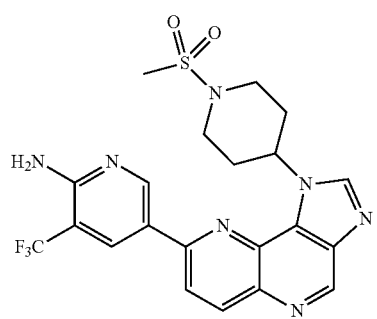 [SMILES: CS(=O)(=O)N1CCC(n2cnc3cnc4ccc(-c5cnc(N)c(C(F)(F)F)c5)nc4c32)CC1] |
| 104 | 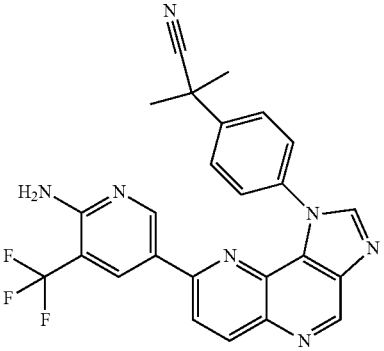 [SMILES: CC(C)(C#N)c1ccc(-n2cnc3cnc4ccc(-c5cnc(N)c(C(F)(F)F)c5)nc4c32)cc1] |

153
-continued
| No. | Structure |
|---|---|
| 105 | 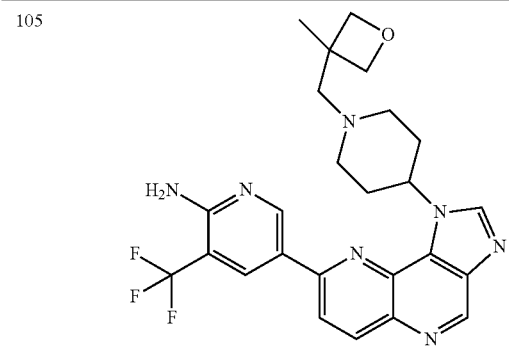 |
| 106 | 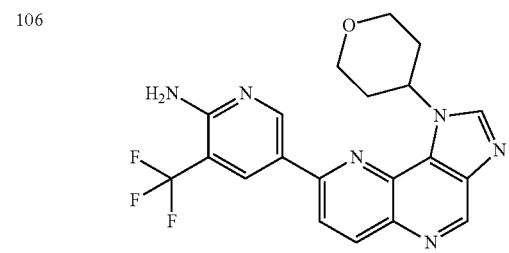 |
| 107 | 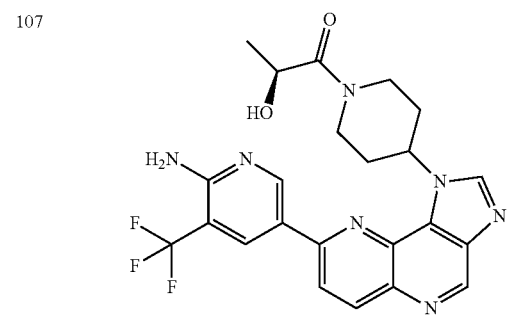 |
| 108 | 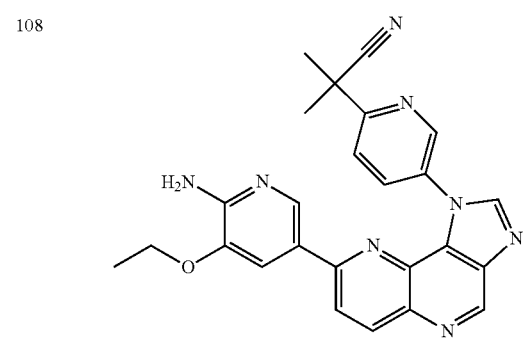 |
| 109 | 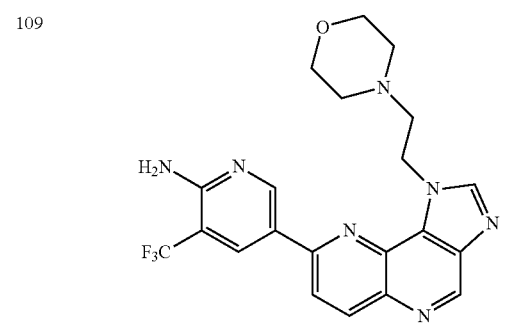 |
154
-continued
| No. | Structure |
|---|---|
| 110 | 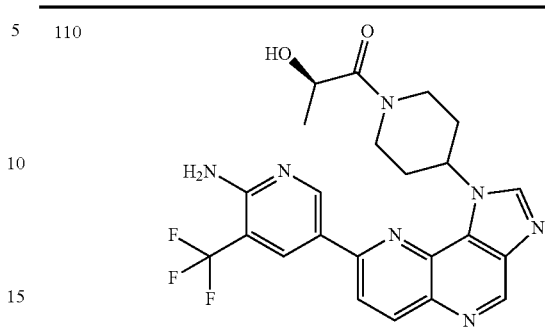 |
| 111 | 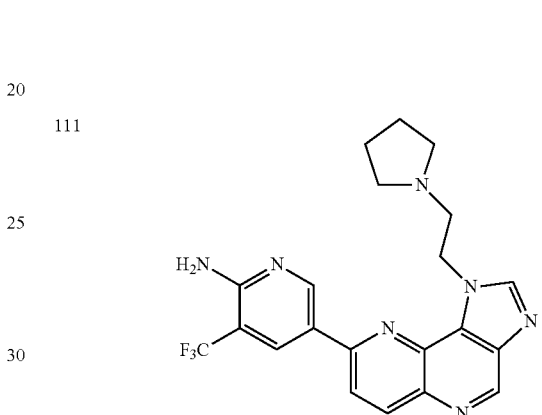 |
| 112 | 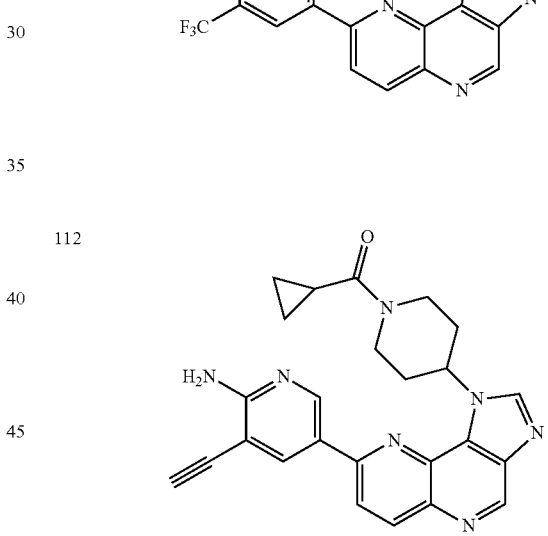 |
| 113 | 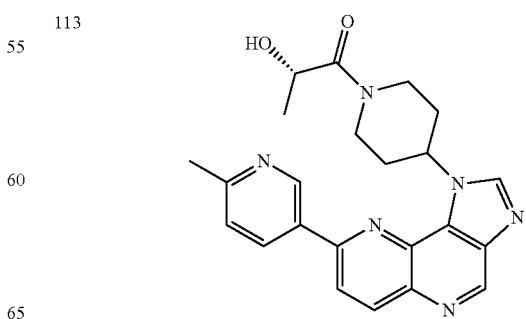 |

-continued
| No. | Structure |
|---|---|
| 114 | 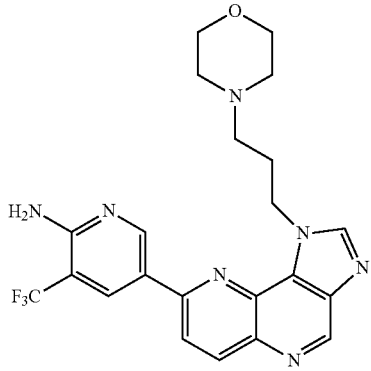 [SMILES: Nc1ncc(-c2ccc3ncc4ncn(CCCN5CCOCC5)c4c3n2)cc1C(F)(F)F] |
| 115 | 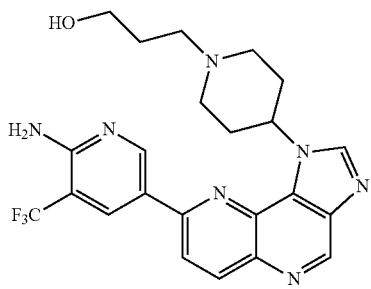 [SMILES: Nc1ncc(-c2ccc3ncc4ncn(C5CCN(CCCO)CC5)c4c3n2)cc1C(F)(F)F] |
| 116 | 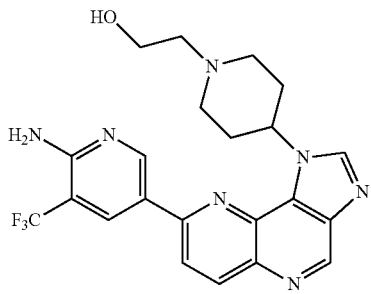 |
| 117 | 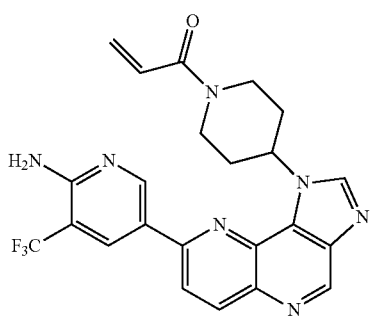 |
| 118 | 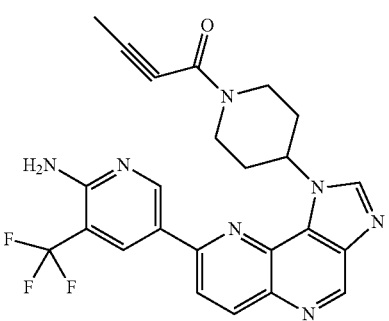 [SMILES: CC#CC(=O)N1CCC(n2cnc3cnc4ccc(-c5cnc(N)c(C(F)(F)F)c5)nc4c32)CC1] |
-continued
| No. | Structure |
|---|---|
| 119 | 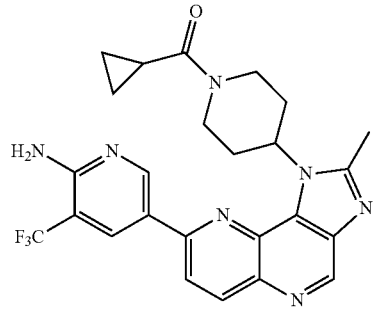 [SMILES: Cc1nc2cnc3ccc(-c4cnc(N)c(C(F)(F)F)c4)nc3c2n1C1CCN(C(=O)C2CC2)CC1] |
| 120 | 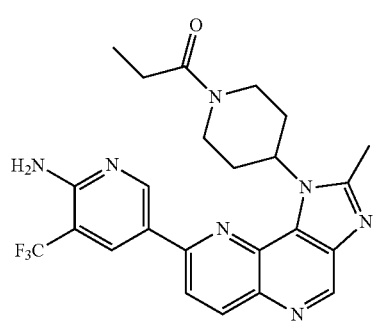 [SMILES: CCC(=O)N1CCC(n2c(C)nc3cnc4ccc(-c5cnc(N)c(C(F)(F)F)c5)nc4c32)CC1] |
| 121 | 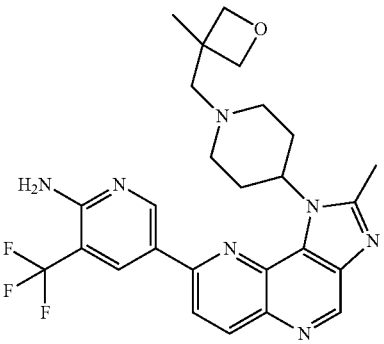 [SMILES: Cc1nc2cnc3ccc(-c4cnc(N)c(C(F)(F)F)c4)nc3c2n1C1CCN(CC2(C)COC2)CC1] |
| 122 | 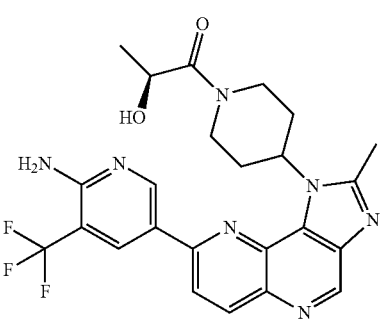 [SMILES: Cc1nc2cnc3ccc(-c4cnc(N)c(C(F)(F)F)c4)nc3c2n1C1CCN(C(=O)[C@H](C)O)CC1] |

-continued

| No. | Structure |
|---|---|
| 123 | 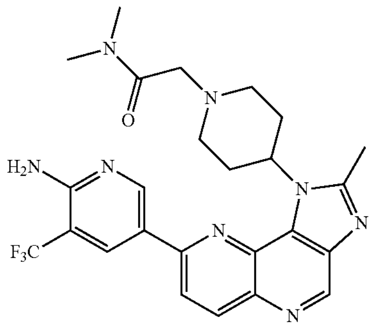 [SMILES: Cc1nc2cnc3ccc(-c4cnc(N)c(C(F)(F)F)c4)nc3c2n1C1CCN(CC(=O)N(C)C)CC1] |
| 124 | 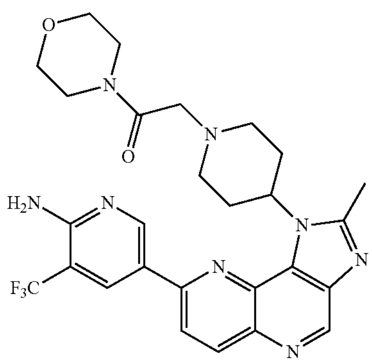 [SMILES: Cc1nc2cnc3ccc(-c4cnc(N)c(C(F)(F)F)c4)nc3c2n1C1CCN(CC(=O)N2CCOCC2)CC1] |
| 125 | 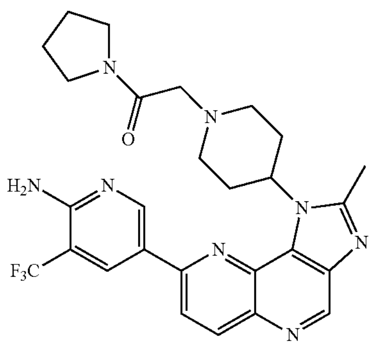 [SMILES: Cc1nc2cnc3ccc(-c4cnc(N)c(C(F)(F)F)c4)nc3c2n1C1CCN(CC(=O)N2CCCC2)CC1] |
| 126 | 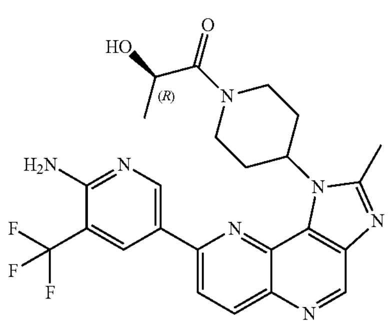 |

-continued

| No. | Structure |
|---|---|
| 127 | 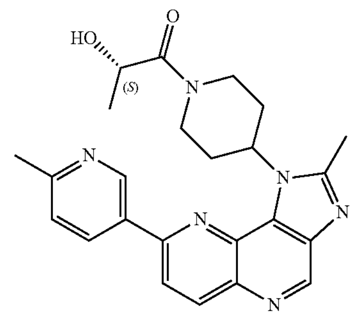 |
| 128 | 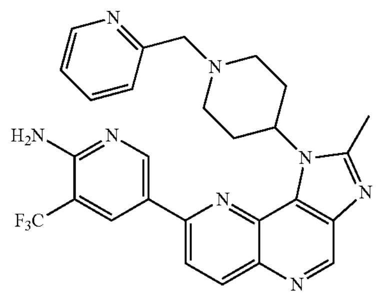 [SMILES: Cc1nc2cnc3ccc(-c4cnc(N)c(C(F)(F)F)c4)nc3c2n1C1CCN(Cc2ccccn2)CC1] |
| 129 | 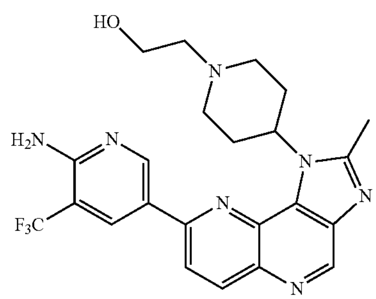 [SMILES: Cc1nc2cnc3ccc(-c4cnc(N)c(C(F)(F)F)c4)nc3c2n1C1CCN(CCO)CC1] |
| 130 | 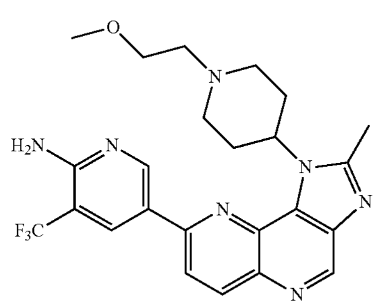 [SMILES: COCCN1CCC(n2c(C)nc3cnc4ccc(-c5cnc(N)c(C(F)(F)F)c5)nc4c32)CC1] |
| 131 | 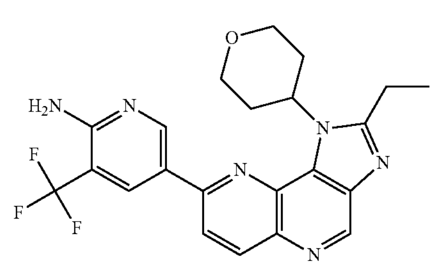 [SMILES: CCc1nc2cnc3ccc(-c4cnc(N)c(C(F)(F)F)c4)nc3c2n1C1CCOCC1] |

159
-continued
| No. | Structure |
|---|---|
| 132 | 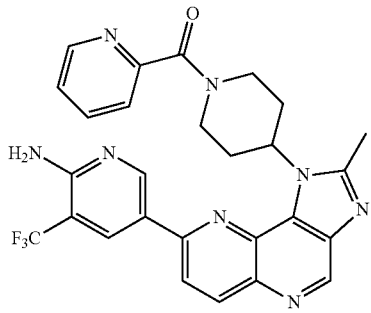 [SMILES: Cc1nc2cnc3ccc(-c4cnc(N)c(C(F)(F)F)c4)nc3c2n1C1CCN(C(=O)c2ccccn2)CC1] |
| 133 | 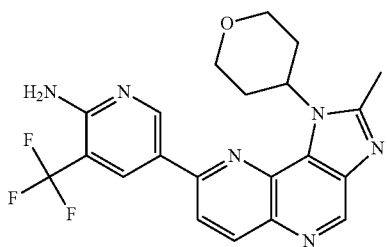 [SMILES: Cc1nc2cnc3ccc(-c4cnc(N)c(C(F)(F)F)c4)nc3c2n1C1CCOCC1] |
| 134 | 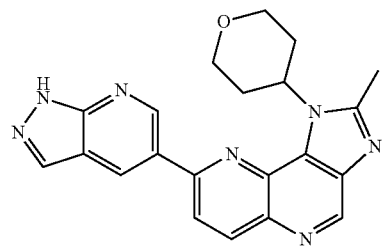 [SMILES: Cc1nc2cnc3ccc(-c4cnc5[nH]ncc5c4)nc3c2n1C1CCOCC1] |
| 135 | 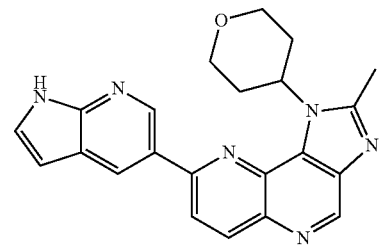 [SMILES: Cc1nc2cnc3ccc(-c4cnc5[nH]ccc5c4)nc3c2n1C1CCOCC1] |
| 136 | 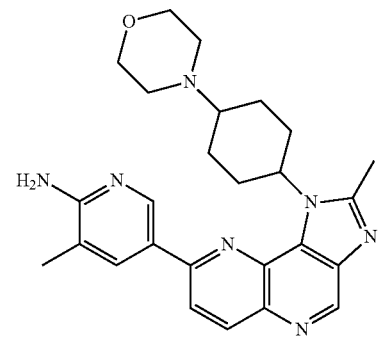 |
160
-continued
| No. | Structure |
|---|---|
| 137 | 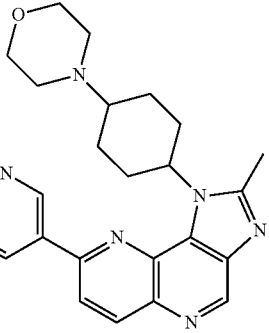 |
| 138 | 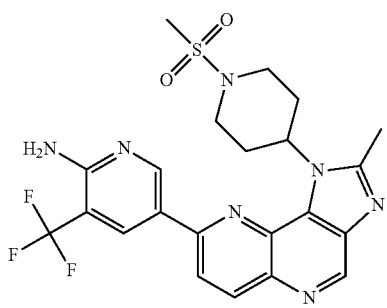 [SMILES: Cc1nc2cnc3ccc(-c4cnc(N)c(C(F)(F)F)c4)nc3c2n1C1CCN(S(C)(=O)=O)CC1] |
| 139 | 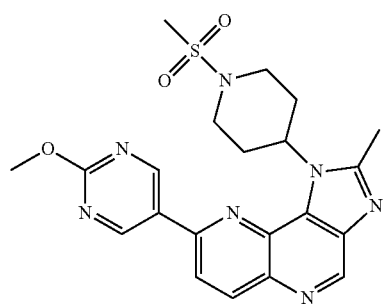 |
| 140 | 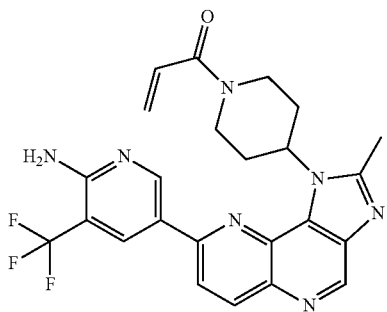 [SMILES: C=CC(=O)N1CCC(n2c(C)nc3cnc4ccc(-c5cnc(N)c(C(F)(F)F)c5)nc4c32)CC1] |
| 141 | 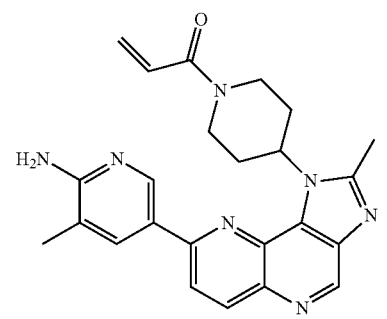 [SMILES: C=CC(=O)N1CCC(n2c(C)nc3cnc4ccc(-c5cnc(N)c(C)c5)nc4c32)CC1] |

161
-continued

| No. | Structure |
|---|---|
| 142 | 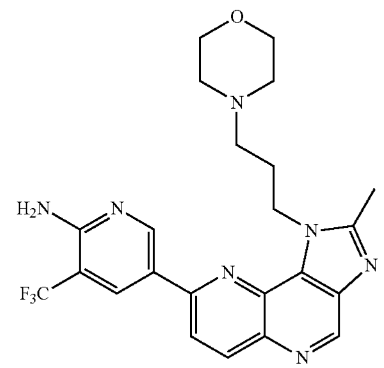 [SMILES: Cc1nc2cnc3ccc(-c4cnc(N)c(C(F)(F)F)c4)nc3c2n1CCCN1CCOCC1] |
| 143 | 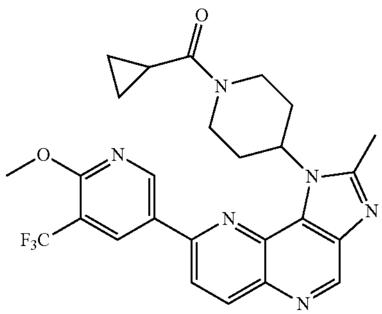 |
| 144 | 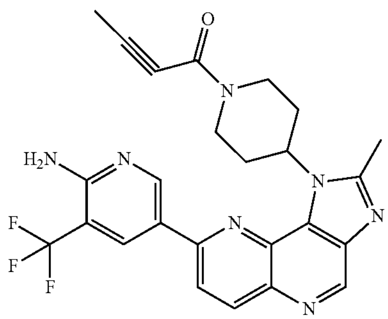 [SMILES: CC#CC(=O)N1CCC(n2c(C)nc3cnc4ccc(-c5cnc(N)c(C(F)(F)F)c5)nc4c32)CC1] |
| 145 | 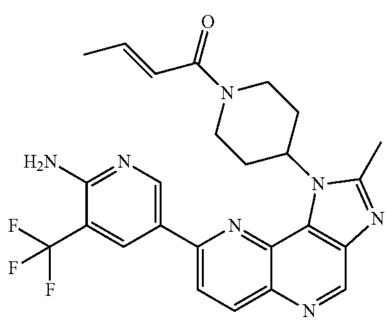 [SMILES: C/C=C/C(=O)N1CCC(n2c(C)nc3cnc4ccc(-c5cnc(N)c(C(F)(F)F)c5)nc4c32)CC1] |
| 146 | 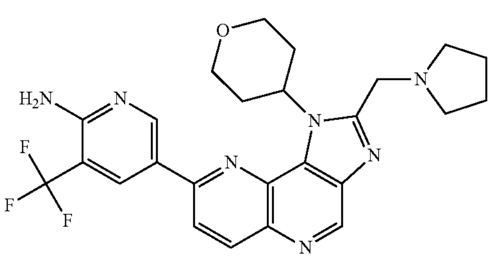 [SMILES: Nc1ncc(-c2ccc3ncc4nc(CN5CCCC5)n(C5CCOCC5)c4c3n2)cc1C(F)(F)F] |

162
-continued

| No. | Structure |
|---|---|
| 147 | 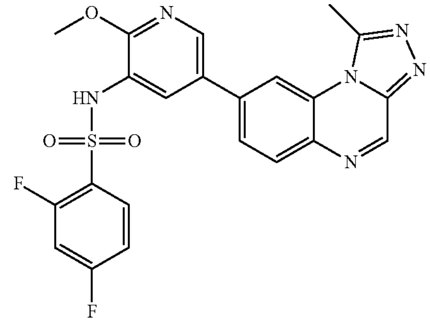 [SMILES: COc1ncc(-c2ccc3ncc4nnc(C)n4c3c2)cc1NS(=O)(=O)c1ccc(F)cc1F] |
| 148 | 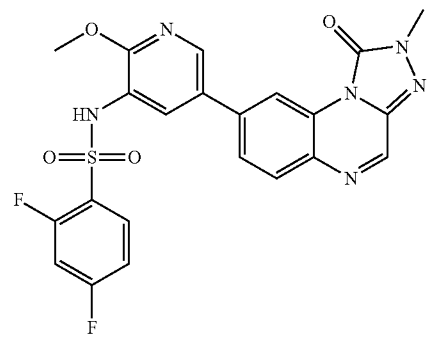 [SMILES: COc1ncc(-c2ccc3ncc4nn(C)c(=O)n4c3c2)cc1NS(=O)(=O)c1ccc(F)cc1F] |
| 149 | 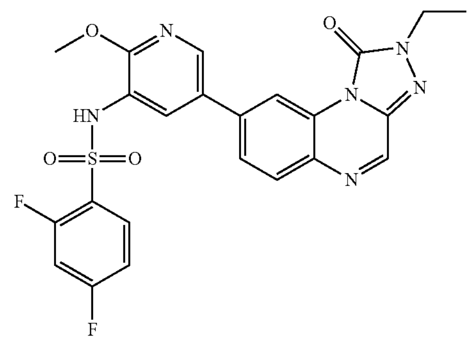 [SMILES: CCn1nc2cnc3ccc(-c4cnc(OC)c(NS(=O)(=O)c5ccc(F)cc5F)c4)cc3n2c1=O] |
| 150 | 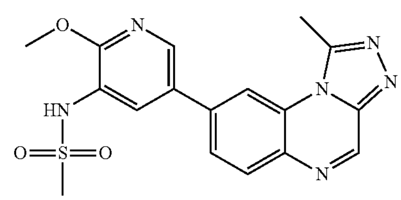 [SMILES: COc1ncc(-c2ccc3ncc4nnc(C)n4c3c2)cc1NS(C)(=O)=O] |
| 151 | 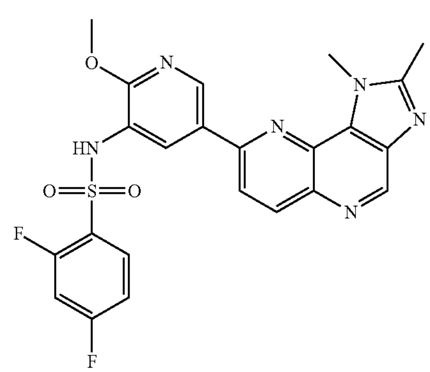 [SMILES: COc1ncc(-c2ccc3ncc4nc(C)n(C)c4c3n2)cc1NS(=O)(=O)c1ccc(F)cc1F] |

| No. | Structure |
|---|---|
| 152 | 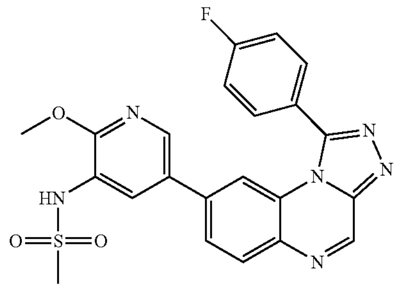 [SMILES: COc1ncc(-c2ccc3ncc4nnc(-c5ccc(F)cc5)n4c3c2)cc1NS(C)(=O)=O] |
| 153 | 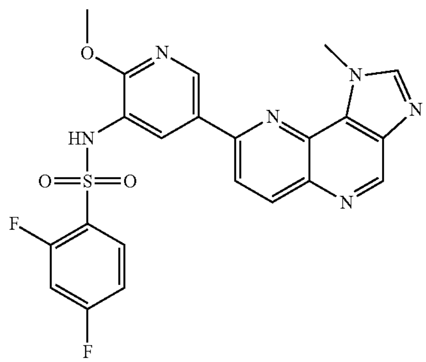 [SMILES: COc1ncc(-c2ccc3ncc4ncn(C)c4c3n2)cc1NS(=O)(=O)c1ccc(F)cc1F] |
| 154 | 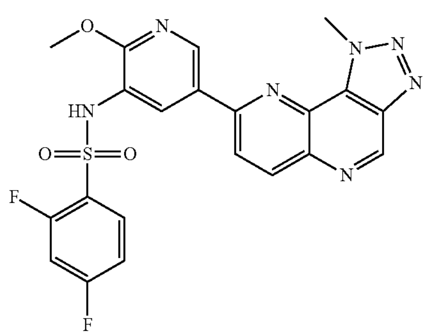 [SMILES: COc1ncc(-c2ccc3ncc4nnn(C)c4c3n2)cc1NS(=O)(=O)c1ccc(F)cc1F] |
| 155 | 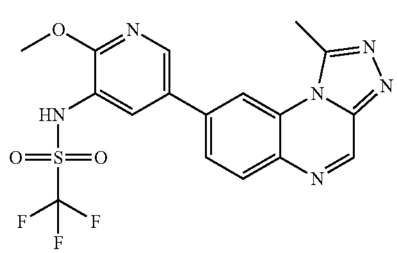 [SMILES: COc1ncc(-c2ccc3ncc4nnc(C)n4c3c2)cc1NS(=O)(=O)C(F)(F)F] |
| 156 | 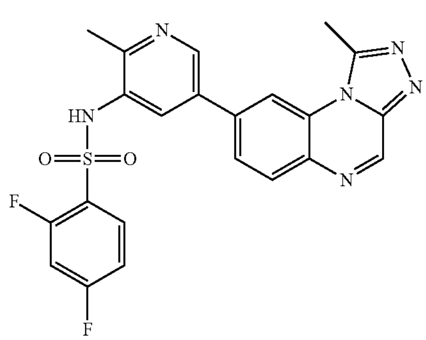 [SMILES: Cc1ncc(-c2ccc3ncc4nnc(C)n4c3c2)cc1NS(=O)(=O)c1ccc(F)cc1F] |

| No. | Structure |
|---|---|
| 157 | 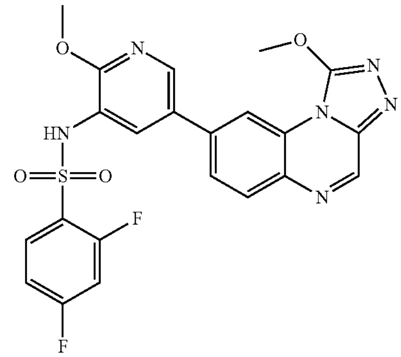 [SMILES: COc1ncc(-c2ccc3ncc4nnc(OC)n4c3c2)cc1NS(=O)(=O)c1ccc(F)cc1F] |
| 158 | 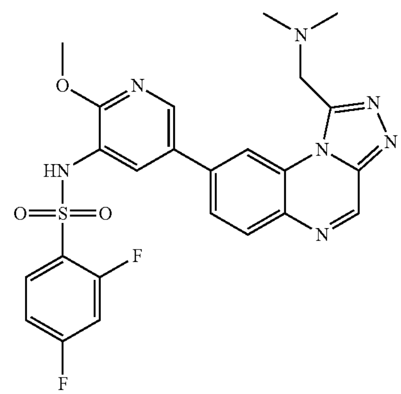 [SMILES: COc1ncc(-c2ccc3ncc4nnc(CN(C)C)n4c3c2)cc1NS(=O)(=O)c1ccc(F)cc1F] |
| 159 | 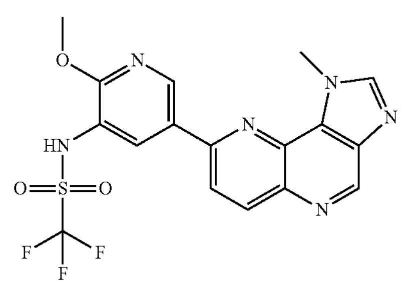 [SMILES: COc1ncc(-c2ccc3ncc4ncn(C)c4c3n2)cc1NS(=O)(=O)C(F)(F)F] |
| 160 | 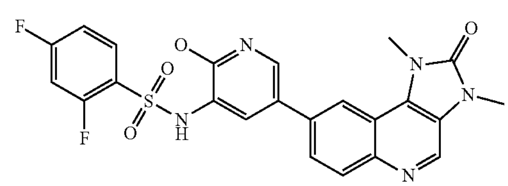 [SMILES: Cn1c(=O)n(C)c2c3cc(-c4cnc(O)c(NS(=O)(=O)c5ccc(F)cc5F)c4)ccc3ncc21] |
| 161 | 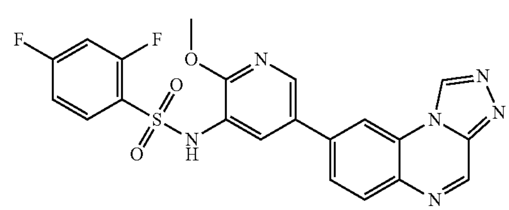 [SMILES: COc1ncc(-c2ccc3ncc4nncn4c3c2)cc1NS(=O)(=O)c1ccc(F)cc1F] |

TABLE-continued
| No. | Structure |
|---|---|
| 162 | 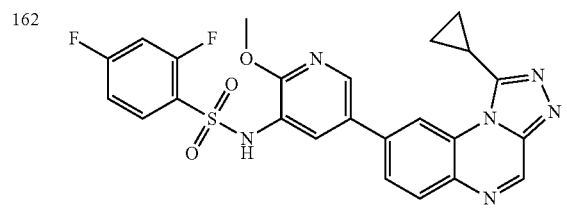 |
| 163 | 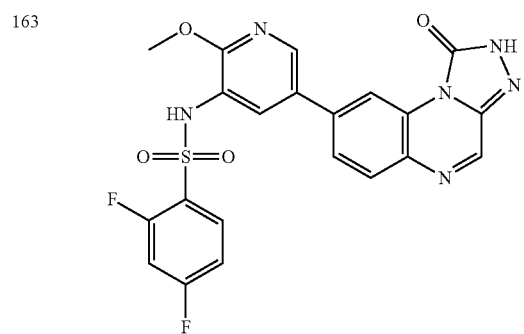 |
| 164 | 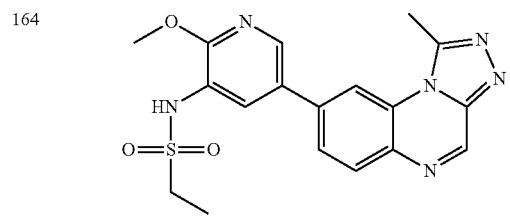 |
| 165 | 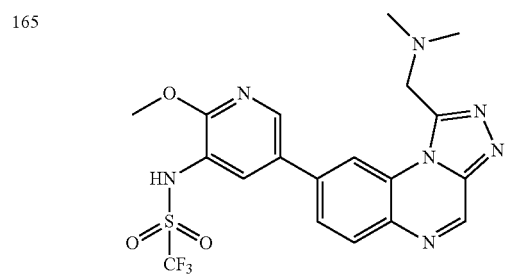 |
| 166 | 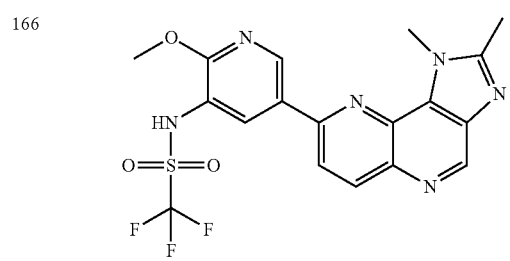 |
TABLE-continued
| No. | Structure |
|---|---|
| 167 | 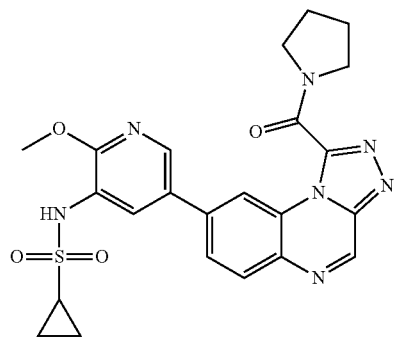 [SMILES: COc1ncc(-c2ccc3ncc4nnc(C(=O)N5CCCC5)n4c3c2)cc1NS(=O)(=O)C1CC1] |
| 168 | 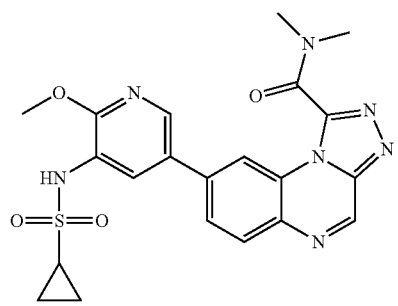 [SMILES: COc1ncc(-c2ccc3ncc4nnc(C(=O)N(C)C)n4c3c2)cc1NS(=O)(=O)C1CC1] |
| 169 | 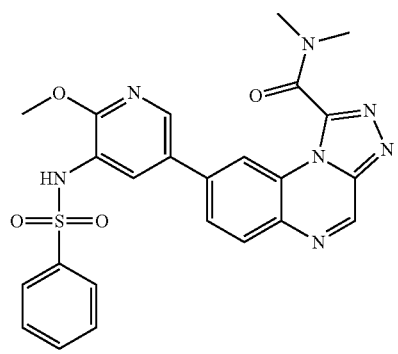 [SMILES: COc1ncc(-c2ccc3ncc4nnc(C(=O)N(C)C)n4c3c2)cc1NS(=O)(=O)c1ccccc1] |
| 170 | 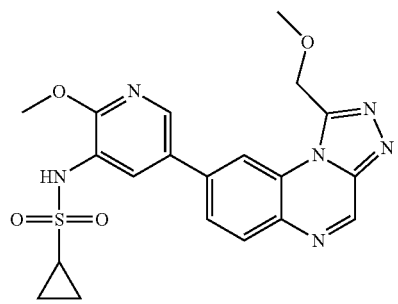 [SMILES: COCc1nnc2cnc3ccc(-c4cnc(OC)c(NS(=O)(=O)C5CC5)c4)cc3n12] |
| 171 | 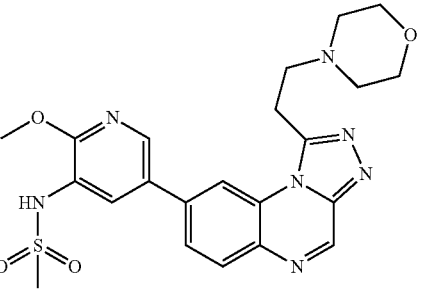 |

| No. | Structure |
|-----|-----------|
| 172 | 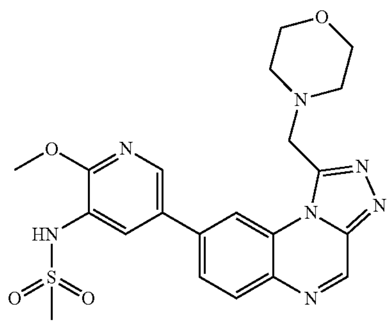 [SMILES: COc1ncc(-c2ccc3ncc4nnc(CN5CCOCC5)n4c3c2)cc1NS(C)(=O)=O] |
| 173 | 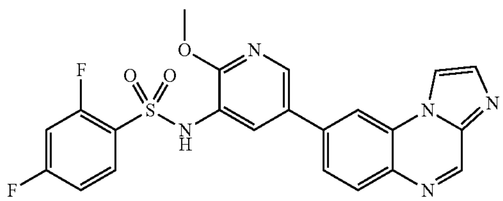 [SMILES: COc1ncc(-c2ccc3ncc4nccn4c3c2)cc1NS(=O)(=O)c1ccc(F)cc1F] |
| 174 | 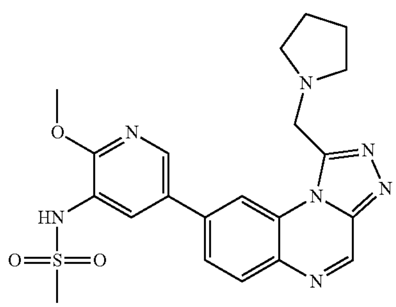 [SMILES: COc1ncc(-c2ccc3ncc4nnc(CN5CCCC5)n4c3c2)cc1NS(C)(=O)=O] |
| 175 | 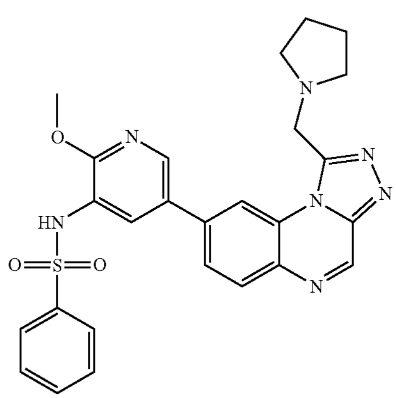 [SMILES: COc1ncc(-c2ccc3ncc4nnc(CN5CCCC5)n4c3c2)cc1NS(=O)(=O)c1ccccc1] |
| 176 | 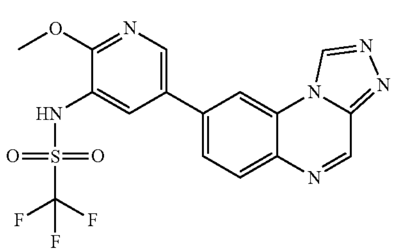 [SMILES: COc1ncc(-c2ccc3ncc4nncn4c3c2)cc1NS(=O)(=O)C(F)(F)F] |

| No. | Structure |
|-----|-----------|
| 177 | 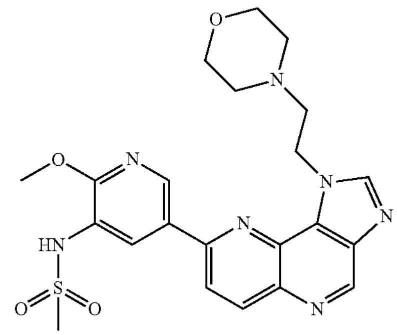 [SMILES: COc1ncc(-c2ccc3ncc4ncn(CCN5CCOCC5)c4c3n2)cc1NS(C)(=O)=O] |
| 178 | 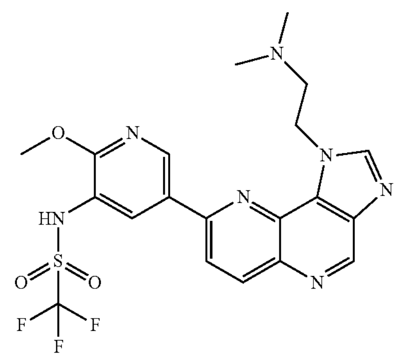 [SMILES: COc1ncc(-c2ccc3ncc4ncn(CCN(C)C)c4c3n2)cc1NS(=O)(=O)C(F)(F)F] |
| 179 | 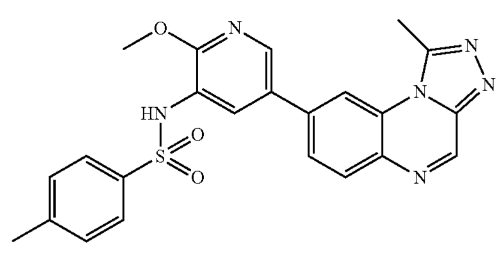 [SMILES: COc1ncc(-c2ccc3ncc4nnc(C)n4c3c2)cc1NS(=O)(=O)c1ccc(C)cc1] |
| 180 | 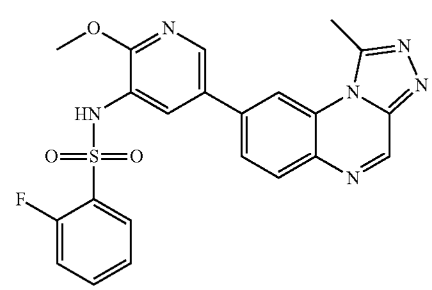 [SMILES: COc1ncc(-c2ccc3ncc4nnc(C)n4c3c2)cc1NS(=O)(=O)c1ccccc1F] |
| 181 | 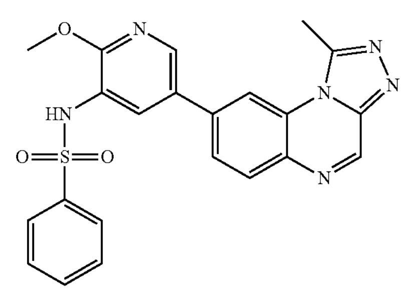 [SMILES: COc1ncc(-c2ccc3ncc4nnc(C)n4c3c2)cc1NS(=O)(=O)c1ccccc1] |

| No. | Structure |
|---|---|
| 182 | |
| 183 | |
| No. | Structure |
|---|---|
| 184 | 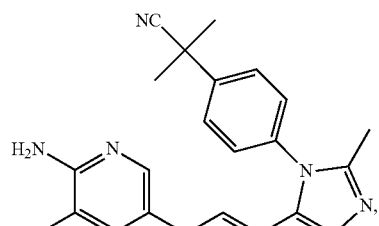 |
and/or at least one pharmaceutically acceptable salt thereof.
2. A pharmaceutical composition comprising at least one compound and/or at least one pharmaceutically acceptable salt thereof according to claim 1 and further comprising at least one pharmaceutically acceptable carrier.
* * * * *